(12) United States Patent
Imaizumi

(10) Patent No.: US 12,201,020 B2
(45) Date of Patent: Jan. 14, 2025

(54) ORGANIC ELECTROLUMINESCENCE DEVICE AND AMINE COMPOUND FOR ORGANIC ELECTROLUMINESCENCE DEVICE

(71) Applicant: Samsung Display Co., Ltd., Yongin-si (KR)

(72) Inventor: Taku Imaizumi, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 582 days.

(21) Appl. No.: 17/011,843

(22) Filed: Sep. 3, 2020

(65) Prior Publication Data

US 2021/0234104 A1 Jul. 29, 2021

(30) Foreign Application Priority Data

Jan. 15, 2020 (KR) .......................... 10-2020-0005457

(51) Int. Cl.
*H10K 85/60* (2023.01)
*C07D 493/04* (2006.01)
*H10K 50/15* (2023.01)

(52) U.S. Cl.
CPC ....... *H10K 85/6576* (2023.02); *C07D 493/04* (2013.01); *H10K 85/633* (2023.02);
(Continued)

(58) Field of Classification Search
CPC .............. H01L 51/0074; H01L 51/006; H01L 51/0061; H01L 51/0067; H01L 51/0073;
(Continued)

(56) References Cited

U.S. PATENT DOCUMENTS 9,564,600 B2 2/2017 Yokoyama et al.
9,738,826 B2 8/2017 Pan et al.
(Continued)

FOREIGN PATENT DOCUMENTS

| CN | 110885334 A | * | 3/2020 | ........ C07F 9/657172 |
| CN | 111655697 A | | 9/2020 | |

(Continued)

OTHER PUBLICATIONS

Chinese Patent Office Examination report dated Apr. 27, 2023, in corresponding CN Patent Application No. 202011462715.0 (10 pages).

*Primary Examiner* — Ruiyun Zhang
(74) *Attorney, Agent, or Firm* — Lewis Roca Rothgerber Christie LLP

(57) ABSTRACT

An organic electroluminescence device of an embodiment includes a first electrode, a second electrode, and a plurality of organic layers disposed between the first electrode and the second electrode, wherein at least one layer among the plurality of organic layers includes an amine compound represented by Formula 1, and the device thereby shows high emission efficiency and improved life span characteristics:

(Continued)

US 12,201,020 B2
Page 2

(56) References Cited

U.S. PATENT DOCUMENTS

| | | |
|---|---|---|
| 10,056,560 B2 | 8/2018 | Lee et al. |
| 10,230,056 B2 | 3/2019 | Cha et al. |
| 10,361,377 B2 | 7/2019 | Kim et al. |
| 10,505,121 B2 | 12/2019 | Song et al. |
| 10,553,800 B2 | 2/2020 | Ito et al. |
| 2017/0342318 A1 | 11/2017 | Kim et al. |
| 2018/0141957 A1 | 5/2018 | Park et al. |
| 2018/0201621 A1 | 7/2018 | Park et al. |
| 2019/0152985 A1 | 5/2019 | Suh et al. |
| 2019/0288040 A1 | 9/2019 | Ujiie et al. |

FOREIGN PATENT DOCUMENTS

| | | | |
|---|---|---|---|
| CN | 111683943 A | | 9/2020 |
| JP | 5493309 B2 | | 5/2014 |
| JP | 2018-85427 A | | 5/2018 |
| JP | 6469246 B2 | | 2/2019 |
| KR | 10-1447959 B1 | | 10/2014 |
| KR | 10-1507002 B1 | | 3/2015 |
| KR | 10-2017-0047653 A | | 5/2017 |
| KR | 10-2017-0056425 A | | 5/2017 |
| KR | 10-2017-0082193 A | | 7/2017 |
| KR | 10-2017-0082459 A | | 7/2017 |
| KR | 10-2017-0111538 A | | 10/2017 |
| KR | 20180096458 A | | 8/2018 |
| KR | 10-1916783 B1 | | 11/2018 |
| KR | 10-2019-0010499 A | | 1/2019 |
| KR | 2019031718 A | * | 3/2019 ............ C09K 11/06 |
| KR | 10-2019-0037772 A | | 4/2019 |
| WO | WO 2018/034444 A1 | | 2/2018 |
| WO | WO 2019/022458 A1 | | 1/2019 |
| WO | 2019225938 A1 | | 11/2019 |

* cited by examiner

Formula 1

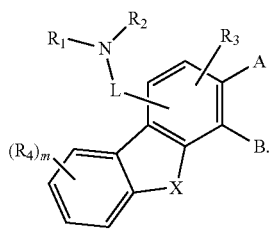

15 Claims, 2 Drawing Sheets

(52) U.S. Cl.
CPC ......... *H10K 85/636* (2023.02); *H10K 85/654* (2023.02); *H10K 85/657* (2023.02); *H10K 85/6574* (2023.02); *H10K 50/156* (2023.02)

(58) Field of Classification Search
CPC ............ H01L 51/5056; H01L 51/5064; H10K 85/6576; H10K 85/633; H10K 85/636; H10K 85/6574; H10K 85/657; C07D 493/04
USPC ......................................................... 257/40
See application file for complete search history.

ORGANIC ELECTROLUMINESCENCE DEVICE AND AMINE COMPOUND FOR ORGANIC ELECTROLUMINESCENCE DEVICE

CROSS-REFERENCE TO RELATED APPLICATION

This application claims priority to and the benefit of Korean Patent Application No. 10-2020-0005457, filed on Jan. 15, 2020, the entire content of which is hereby incorporated by reference.

BACKGROUND

One or more aspects of embodiments of the present disclosure relate to an organic electroluminescence device and an amine compound used therein.

Organic electroluminescence displays are recently being developed as image display devices. An organic electroluminescence display is a so-called self-luminescent display, in which holes and electrons respectively injected from a first electrode and a second electrode recombine in an emission layer to produce excitons, and light is emitted by the transition of excitons to the ground state, thereby achieving display.

In the application of an organic electroluminescence device to a display, a decrease in driving voltage and/or an increase in emission efficiency and/or life span of the organic electroluminescence device are desired, and development of materials for an organic electroluminescence device stably attaining such demands are desired.

Amine compounds have been developed as hole transport region materials. However, development of improved amine compounds having high efficiency and/or long life span for an organic electroluminescence device including the same is desired.

SUMMARY

One or more aspects of embodiments of the present disclosure are directed toward an organic electroluminescence device having excellent emission efficiency and increased life.

One or more aspects of embodiments of the present disclosure are directed toward an amine compound for use in an organic electroluminescence device having excellent emission efficiency and/or increased lifespan.

One or more example embodiments of the present disclosure provide an organic electroluminescence device including a first electrode; a second electrode oppositely disposed to the first electrode; and a plurality of organic layers disposed between the first electrode and the second electrode, wherein at least one functional layer among the plurality of organic layers includes an amine compound represented by Formula 1:

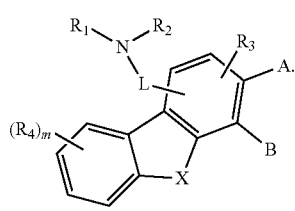

Formula 1

In Formula 1, X may be O or S, $R_1$ and $R_2$ may each independently be a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, $R_3$ and $R_4$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, where when $R_3$ and $R_4$ are each a heteroaryl group, a carbazole group is excluded, L may be a direct linkage, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, "m" may be an integer of 0 to 4, and A and B are points of connection to a substituent represented by Formula 2:

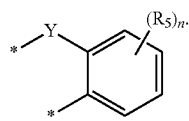

Formula 2

In Formula 2, Y may be O or S, where at least one of X (in Formula 1) or Y is O, $R_5$ may be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, where when $R_5$ is a heteroaryl group, a carbazole group is excluded, "n" may be an integer of 0 to 4, and "—*" refers to a position connected to positions A or B of Formula 1.

In an embodiment, the amine compound may be a monoamine compound.

In an embodiment, $R_1$ and $R_2$ may each independently be a substituted or unsubstituted aryl group of 6 to 30 carbon atoms for forming a ring, or a substituted or unsubstituted heteroaryl group of 2 to 30 carbon atoms for forming a ring.

In an embodiment, $R_1$ and $R_2$ may each independently be a substituted or unsubstituted cyclohexyl group, a substituted or unsubstituted adamantyl group, a substituted or unsubstituted phenyl group, a substituted or unsubstituted biphenyl group, a substituted or unsubstituted terphenyl group, a substituted or unsubstituted naphthalene group, a substituted or unsubstituted fluorenyl group, a substituted or unsubstituted phenanthryl group, a substituted or unsubstituted dibenzofuran group, or a substituted or unsubstituted dibenzothiophene group.

In an embodiment, L may be a substituted or unsubstituted aryl group of 6 to 30 carbon atoms for forming a ring, or a substituted or unsubstituted heteroaryl group of 2 to 30 carbon atoms for forming a ring.

In an embodiment, any one among X and Y (e.g., X and/or Y) may be substituted at (e.g., connected to) a para position or a meta position with respect to a nitrogen atom in the amine compound.

In an embodiment, $R_4$ and $R_5$ may each independently be a hydrogen atom, a deuterium atom, or a phenyl group.

In an embodiment, the amine compound represented by Formula 1 may be represented by one of Formula 3-1 to Formula 3-3:

Formula 3-1

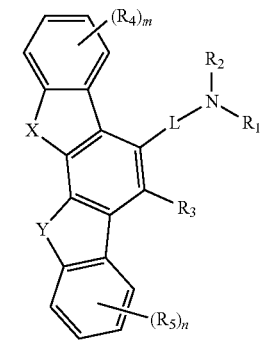

Formula 3-2

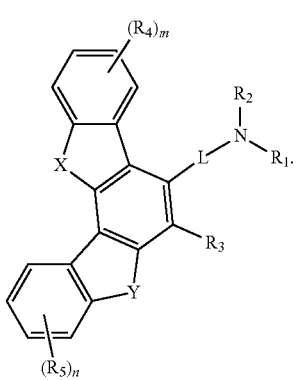

Formula 3-3

In Formula 3-1 to Formula 3-3, X, Y, $R_1$ to $R_5$, L, "m" and "n" may each independently be the same as defined in Formula 1 and Formula 2.

In an embodiment, the amine compound represented by Formula 1 may be represented by one of Formula 4-1 to Formula 4-9:

Formula 4-1

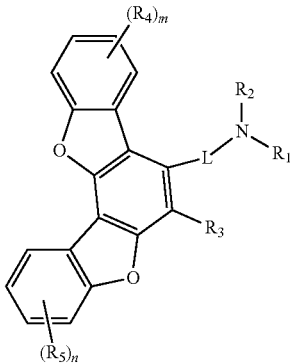

Formula 4-2

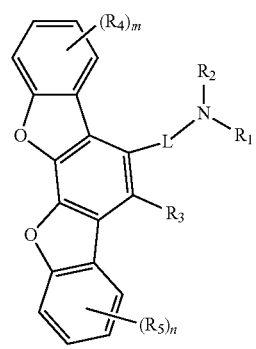

Formula 4-3

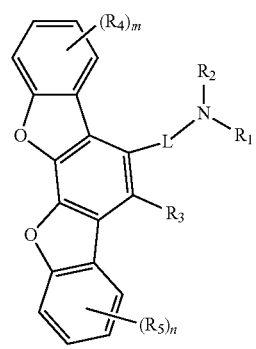

Formula 4-4

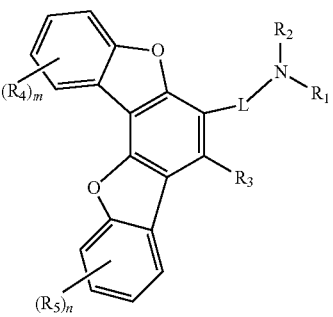

Formula 4-5

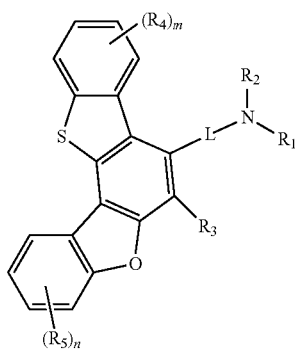

Formula 4-6

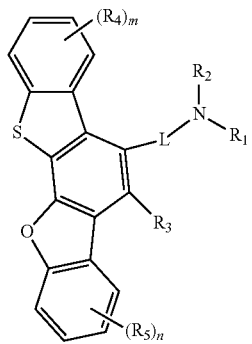

Formula 4-7

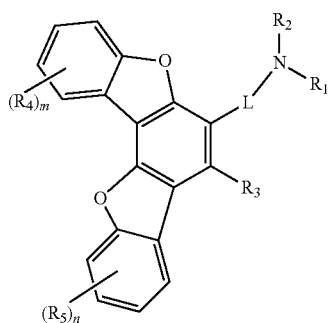

Formula 4-8

Formula 4-9

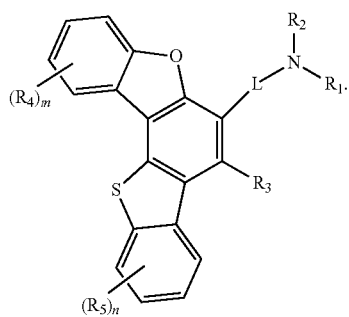

In Formula 4-1 to Formula 4-9, $R_1$ to $R_5$, L, "m" and "n" may each independently be the same as defined in Formula 1 and Formula 2.

In an embodiment, the plurality of the organic layers may include a hole transport region, an emission layer, and an electron transport region, and the hole transport region may include the amine compound.

In an embodiment, the hole transport region may include a hole injection layer, a hole transport layer, and an electron blocking layer, and the hole transport layer may include the amine compound.

In an embodiment, the amine compound represented by Formula 1 may be any (e.g., at least) one among the compounds in Compound Group A to Compound Group F:

Compound Group A

A1

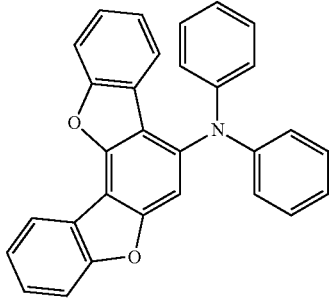

A2

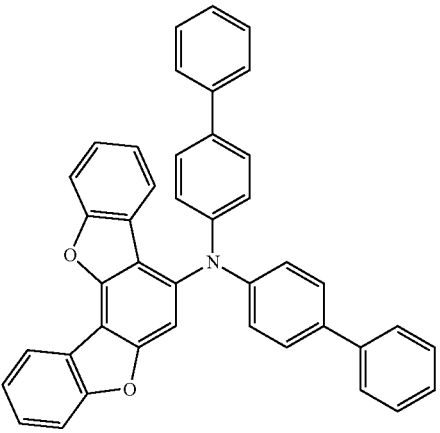

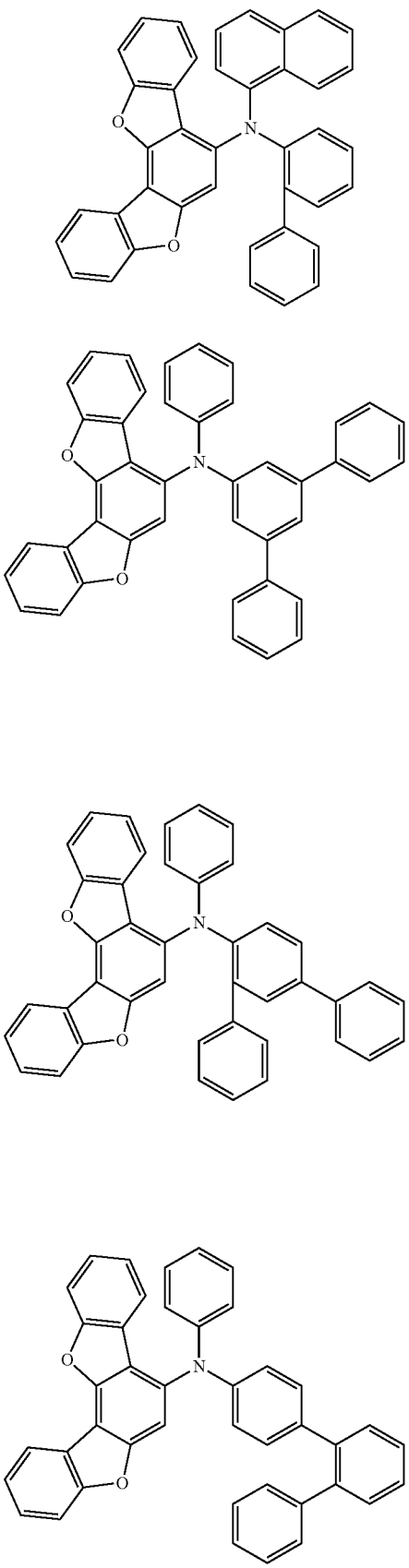
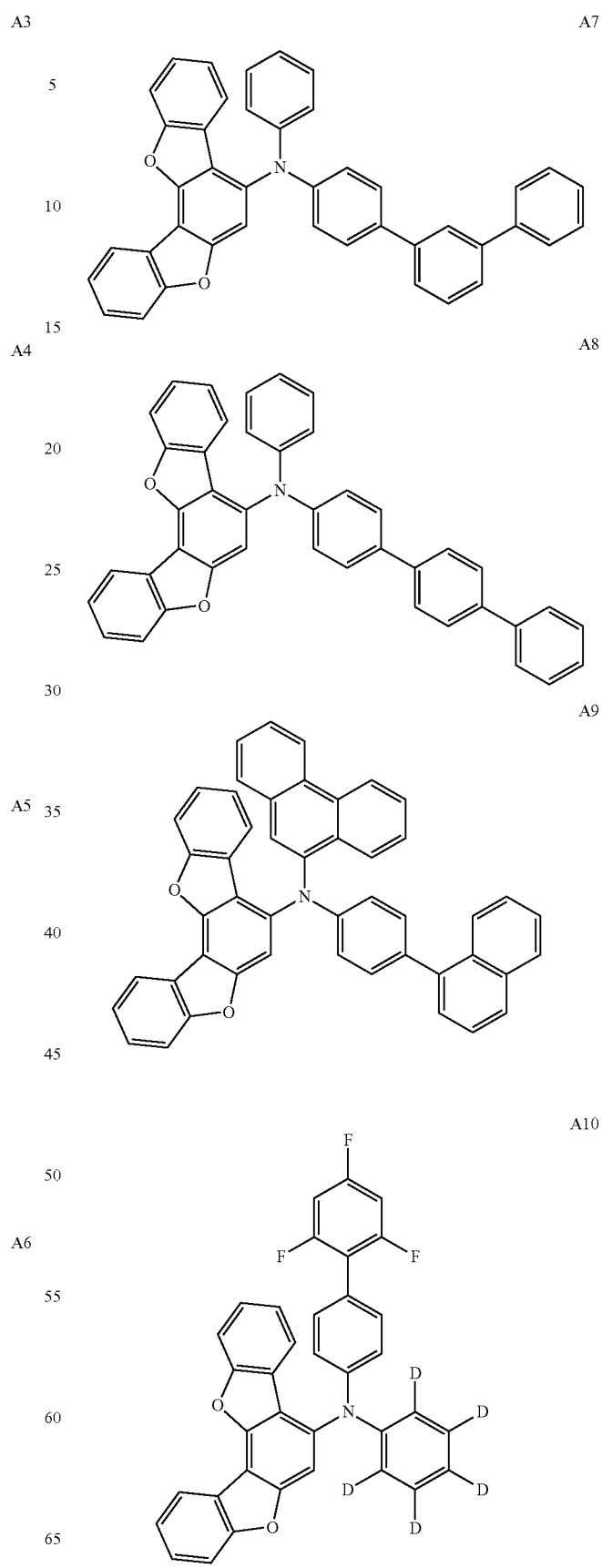

A11
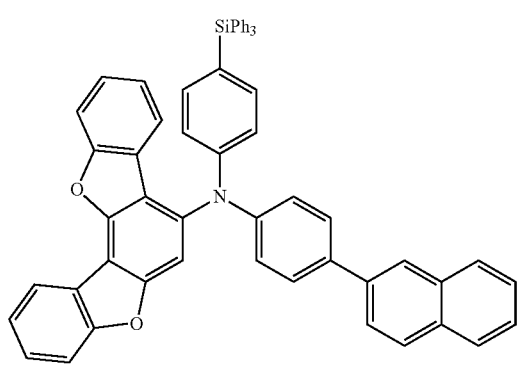
A12
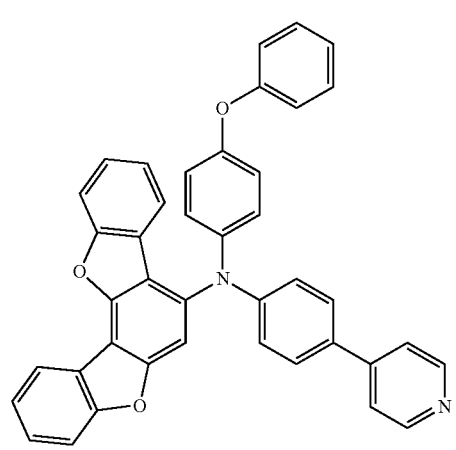
A13
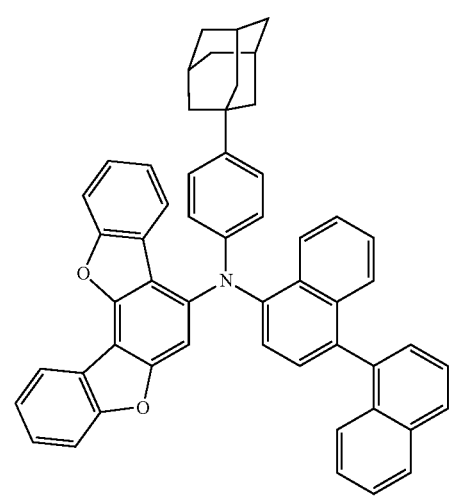
A14
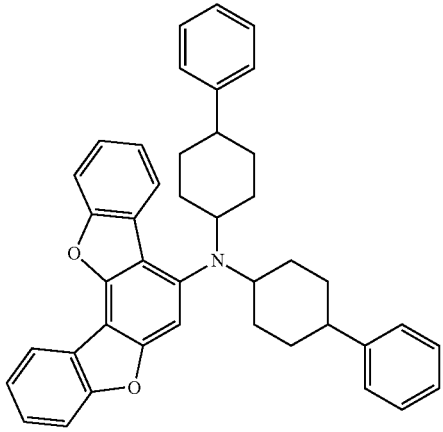
A15
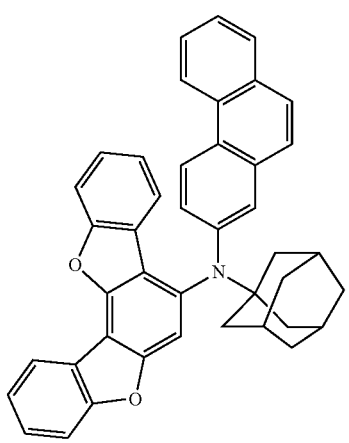
A16
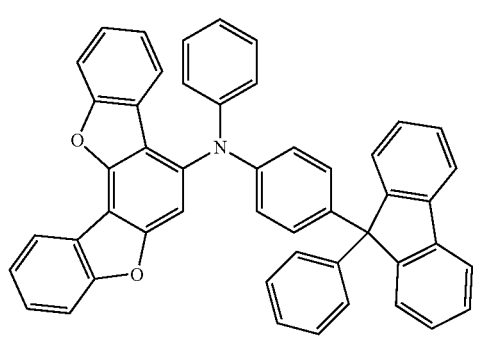
A17
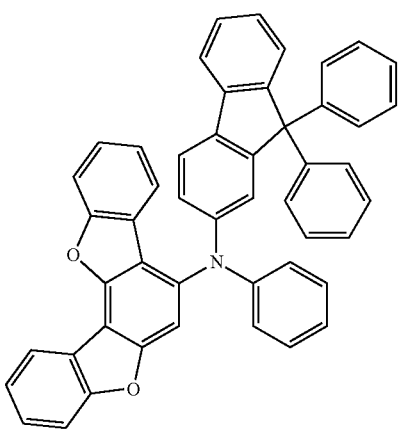

A18
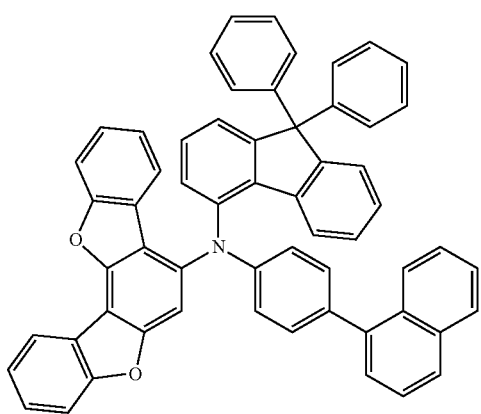
A19
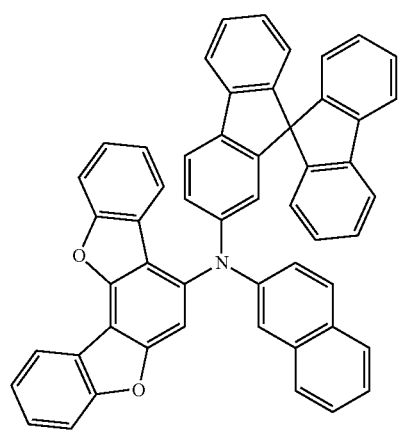
A20
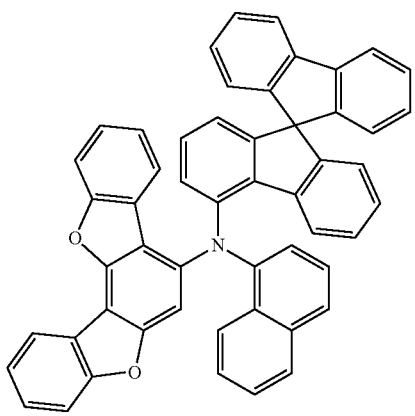
A21
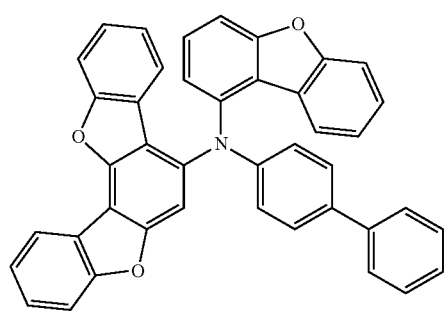
A22
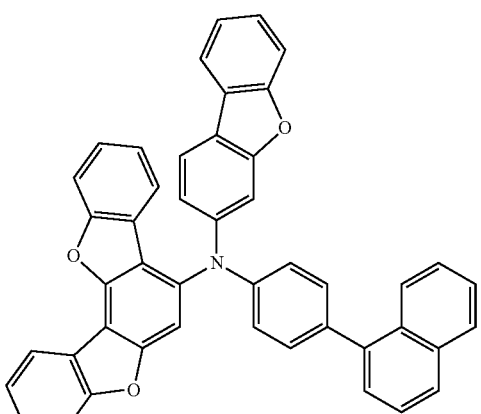
A23
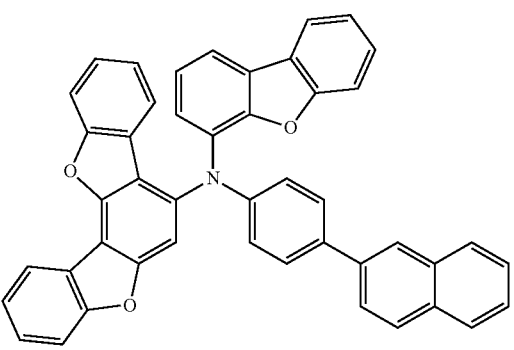
A24

A25
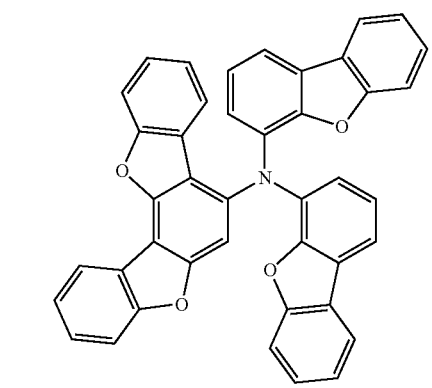

-continued
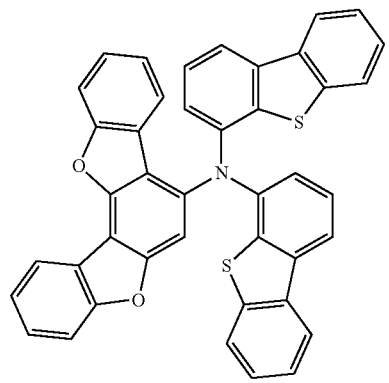
A26
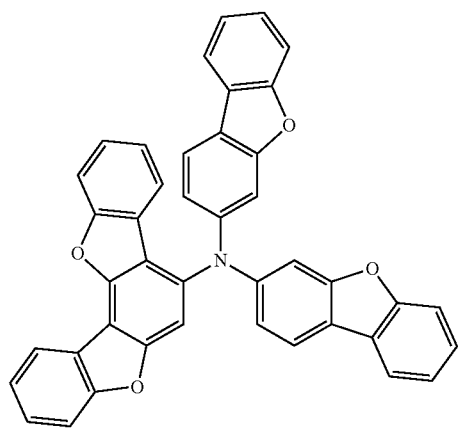
A27
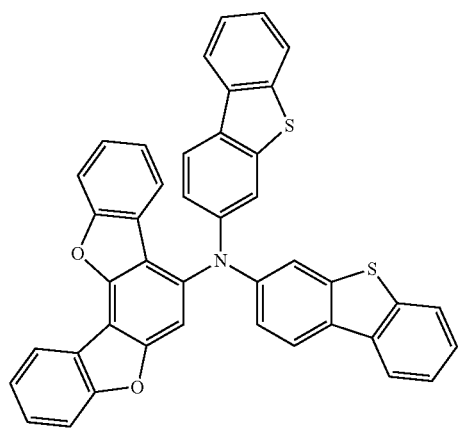
A28
-continued
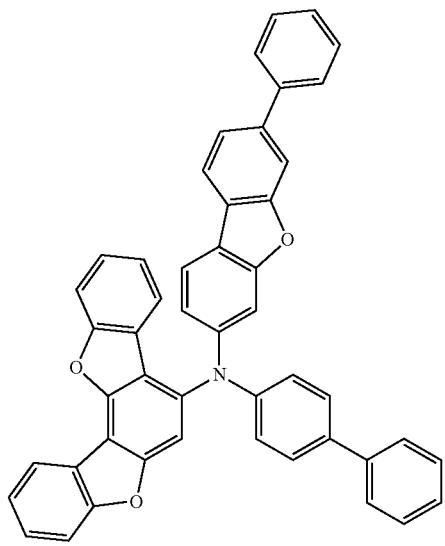
A29
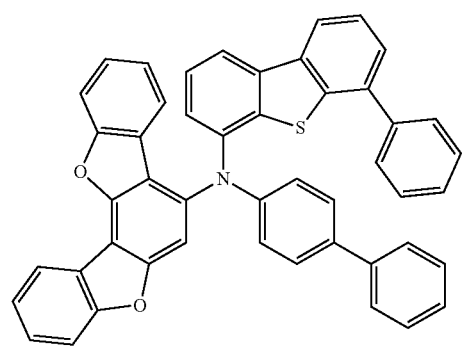
A30
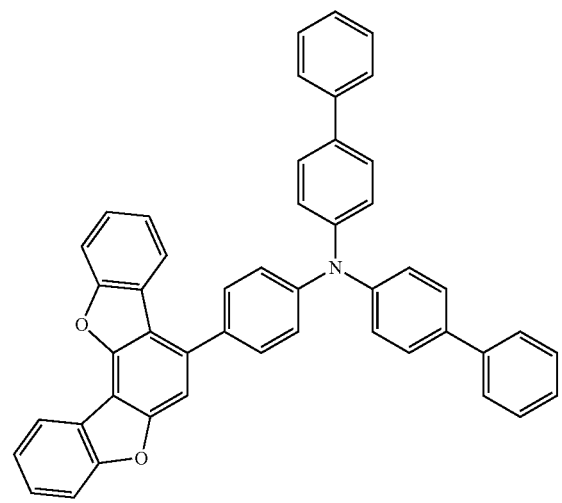
A31

A32
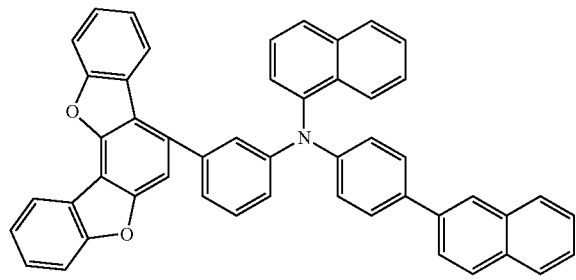
A33
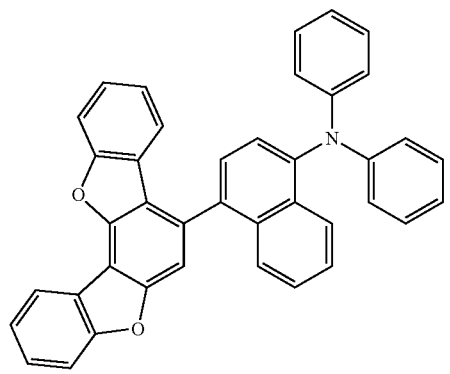
A34
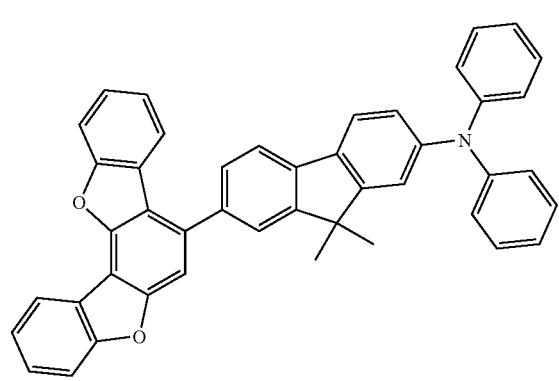
A36
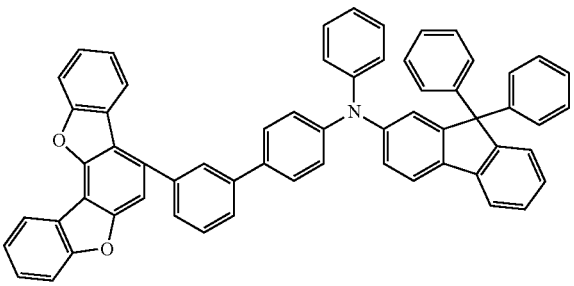
A37
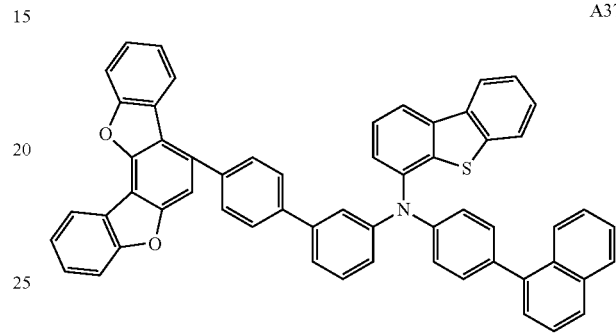
A38
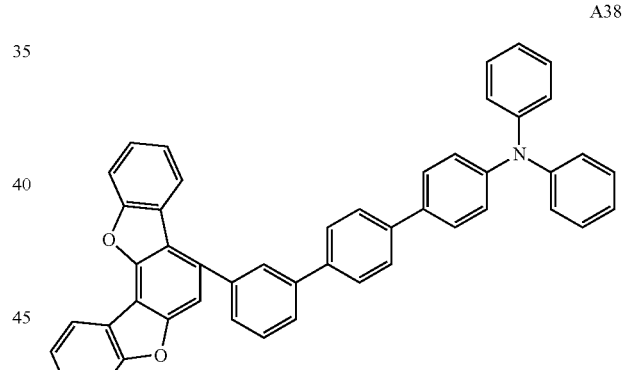
A35
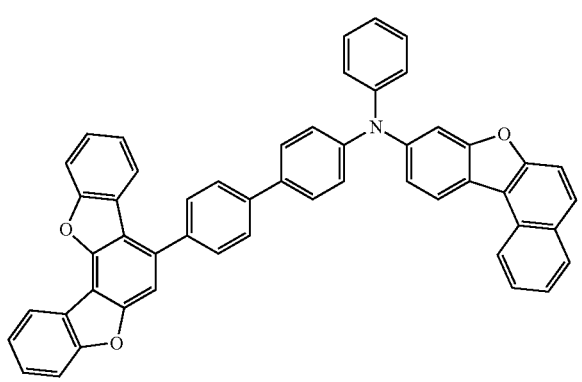
A39
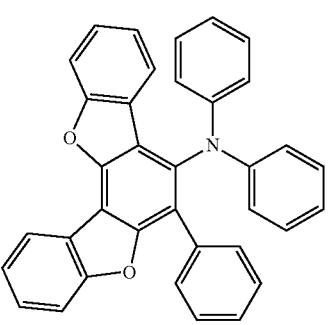

A40
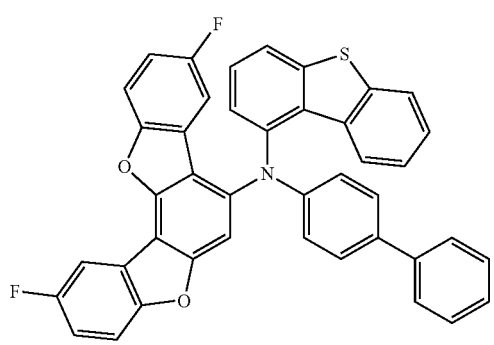
A41
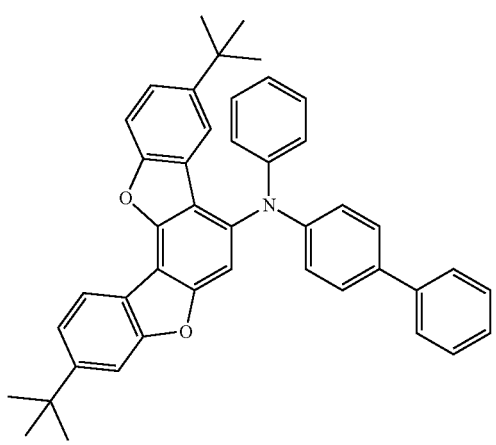
A42
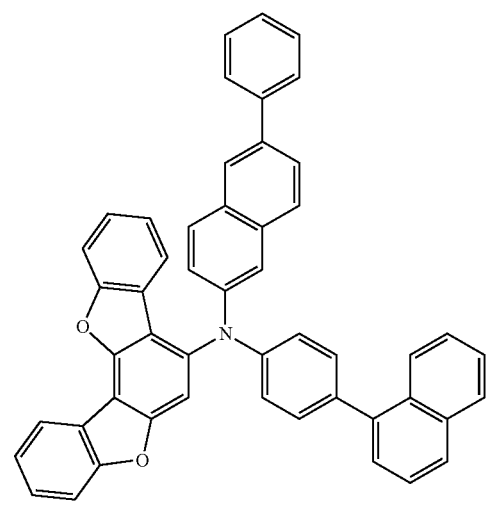
A43
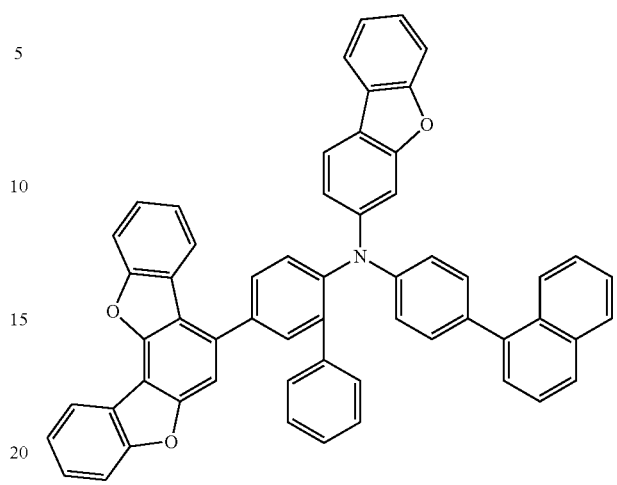
A44
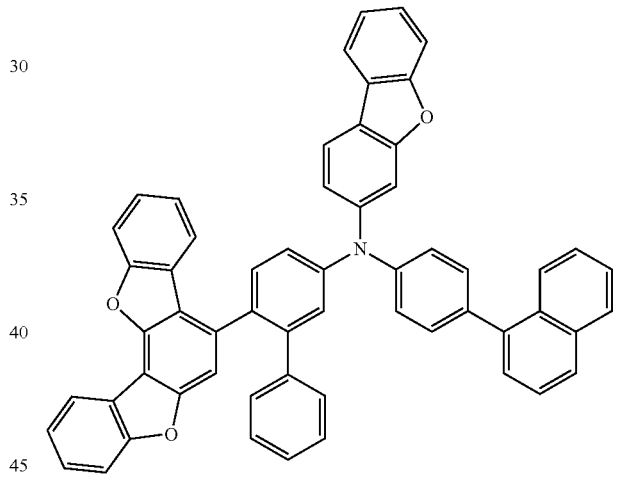
A45
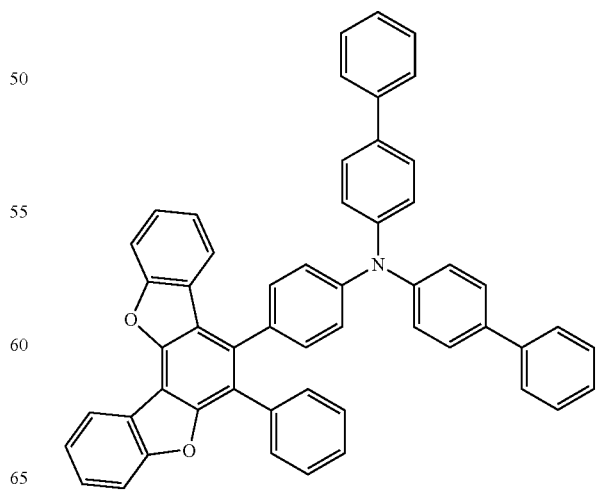

-continued
A46
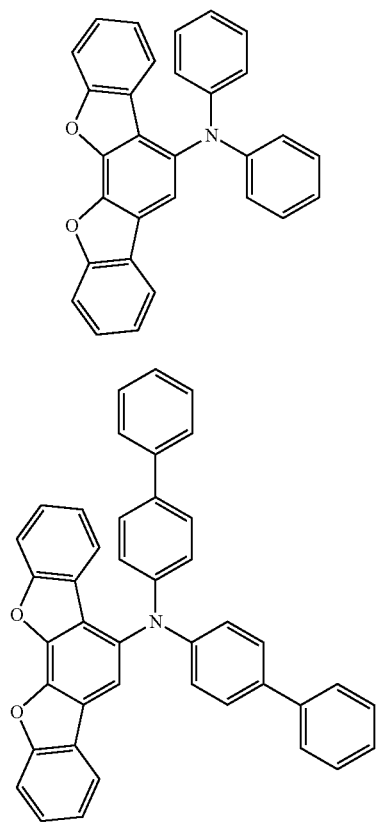
A47
A48
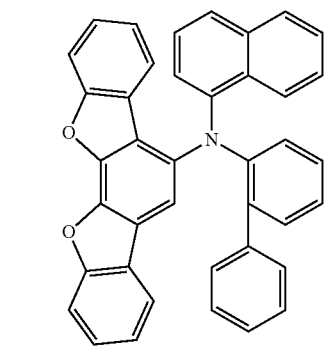
A49
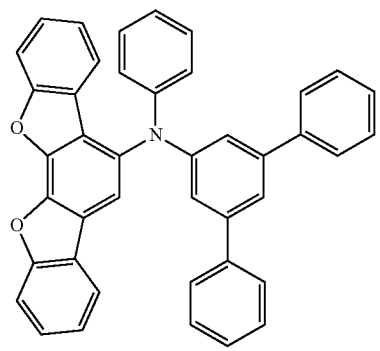
-continued
A50
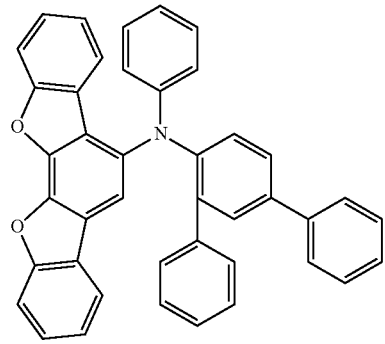
A51
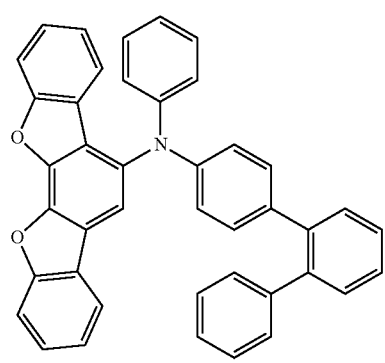
A52
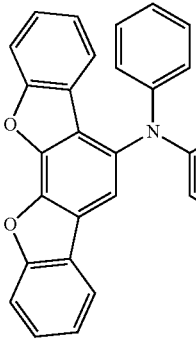
A53
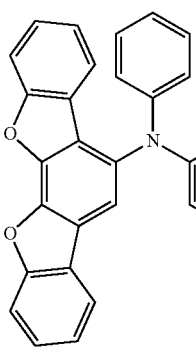

A54
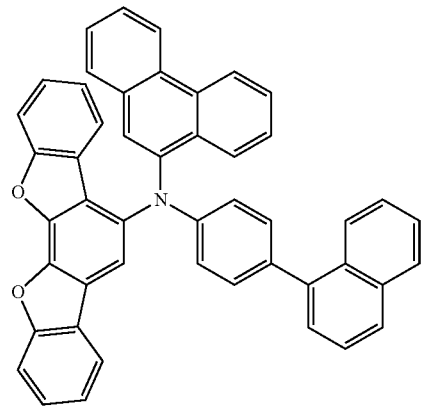
A55
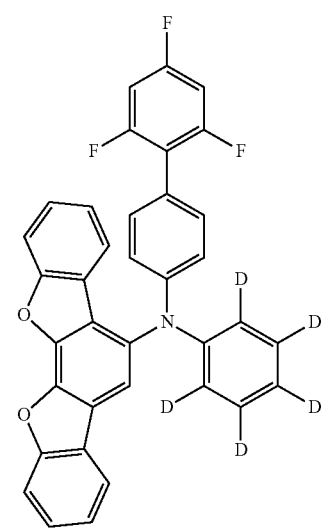
A56
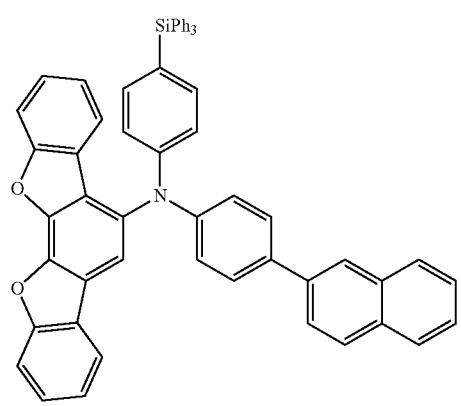
A57
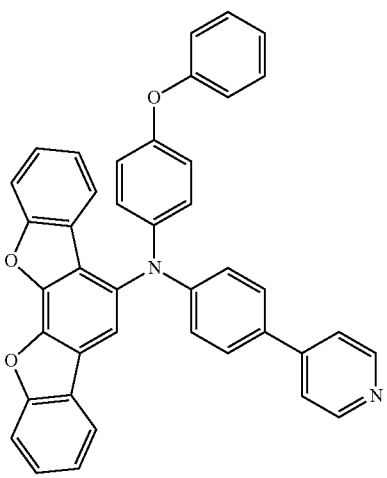
A58
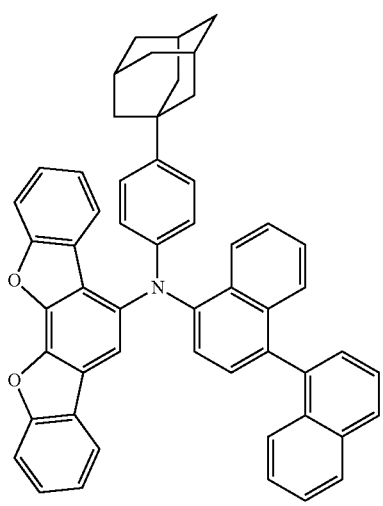
A59
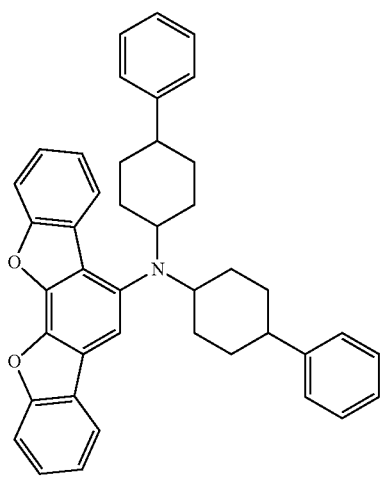

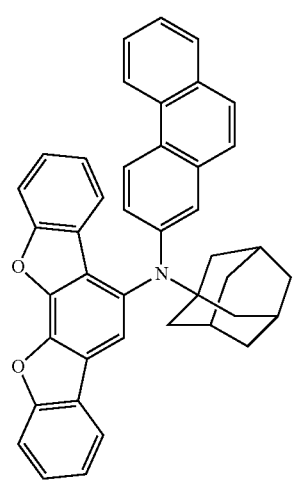
A60
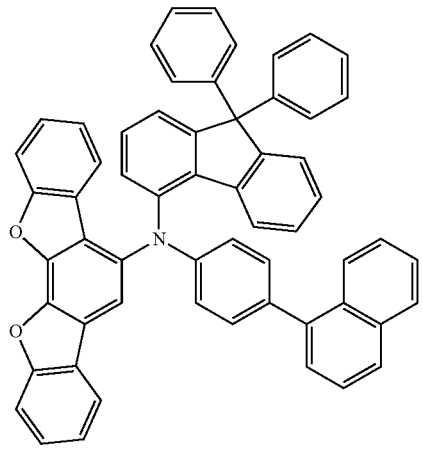
A63
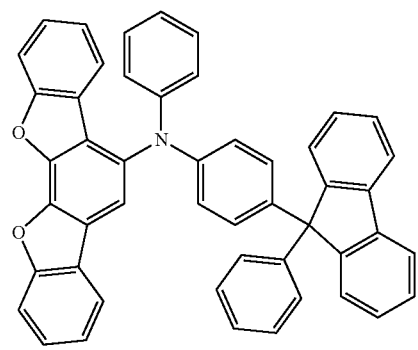
A61
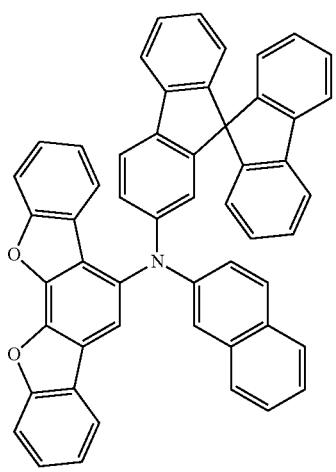
A64
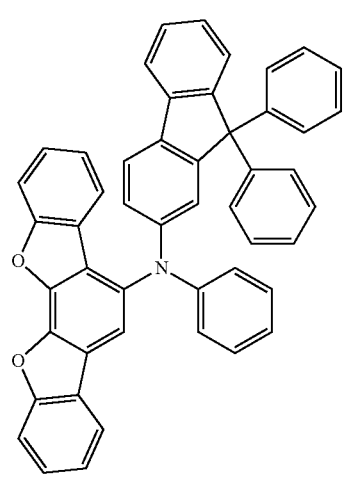
A62
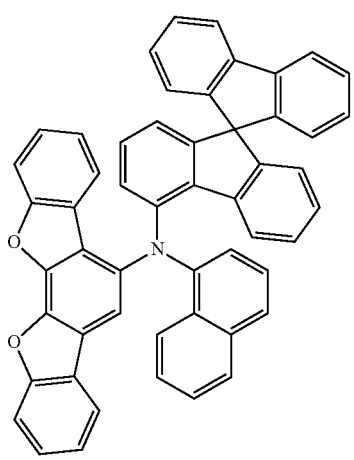
A65

-continued
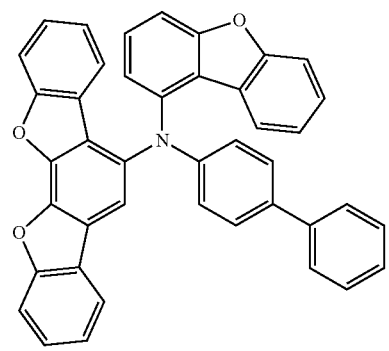
A66
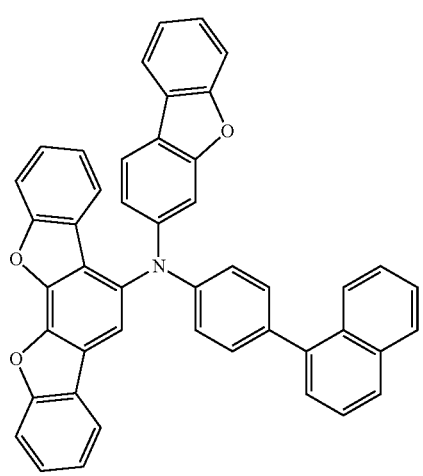
A67
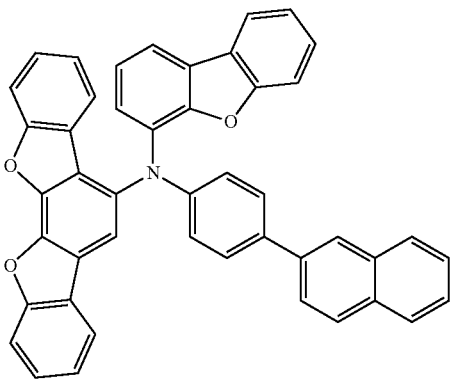
A68

A69
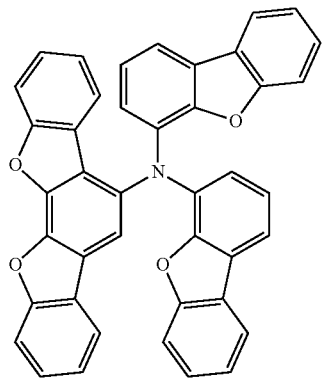
A70
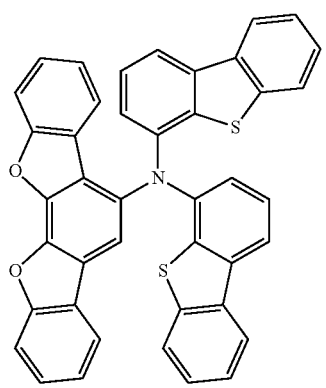
A71
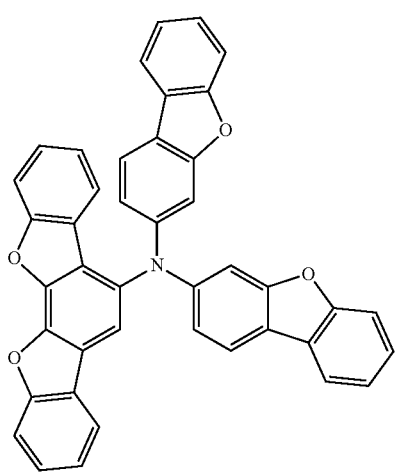
A72

-continued
A73
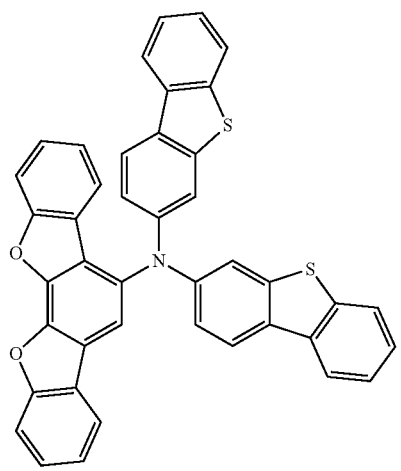
A74
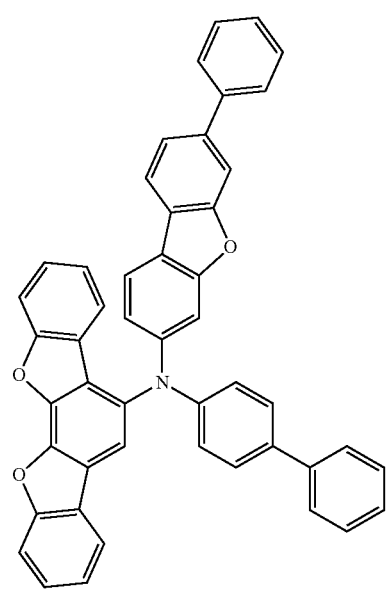
A75
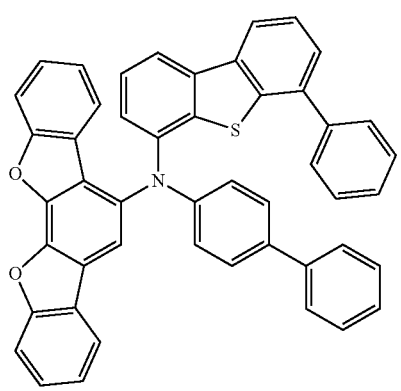
-continued
A76
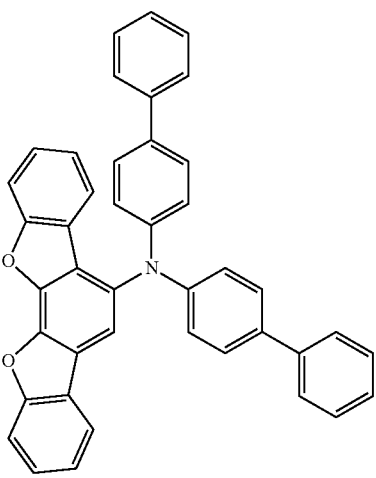
A77
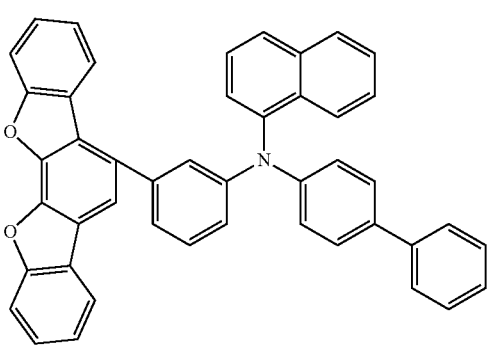
A78
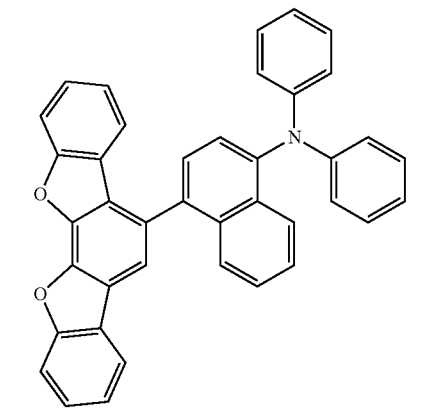
A79
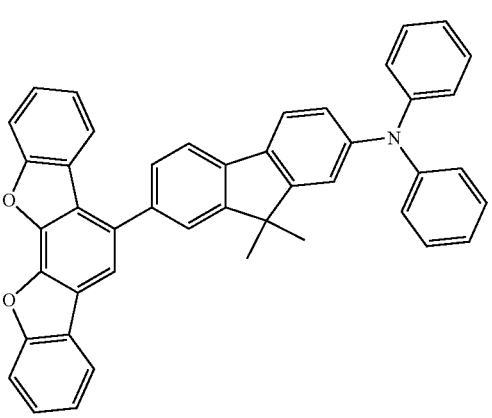

A80
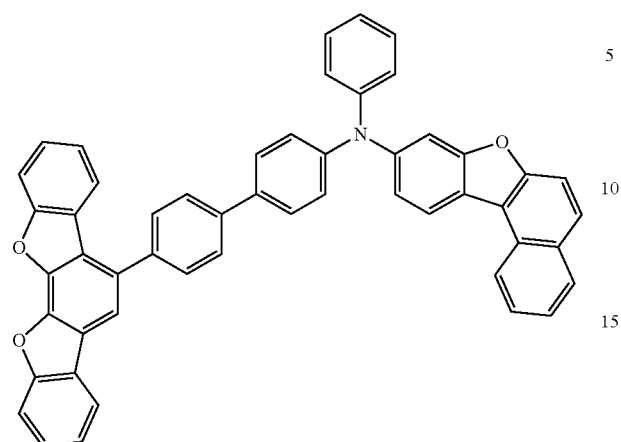
A81
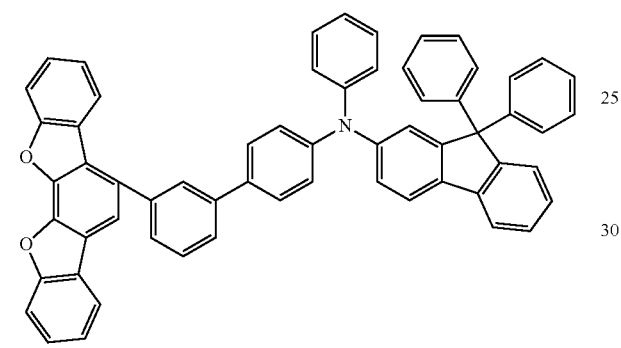
A82
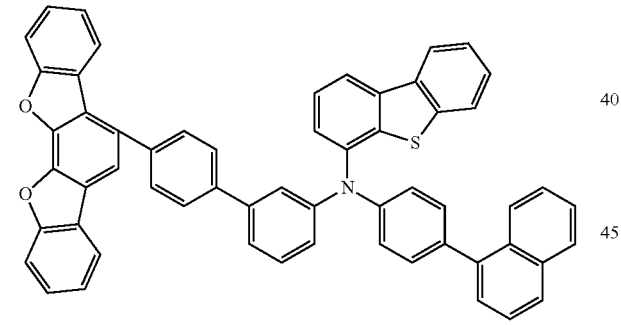
A83
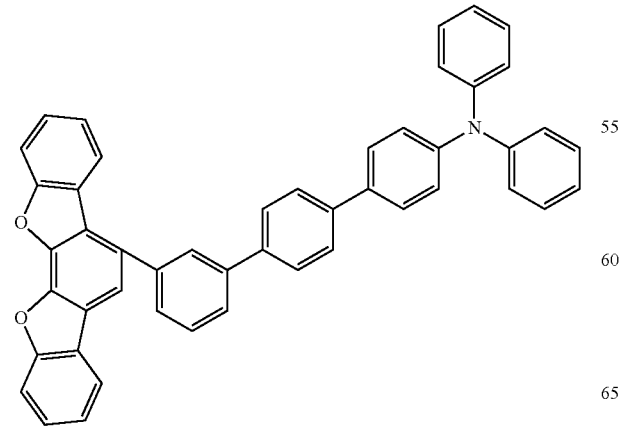
A84
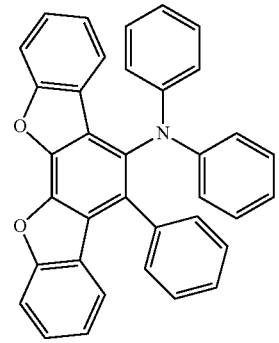
A85
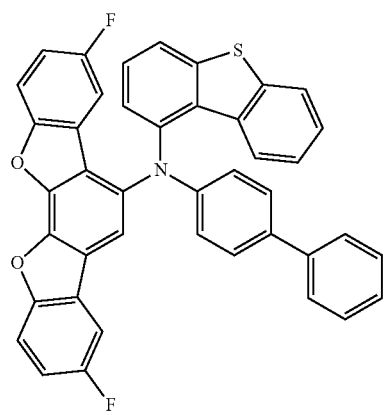
A86
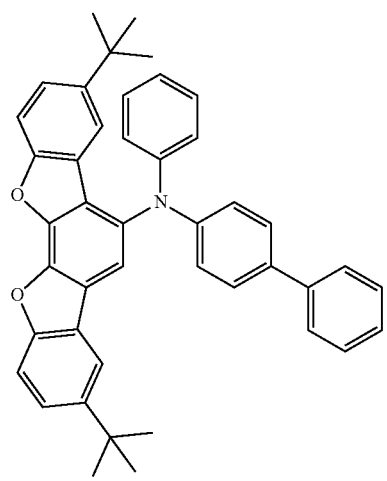

A87
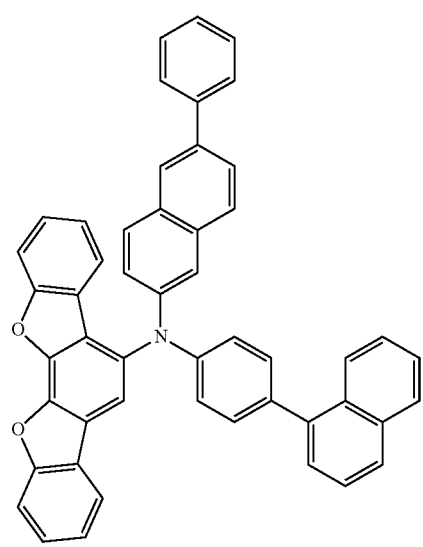
A88
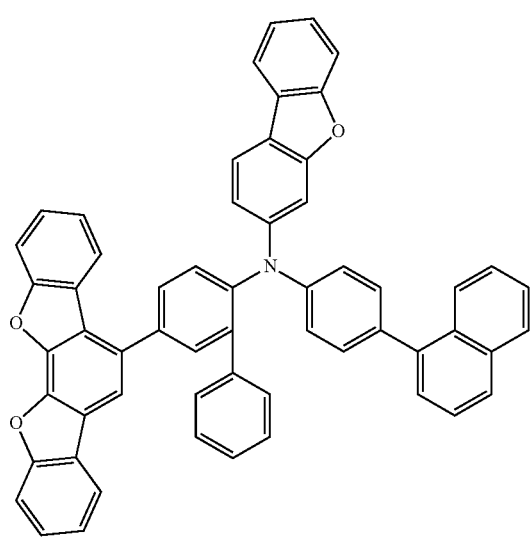
A89
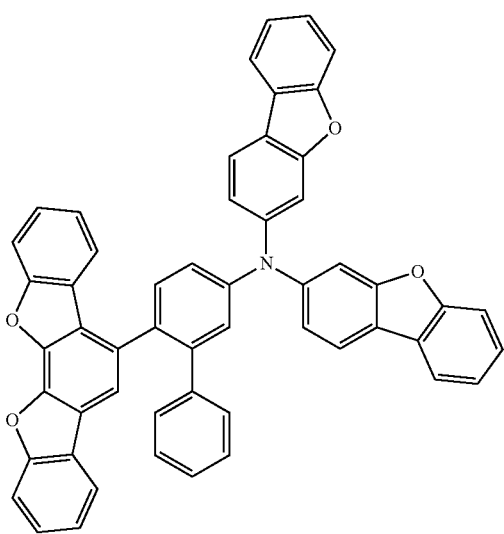
A90
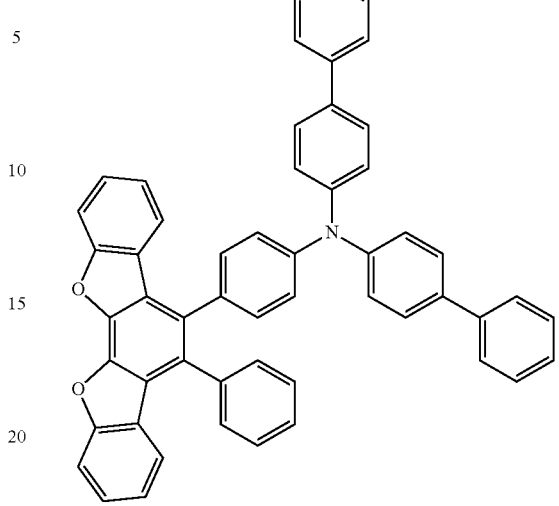
A91
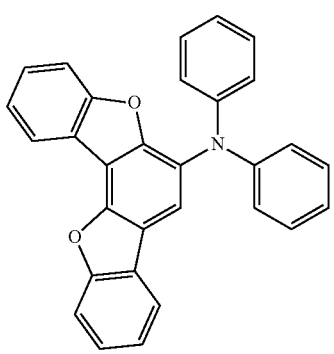
A92
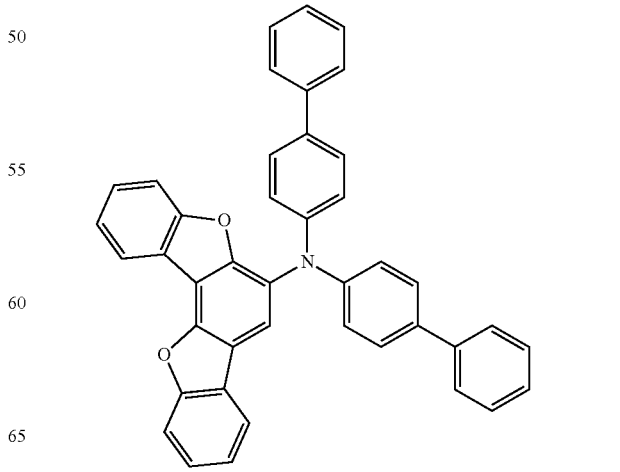

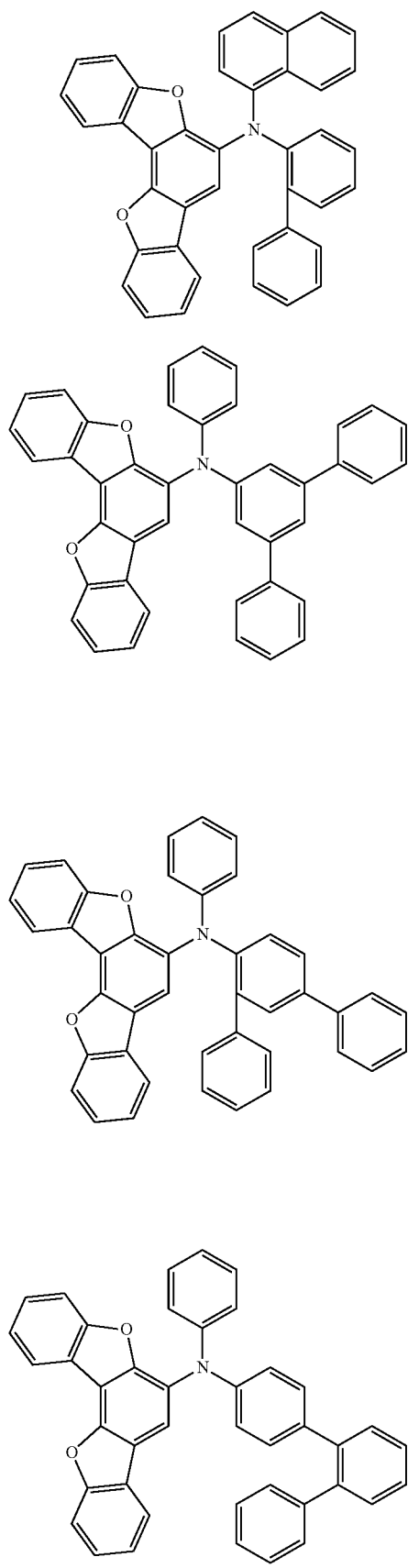
A93
A94
A95
A96
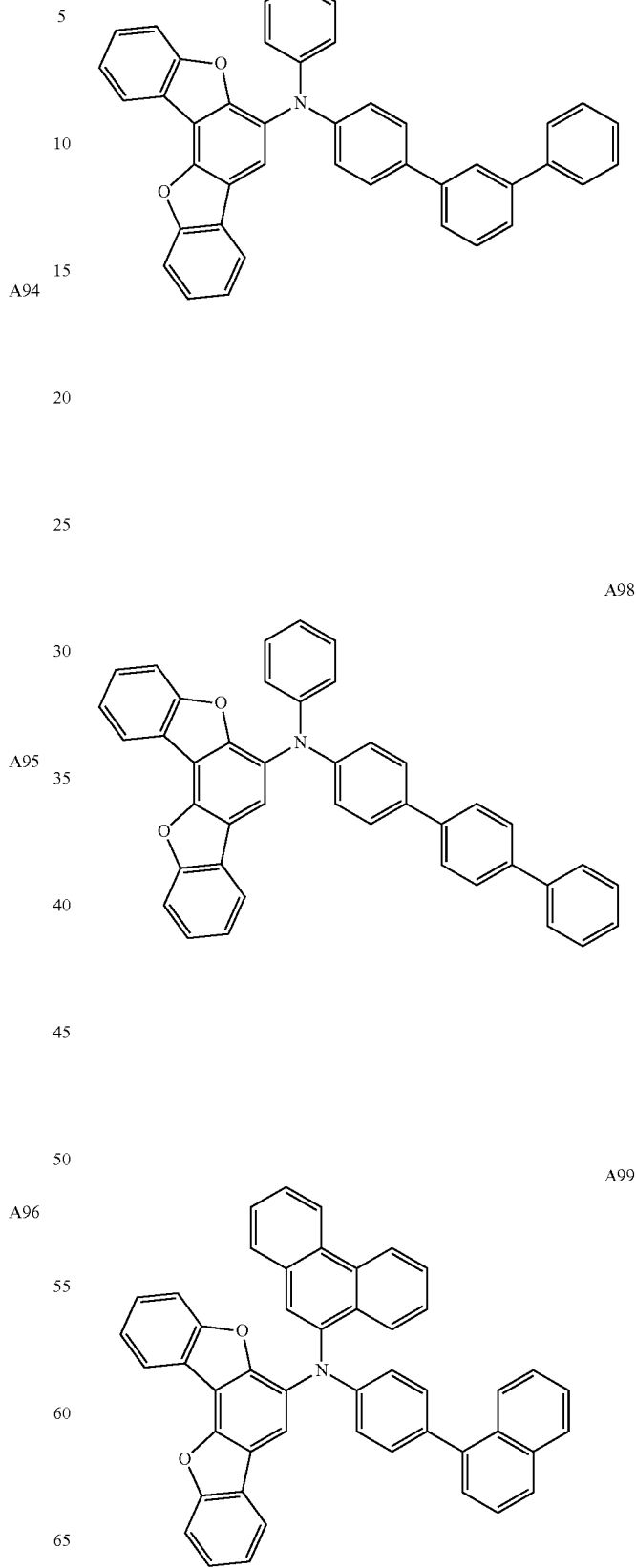
A97
A98
A99

A100
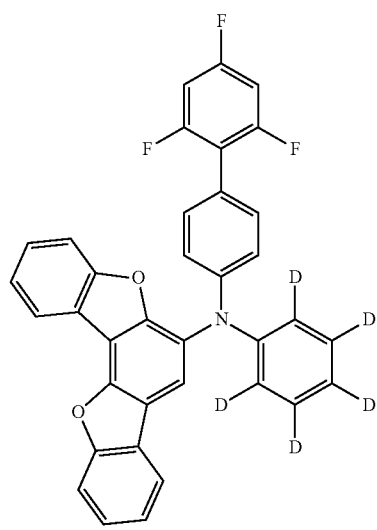
A101
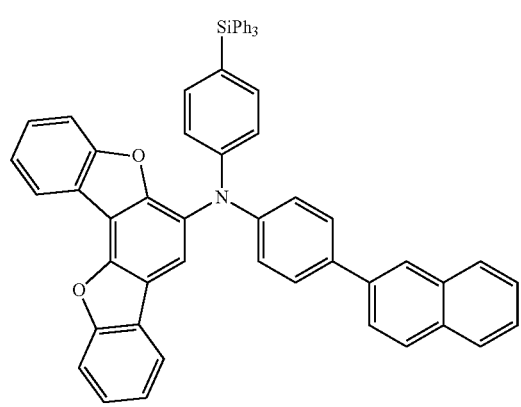
A102
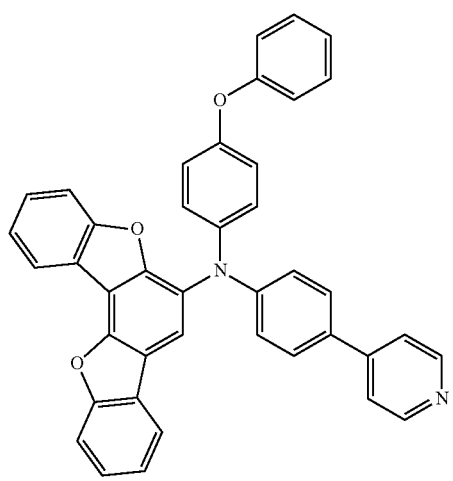
A103
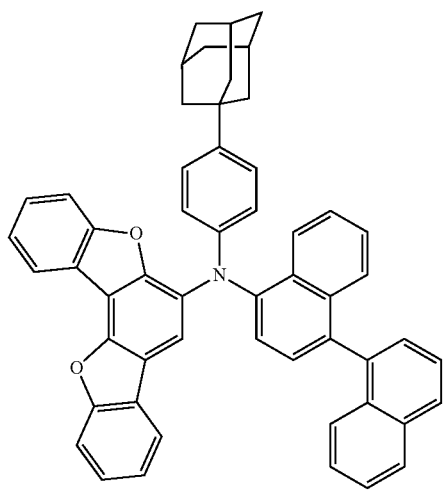
A104
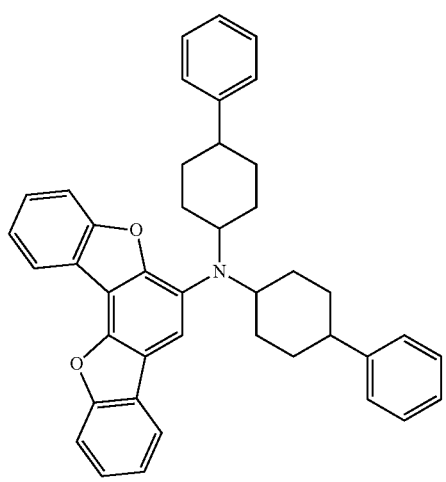
A105
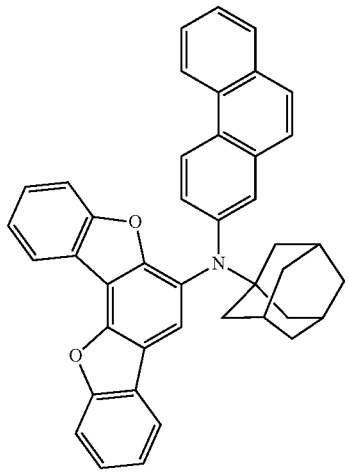

A106
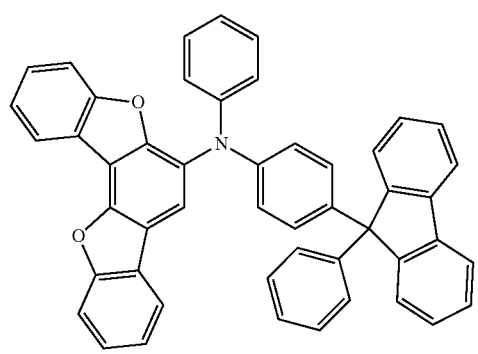
A107
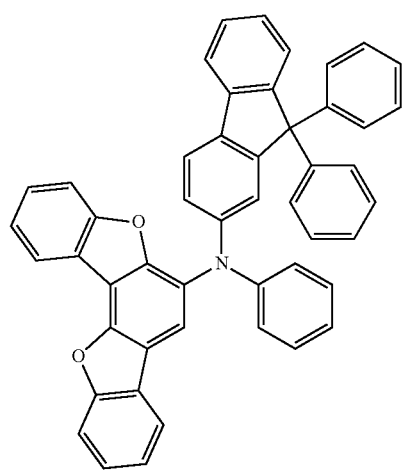
A108
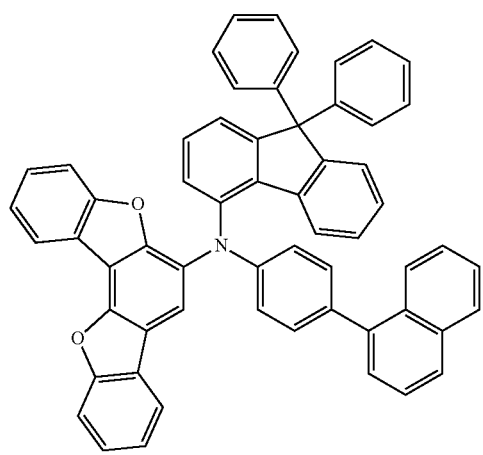
A109
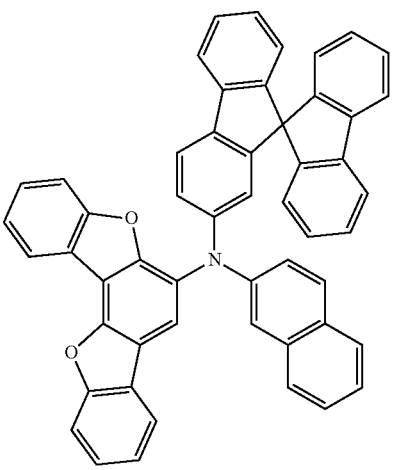
A110
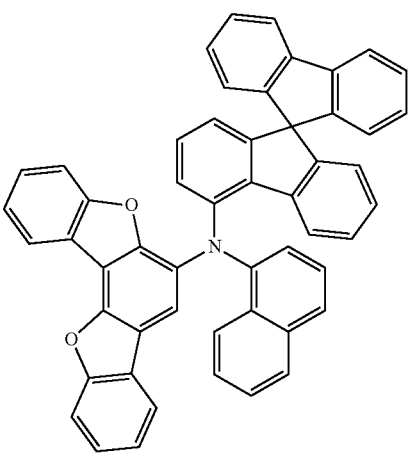
A111
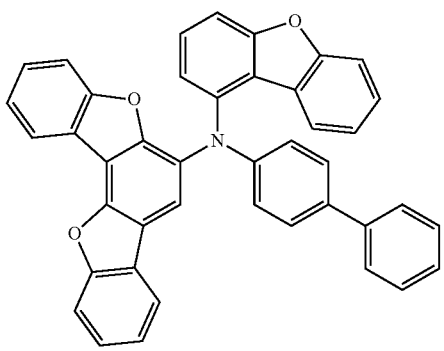

A112
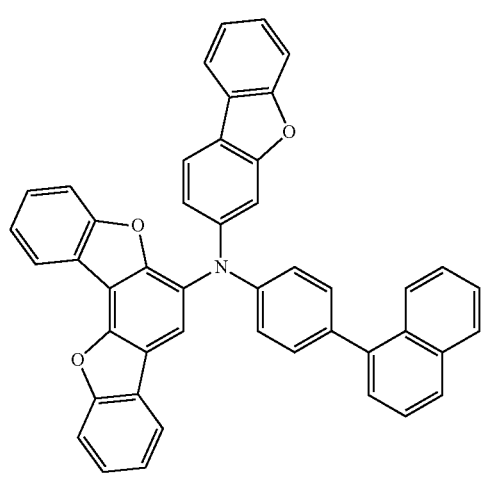
A113
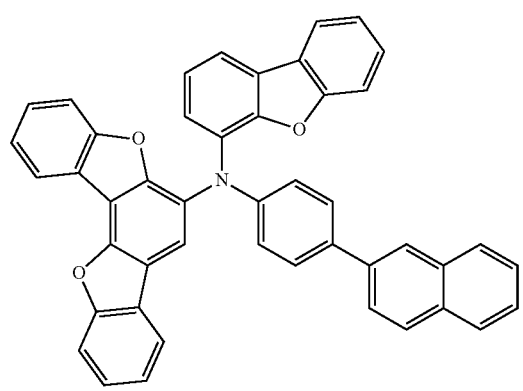
A114
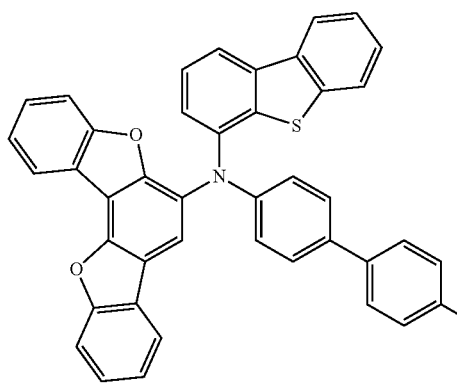
A115
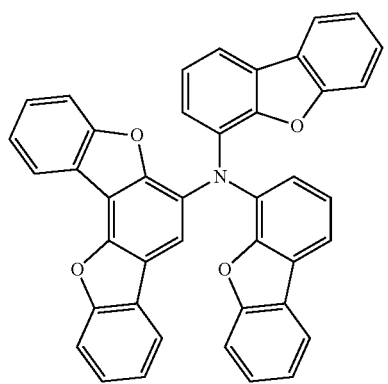
A116
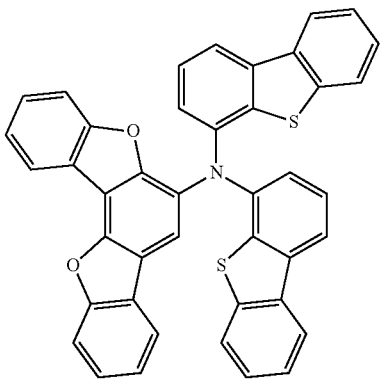
A117
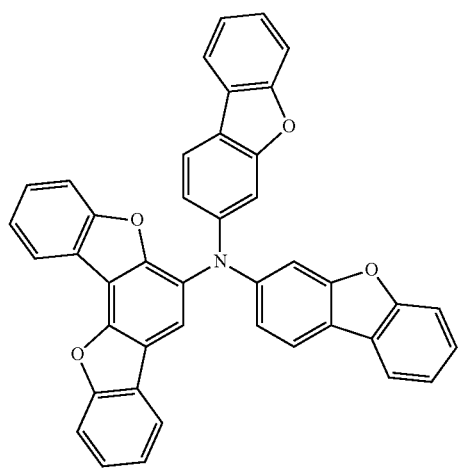
A118
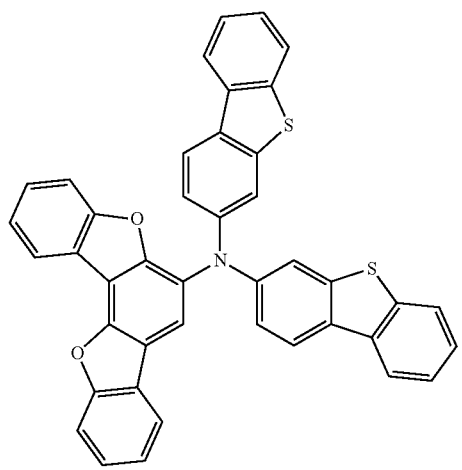

A119
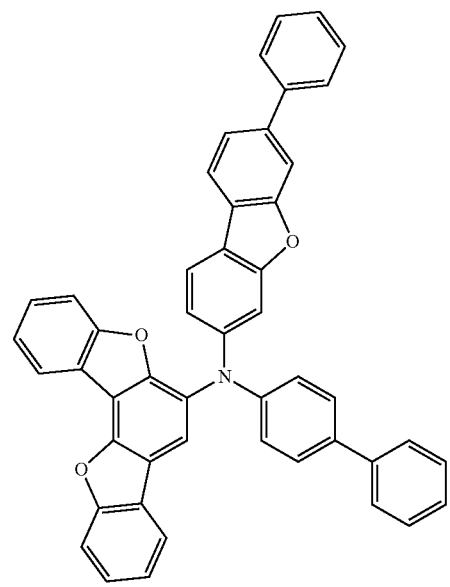
A122
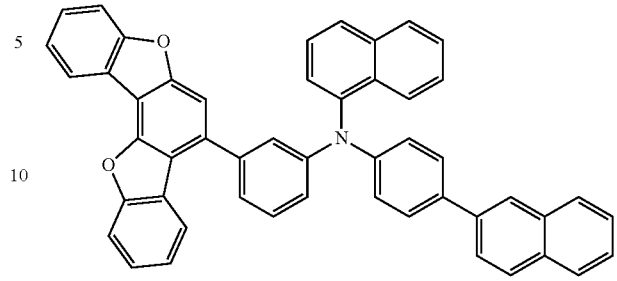
A123
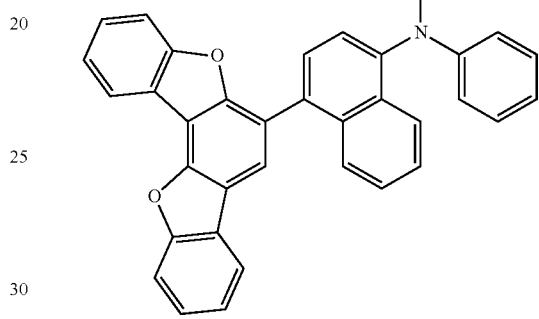
A120
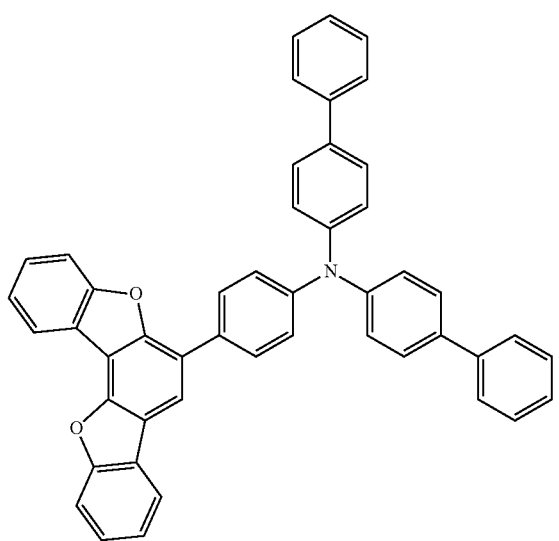
A124
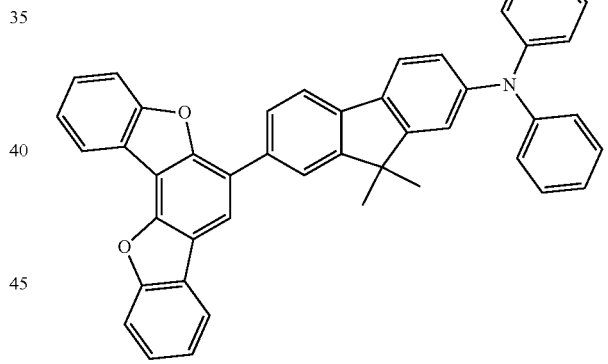
A121
A125
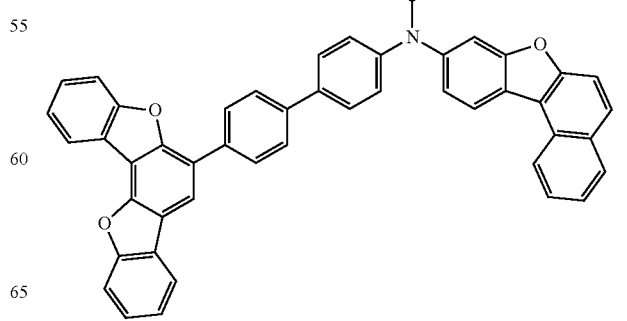

A126
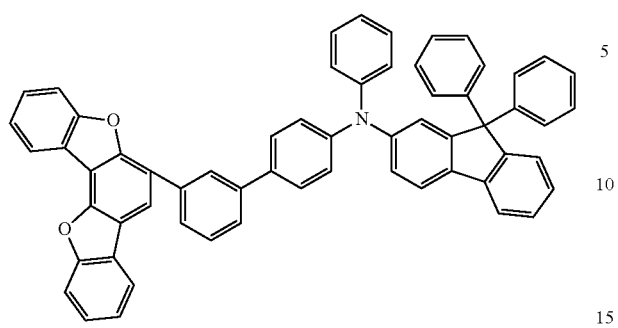
A127
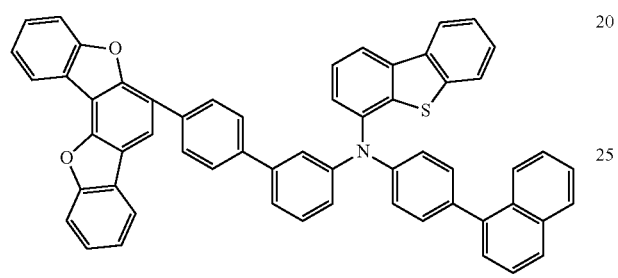
A128
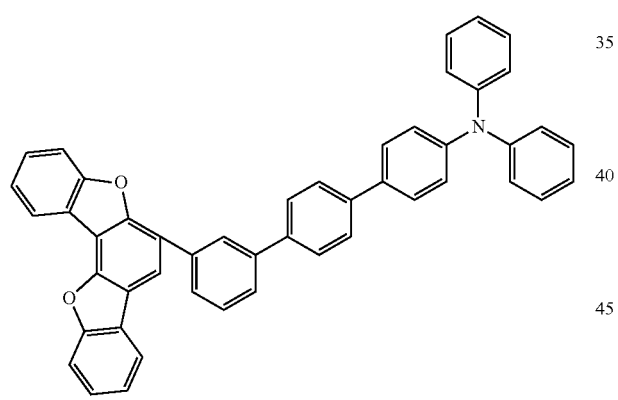
A129
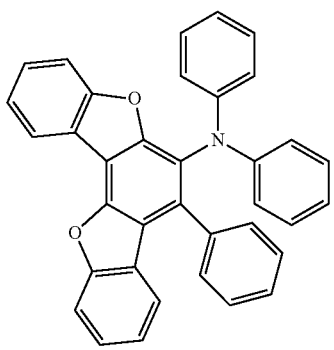
A130
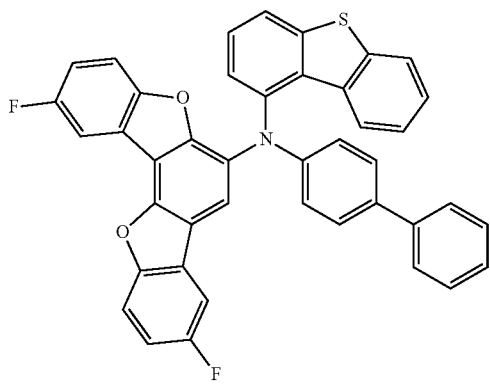
A131
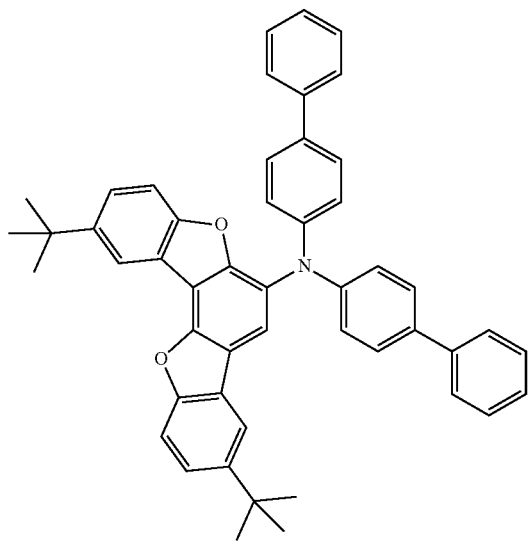
A132
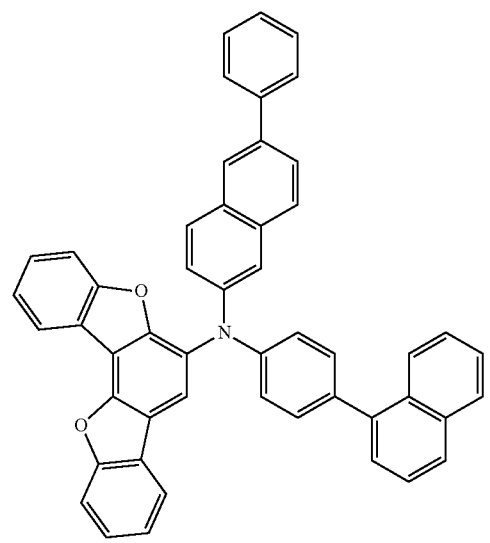

A132
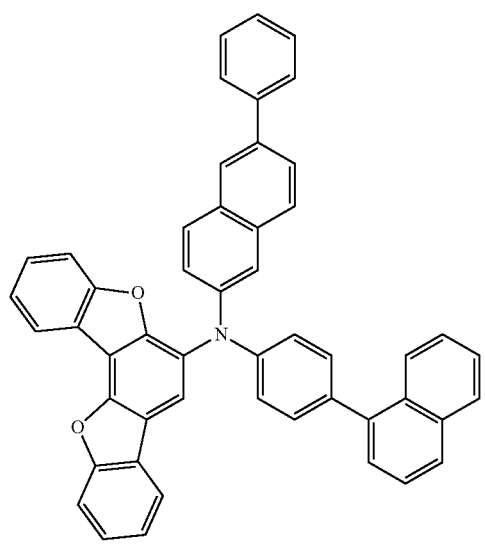
A135
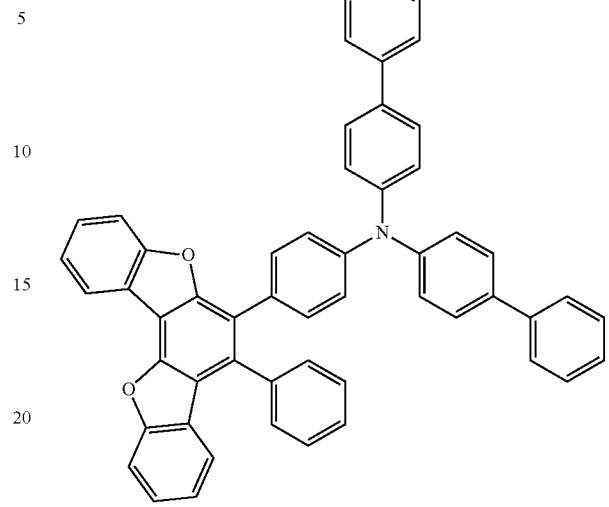
A133
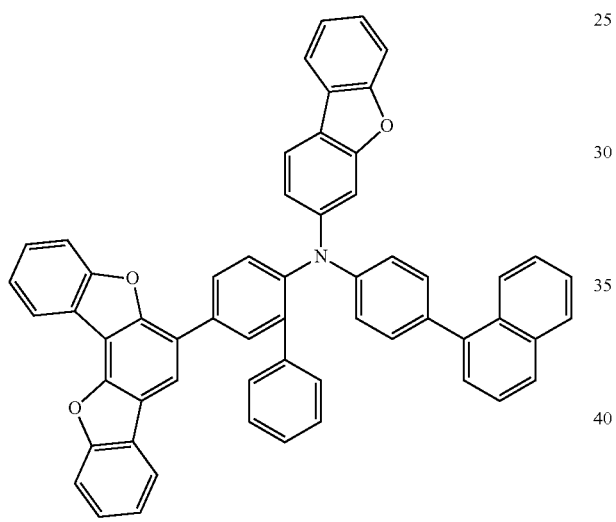
A136
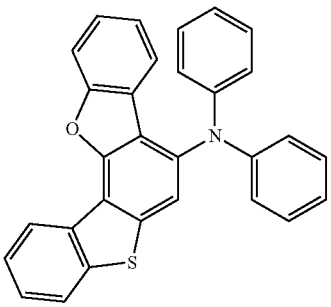
A137
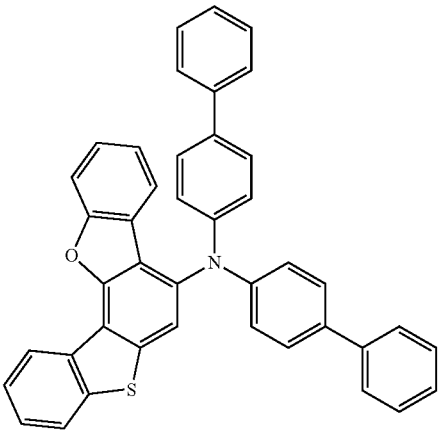
A134
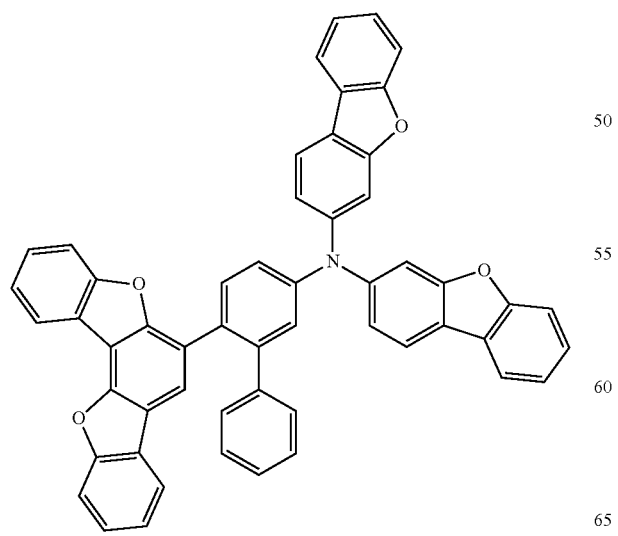
A138
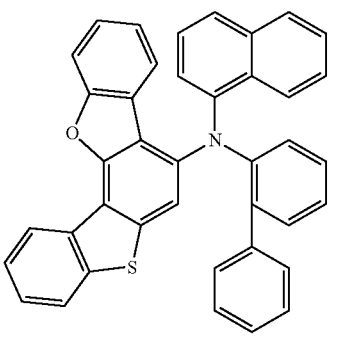

A139
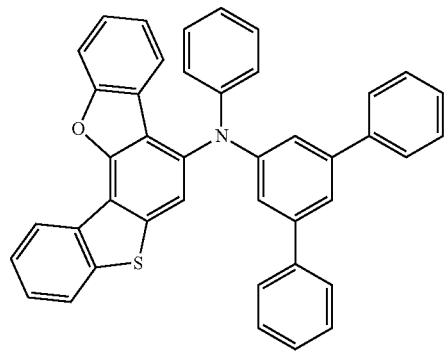
A140
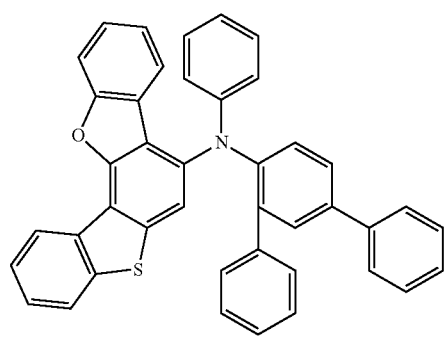
A141
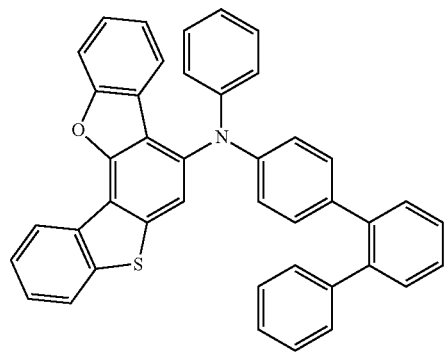
A142
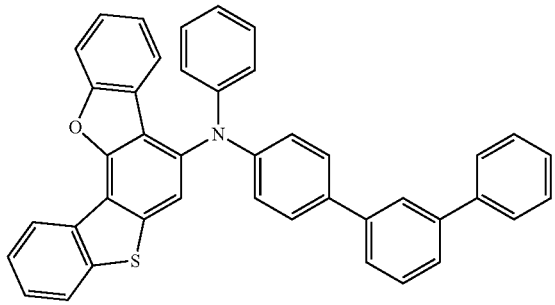
A143
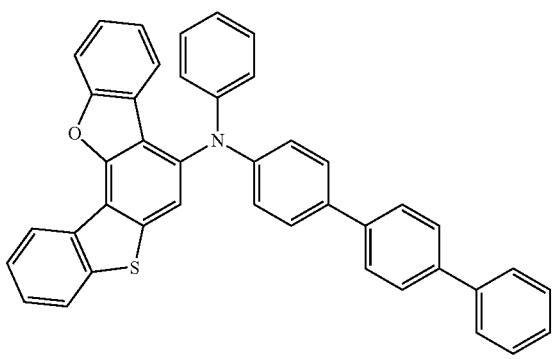
A144
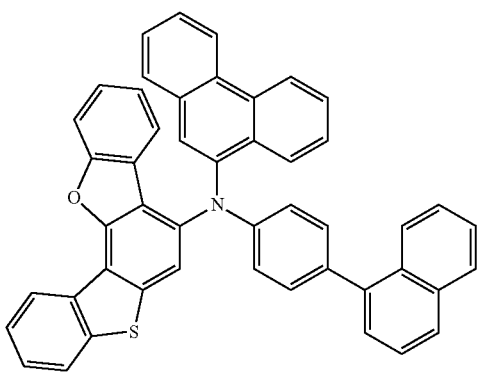
A145
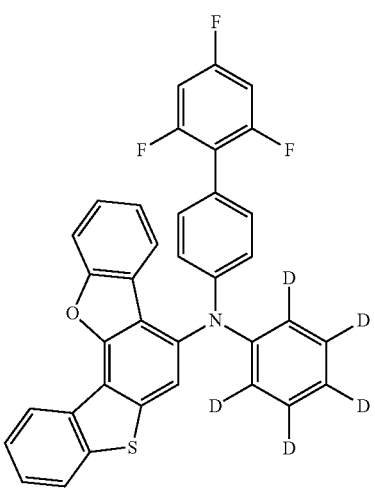
A146
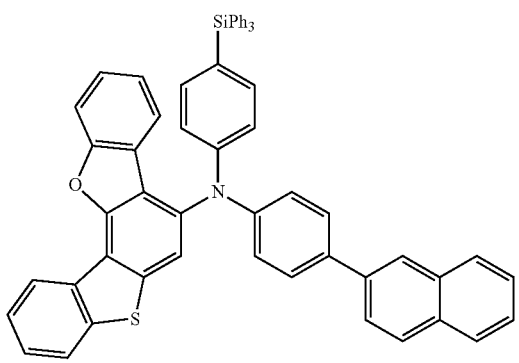

A147
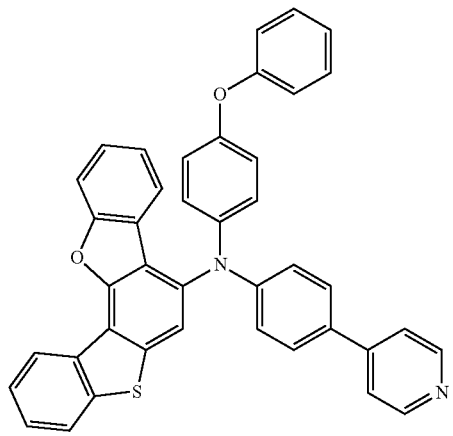
A148
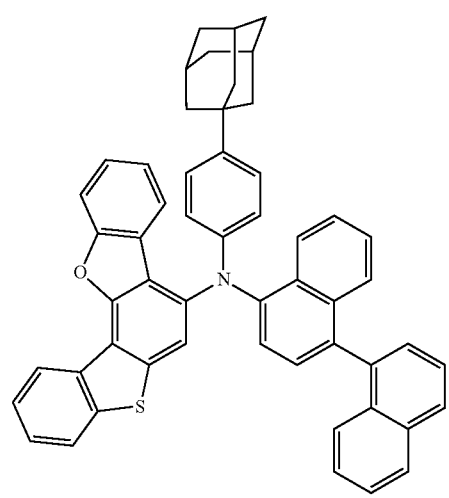
A149
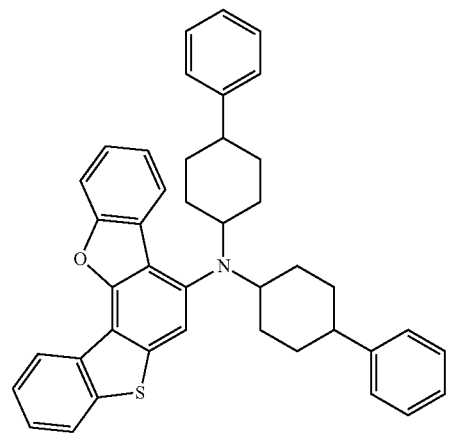
A150
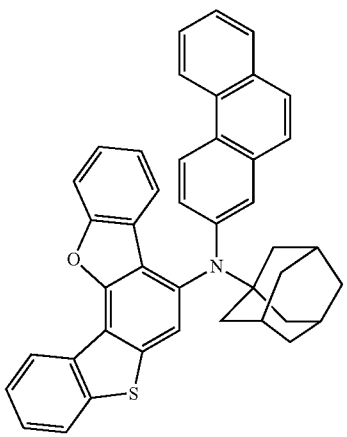
A151
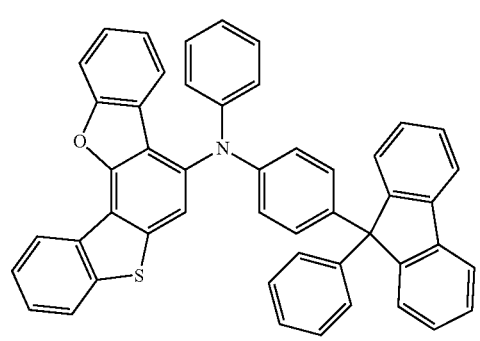
A152
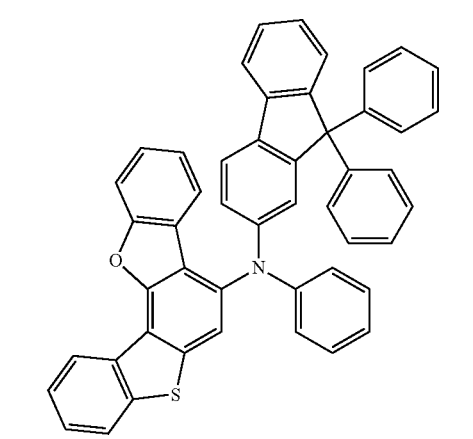
A153
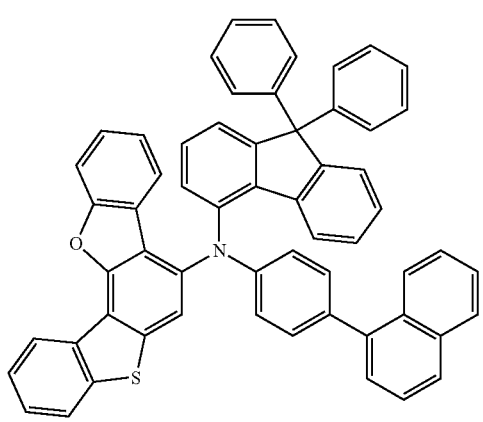

A154
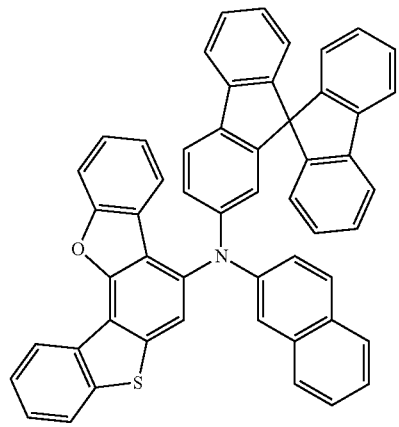
A155
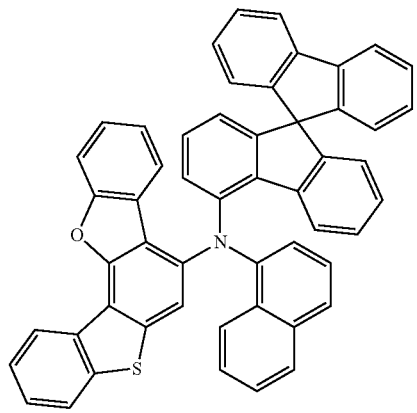
A156
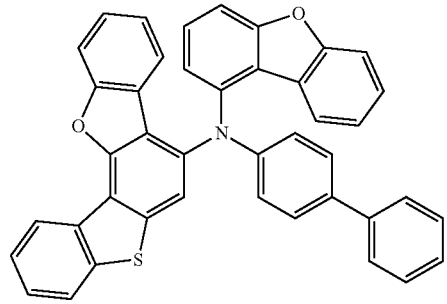
A157
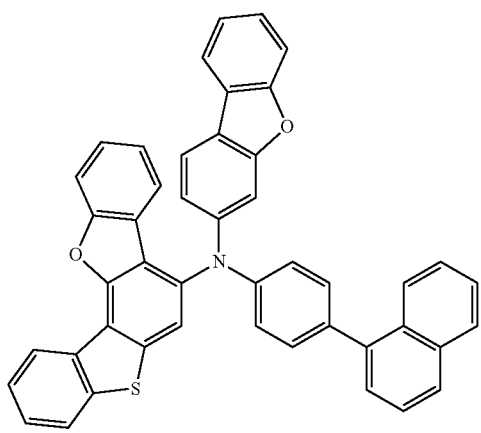
A158
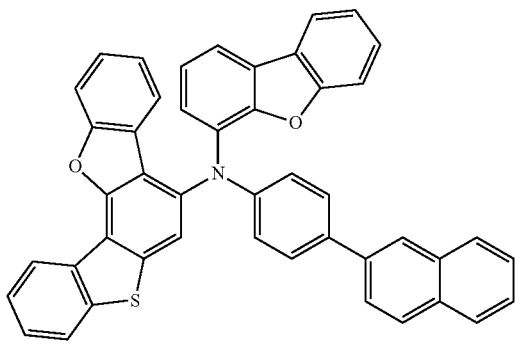
A159
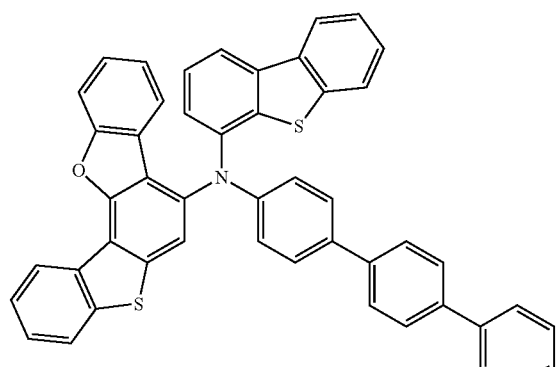
A160
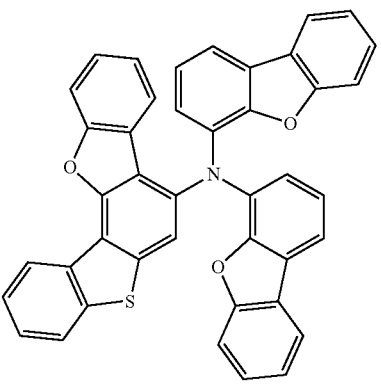
A161
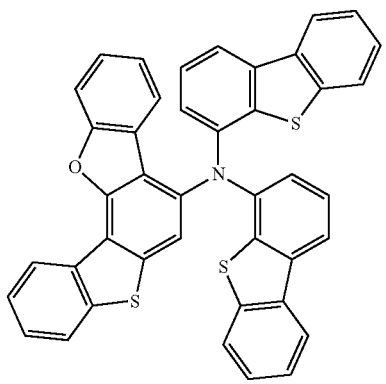

A162
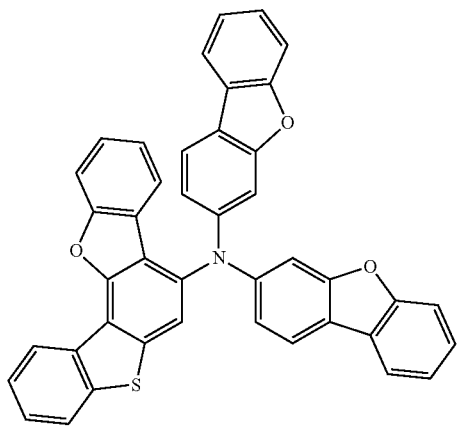
A163
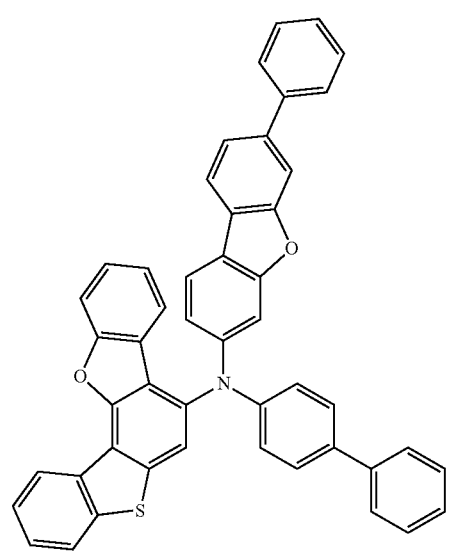
A164
A165
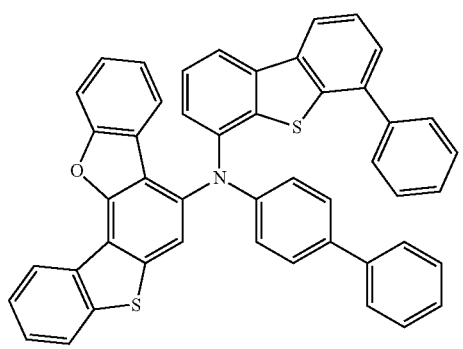
Compound Group B
B1
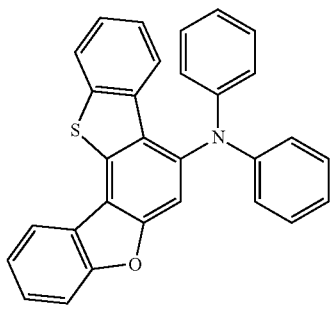
B2
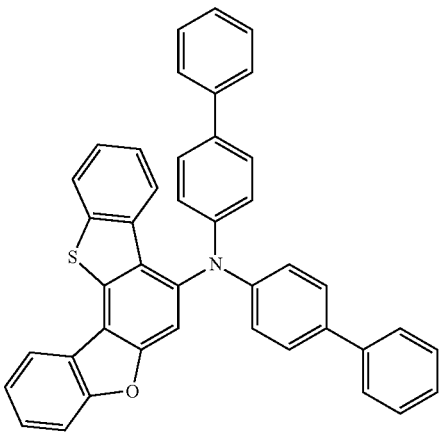
B3
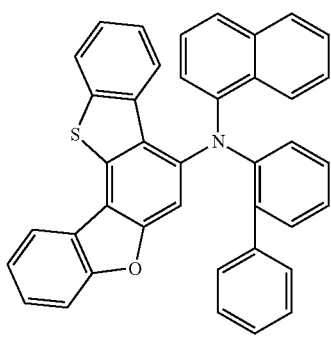

B4
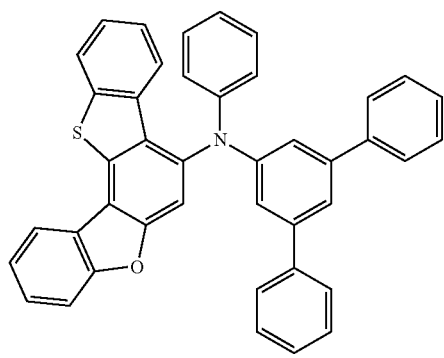
B8
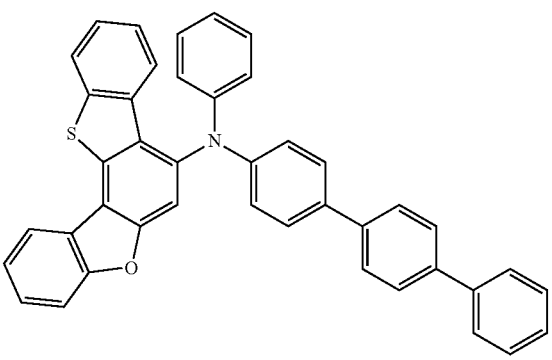
B5
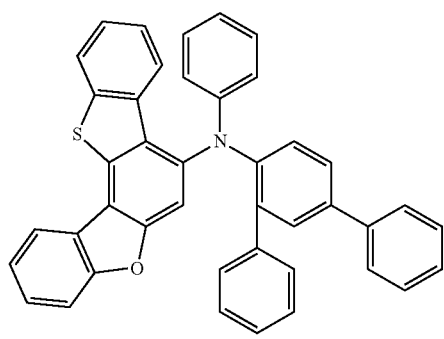
B9
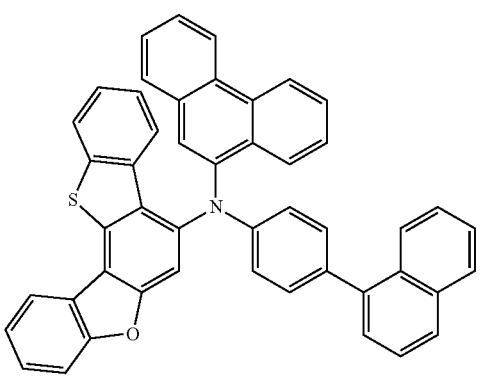
B6
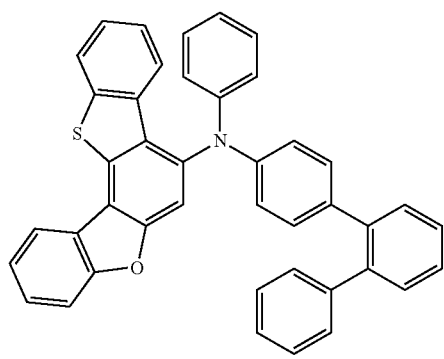
B10
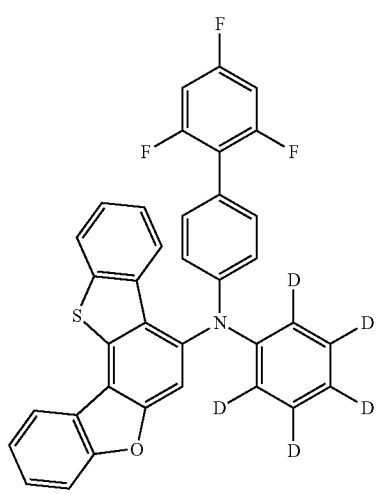
B7
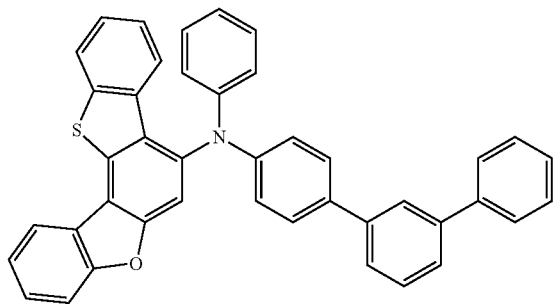
B11
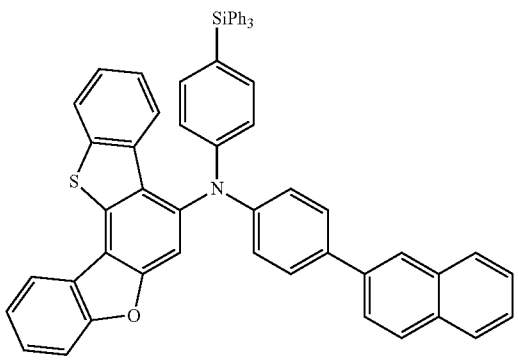

B12
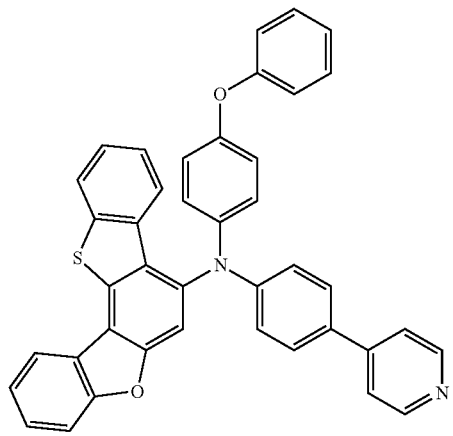
B13
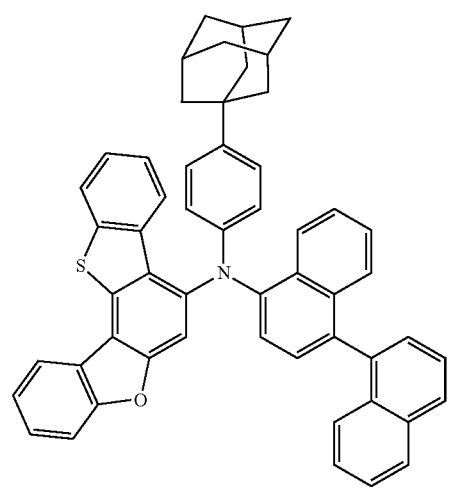
B14
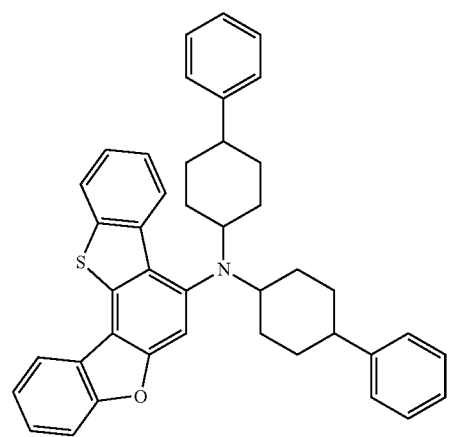
B15
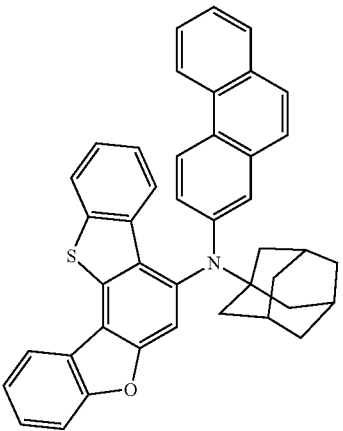
B16
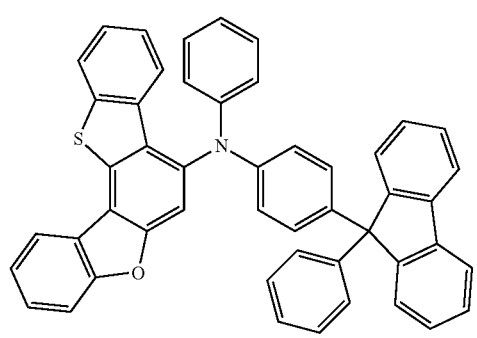
B17
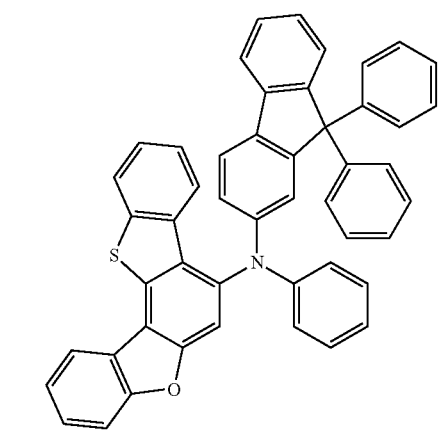
B18
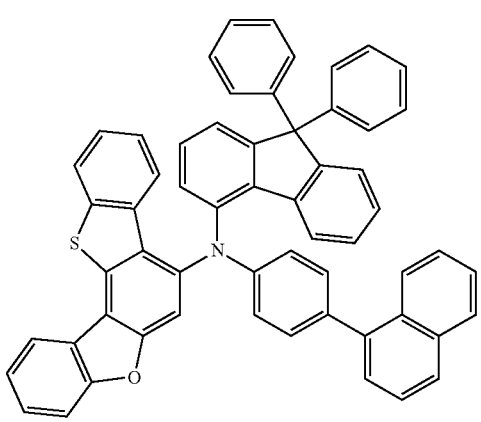

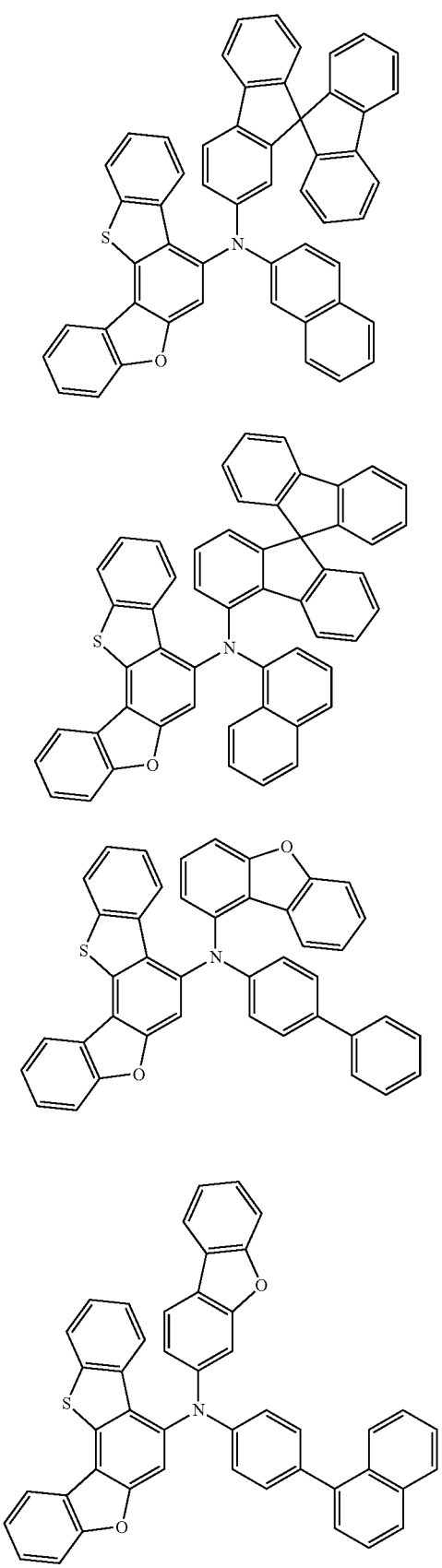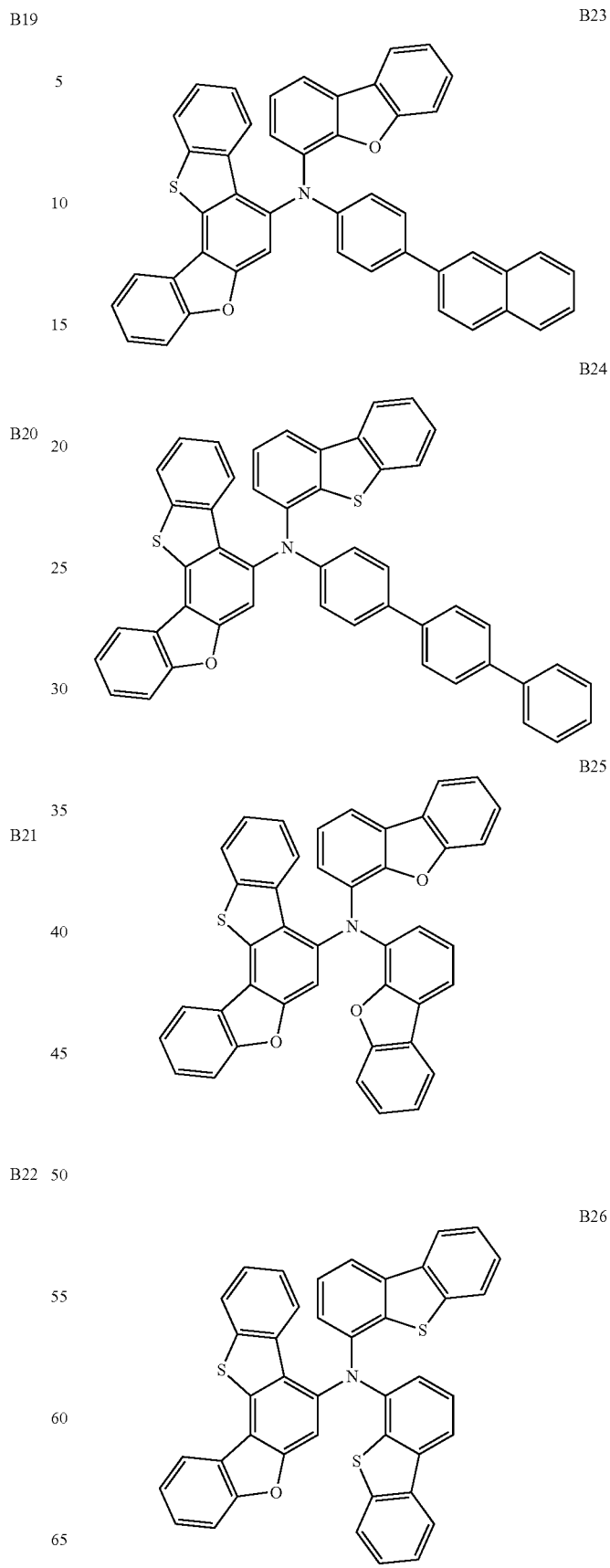

B27
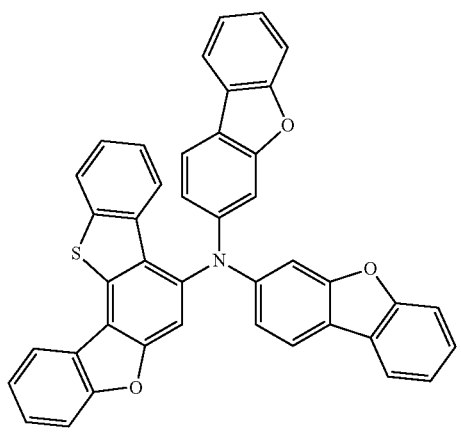
B28
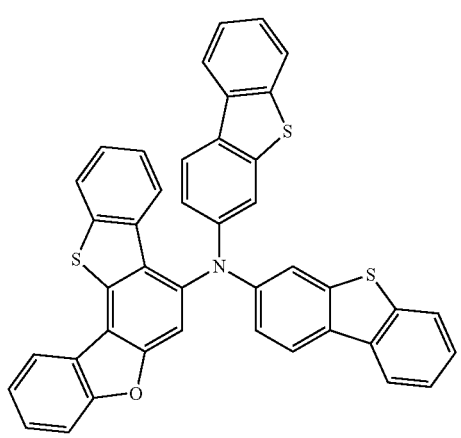
B29
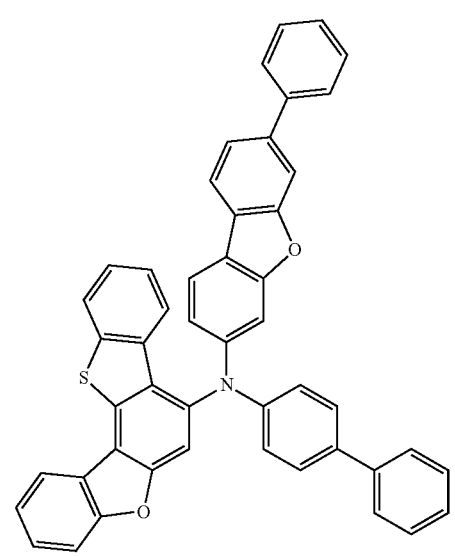
B30
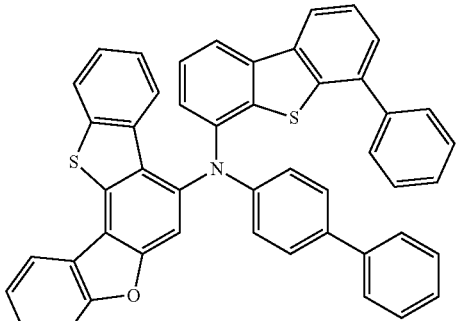
B31
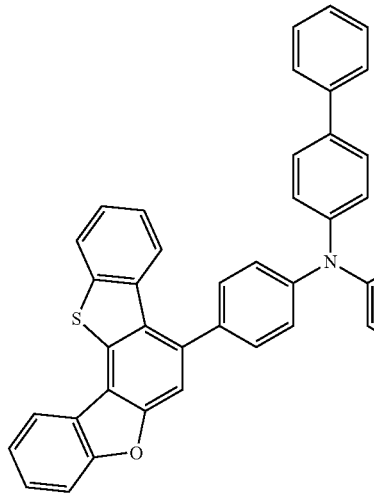
B32
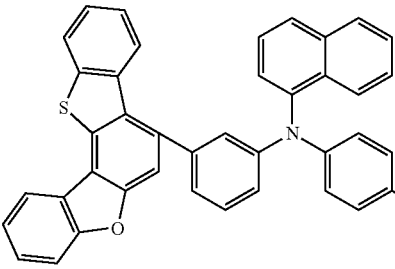
B33
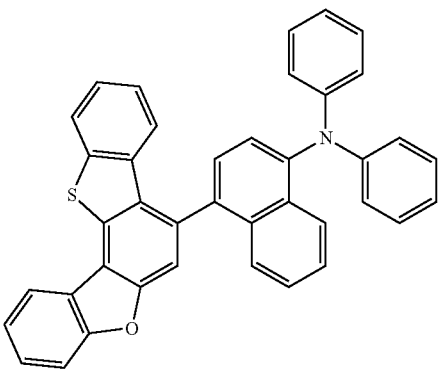

B34
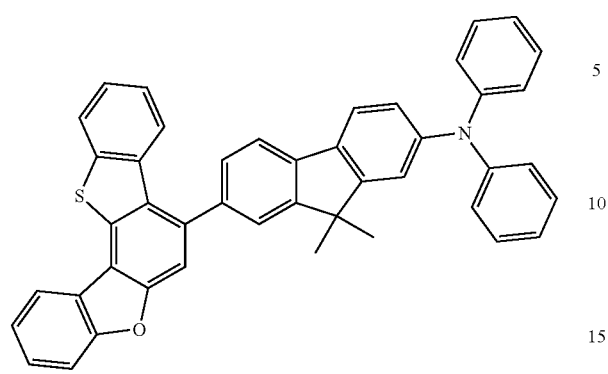
B38
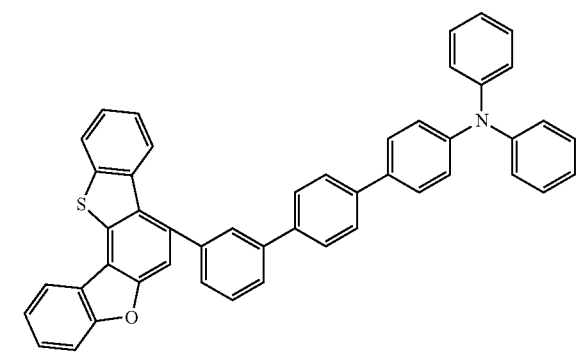
B35
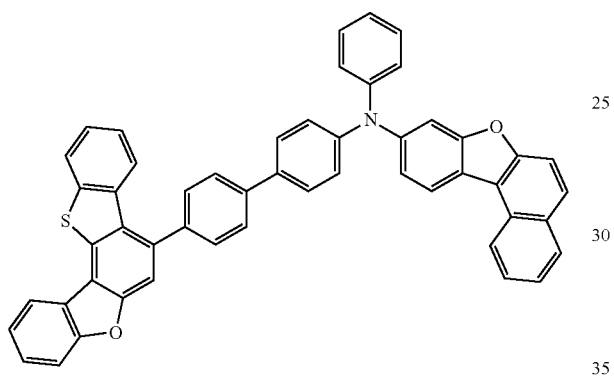
B39
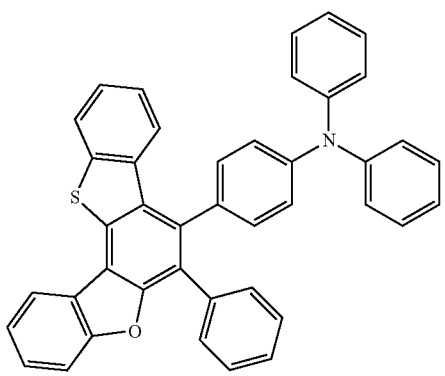
B36
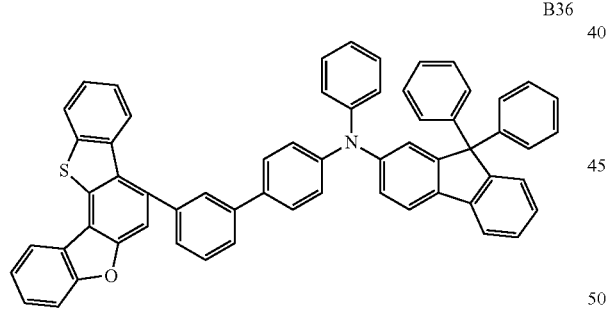
B40
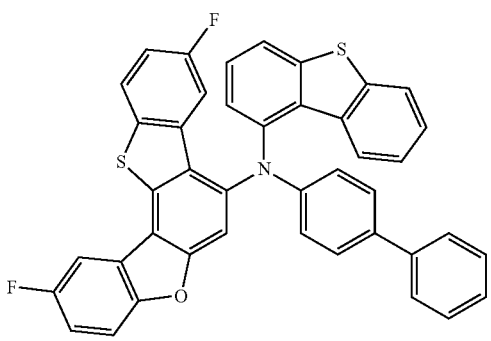
B37
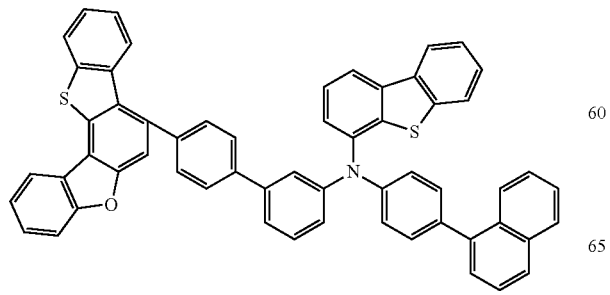
B41
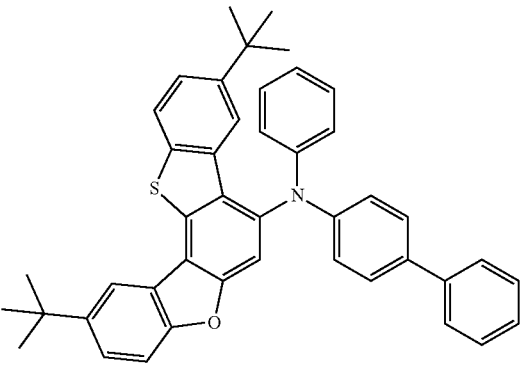

-continued
B42
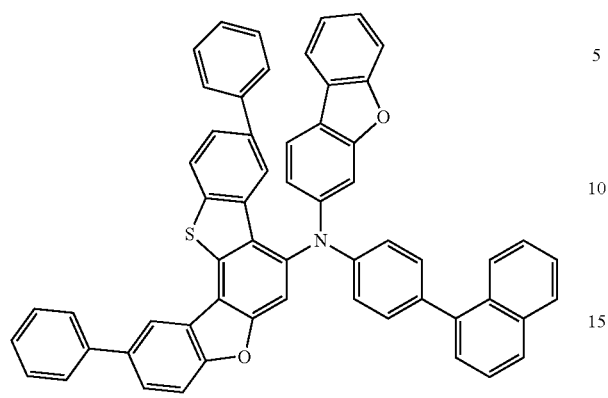
Compound Group C
C1
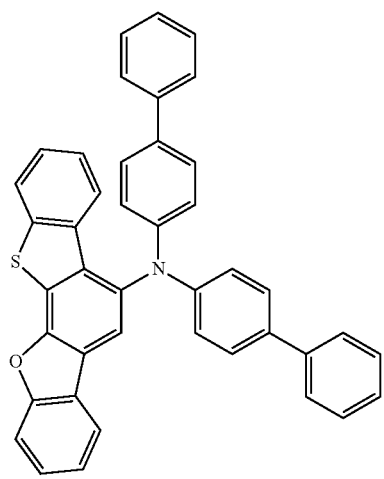
C2
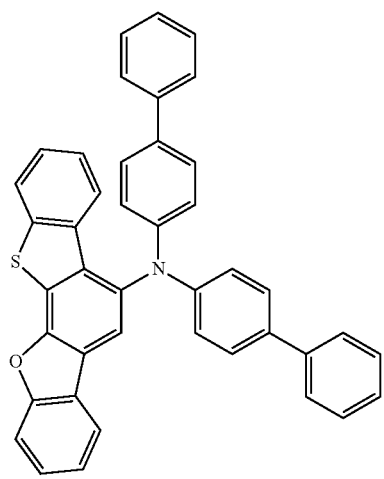
-continued
C3
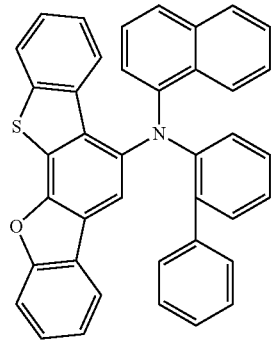
C4
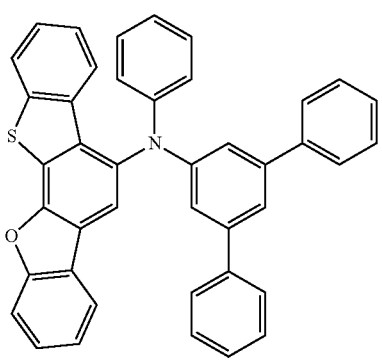
C5
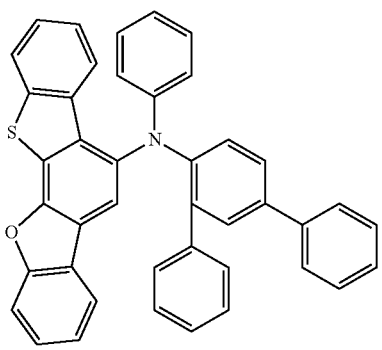
C6
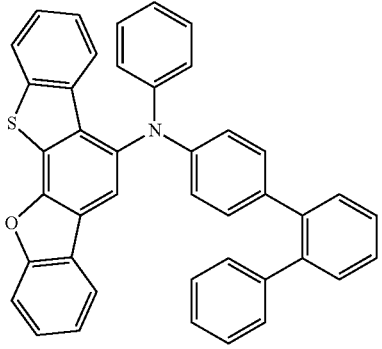

-continued
C7
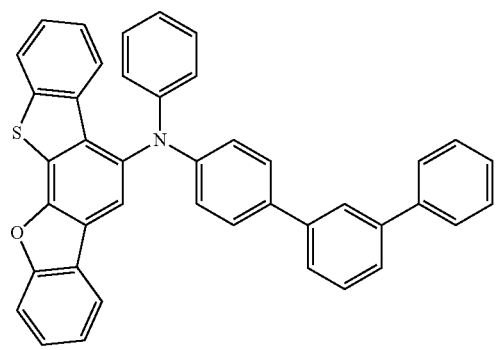
C8
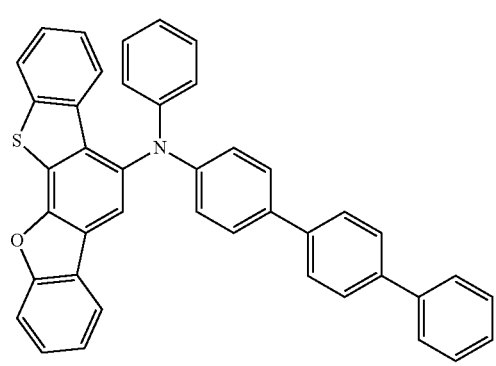
C9
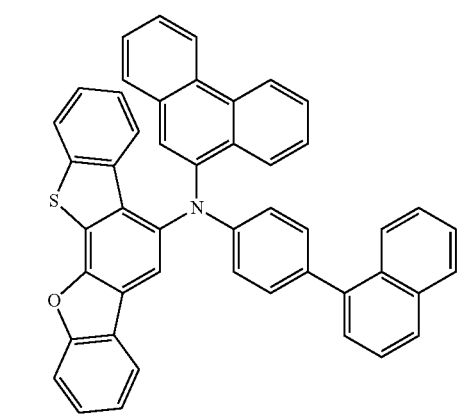
C10
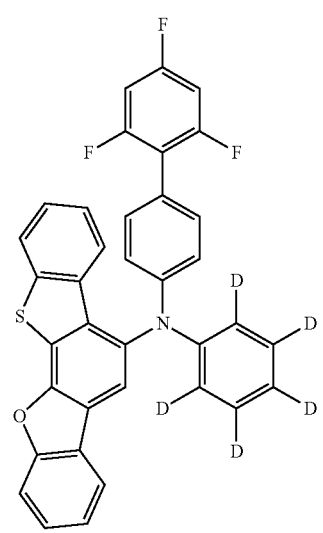
C11
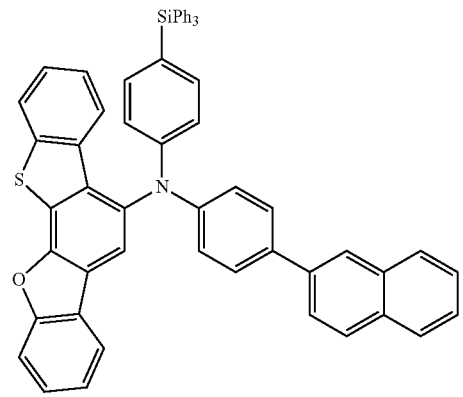
C12
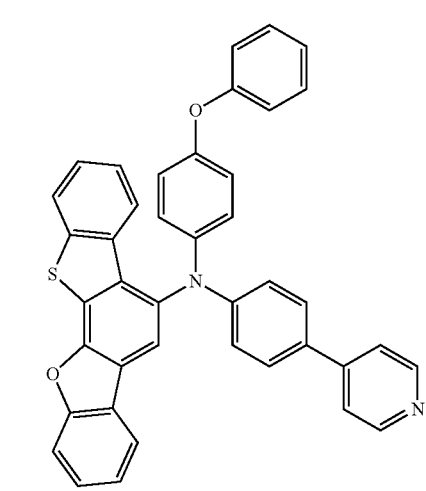
C13
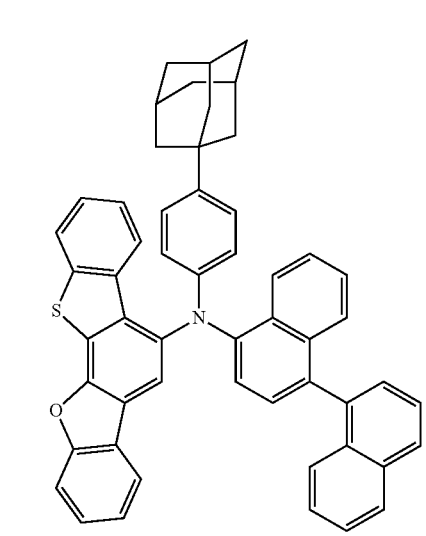

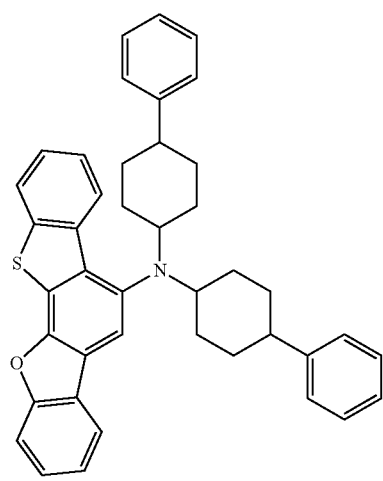
C14
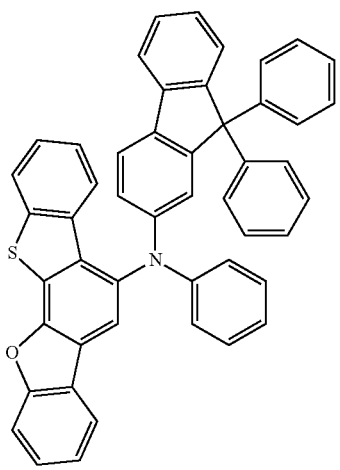
C17
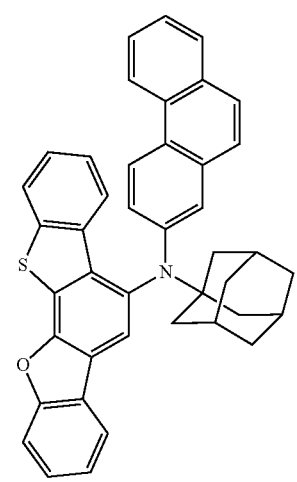
C15
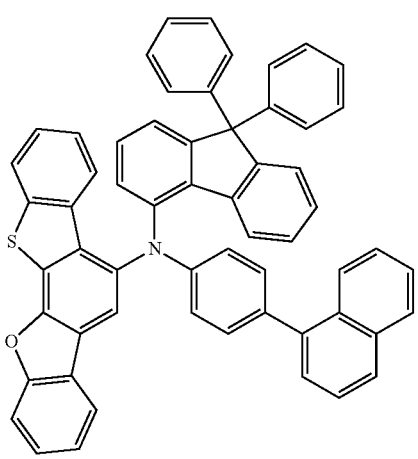
C18
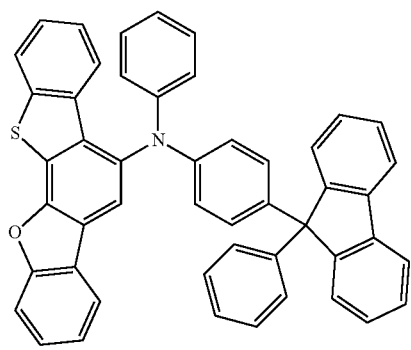
C16
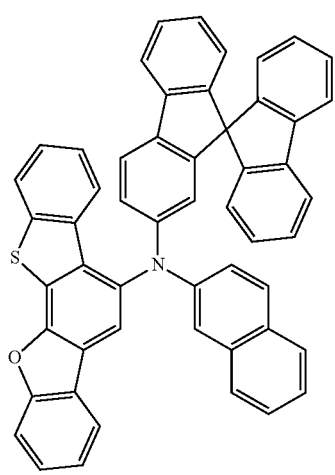
C19

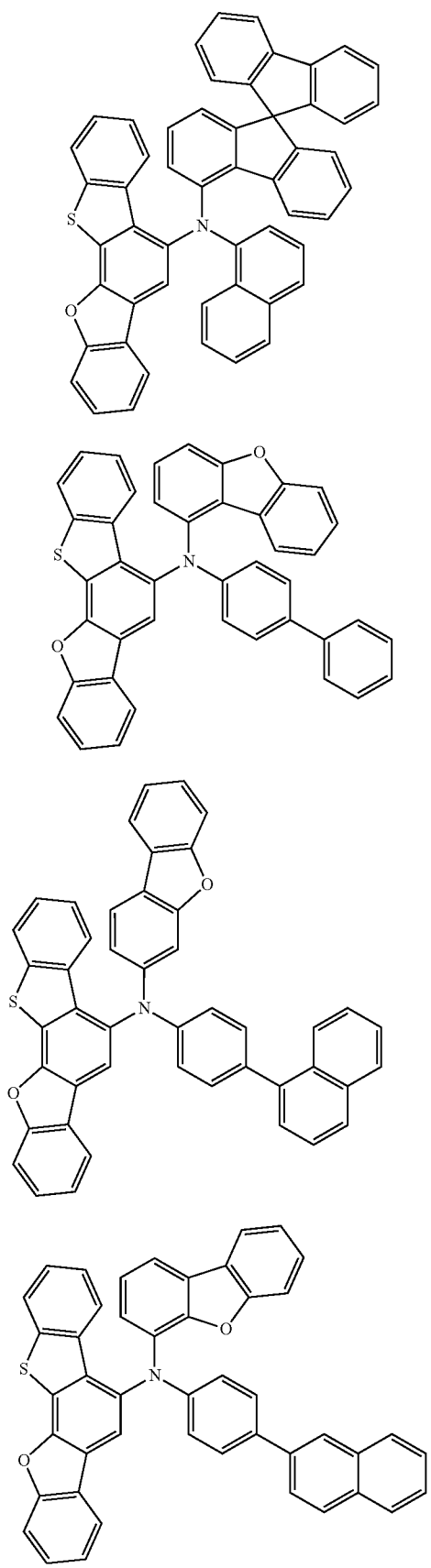
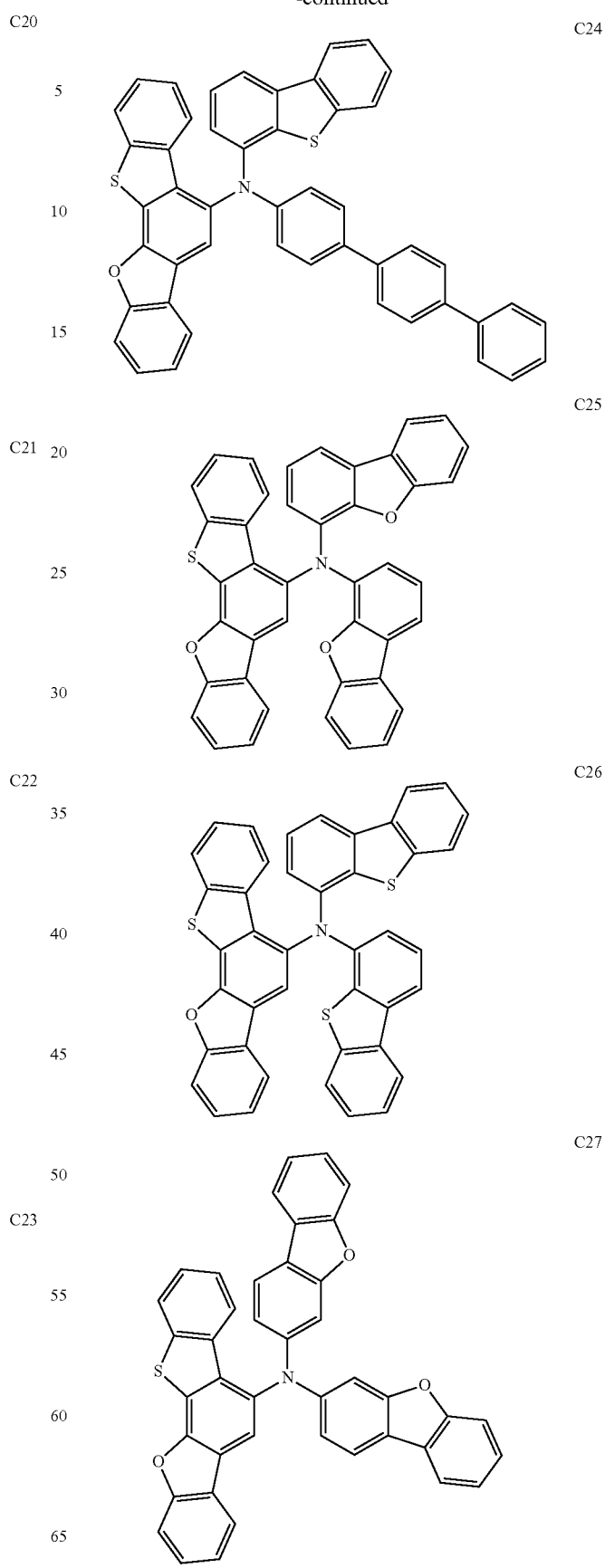

C28
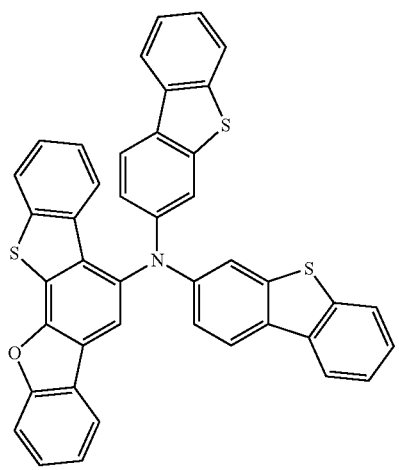
C31
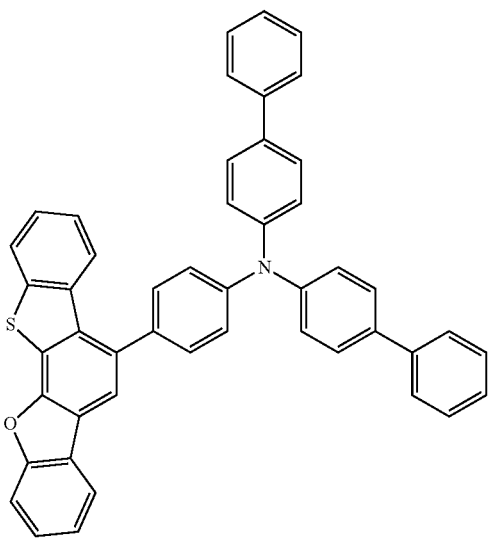
C29
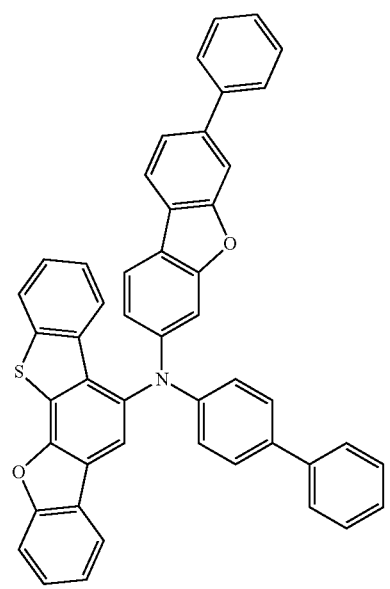
C32
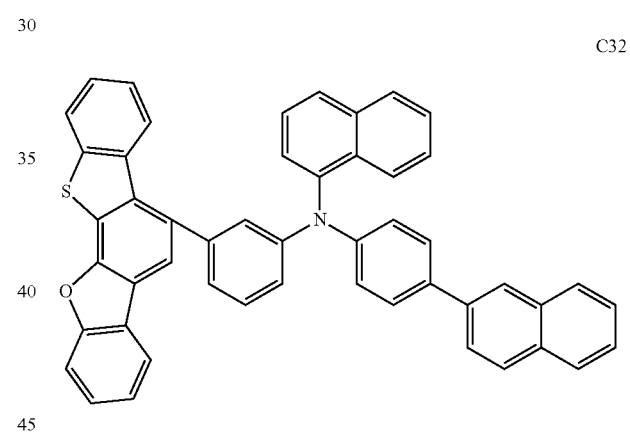
C30
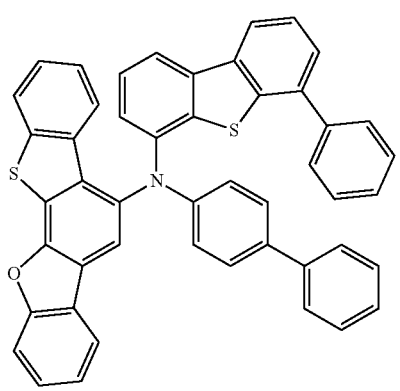
C33
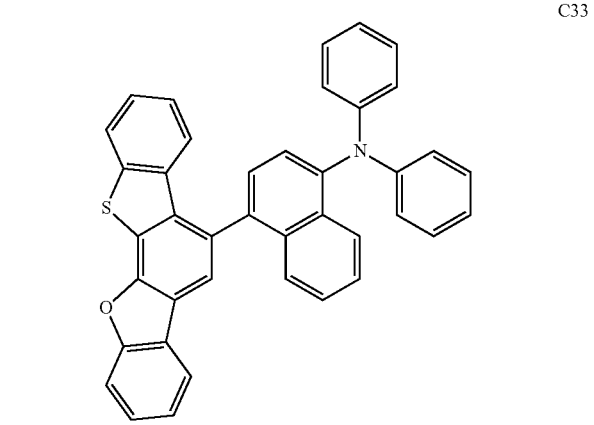

C34
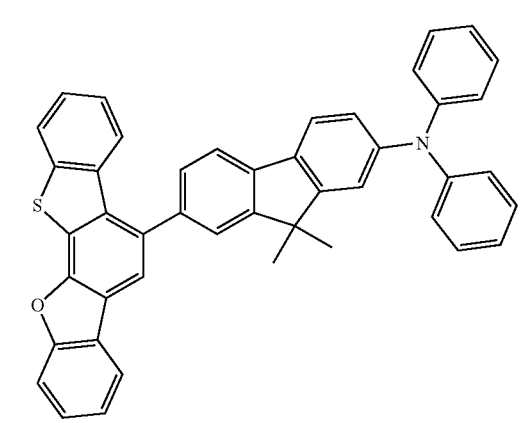
C35
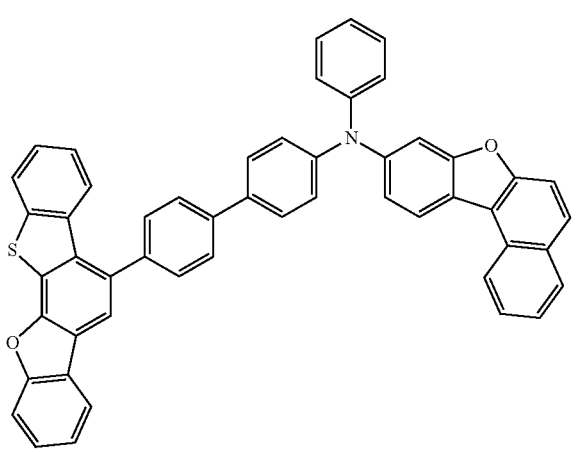
C36
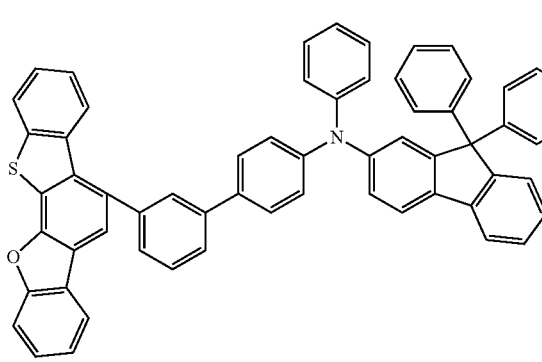
C37
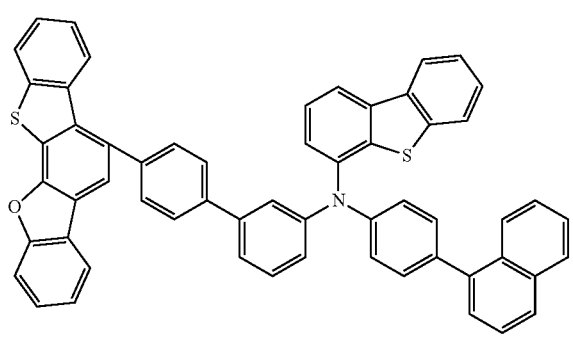
C38
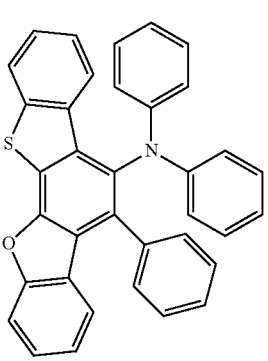
C39
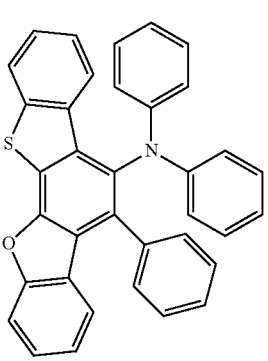
C40
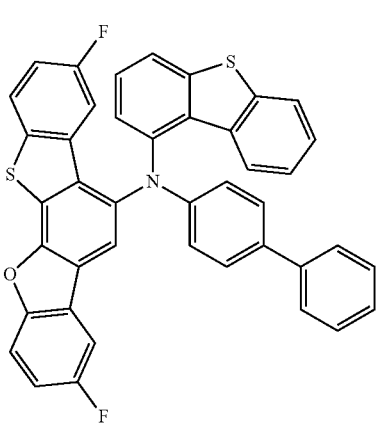

C41
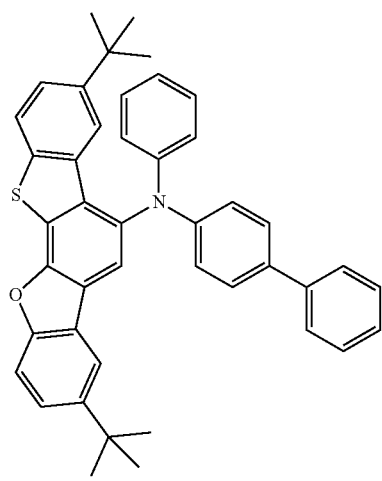
C42
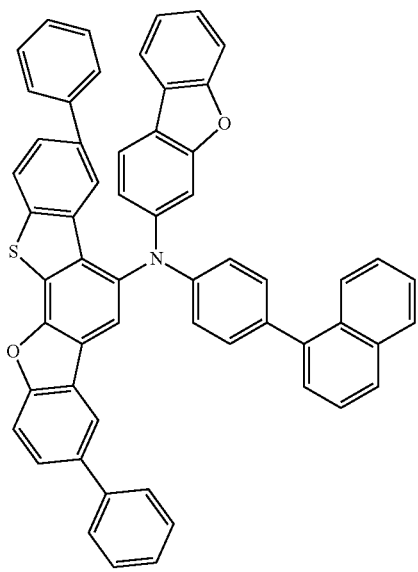
Compound Group D
D1
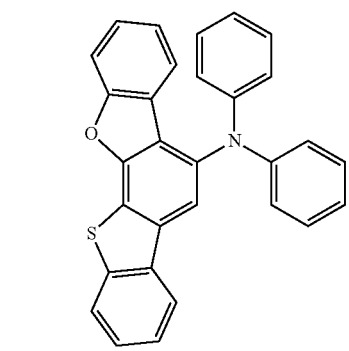
D2
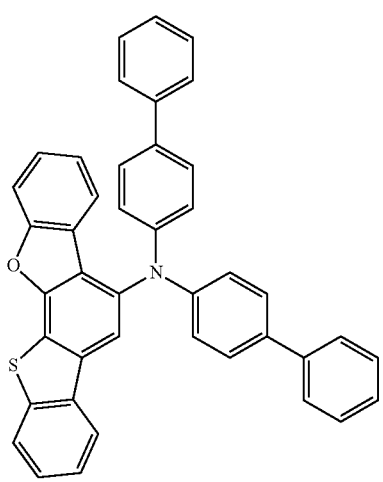
D3
D4
D5
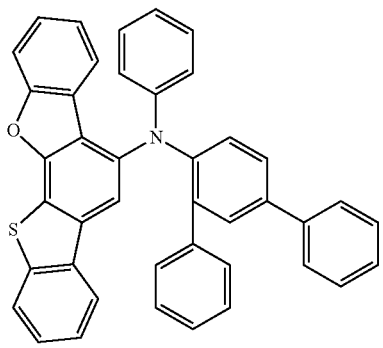

D6
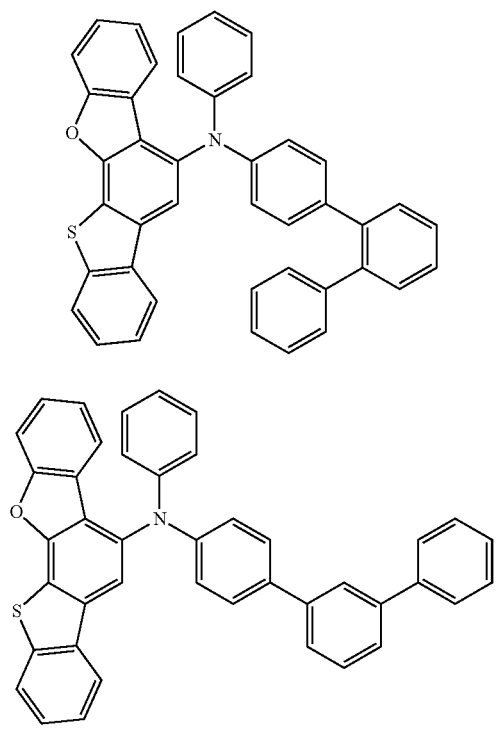
D7
D8
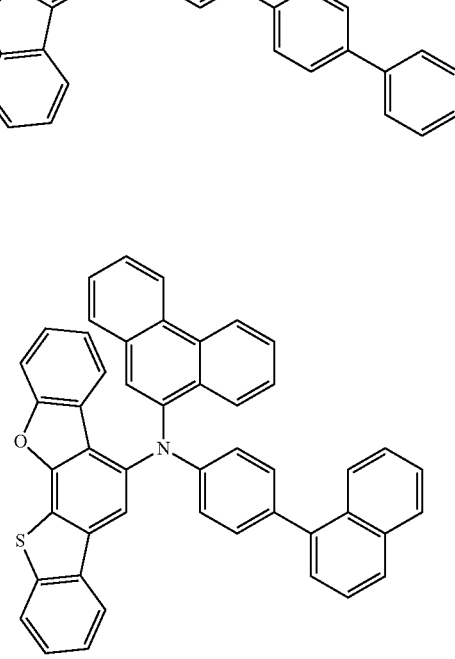
D9
D10
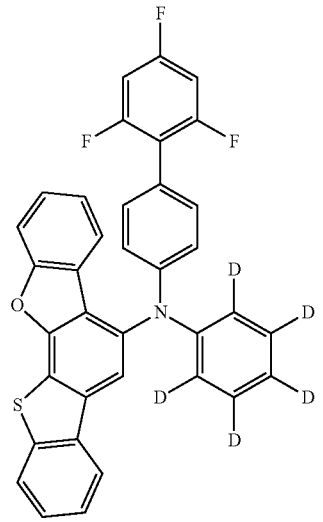
D11
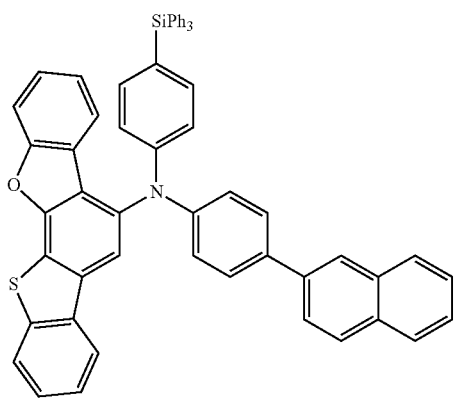
D12
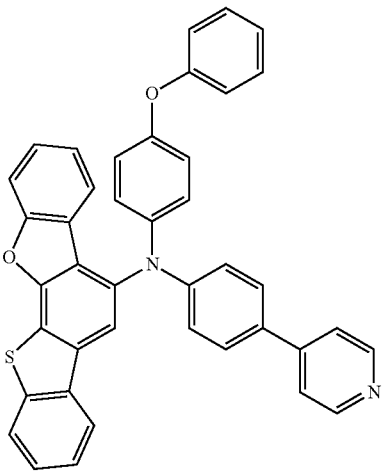

D13 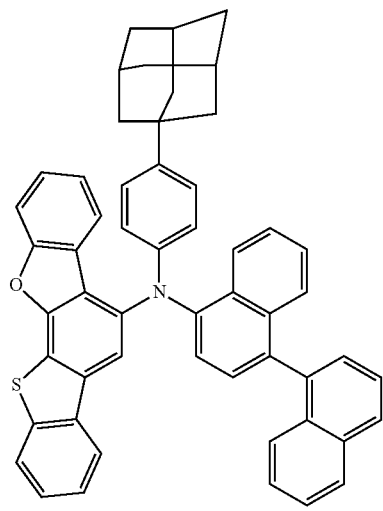
D14 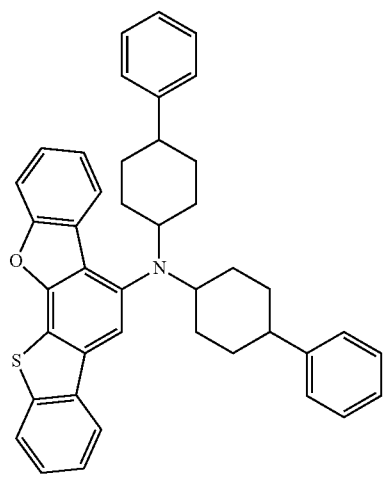
D15 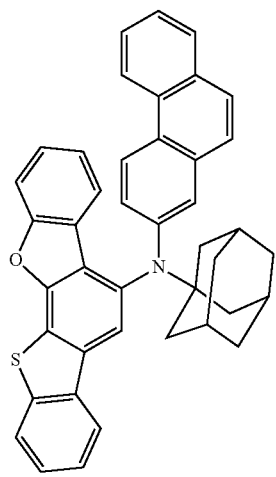
D16 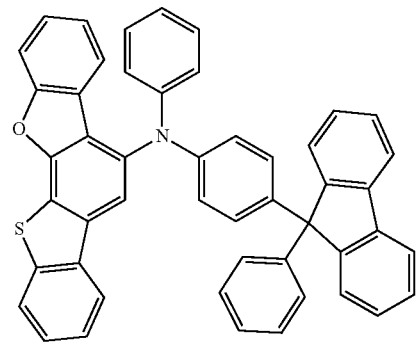
D17 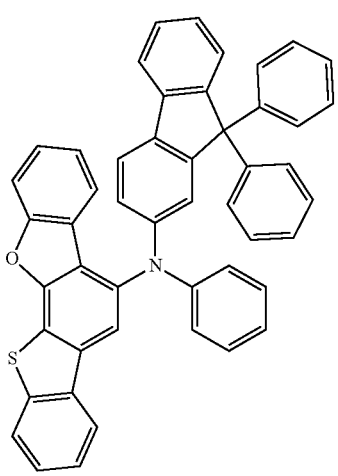
D18 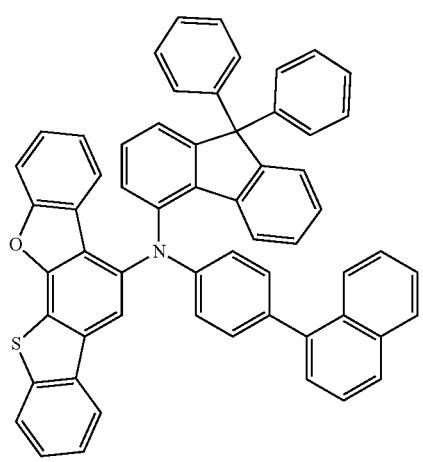

D19 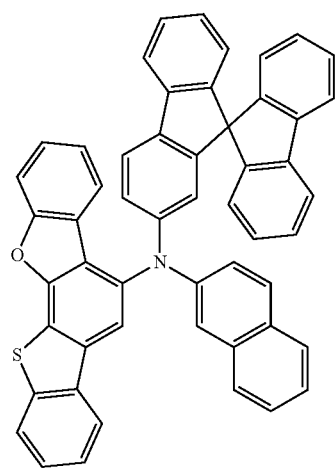
D20 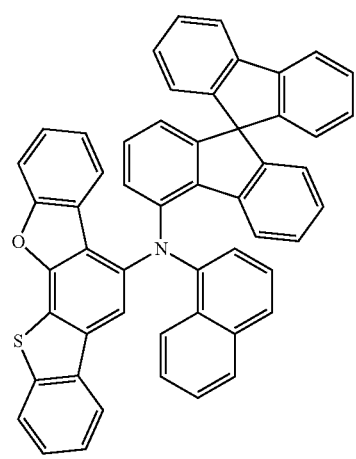
D21 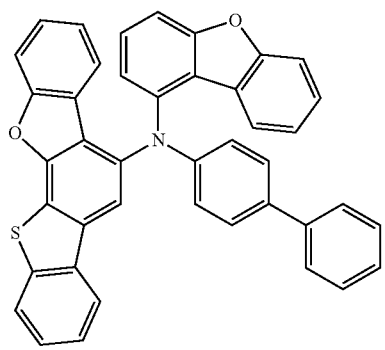
D22 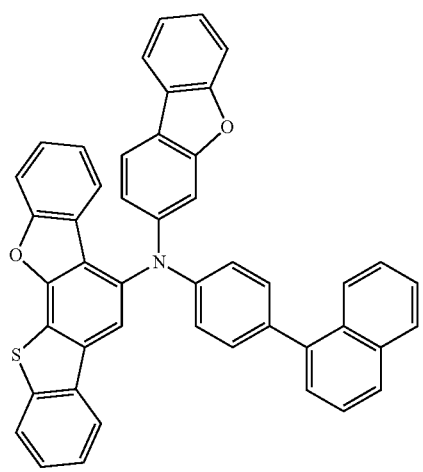
D23 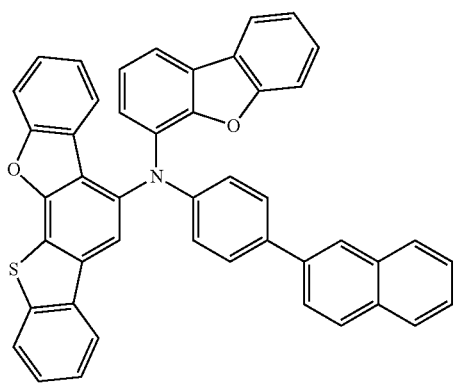
D24 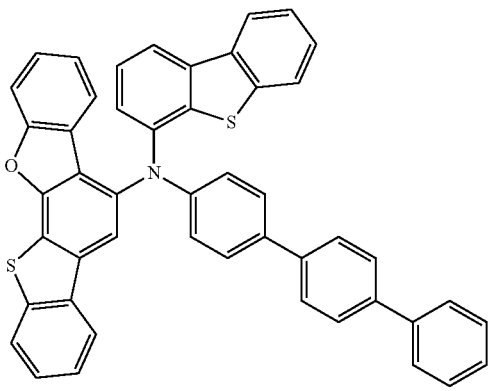
D25 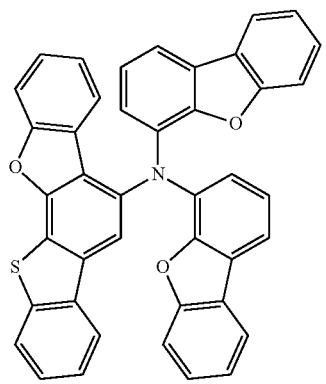

D26
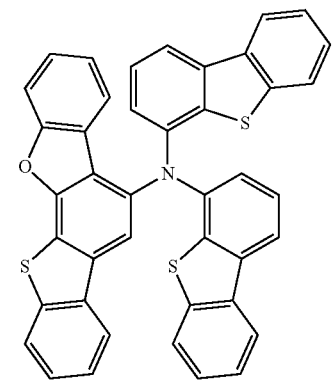
D27
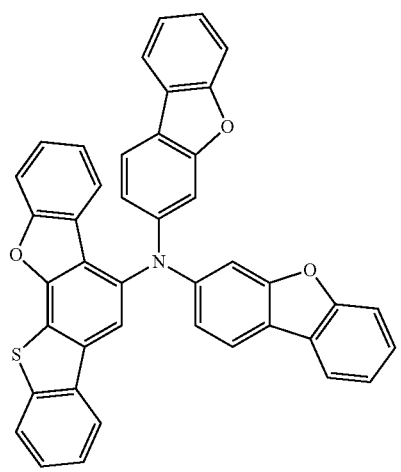
D28
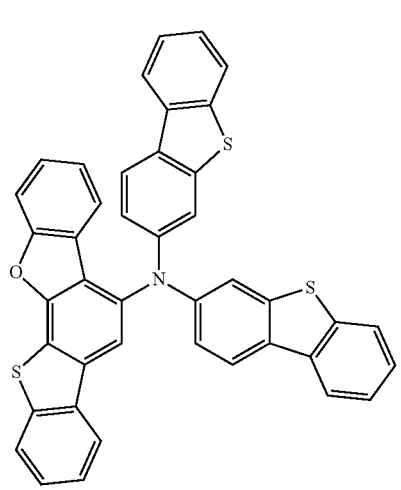
D29
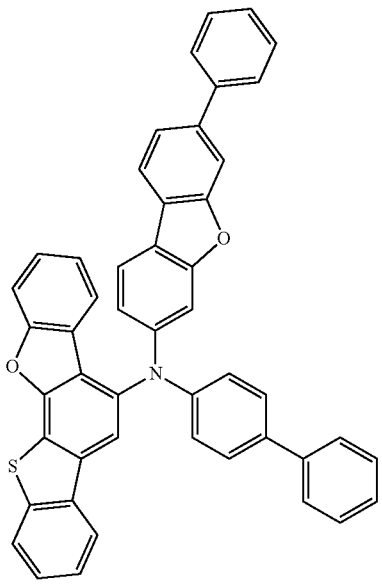
D30
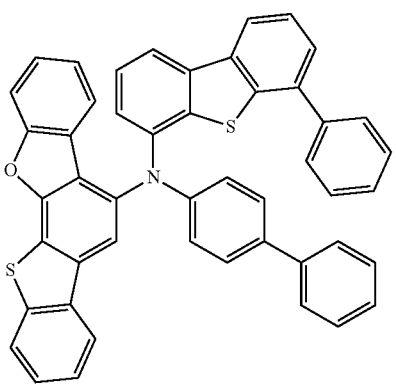
D31
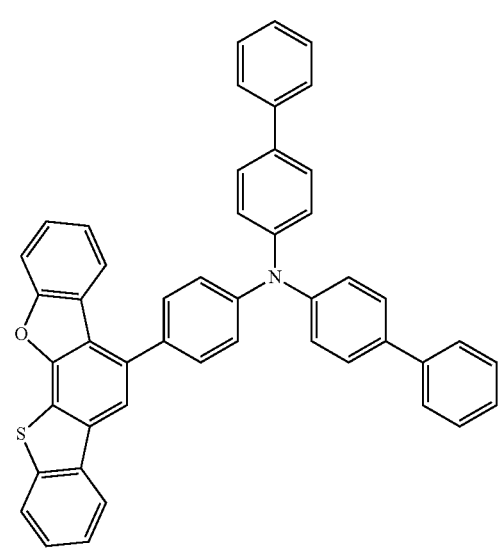

-continued
D32
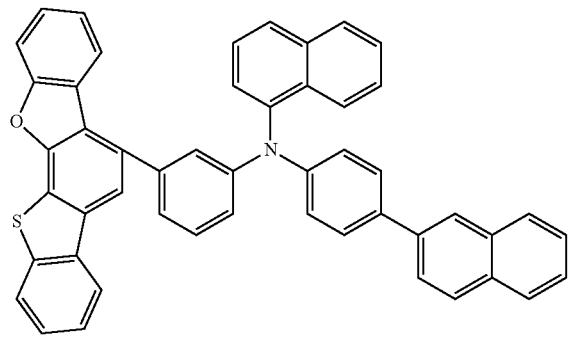
D33
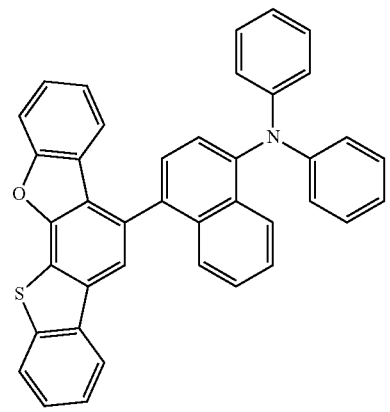
D34
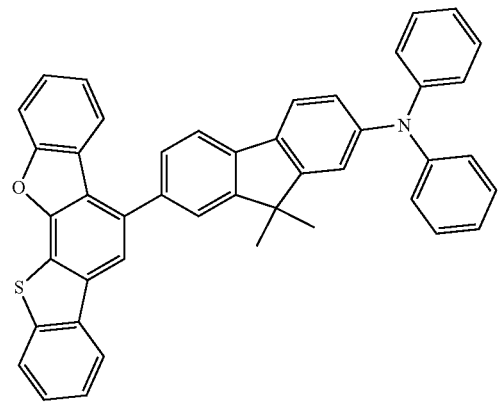
D35
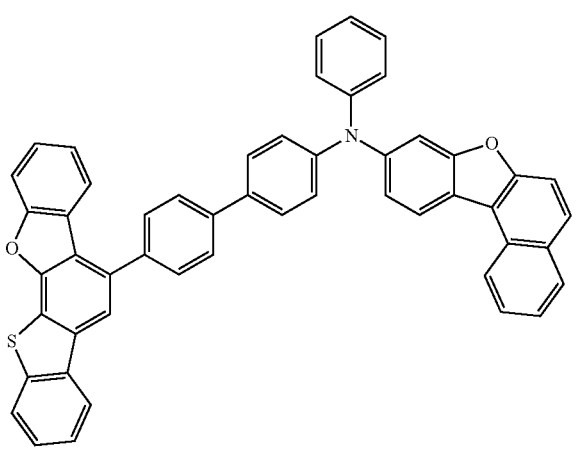
-continued
D36
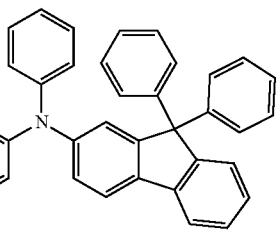
D37
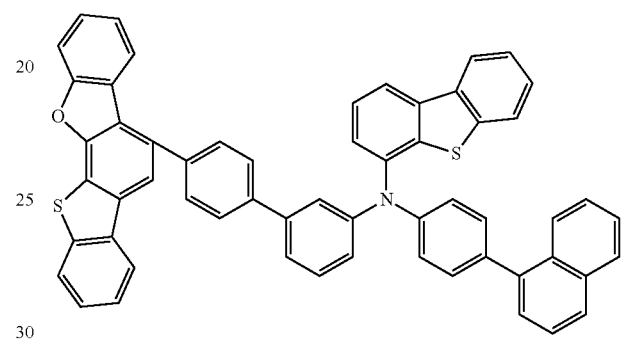
D38
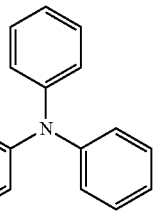
D39
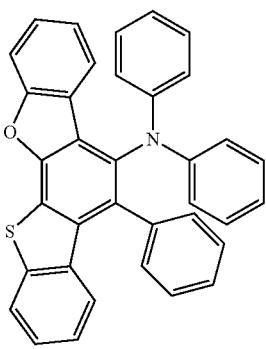

Compound Group E
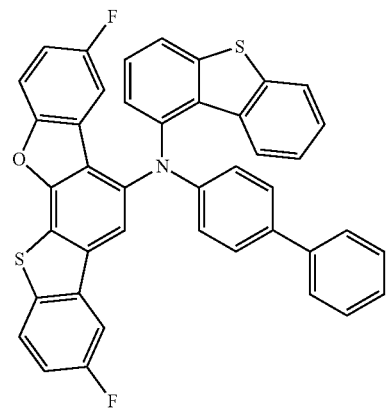
D40
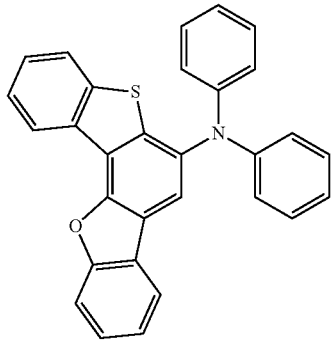
E1
D41
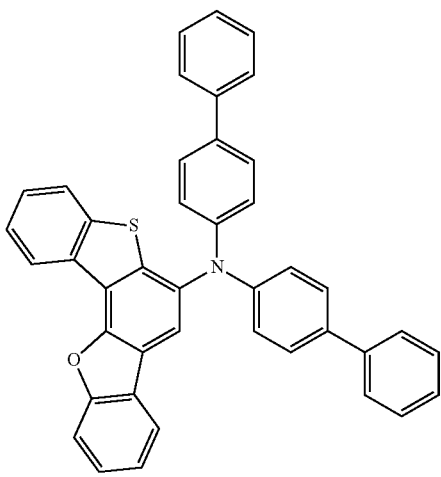
E2
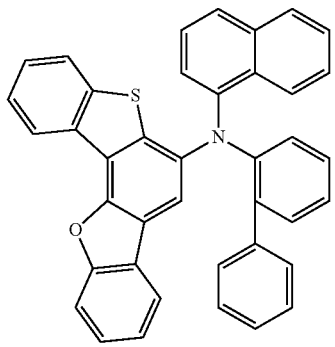
E3
D42
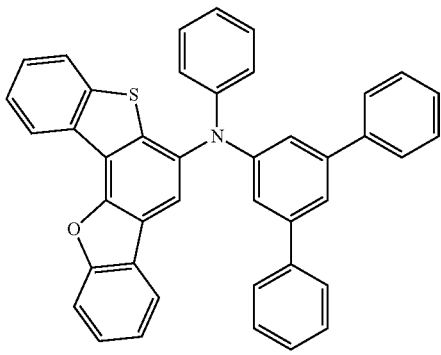
E4

E5
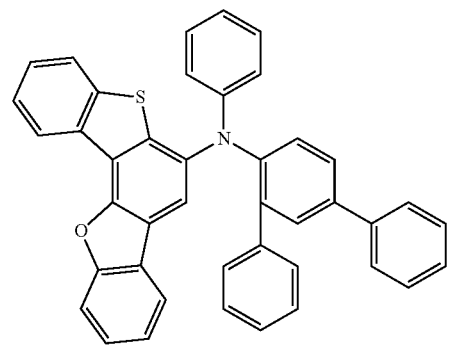
E6
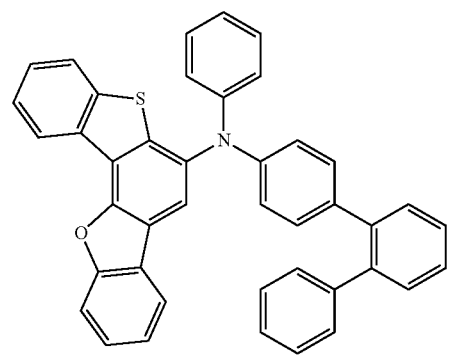
E7
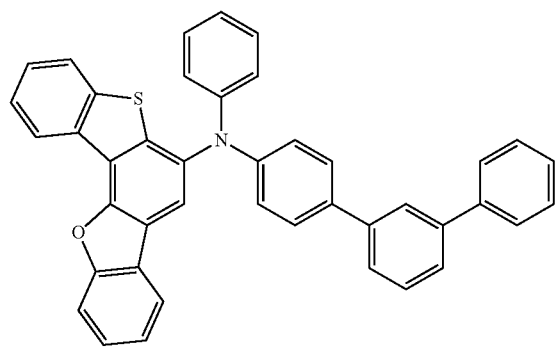
E8
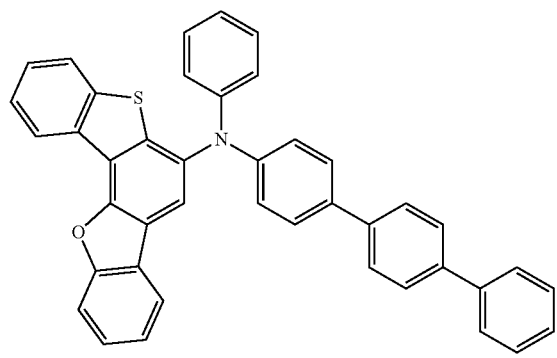
E9
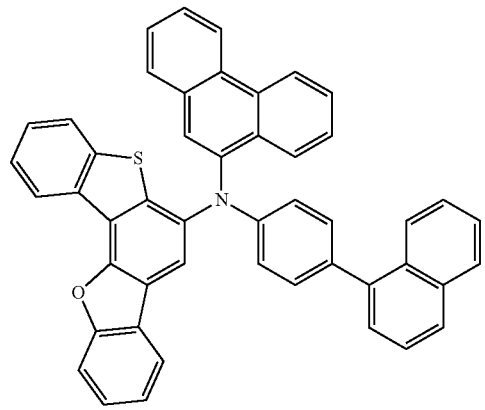
E10
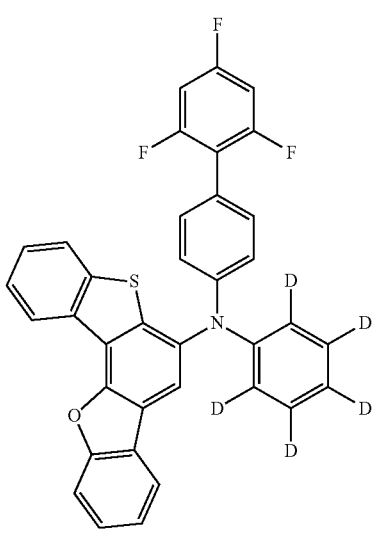
E11
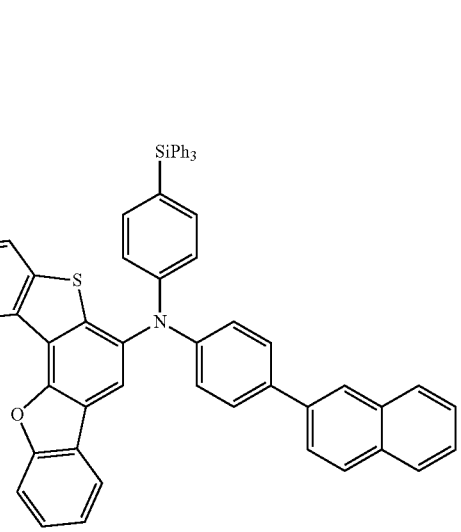

E12
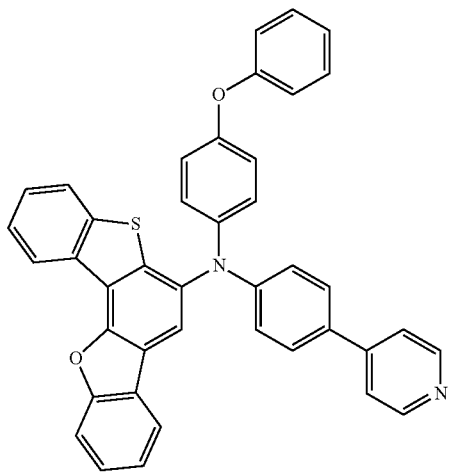
E13
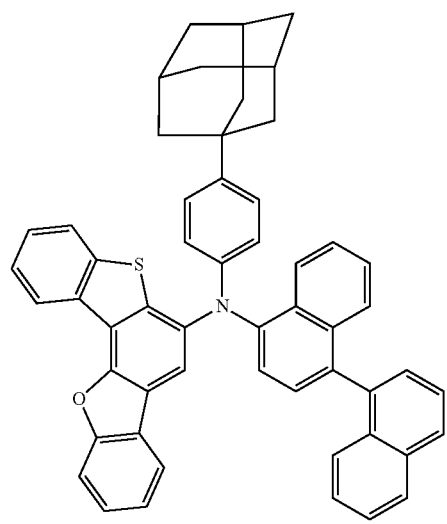
E14
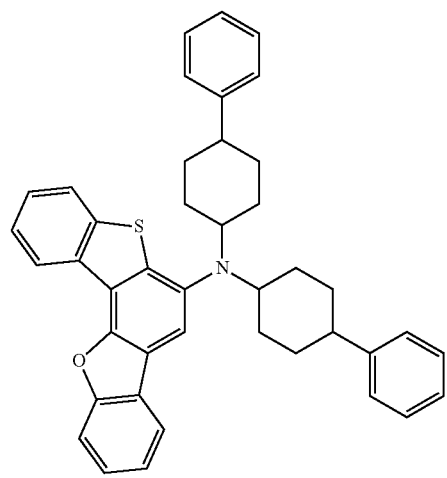
E15
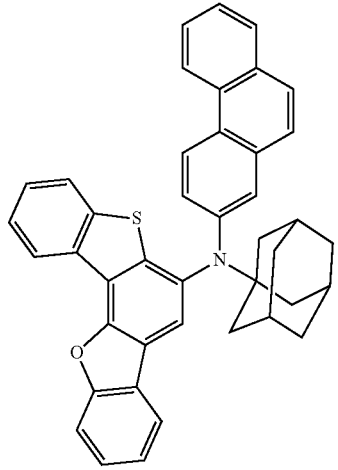
E16
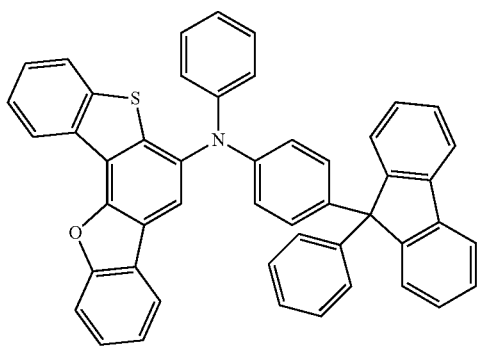
E17
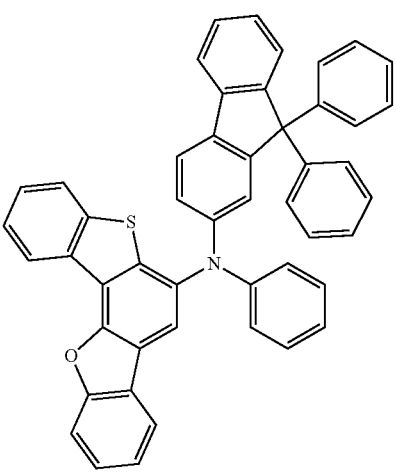

E18
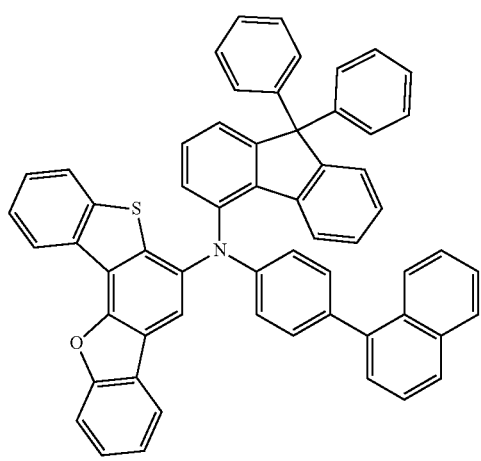
E19
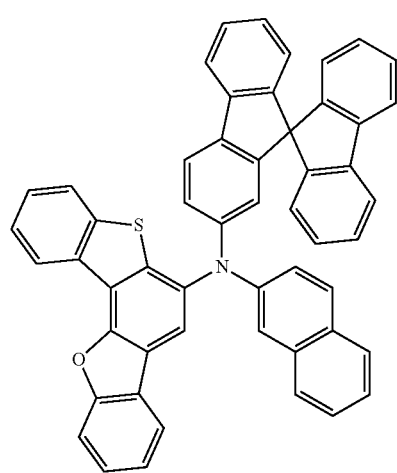
E20
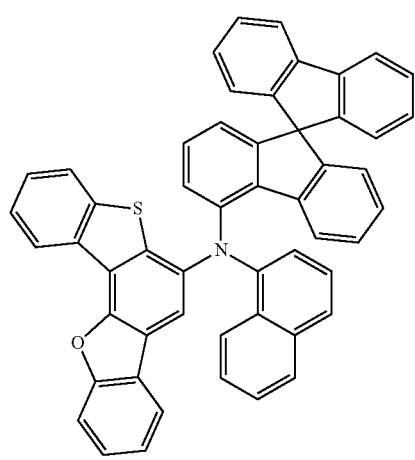
E21
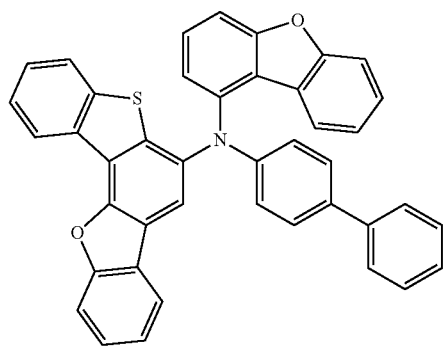
E22
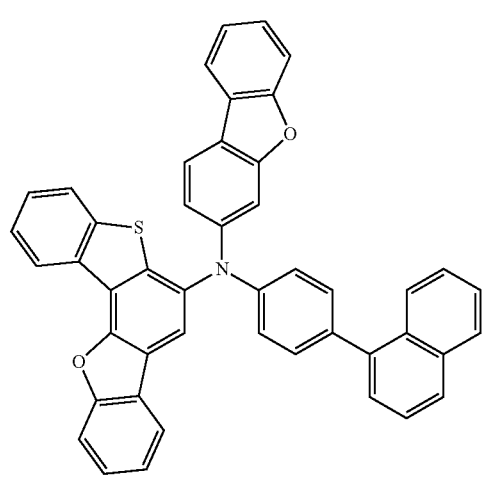
E23
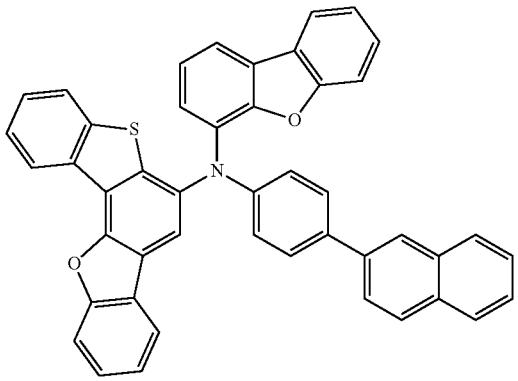
E24
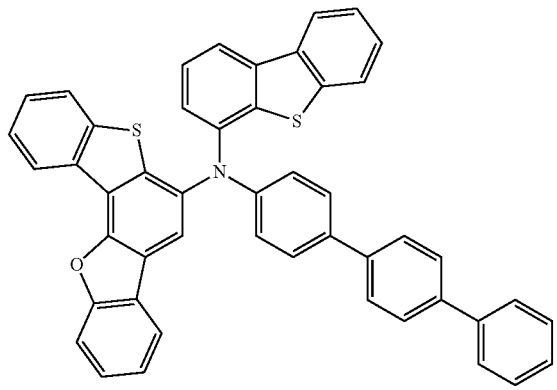

E25
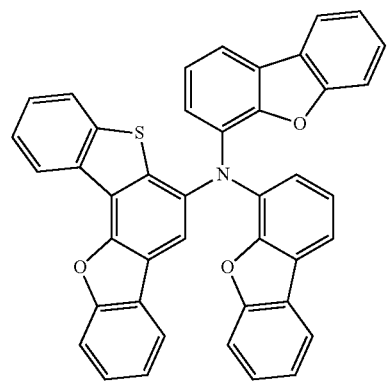
E26
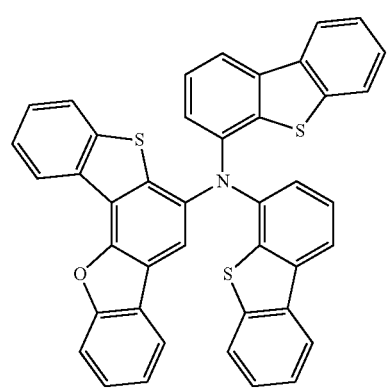
E27
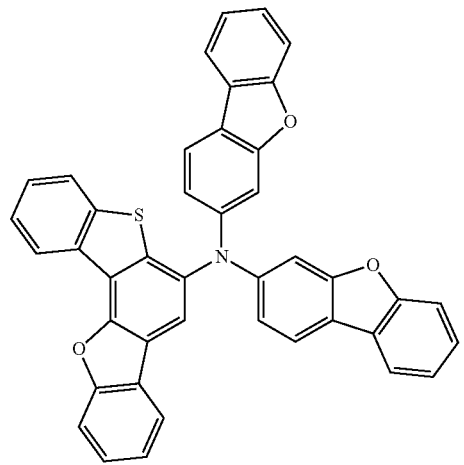
E28
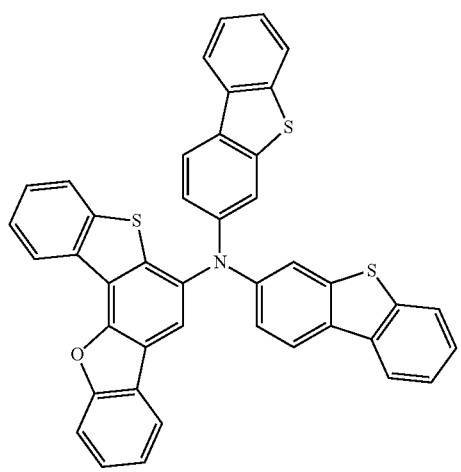
E29
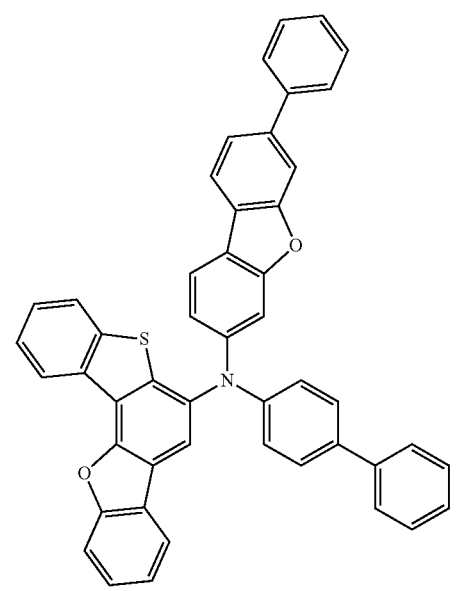
E30
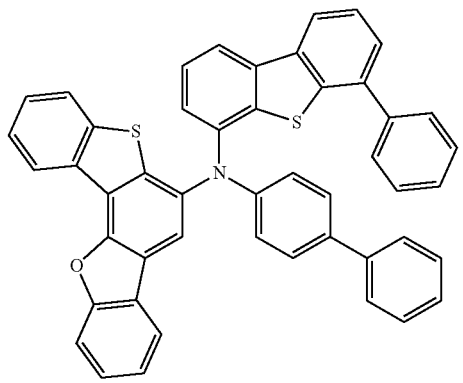

E31
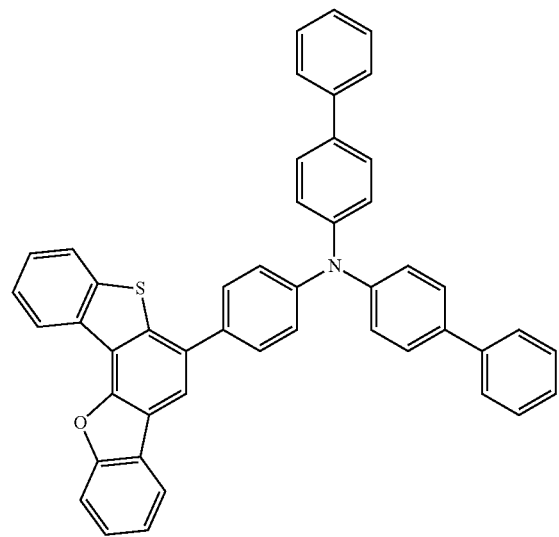
E32
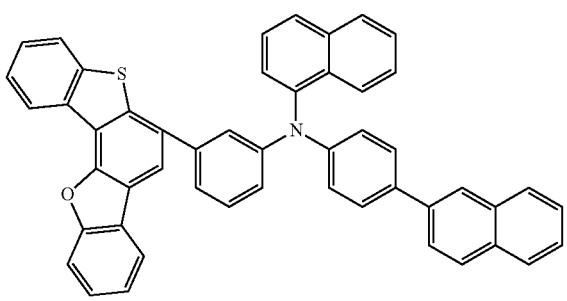
E33
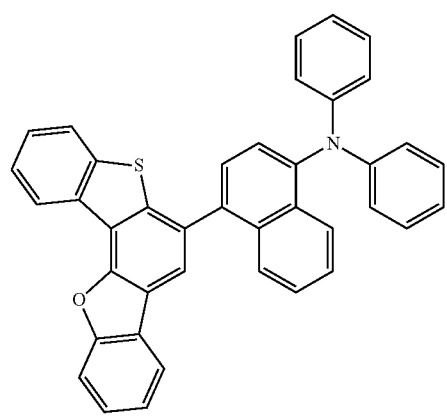
E34
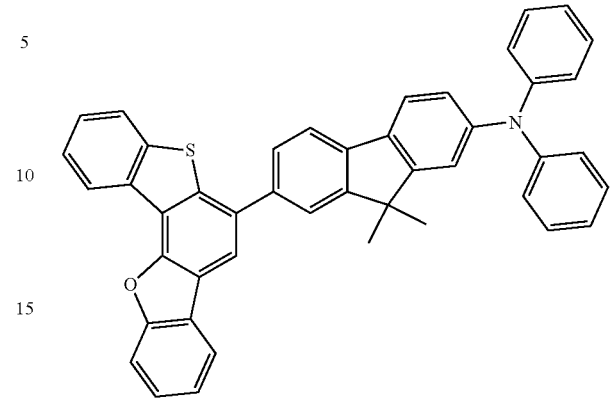
E35
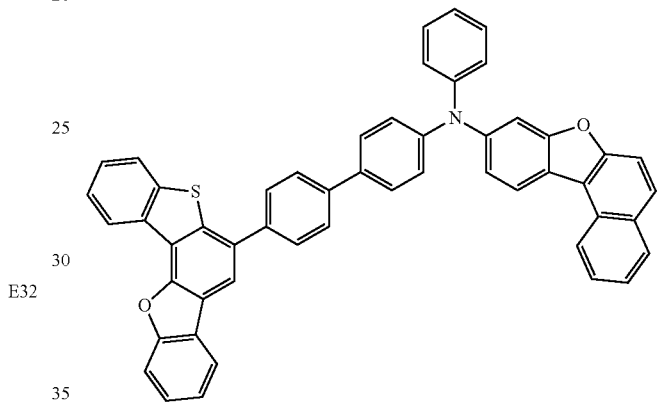
E36
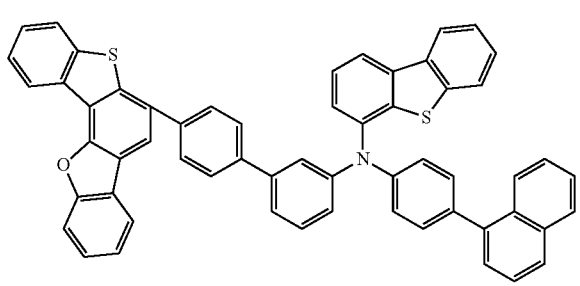
E37

E38
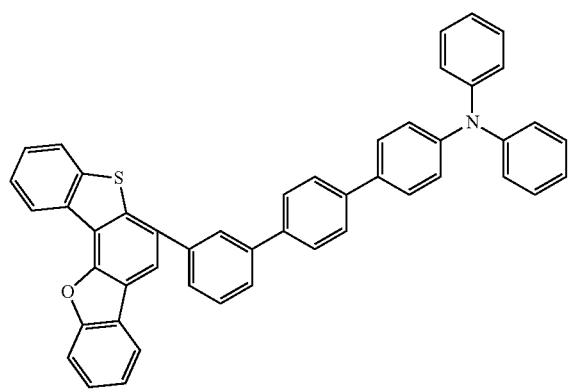
E39
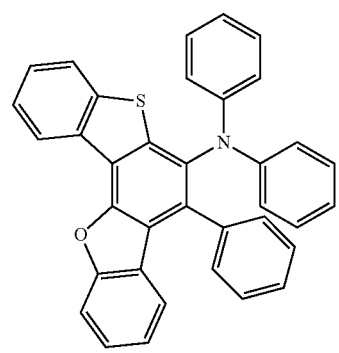
E40
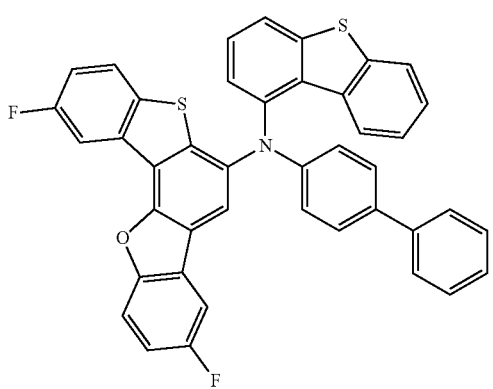
E41
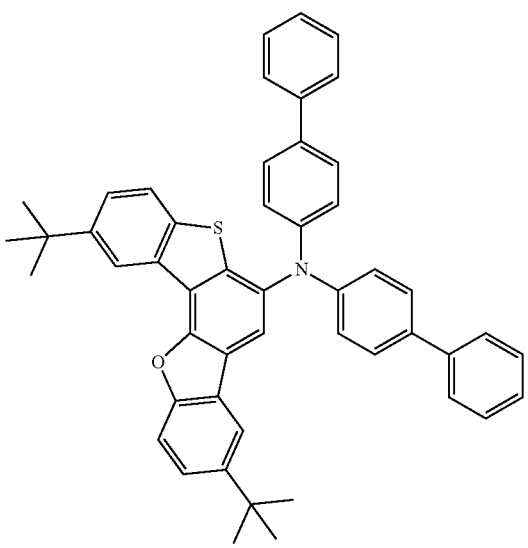
E42
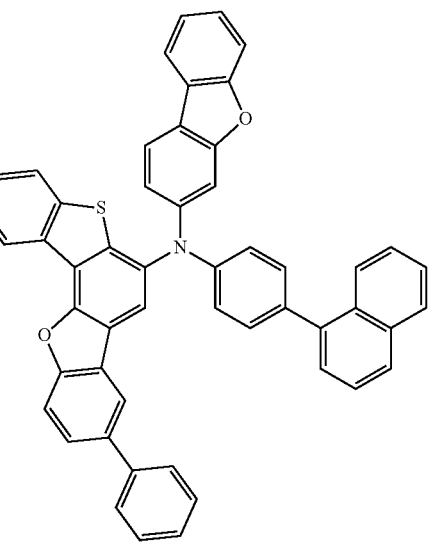
Compound Group F
F1
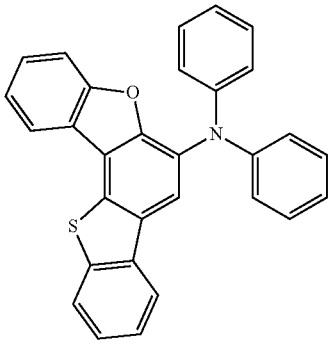

103
-continued
F2
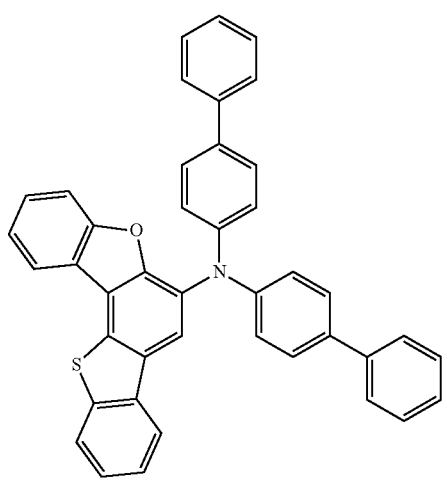
F3
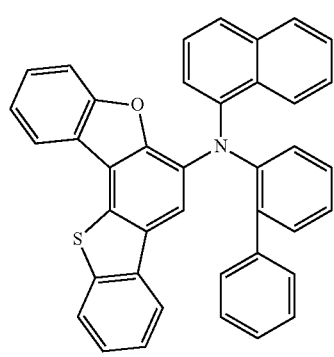
F4
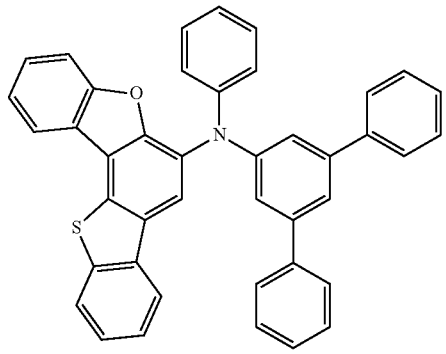
F5
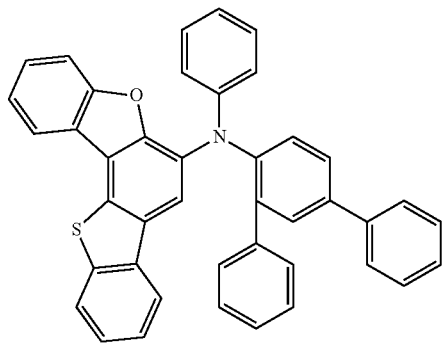
104
-continued
F6
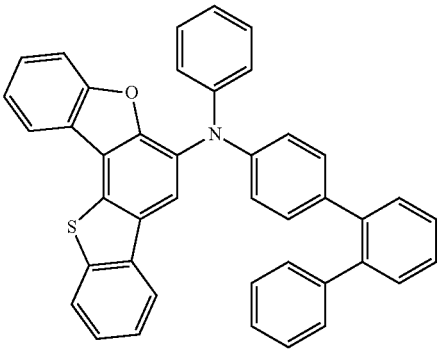
F7
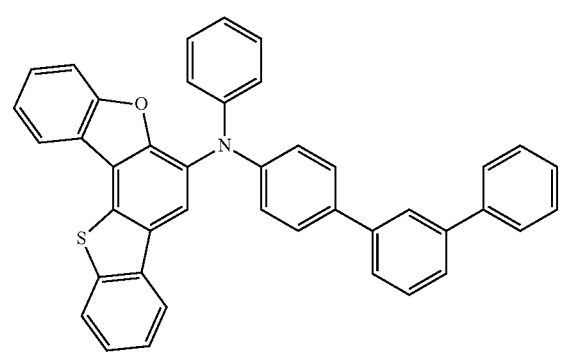
F8
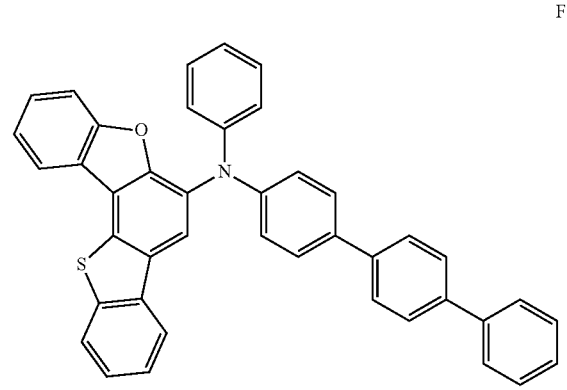
F9
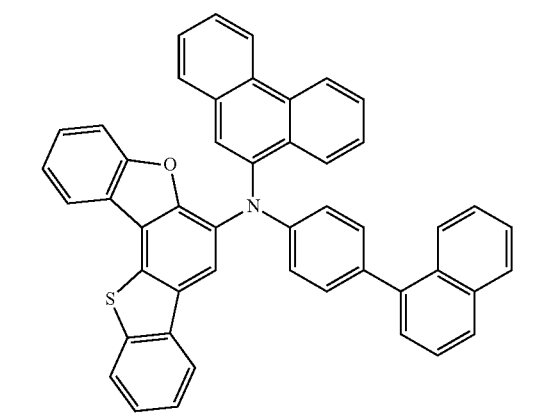

105
-continued
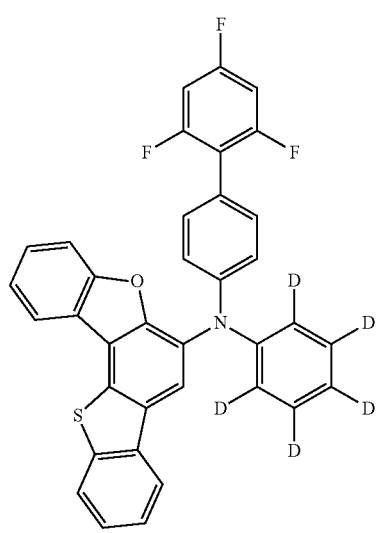
F10
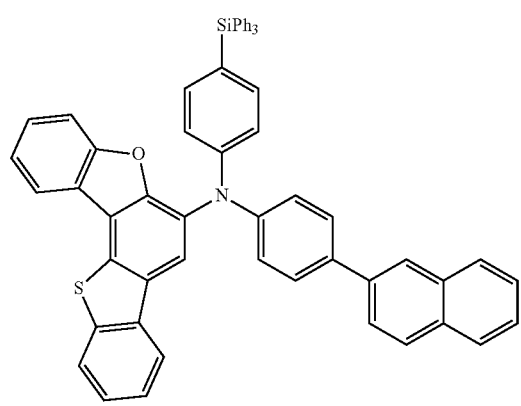
F11
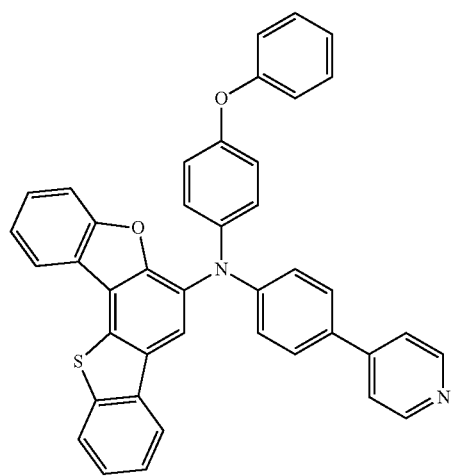
F12
106
-continued
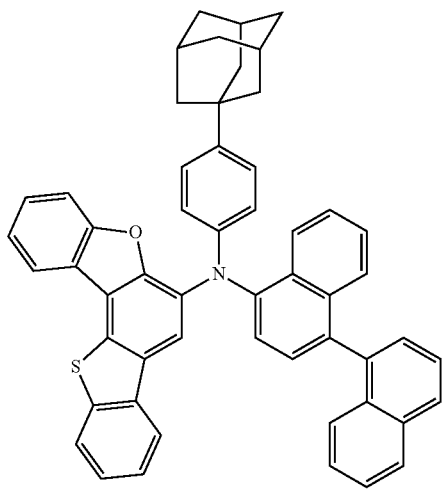
F13
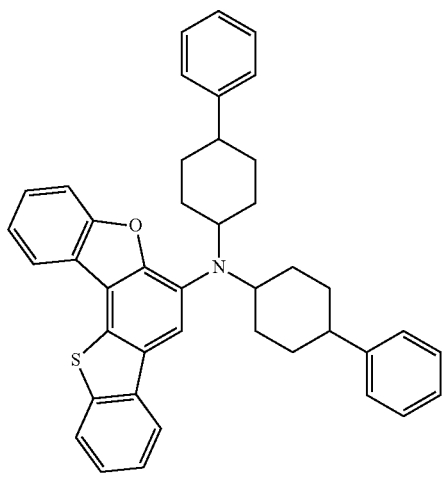
F14
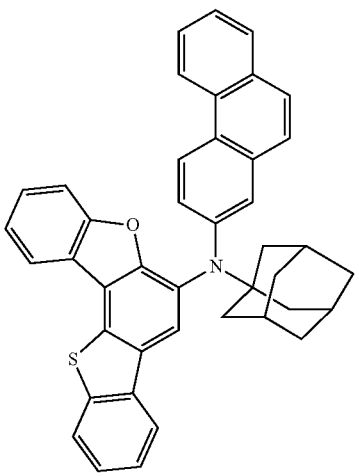
F15

-continued
F16
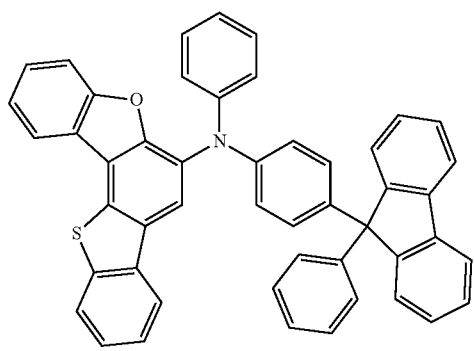
F17
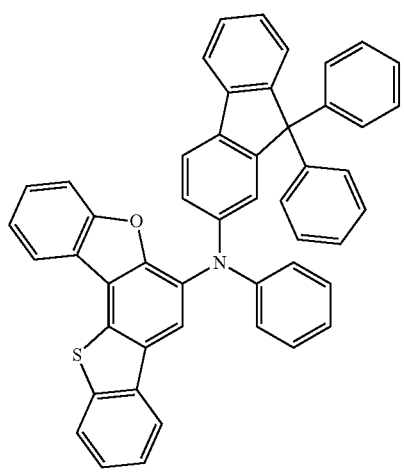
F18
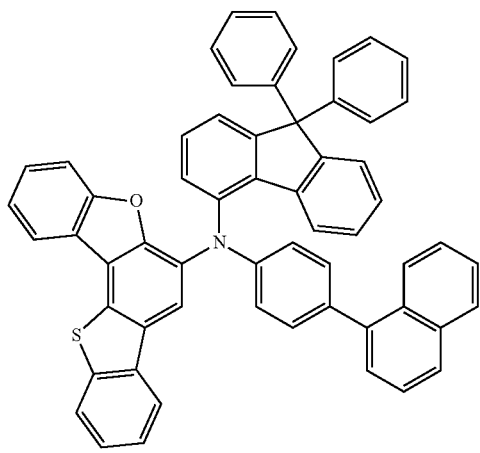
F19
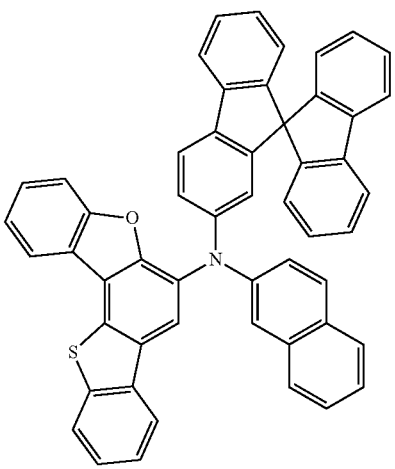
F20
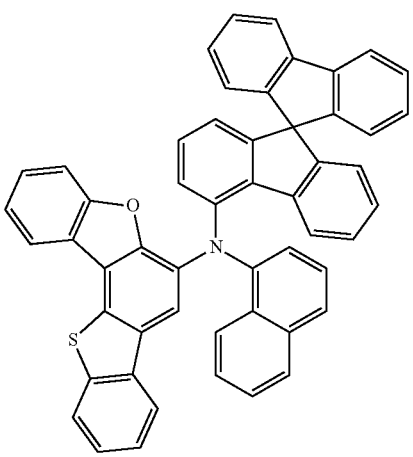
F21
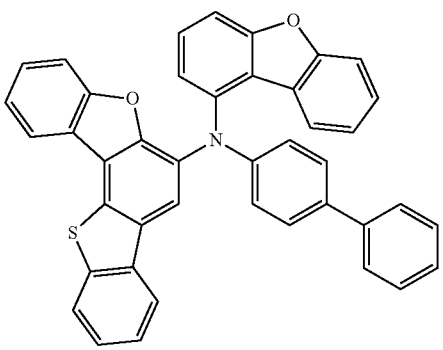

-continued
F22
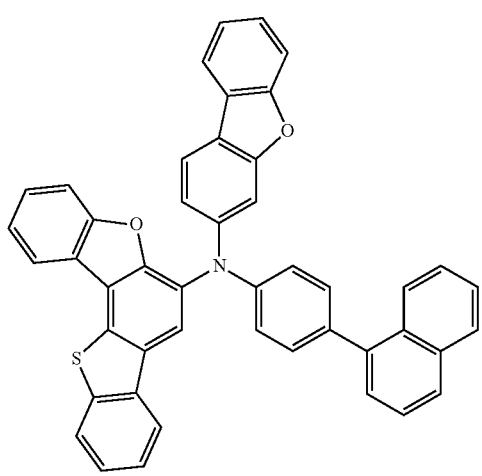
F23
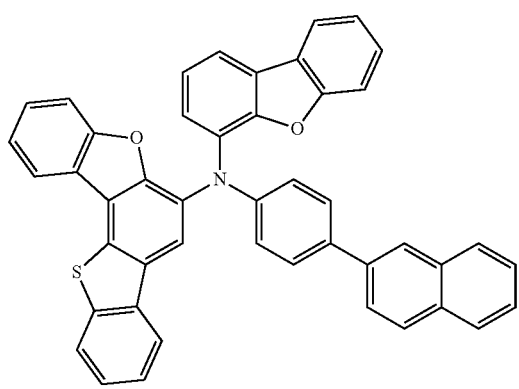
F24
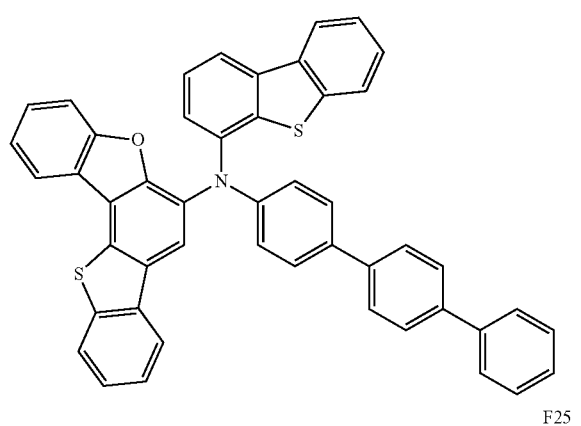
F25
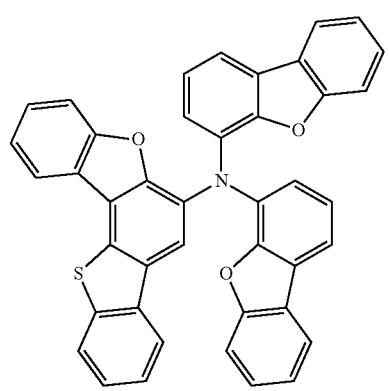
-continued
F26
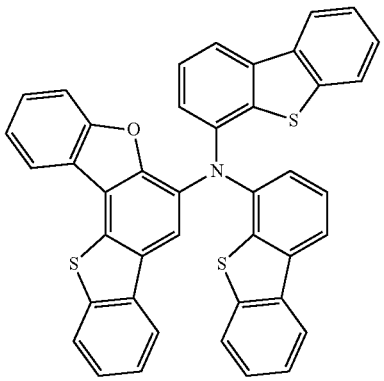
F27
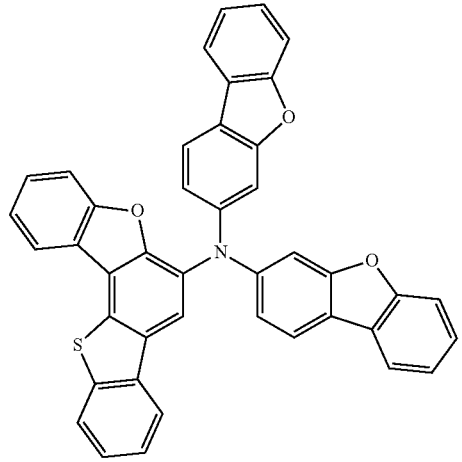
F28
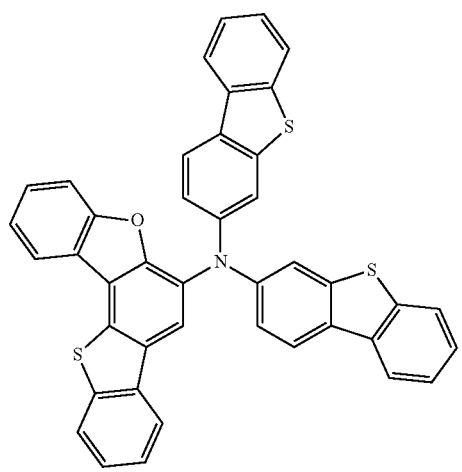

-continued
F29
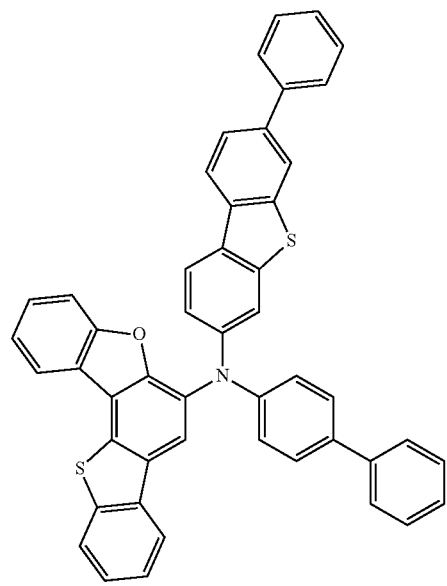
F30
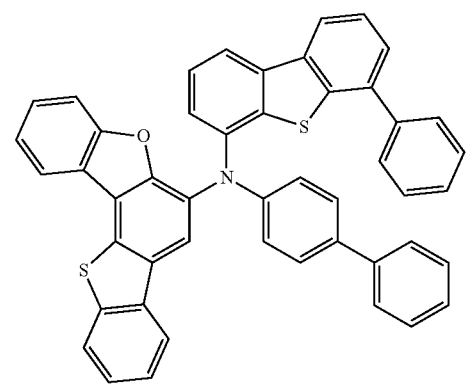
F31
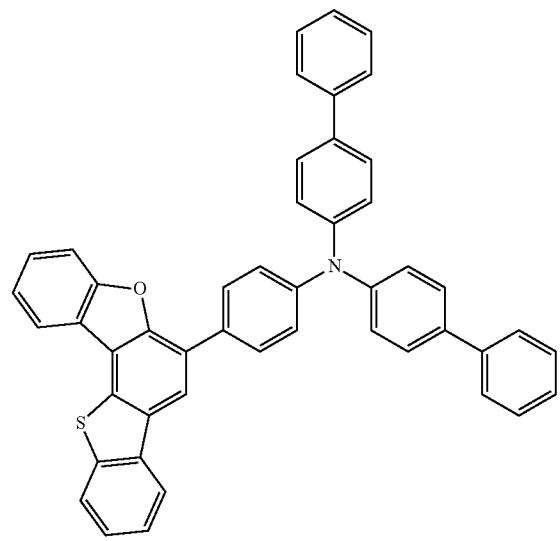
-continued
F32
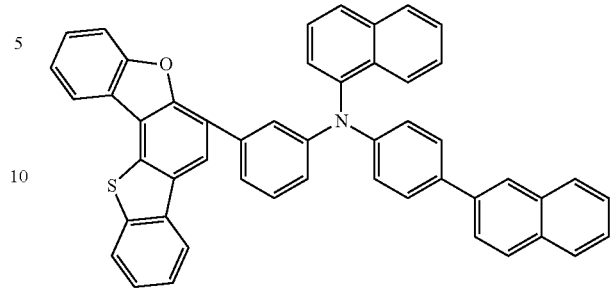
F33
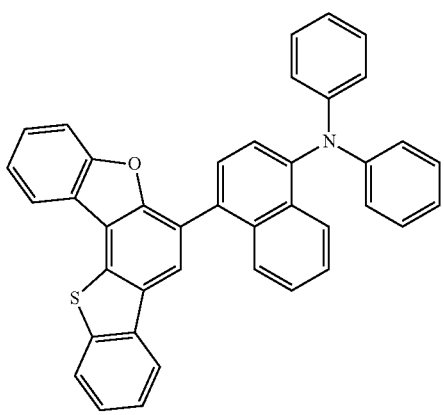
F34
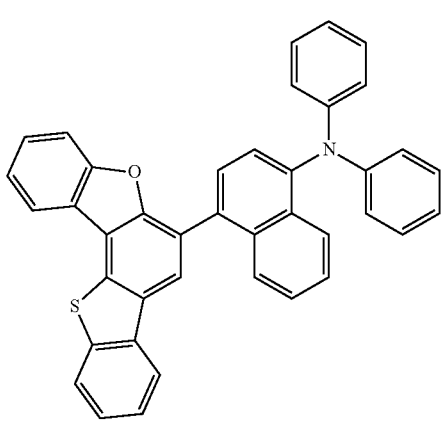
F35
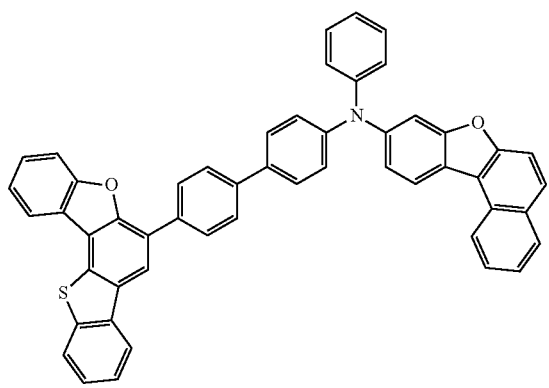

-continued
F36
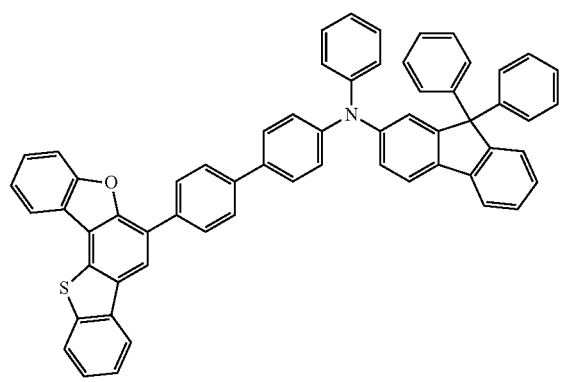
F37
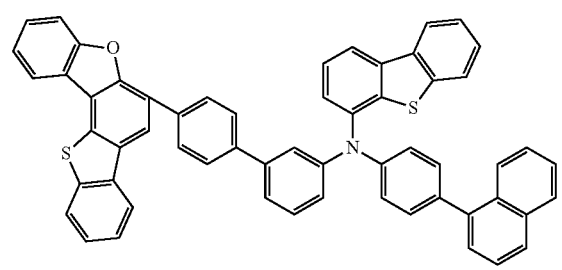
F38
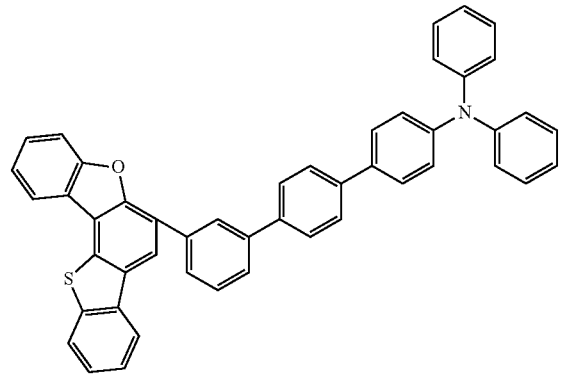
F39
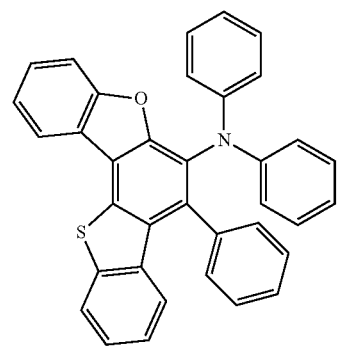
-continued
F40
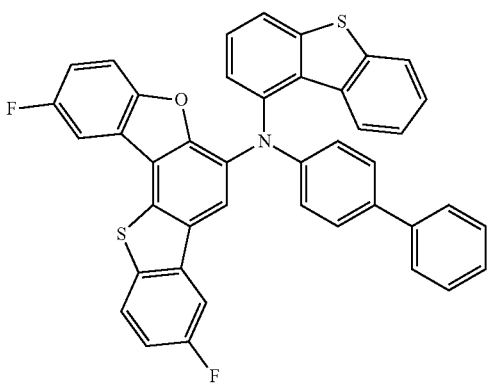
F41
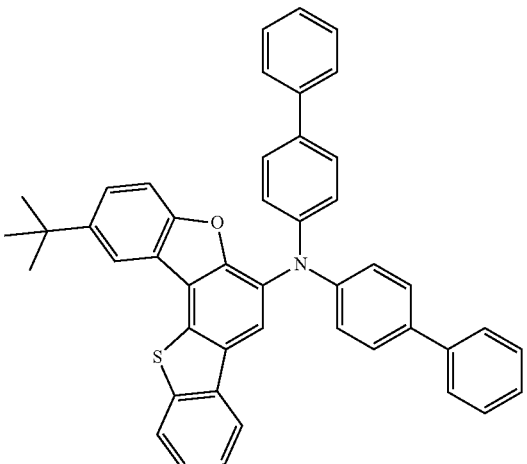
F42
BRIEF DESCRIPTION OF THE DRAWINGS
The accompanying drawings are included to provide a further understanding of the present disclosure, and are incorporated in and constitute a part of this specification. The drawings illustrate example embodiments of the present disclosure and, together with the description, serve to explain principles of the present disclosure. In the drawings.

DETAILED DESCRIPTION

Figure 1:
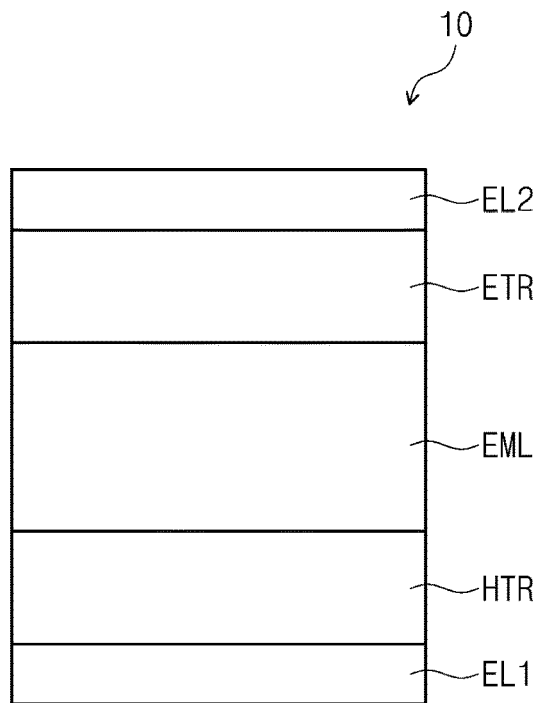
FIG. 1 is a cross-sectional view schematically illustrating an organic electroluminescence device according to an embodiment of the present disclosure.

The present disclosure may have various modifications and may be embodied in different forms, and example embodiments will be explained in more detail with reference to the accompanying drawings. The present disclosure may, however, be embodied in different forms and should not be construed as being limited to the embodiments set forth herein. Rather, all modifications, equivalents, and substituents that are included in the spirit and technical scope of the present disclosure should be included in the present disclosure.

It will be understood that when an element is referred to as being "on," "connected to," or "coupled to" another element, it can be directly on, connected, or coupled to the other element, or intervening elements may be present.

Like reference numerals refer to like elements throughout, and duplicative descriptions thereof may not be provided. In addition, in the drawings, the thicknesses, ratios, and dimensions of constituent elements may be exaggerated for effective explanation of technical contents.

As used herein, the singular forms "a," "an," and "the" are intended to include the plural forms as well, unless the context clearly indicates otherwise. As used herein, expressions such as "at least one of," "one of," and "selected from," when preceding a list of elements, modify the entire list of elements and do not modify the individual elements of the list.

The term "and/or" includes one or more (all possible) combinations of the listed elements. Further, the use of "may" when describing embodiments of the present disclosure refers to "one or more embodiments of the present disclosure".

It will be understood that, although the terms first, second, etc. may be used herein to describe various elements, these elements should not be limited by these terms. These terms are only used to distinguish one element from another element. Thus, a first element could be alternatively termed a second element without departing from the teachings of the present disclosure. Similarly, a second element could be alternatively termed a first element. As used herein, the singular forms are intended to include the plural forms as well, unless the context clearly indicates otherwise.

In addition, the terms "below," "beneath," "on," and "above" are used for explaining the relation of elements shown in the drawings. The terms are relative concept and are explained on the basis of the direction shown in the drawing.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It will be further understood that the terms "includes," "including," "comprises," and/or "comprising," when used in this specification, specify the presence of stated features, numerals, steps, operations, elements, parts, or combinations thereof, but do not preclude the presence or addition of one or more other features, numerals, steps, operations, elements, parts, or combinations thereof.

Hereinafter, the organic electroluminescence device according to an embodiment of the present disclosure and an amine compound of an embodiment included therein will be explained with reference to attached drawings.

FIG. 1 to FIG. 4 are cross-sectional views schematically showing organic electroluminescence devices according to example embodiments of the present disclosure. Referring to FIGS. 1 to 4, in an organic electroluminescence device 10 according to an embodiment, a first electrode EL1 and a second electrode EL2 are oppositely disposed, and between the first electrode EL1 and the second electrode EL2, an emission layer EML may be disposed.

In some embodiments, the organic electroluminescence device 10 of an embodiment may further include a plurality of functional layers between the first electrode EL1 and the second electrode EL2 in addition to the emission layer EML. The plurality of functional layers may include a hole transport region HTR and an electron transport region ETR. For example, the organic electroluminescence device 10 of an embodiment may include a first electrode EL1, a hole transport region HTR, an emission layer EML, an electron transport region ETR, and a second electrode, stacked one by one. In some embodiments, the organic electroluminescence device 10 of an embodiment may include a capping layer CPL disposed on the second electrode EL2.

The organic electroluminescence device 10 of an embodiment may include an amine compound of an embodiment, which will be explained later, in a plurality of organic layers disposed between the first electrode EL1 and the second electrode EL2. For example, the amine compound of an embodiment may be included in an emission layer EML and/or an electron transport region ETR. However, embodiments of the present disclosure are not limited thereto, and the organic electroluminescence device 10 of an embodiment may include the amine compound of an embodiment in the hole transport region HTR (which is one of the plurality of organic layers disposed between the first electrode EL1 and the second electrode EL2), in addition to the emission layer EML and the electron transport region ETR.

Figure 2:
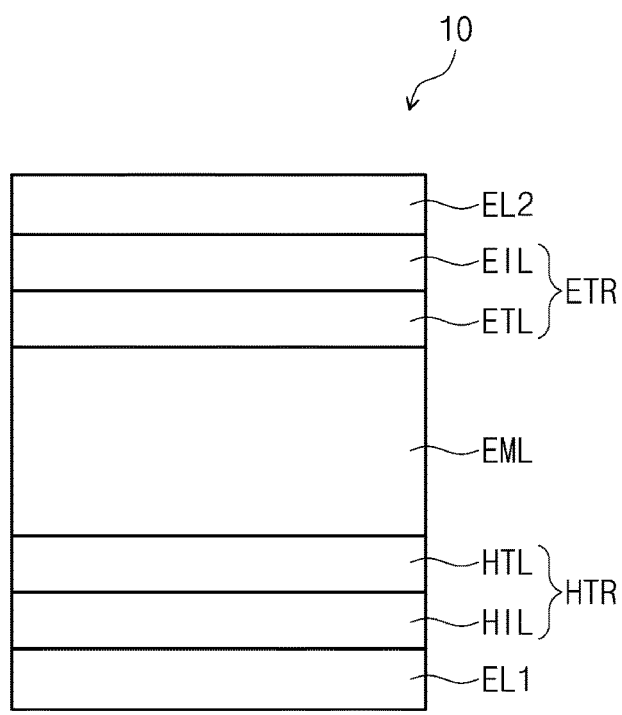
FIG. 2 is a cross-sectional view schematically illustrating an organic electroluminescence device according to an embodiment of the present disclosure.
Figure 3:
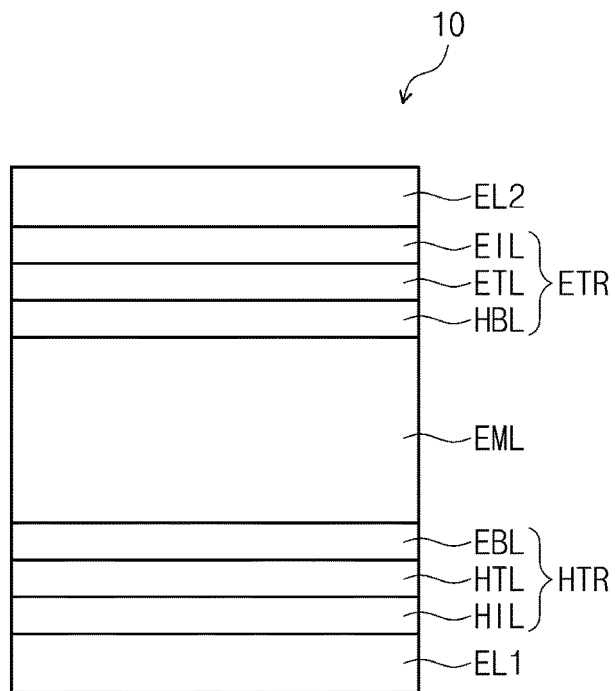
FIG. 3 is a cross-sectional view schematically illustrating an organic electroluminescence device according to an embodiment of the present disclosure.
Figure 4:
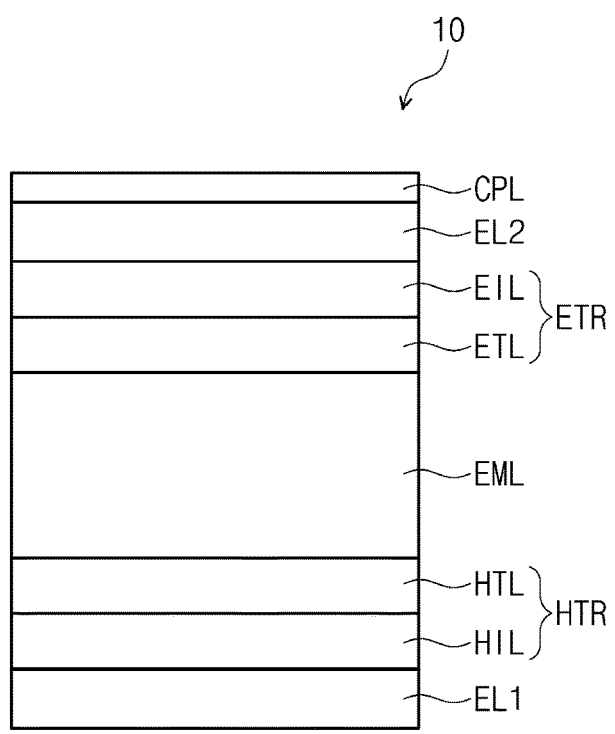
FIG. 4 is a cross-sectional view schematically illustrating an organic electroluminescence device according to an embodiment of the present disclosure.

Compared with FIG. 1, FIG. 2 shows the cross-sectional view of an organic electroluminescence device 10 of an embodiment, wherein the hole transport region HTR includes a hole injection layer HIL and a hole transport layer HTL, and the electron transport region ETR includes an electron injection layer EIL and an electron transport layer ETL. Compared with FIG. 1, FIG. 3 shows the cross-sectional view of an organic electroluminescence device 10 of an embodiment, wherein the hole transport region HTR includes the hole injection layer HIL, the hole transport layer HTL, and an electron blocking layer EBL, and the electron transport region ETR includes the electron injection layer EIL, the electron transport layer ETL, and a hole blocking layer HBL. Compared with FIG. 2, FIG. 4 shows the cross-sectional view of an organic electroluminescence device 10 of an embodiment including a capping layer CPL disposed on the second electrode EL2.

The first electrode EL1 may have conductivity (e.g., be conductive). The first electrode EL1 may be formed using a metal alloy and/or a conductive compound. The first electrode EL1 may be an anode. In some embodiments, the first electrode EL1 may be a pixel electrode. The first electrode EL1 may be a transmissive electrode, a transflective electrode, or a reflective electrode. When the first electrode EL1 is a transmissive electrode, the first electrode EL1 may be formed using a transparent metal oxide such as indium tin oxide (ITO), indium zinc oxide (IZO), zinc oxide (ZnO), and/or indium tin zinc oxide (ITZO). When the first electrode EL1 is a transflective electrode or the reflective electrode, the first electrode EL1 may include silver (Ag), magnesium (Mg), copper (Cu), aluminum (Al), platinum (Pt), palladium (Pd), gold (Au), nickel (Ni), neodymium (Nd), iridium (Ir), chromium (Cr), lithium (Li), calcium (Ca), LiF/Ca, LiF/Al, molybdenum (Mo), titanium (Ti), a compound thereof, or a mixture thereof (for example, a mixture of Ag and Mg). In some embodiments, the first electrode EL1 may have a structure including a plurality of layers including a reflective layer or a transflective layer formed using the above materials, and a transmissive conductive layer formed using ITO, IZO, ZnO, or ITZO. For example, the first electrode EL1 may include a three-layer structure of ITO/Ag/ITO. However, embodiments of the present disclosure are not limited thereto. The thickness of the first electrode EL1 may be about 1,000 Å to about 10,000 Å, for example, about 1,000 Å to about 3,000 Å.

The hole transport region HTR may be provided on the first electrode EL1. The hole transport region HTR may include at least one of a hole injection layer HIL, a hole transport layer HTL, a hole buffer layer, or an electron blocking layer EBL. The thickness of the hole transport region HTR may be about 50 Å to about 15,000 Å

The hole transport region HTR may have a single layer formed using a single material, a single layer formed using a plurality of different materials, or a multilayer structure including a plurality of layers formed using a plurality of different materials.

For example, the hole transport region HTR may have the structure of a single layer of a hole injection layer HIL or a hole transport layer HTL, or may have a structure of a single layer formed using a hole injection material and a hole transport material. In some embodiments, the hole transport region HTR may have a structure of a single layer formed using a plurality of different materials, or a structure stacked from the first electrode EL1 of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer EBL, without limitation.

The hole transport region HTR may be formed using any suitable method (such as a vacuum deposition method, a spin coating method, a cast method, a Langmuir-Blodgett (LB) method, an inkjet printing method, a laser printing method, and/or a laser induced thermal imaging (LITI) method).

The hole transport region HTR of an embodiment may include an amine compound of an embodiment, which will be explained later. For example, the hole transport layer HTL may include the amine compound of an embodiment.

In the description, the term "substituted or unsubstituted" refers to a state of being unsubstituted, or substituted with at least one substituent selected from the group consisting of a deuterium atom, a halogen atom, a cyano group, a nitro group, an amine group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the above substituents may be further substituted or unsubstituted. For example, a biphenyl group may be interpreted as a named aryl group, or as a phenyl group substituted with a phenyl group.

In the description, the terms "forming a ring via combination with an adjacent group" or "combined with an adjacent group to form a ring" may refer to forming a substituted or unsubstituted hydrocarbon ring, or a substituted or unsubstituted heterocycle via combination with an adjacent group. The hydrocarbon ring may be an aliphatic hydrocarbon ring or an aromatic hydrocarbon ring. The heterocycle may be an aliphatic heterocycle or an aromatic heterocycle. The ring formed by combination with an adjacent group may be a monocyclic ring or a polycyclic ring. In some embodiments, the ring formed via combination with an adjacent group may be combined with another ring to form a spiro structure.

In the description, the term "adjacent group" may refer to a substituent on the same atom or point, a substituent on an atom that is directly connected to the base atom or point, or a substituent sterically positioned (e.g., within intramolecular bonding distance) to the corresponding substituent. For example, in 1,2-dimethylbenzene, two methyl groups may be interpreted as "adjacent groups" to each other, and in 1,1-diethylcyclopentane, two ethyl groups may be interpreted as "adjacent groups" to each other.

In the description, the halogen atom may be a fluorine atom, a chlorine atom, a bromine atom or an iodine atom.

In the description, the alkyl group may be a linear chain, a branched chain or a cyclic alkyl group. The alkyl group may include a cycloalkyl group. The cycloalkyl group may include a monocycloalkyl group, and/or a polycyclic cycloalkyl group (such as a bicycloalkyl group and/or a tricycloalkyl group). For example, the tricycloalkyl group may include adamantane.

The carbon number of the alkyl group may be 1 to 50, 1 to 30, 1 to 20, 1 to 10, or 1 to 6. Non-limiting examples of the alkyl include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldocecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyleicosyl, 2-butyleicosyl, 2-hexyleicosyl, 2-octyleicosyl, n-henicosyl, n-docosyl, n-tricosyl, n-tetracosyl, n-pentacosyl, n-hexacosyl, n-heptacosyl, n-octacosyl, n-nonacosyl, n-triacontyl, etc.

In the description, the term "hydrocarbon ring group" may refer to an optional functional group or substituent derived from an aliphatic hydrocarbon ring.

In the description, the term "aryl group" may refer to an optional functional group or substituent derived from an aromatic hydrocarbon ring. The aryl group may be a monocyclic aryl group or a polycyclic aryl group. The carbon number for forming a ring in the aryl group may be 6 to 30, 6 to 20, or 6 to 15. Non-limiting examples of the aryl group include phenyl, naphthyl, fluorenyl, anthracenyl, phenanthryl, biphenyl, terphenyl, quaterphenyl, quinquephenyl, sexiphenyl, triphenylenyl, pyrenyl, benzofluoranthenyl, chrysenyl, etc.

In the description, the fluorenyl group may be substituted (e.g., at the 9H position), and two substituents may be combined with each other to form a spiro structure. Examples of a substituted fluorenyl group are as follows. However, an embodiment of the present disclosure is not limited thereto:

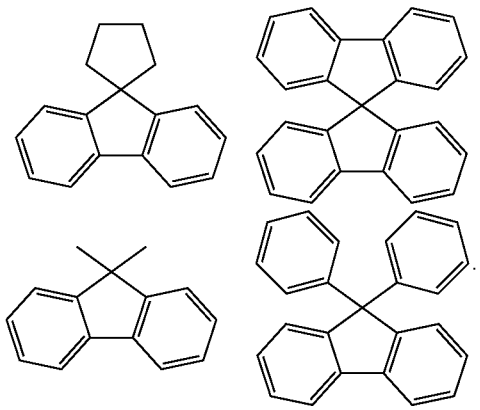

In the description, the term "heterocyclic group" may refer to an optional functional group or substituent derived from a ring including one or more among boron (B), oxygen (O), nitrogen (N), phosphorus (P), silicon (Si), or sulfur (S) as heteroatoms. The heterocyclic group may be an aliphatic heterocyclic group or an aromatic heterocyclic group. The aromatic heterocyclic group may be a heteroaryl group. The aliphatic heterocyclic group and the aromatic heterocyclic group may each independently be a monocycle or a polycycle.

When the heterocyclic group includes two or more heteroatoms, the two or more heteroatoms may be the same or different. The heterocyclic group may be a monocyclic heterocyclic group or a polycyclic heterocyclic group and has a concept including a heteroaryl group. The carbon number for forming a ring of the heterocycle may be 2 to 30, 2 to 20, or 2 to 10.

The carbon number for forming a ring of the aliphatic heterocyclic group may be 2 to 30, 2 to 20, or 2 to 10. Non-limiting examples of the aliphatic heterocyclic group include an oxirane group, a thiirane group, a pyrrolidine group, a piperidine group, a tetrahydrofuran group, a tetrahydrothiophene group, a thiane group, a tetrahydropyran group, a 1,4-dioxane group, etc.

When the heteroaryl group includes two or more heteroatoms, the two or more heteroatoms may be the same or different. The heteroaryl group may be a monocyclic heterocyclic group or a polycyclic heterocyclic group. The carbon number for forming a ring of the heteroaryl group may be 2 to 30, 2 to 20, or 2 to 10. Non-limiting examples of the heteroaryl group include thiophene, furan, pyrrole, imidazole, thiazole, pyridine, bipyridine, pyrimidine, triazine, triazole, acridyl, pyridazine, pyrazinyl, quinoline, quinazoline, quinoxaline, phenoxazine, phthalazine, pyrido pyrimidine, pyrido pyrazine, pyrazino pyrazine, isoquinoline, indole, carbazole, N-arylcarbazole, N-heteroarylcarbazole, N-alkylcarbazole, benzoxazole, benzimidazole, benzothiazole, benzocarbazole, benzothiophene, dibenzothiophene, thienothiophene, benzofuran, phenanthroline, thiazole, isooxazole, oxadiazole, thiadiazole, phenothiazine, dibenzosilole, dibenzofuran, etc.

In the description, the oxy group may include an alkoxy group and an aryl oxy group. The alkoxy group may be a linear chain, a branched chain or a cyclic chain. The carbon number of the alkoxy group is not specifically limited, but may be, for example, 1 to 20 or 1 to 10. The carbon number for forming a ring of the aryl oxy group is not specifically limited, but may be, for example, 6 to 30, 6 to 20, or 6 to 15. Non-limiting examples of the oxy group include methoxy, ethoxy, n-propoxy, isopropoxy, butoxy, pentyloxy, hexyloxy, octyloxy, nonyloxy, decyloxy, benzyloxy, etc.

In the description, the boryl group may be an alkyl boryl group or an aryl boryl group. Non-limiting examples of the boryl group include a trimethylboryl group, a triethylboryl group, a t-butyldimethylboryl group, a triphenylboryl group, a diphenylboryl group, a phenylboryl group, etc. Examples of the alkyl group in the alkyl boryl group may be the same as the examples of the above-described alkyl group, and examples of the aryl group in the aryl boryl group may be the same as the examples of the above-described aryl group.

In the description, the carbon number of the amine group is not specifically limited, but may be 1 to 30. The amine group may include an alkyl amine group and an aryl amine group. Non-limiting examples of the amine group include a methylamine group, a dimethylamine group, a phenylamine group, a diphenylamine group, a naphthylamine group, a 9-methyl-anthracenylamine group, a triphenylamine group, etc.

In the description, the alkyl group in the alkyl amine group may be the same as the examples of the above-described alkyl group.

In the description, the aryl group in the aryl amine group may be the same as the examples of the above-described aryl group.

In the description, the term "direct linkage" may refer to a single bond.

In the description, "—*" may refer to a point of connection to another formula, moiety, or group.

The amine compound according to an embodiment may be represented by Formula 1:

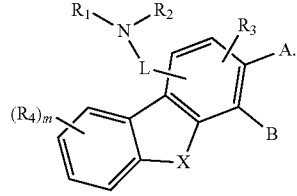

Formula 1

In Formula 1, X may be O or S.

In Formula 1, $R_1$ and $R_2$ may each independently be a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring.

In some embodiments, $R_1$ and $R_2$ may each independently be an alkyl group of 6 to 10 carbon atoms. For example, $R_1$ and $R_2$ may each independently be a substituted or unsubstituted cyclohexyl group or a substituted or unsubstituted adamantane (e.g., adamantyl group).

In some embodiments, $R_1$ and $R_2$ may each independently be an aryl group of 6 to 25 carbon atoms for forming a ring, or a substituted or unsubstituted heteroaryl group of 2 to 18 carbon atoms for forming a ring. For example, $R_1$ and $R_2$ may each independently be a substituted or unsubstituted phenyl group, a substituted or unsubstituted biphenyl group, a substituted or unsubstituted terphenyl group, a substituted or unsubstituted naphthalene group, a substituted or unsubstituted dibenzofuran group, a substituted or unsubstituted dibenzothiophene group, a substituted or unsubstituted fluorenyl group, or a substituted or unsubstituted phenanthryl group. In some embodiments, $R_1$ and $R_2$ may each independently be a substituted or unsubstituted dibenzofuran group, or a substituted or unsubstituted dibenzothiophene group.

In the amine compound of an embodiment, both $R_1$ and $R_2$ may be selected (e.g., simultaneously) from a substituted or unsubstituted aryl group of 6 to 30 carbon atoms for forming a ring, or a substituted or unsubstituted heteroaryl group of 2 to 30 carbon atoms for forming a ring. However, an embodiment of the present disclosure is not limited thereto.

In Formula 1, $R_3$ and $R_4$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring. However, when either $R_3$ or $R_4$ is a heteroaryl group (e.g., a substituted or unsubstituted heteroaryl group of 2 to 30 carbon atoms for forming a ring), a carbazole group is excluded (e.g., $R_3$ and $R_4$ are each not a carbazolyl group, and/or do not form a carbazolyl group). For example, $R_3$ and $R_4$ may each independently be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, excluding carbazolyl group. For example, $R_3$ and $R_4$ may each independently be a hydrogen atom or a deuterium atom. In some embodiments, $R_4$ may be an alkyl group of 1 to 5 carbon atoms. For example, $R_4$ may be a t-butyl group. In some embodiments, $R_4$ may be a halogen atom. For example, $R_4$ may be a fluorine atom (F). In some embodiments, $R_4$ may be an aryl group of 1 to 6 carbon atoms. For example, $R_4$ may be an unsubstituted phenyl group. However, embodiments of the present disclosure are not limited thereto.

In Formula 1, L may be a direct linkage, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring. For example, L may be a substituted or unsubstituted aryl group of 6 to 30 carbon atoms for forming a ring, or a substituted or unsubstituted heteroaryl group of 2 to 30 carbon atoms for forming a ring.

In some embodiments, L may be a direct linkage, an aryl group of 1 to 18, an unsubstituted phenylene group, an unsubstituted divalent biphenyl group, an unsubstituted divalent terphenyl group, an unsubstituted naphthalene group, a 9,9-dimethylfluorenylene group, a 9,9-diphenylfluorenylene group, a dibenzofuranylene group, or a dibenzothiophenylene group.

In Formula 1, "m" may be an integer of 0 to 4. For example, "m" may be 0 or 1.

In Formula 1, A and B are points of connection to a substituent represented by Formula 2:

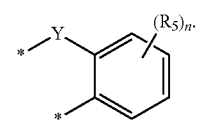

Formula 2

In Formula 2, Y may be O or S, and at least one of X or Y may be O. For example, in the amine compound according to an embodiment, a case where both X and Y are S (e.g., simultaneously) is excluded.

In Formula 2, $R_5$ may be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring. However, when $R_5$ is a heteroaryl group, a carbazolyl group is excluded. For example, $R_5$ may be a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, excluding a carbazolyl group.

In some embodiments, $R_5$ may be an alkyl group of 1 to 5 carbon atoms. For example, $R_5$ may be a t-butyl group. In some embodiments, $R_5$ may be a halogen atom. For example, $R_5$ may be a fluorine atom. In some embodiments, $R_5$ may be an aryl group of 1 to 6 carbon atoms. For example, $R_5$ may be an unsubstituted phenyl group. However, an embodiment of the present disclosure is not limited thereto.

In Formula 2, "n" may be an integer of 0 to 4. For example, "n" may be 0 or 1.

In Formula 2, "—*" may be a point of connection to positions A or B of Formula 1.

In some embodiments, the amine compound of an embodiment may be a monoamine compound. For example, the amine compound of an embodiment may not include a separate (e.g., second or additional) amine moiety or carbazole moiety other than the nitrogen atom represented in Formula 1.

In an embodiment, the amine compound represented by Formula 1 may be represented by one of Formula 3-1 to Formula 3-3:

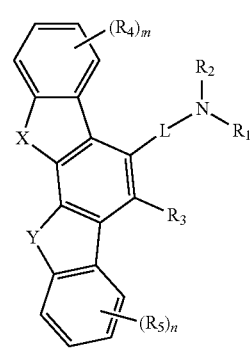

Formula 3-1

Formula 3-2

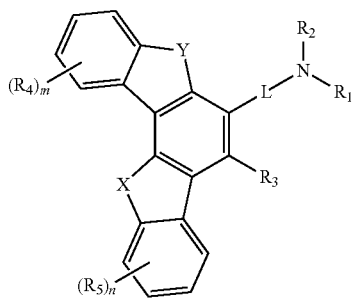

Formula 3-3

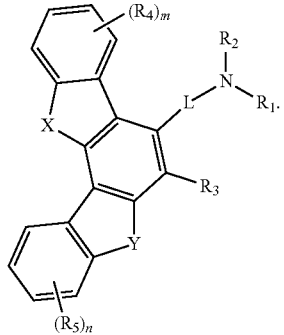

Formula 3-1 to Formula 3-3 are examples in which the connectivity between Formula 1 and the substituent represented by Formula 2 is embodied (e.g. explicitly fixed or specified). In these example structures, the positioning of the nitrogen atom in Formula 1 with respect to the benzene ring is embodied (e.g. explicitly fixed or specified). For example, Formula 3-1 is a case where Y is substituted at a para position with respect to the nitrogen atom in Formula 1 and Formula 2. Formula 3-2 is a case where X is substituted at a para position with respect to the nitrogen atom in Formula 1 and Formula 2. Formula 3-3 is a case where X or Y is (e.g., both X and Y simultaneously are) substituted at a meta position with respect to the nitrogen atom in Formula 1 and Formula 2.

In Formula 3-1 to Formula 3-3, X, Y, $R_1$ to $R_5$, L, "m" and "n" may each independently be the same as defined in Formula 1 and Formula 2.

In an embodiment, the amine compound represented by Formula 1 may be represented by one of Formula 4-1 to Formula 4-9:

Formula 4-1

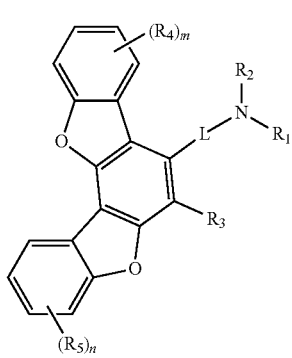

Formula 4-2

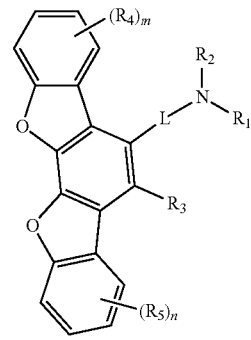

Formula 4-3

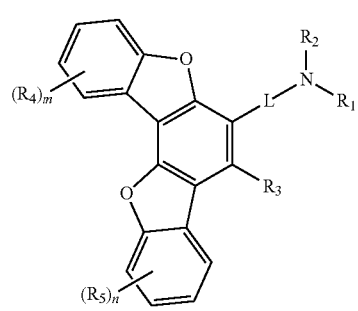

Formula 4-4

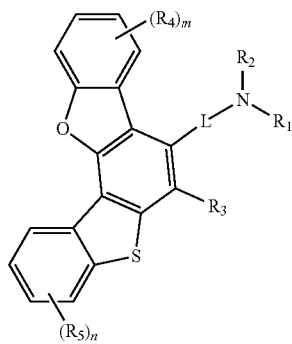

Formula 4-5

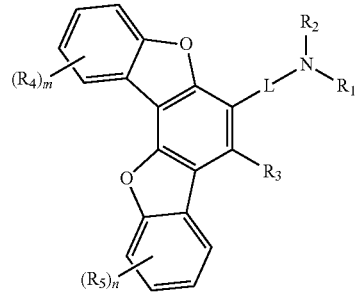

125
-continued

Formula 4-6

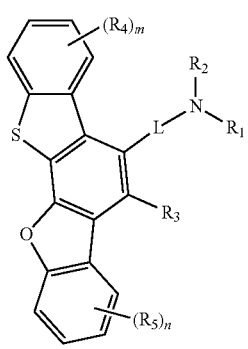

Formula 4-7

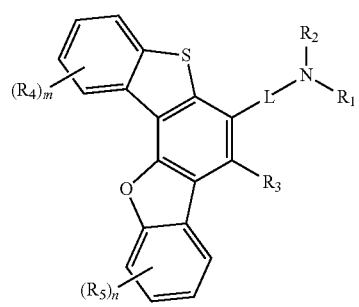

Formula 4-8

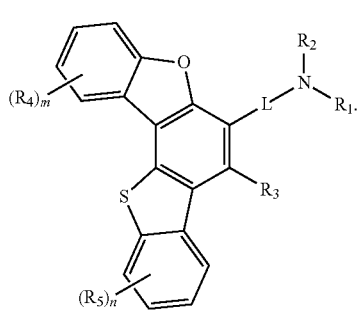

Formula 4-9

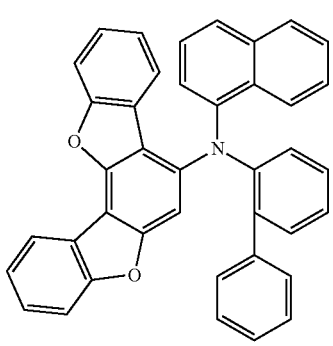

In Formula 4-1 to Formula 4-9, X and Y may each independently be O or S in Formula 1 and Formula 2.

In Formula 4-1 to Formula 4-9, $R_1$ to $R_5$, L, "m" and "n" may each independently be the same as defined in Formula 1 and Formula 2.

126

In an embodiment, the amine compound represented by Formula 1 may be any (e.g., at least) one among the compounds in Compound Group A to Compound Group F:

Compound Group A

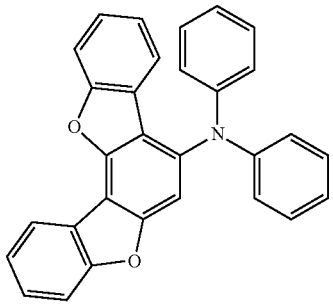
A1

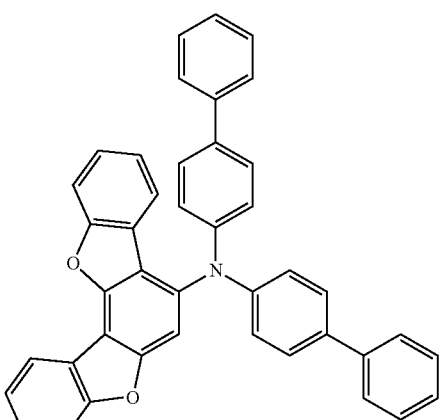
A2

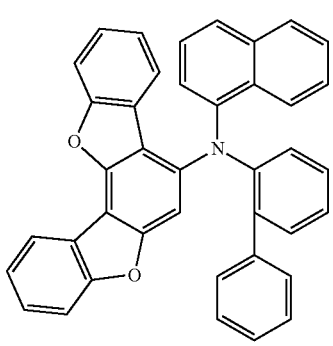
A3

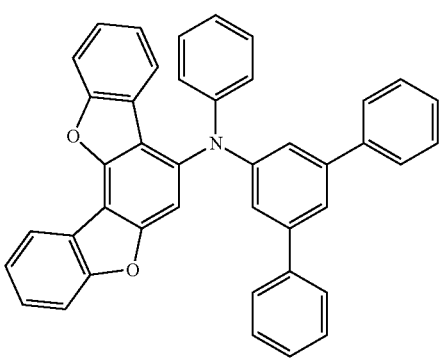
A4

-continued
A5
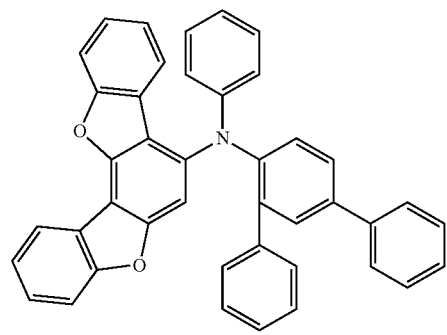
A6
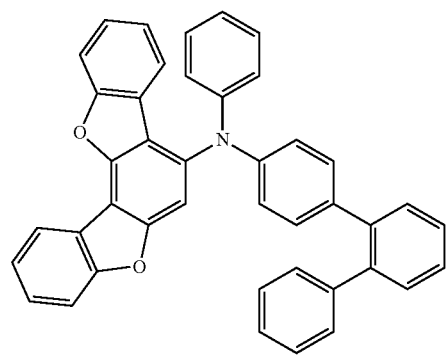
A7
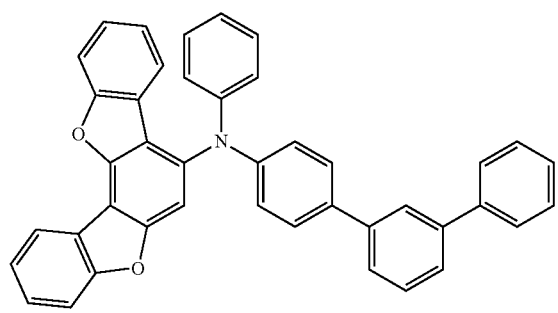
A8
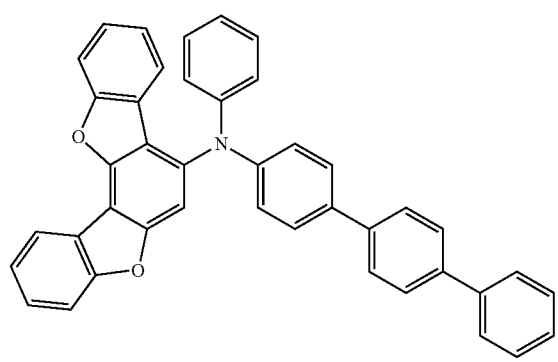
-continued
A9
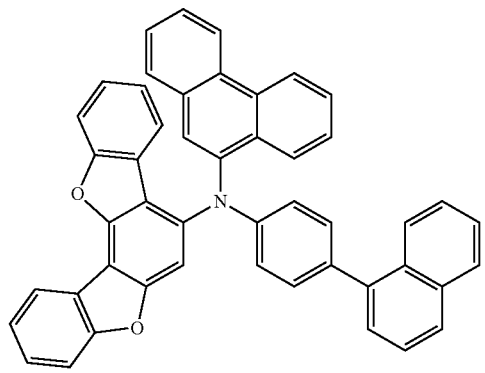
A10
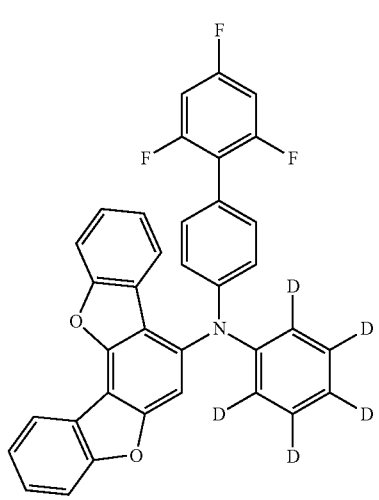
A11
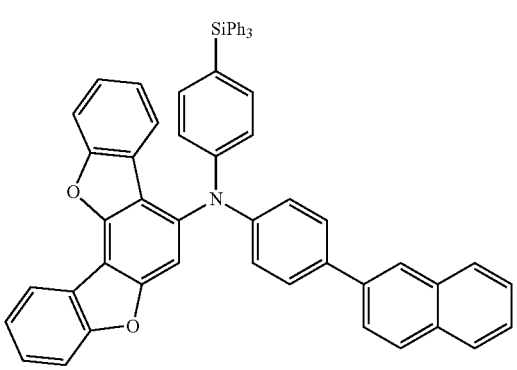

129
-continued
A12
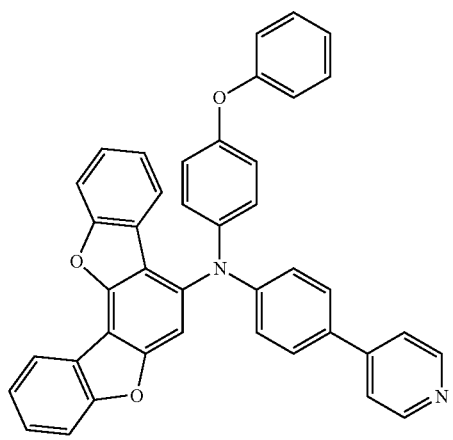
A13
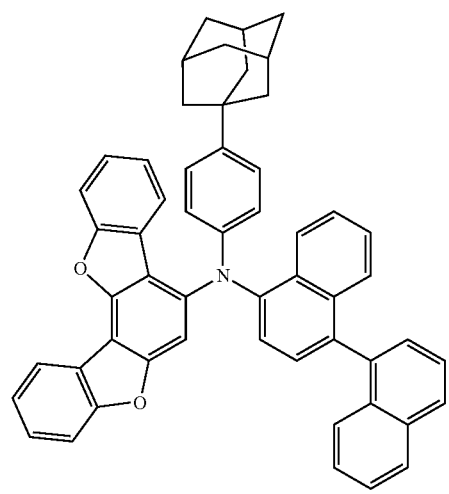
A14
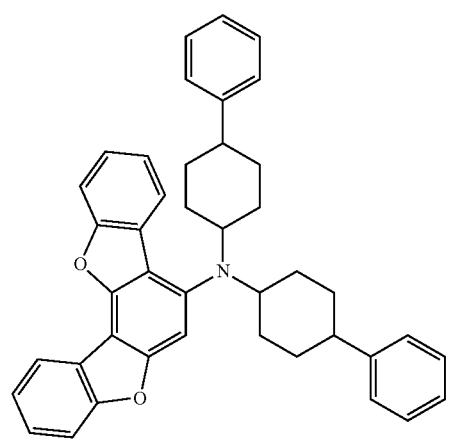
130
-continued
A15
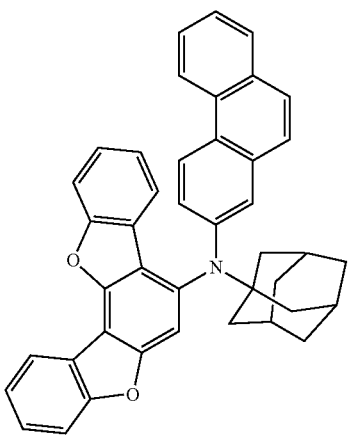
A16
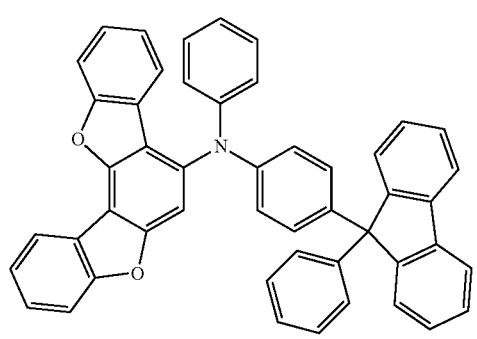
A17
A18
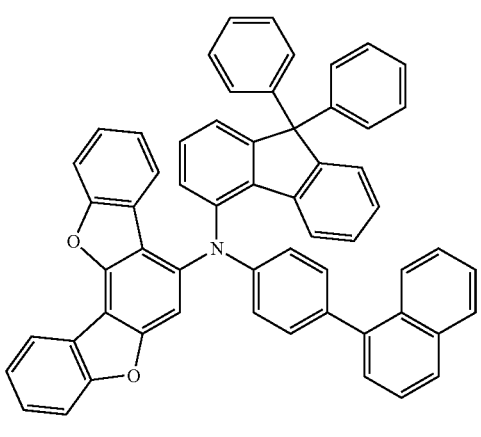

-continued
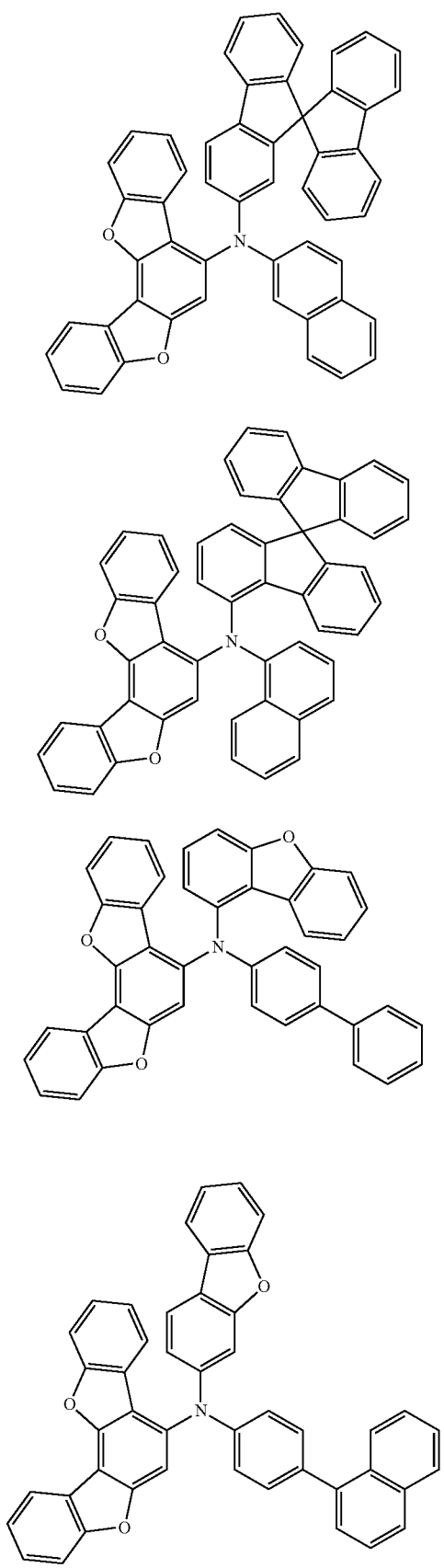
A19
A20
A21
A22
-continued
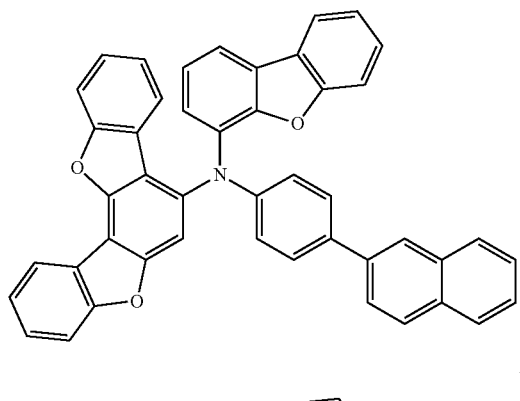
A23
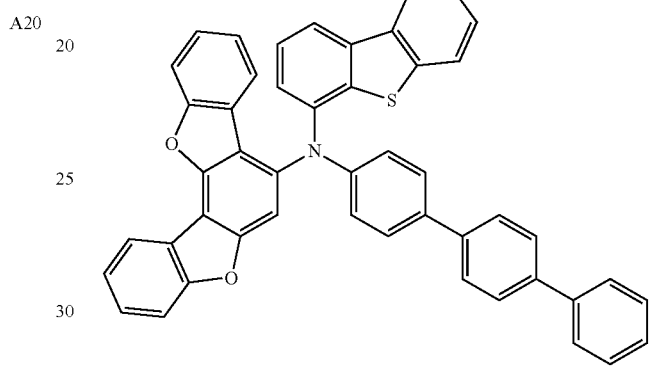
A24
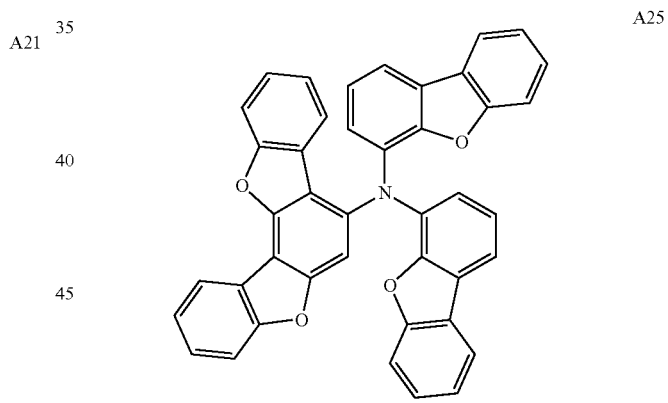
A25
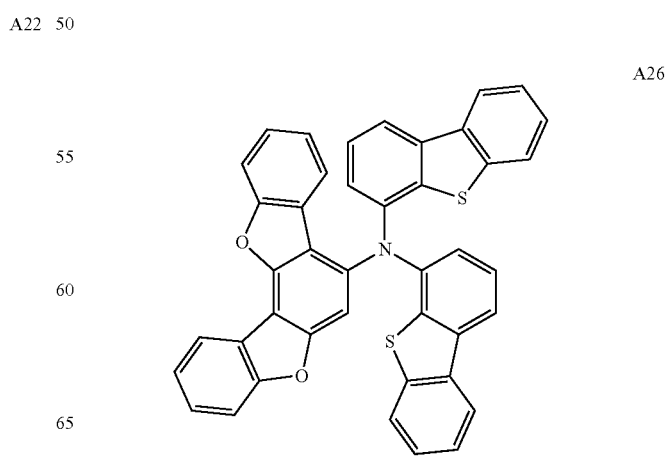
A26

A27
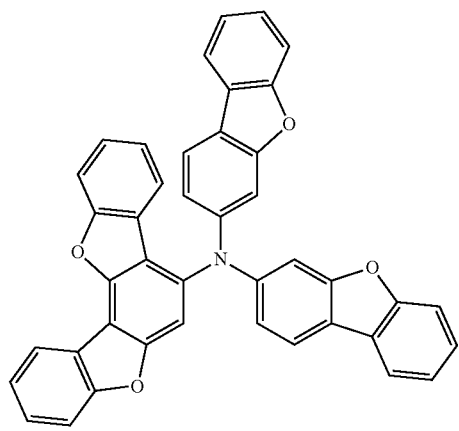
A28
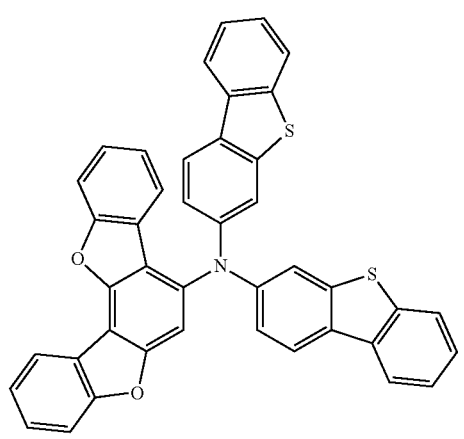
A29
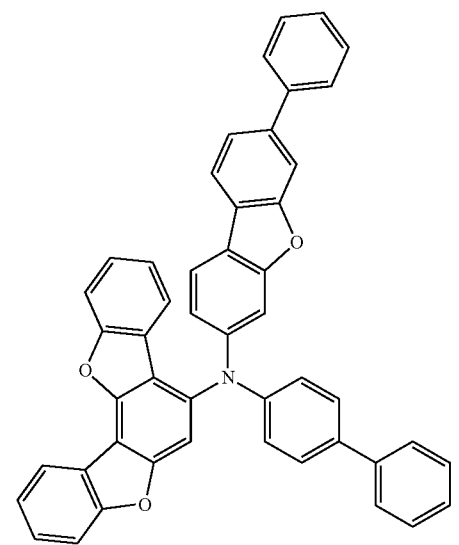
A30
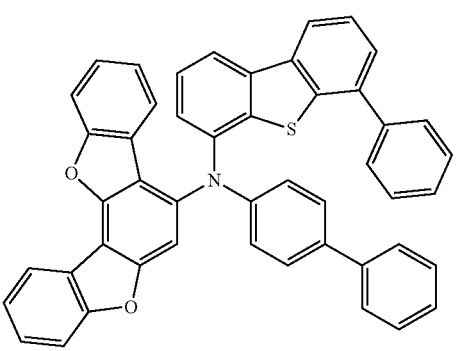
A31
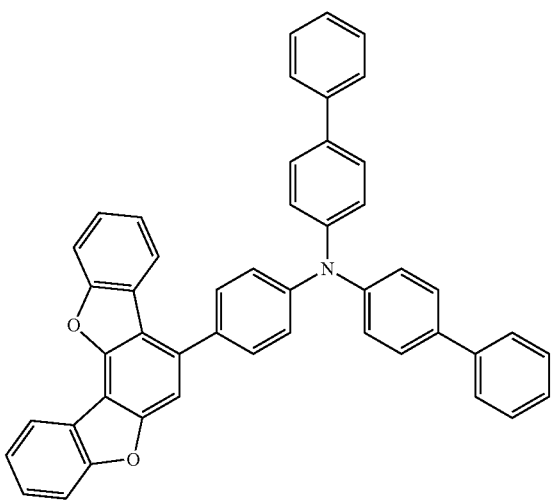
A32
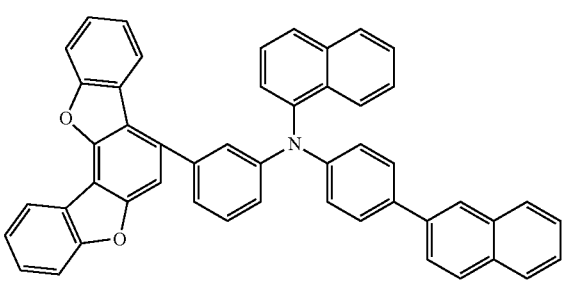
A33
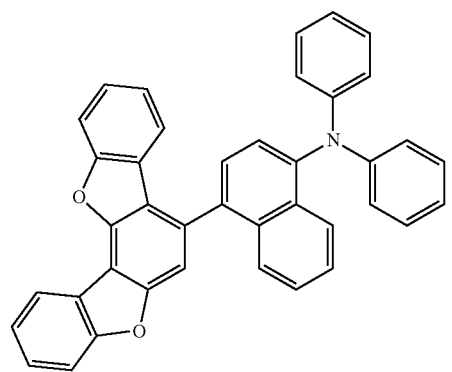

A34
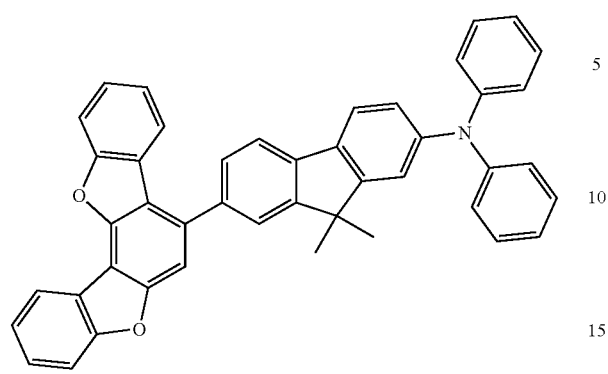
A38
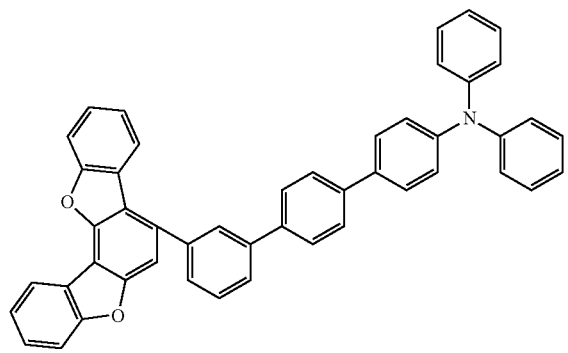
A35
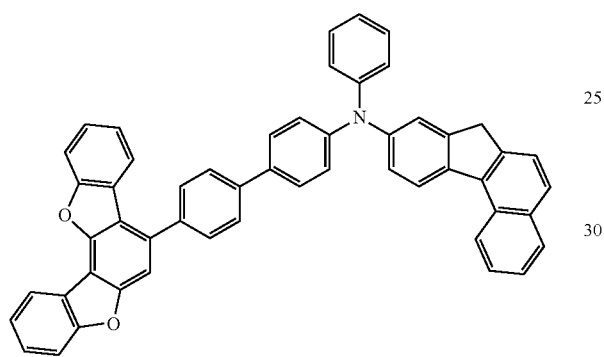
A39
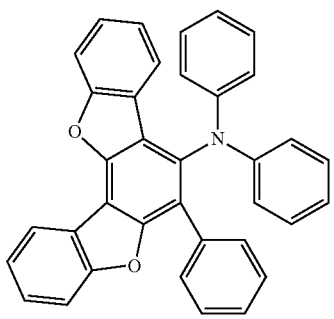
A36
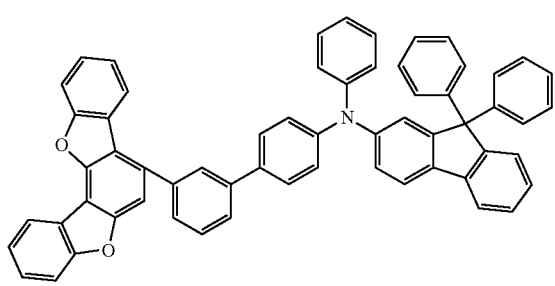
A40
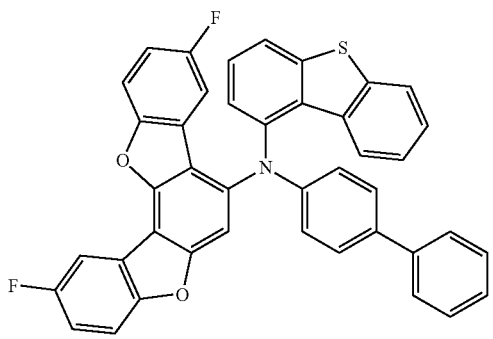
A37
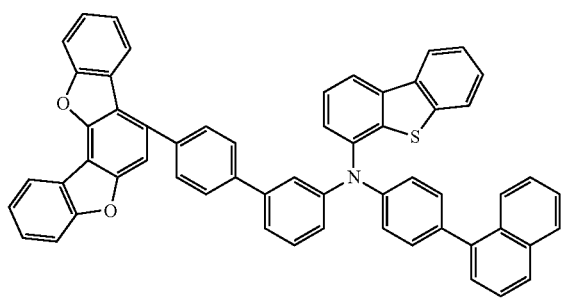
A41
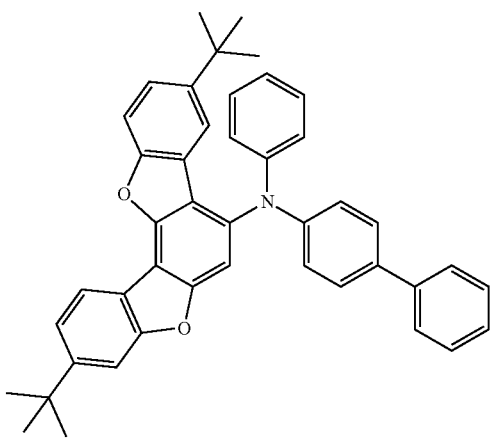

-continued
A42
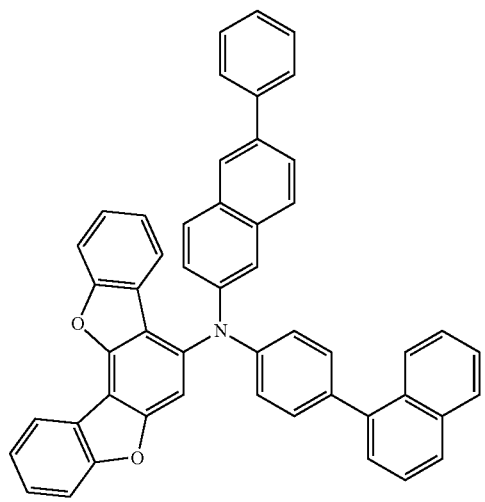
A43
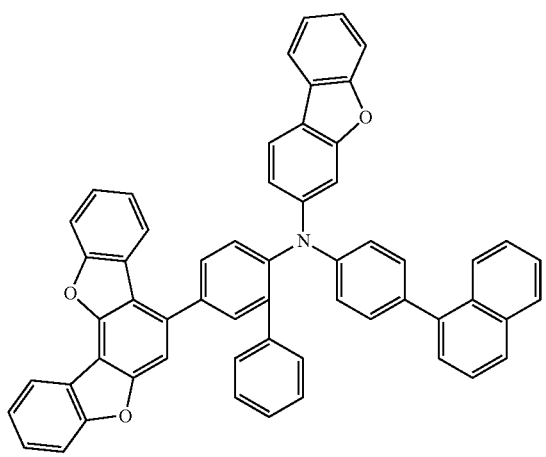
A44
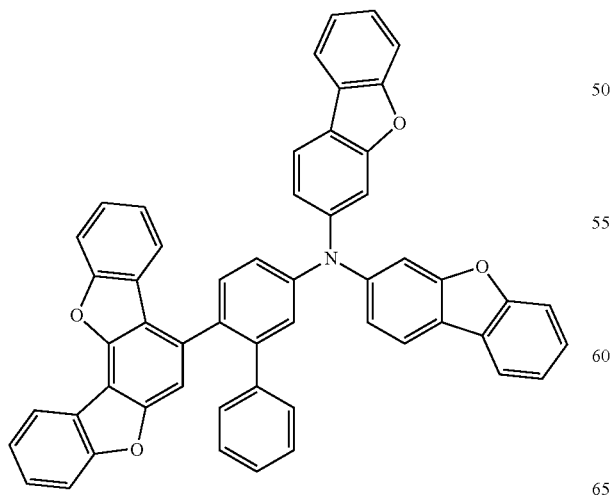
-continued
A45
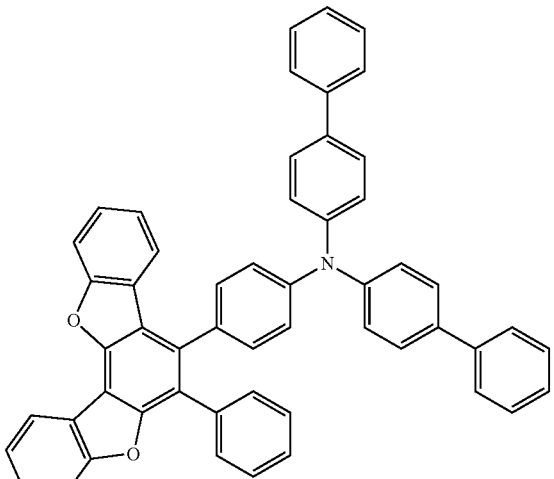
A46
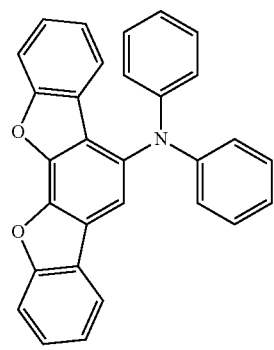
A47
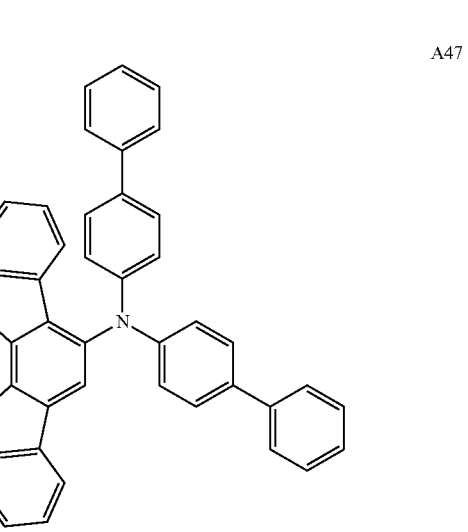

A48
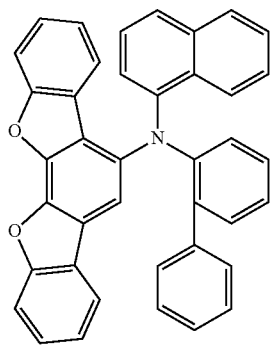
A49
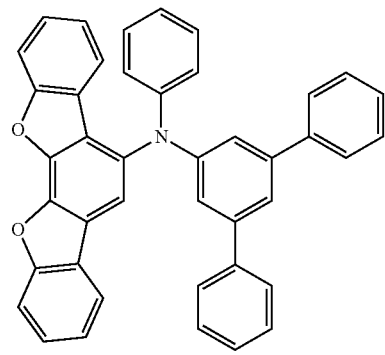
A50
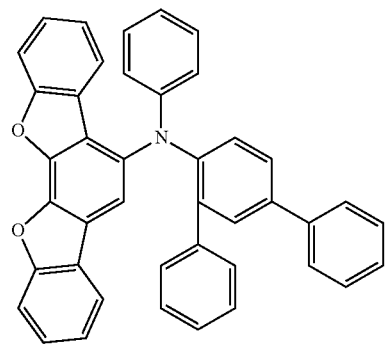
A51
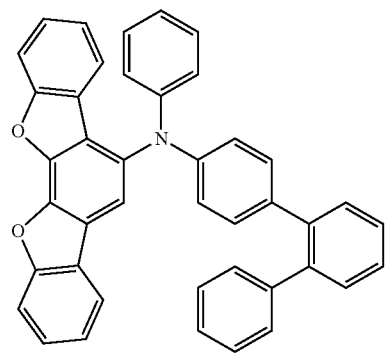
A52
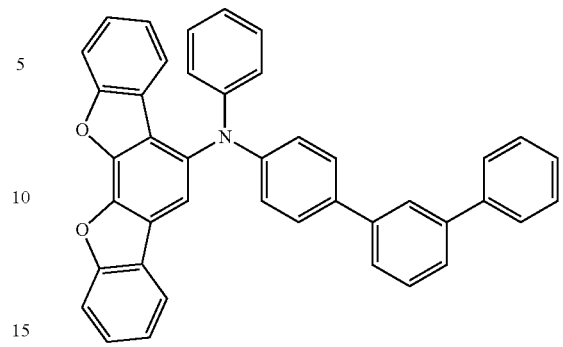
A53
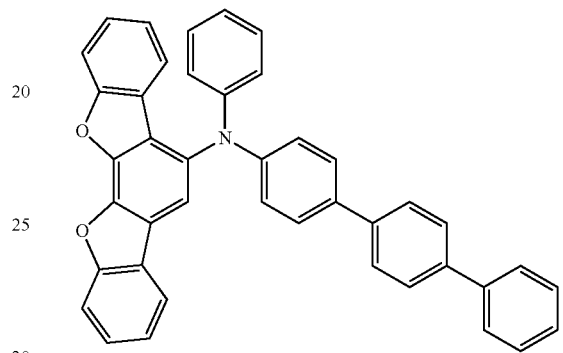
A54
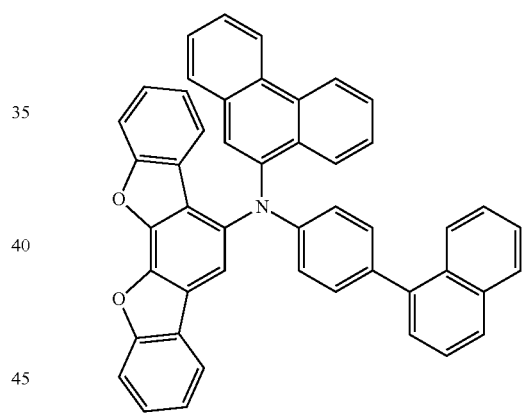
A55
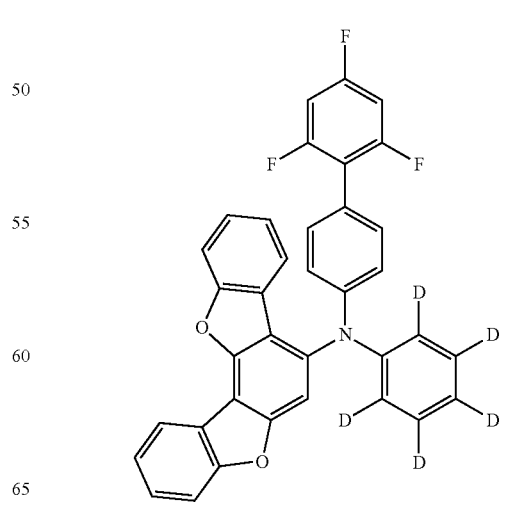

A56
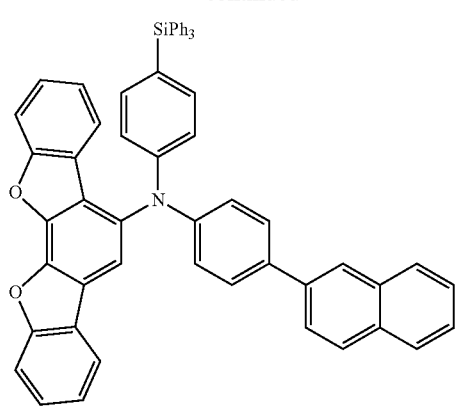
A57
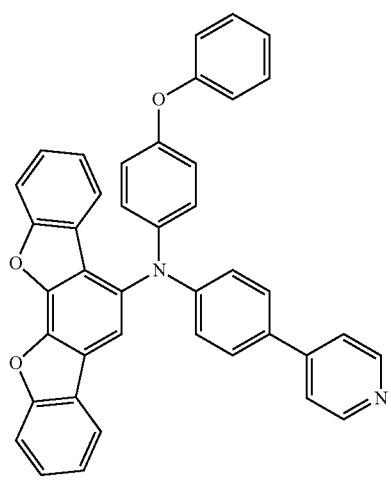
A58
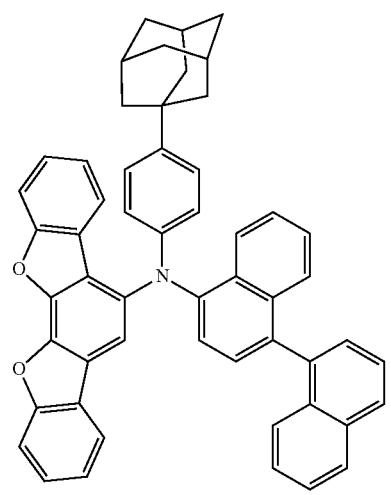
A59
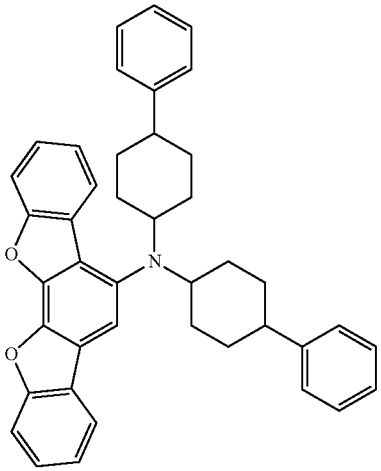
A60
A61

A62
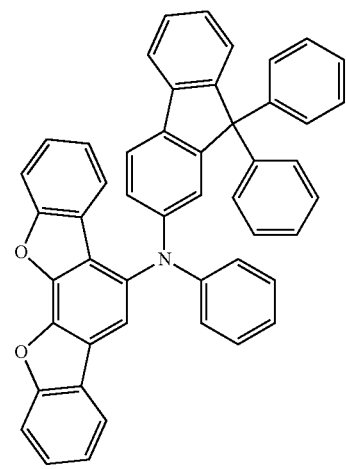
A63
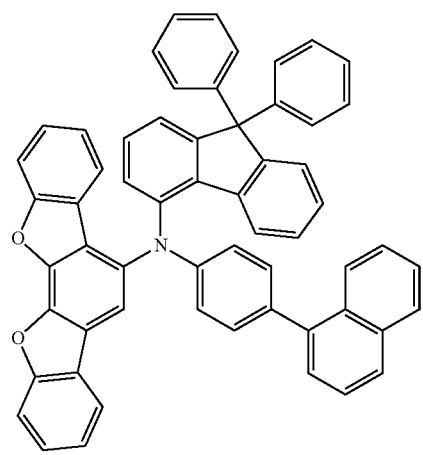
A64
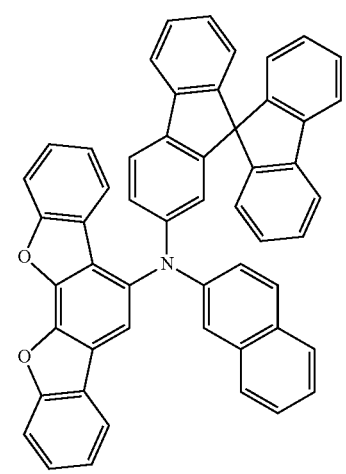
A65
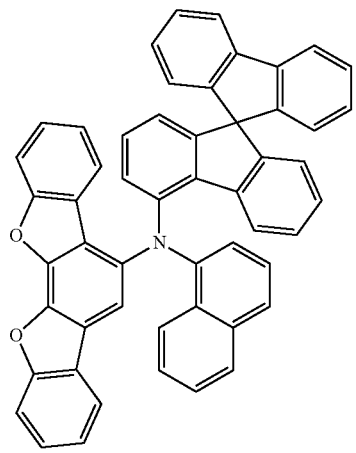
A66
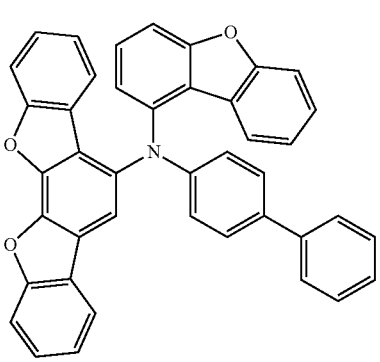
A67
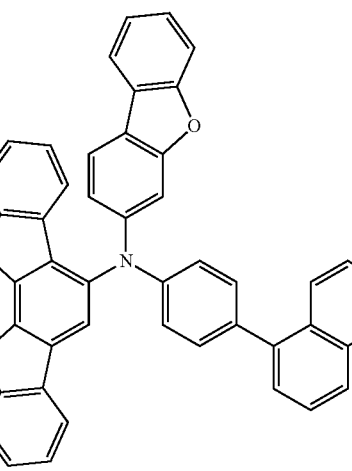
A68
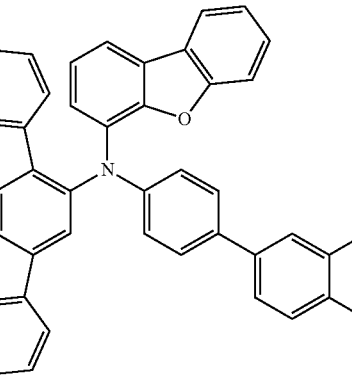

A69
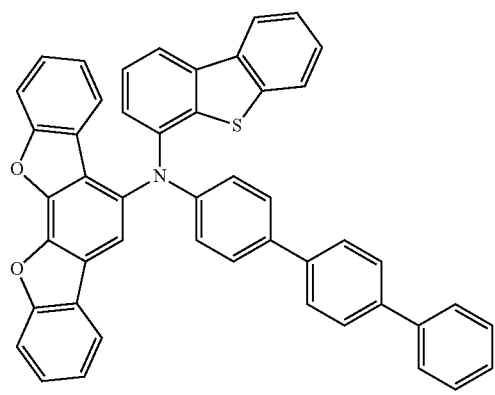
A70
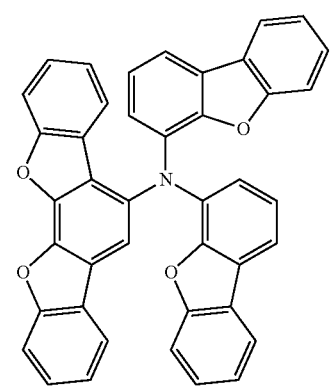
A71
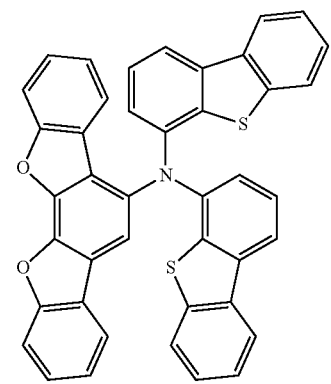
A72
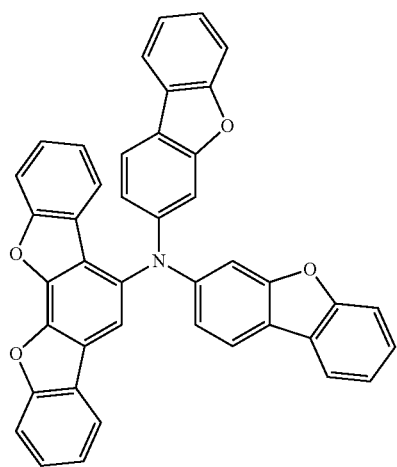
A73
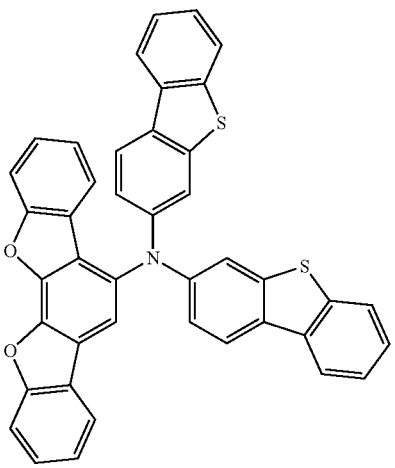
A74
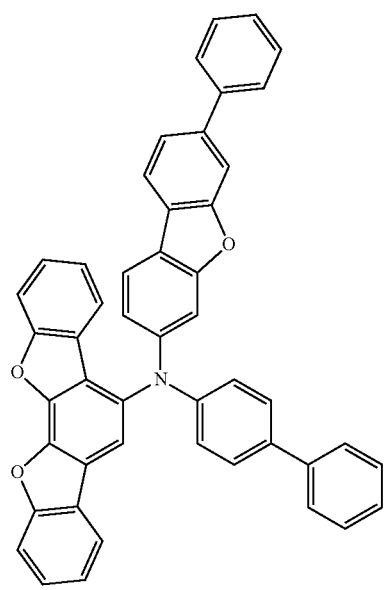
A75
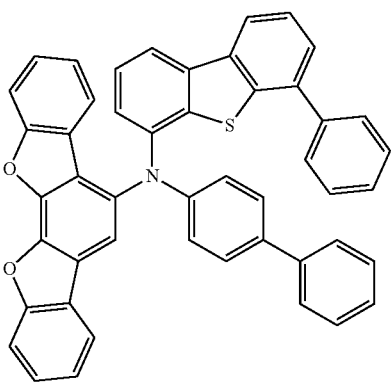

-continued
A76
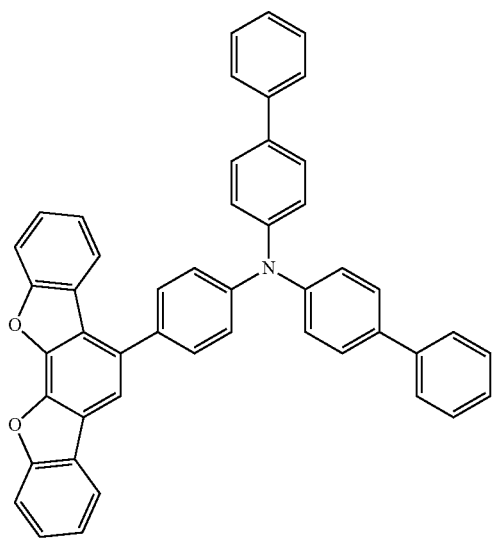
A77
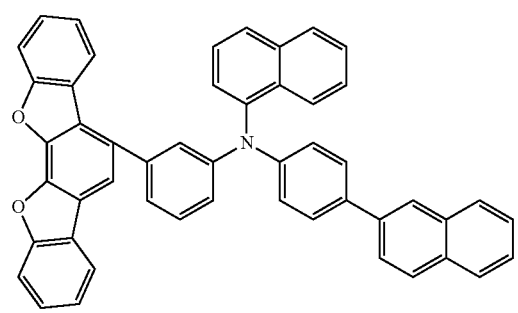
A78
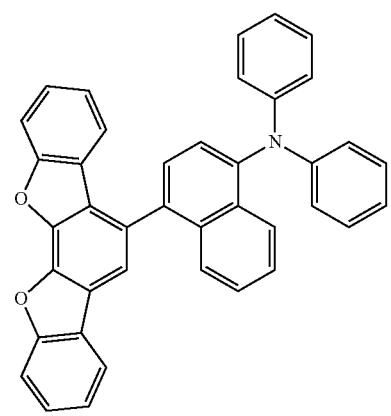
-continued
A79
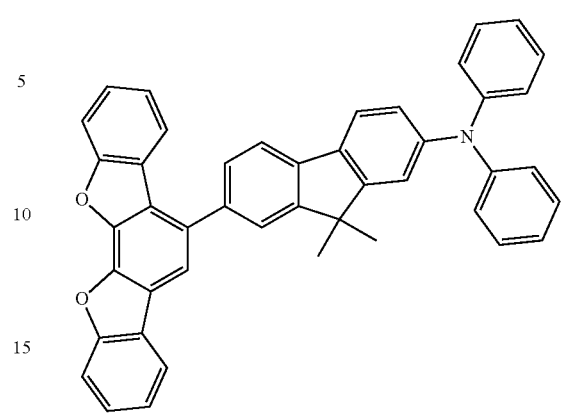
A80
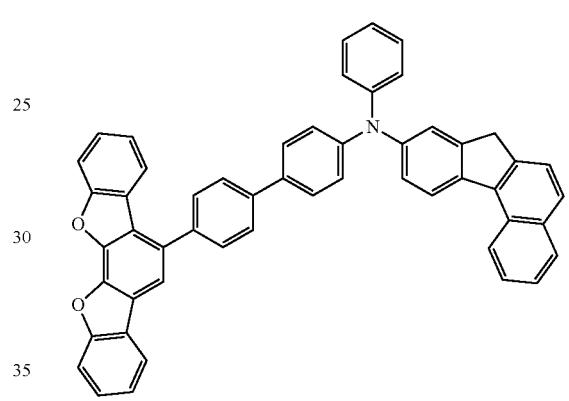
A81
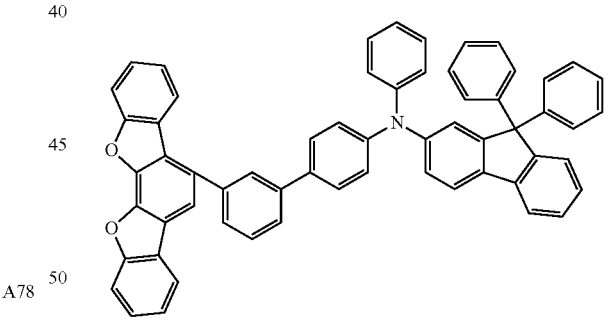
A82
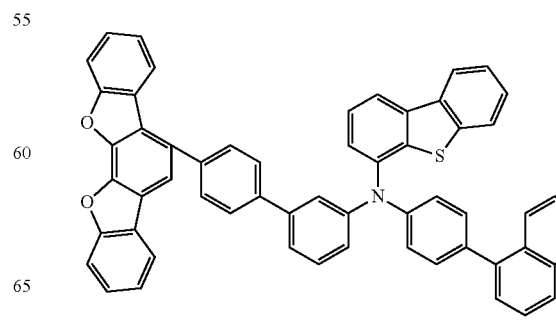

-continued
A83
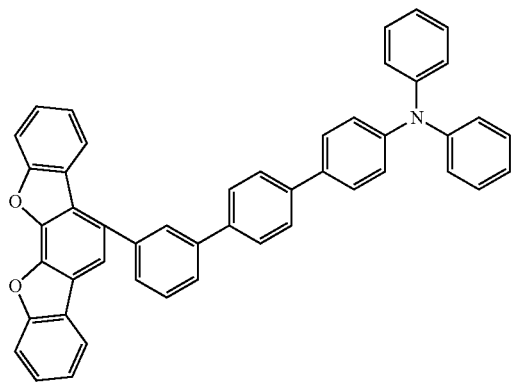
A84
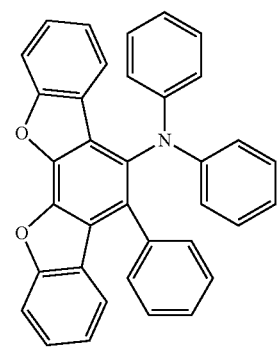
A85
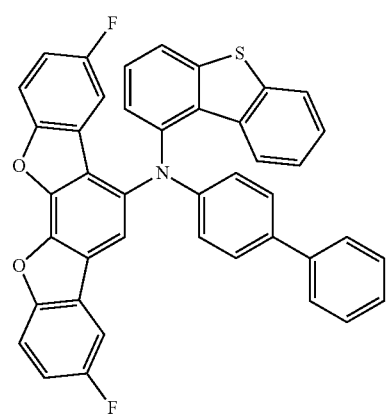
A86
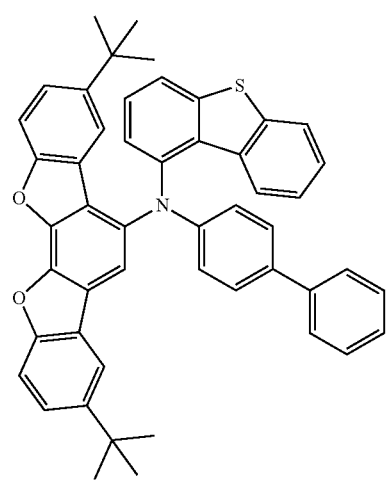
-continued
A87
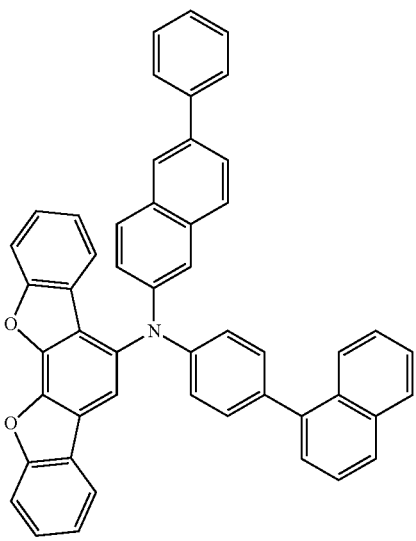
A88
A89

A90
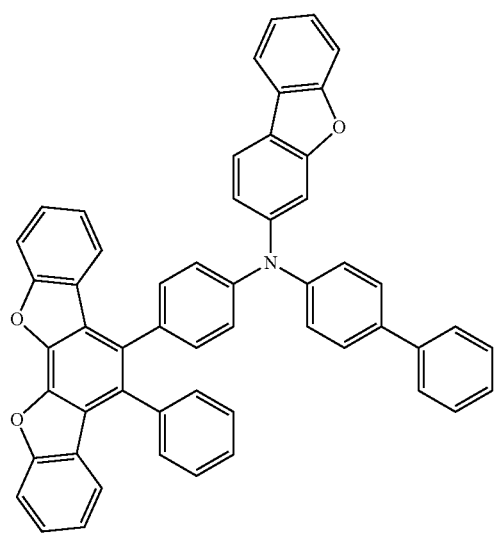
A91
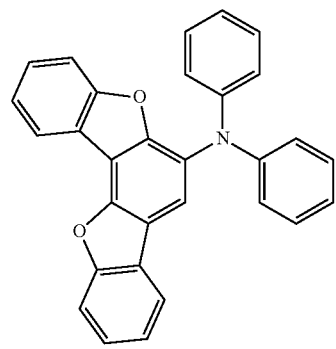
A92
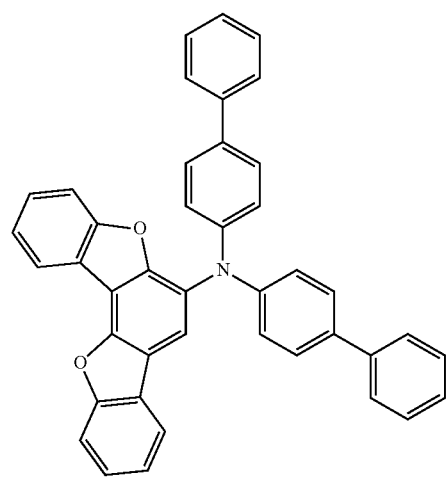
A93
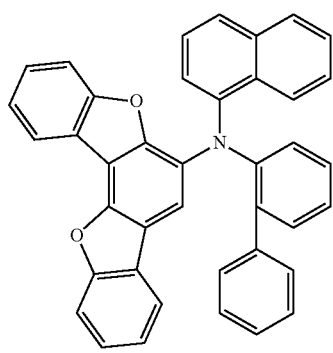
A94
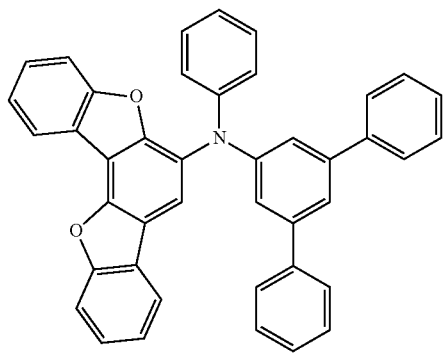
A95
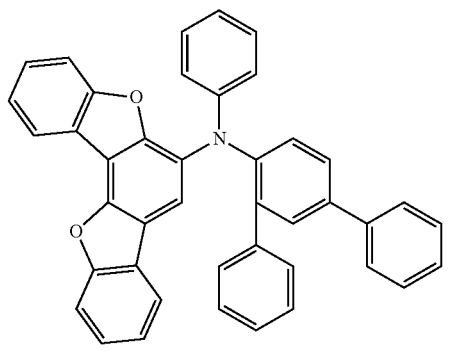
A96
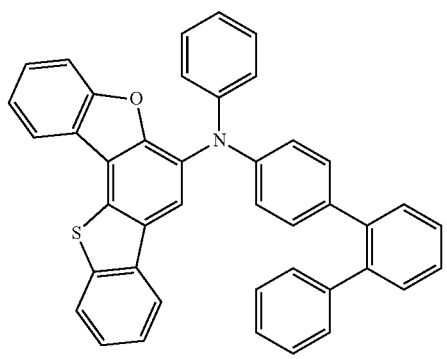

A97
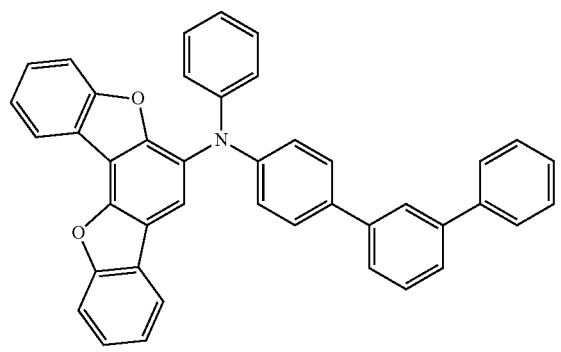
A98
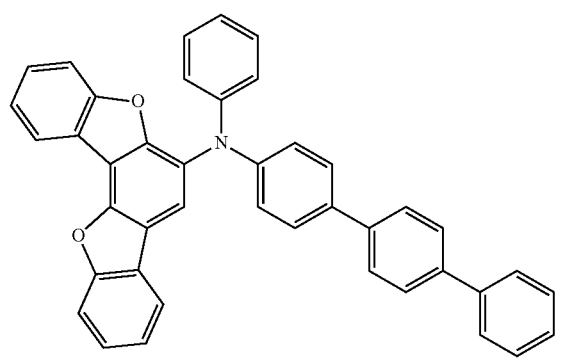
A99
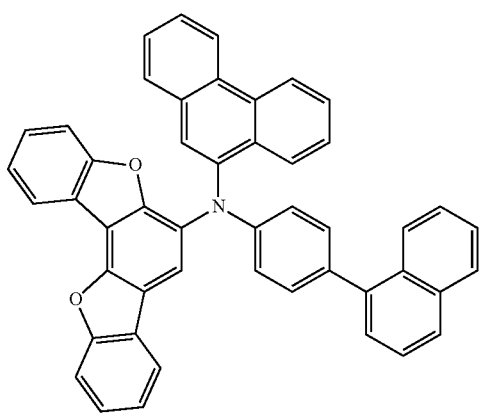
A100
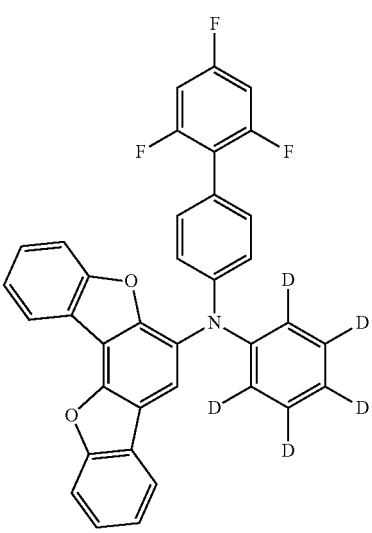
A101
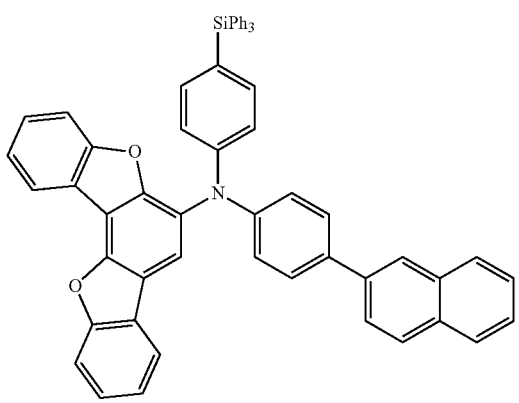
A102
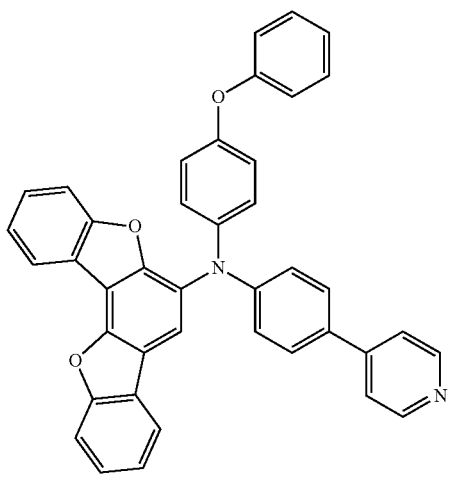

-continued
A103
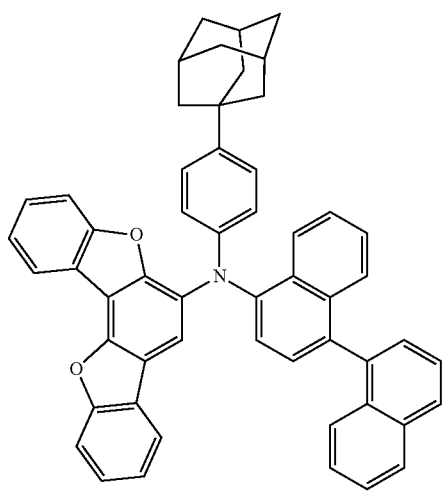
A104
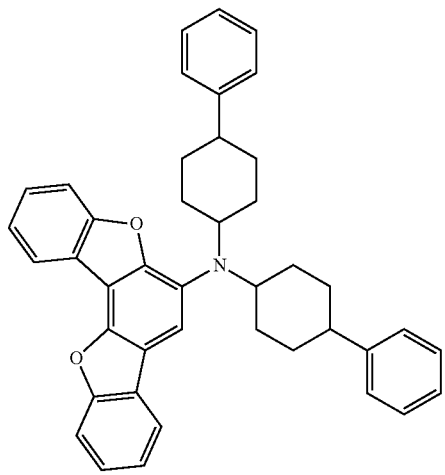
A105
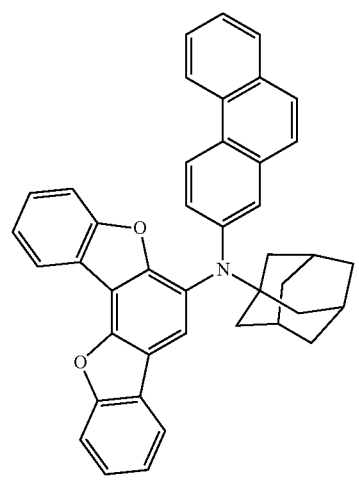
-continued
A106
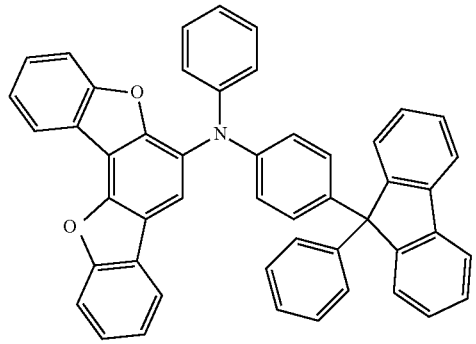
A107
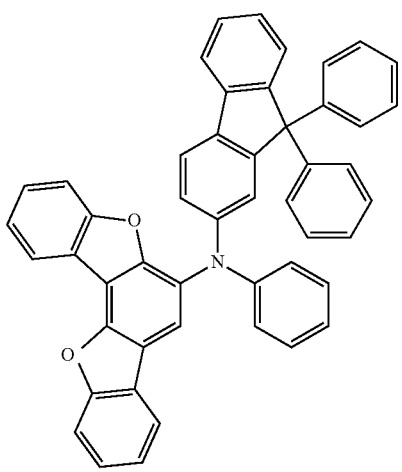
A108
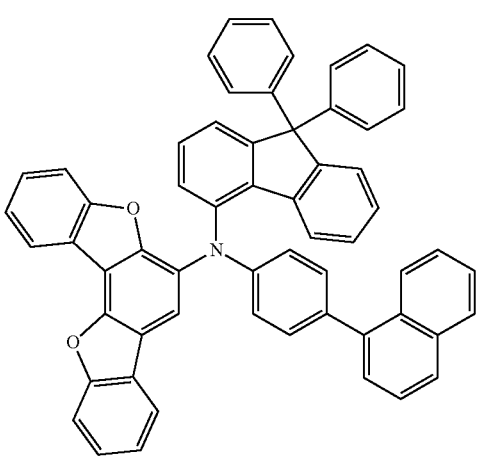

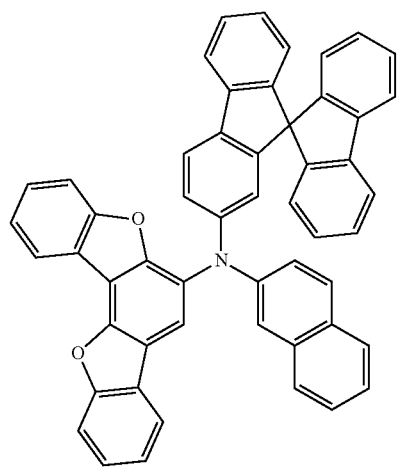
A109
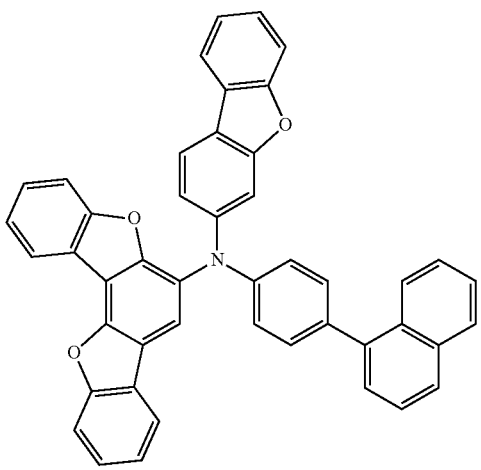
A112
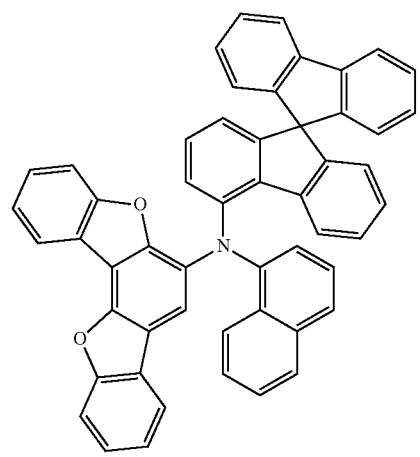
A110
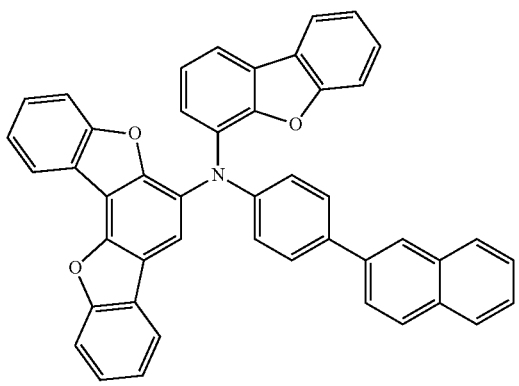
A113
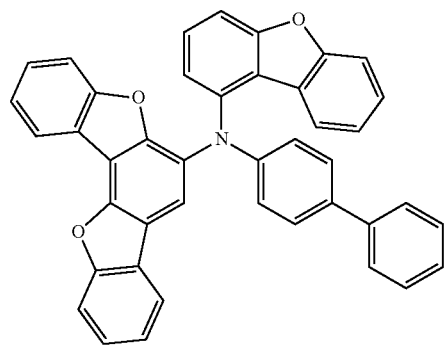
A111
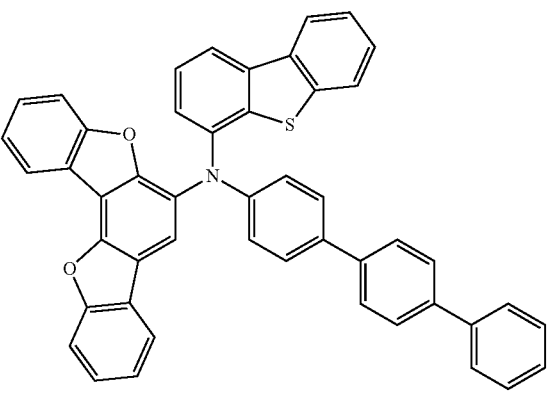
A114

A115
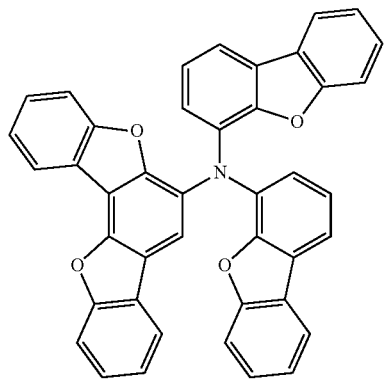
A118
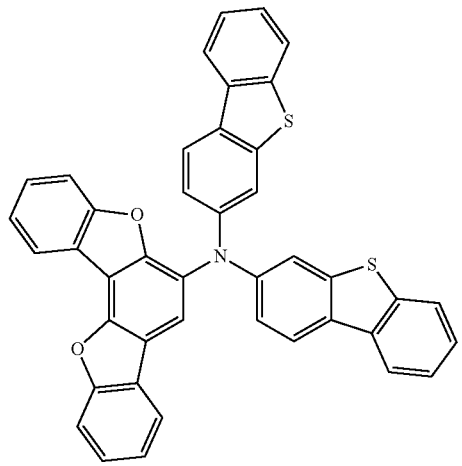
A116
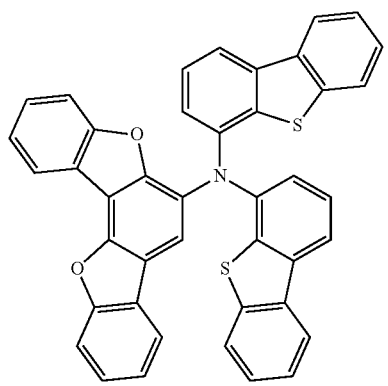
A119
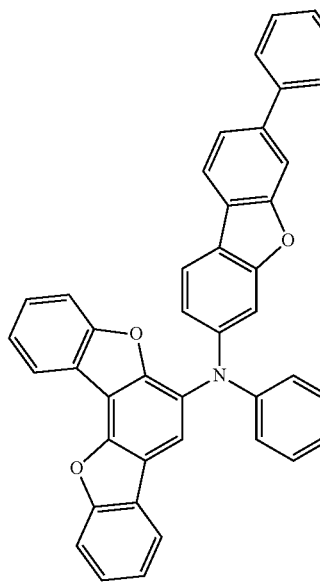
A117
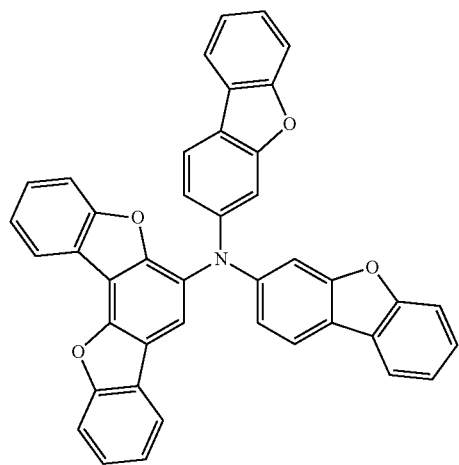
A120
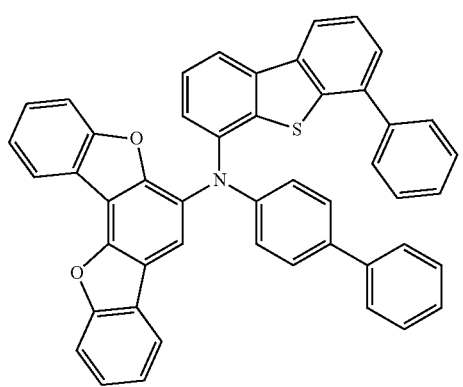

-continued
A121
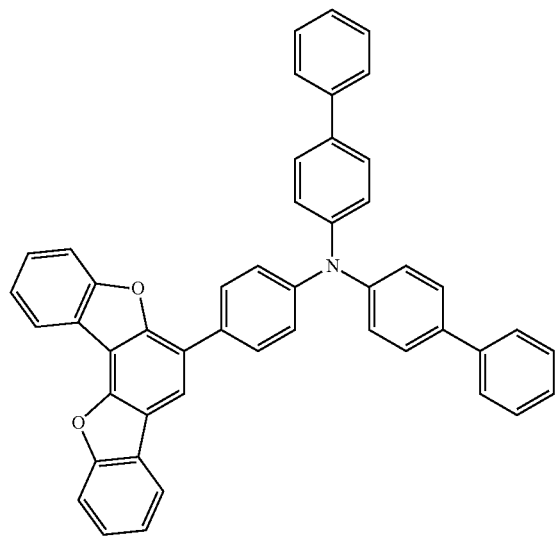
A122
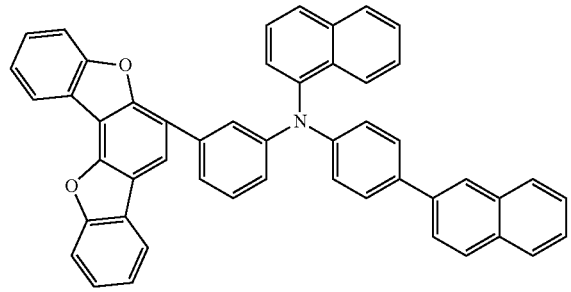
A123
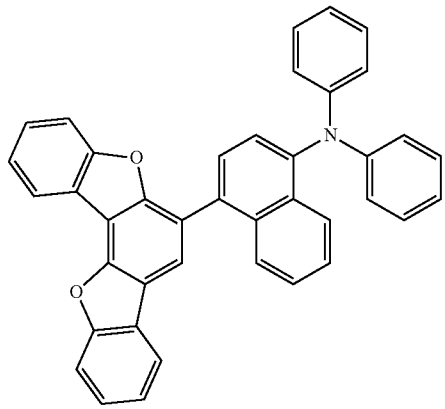
-continued
A124
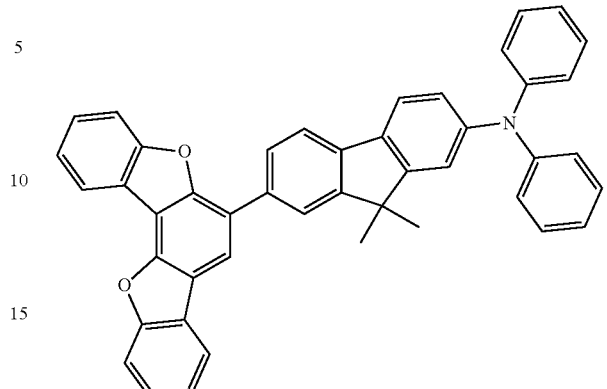
A125
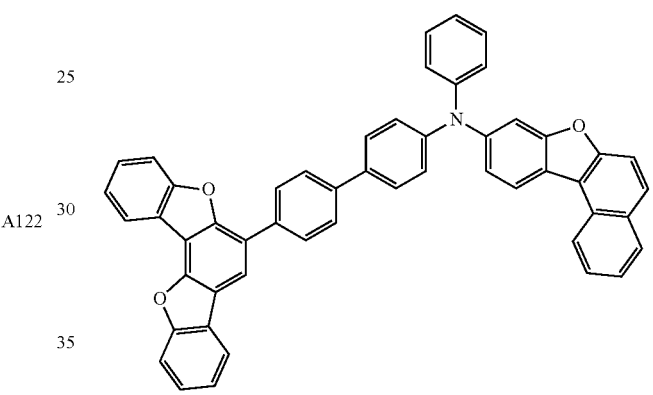
A126
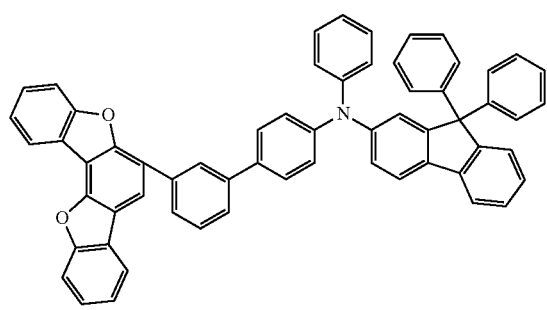
A127
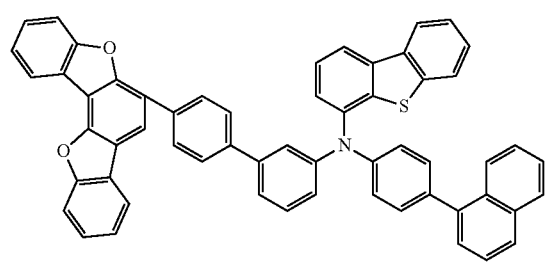

A128
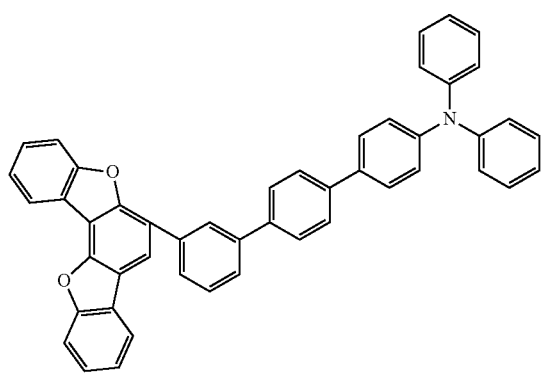
A129
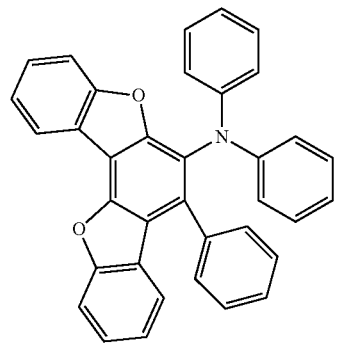
A130
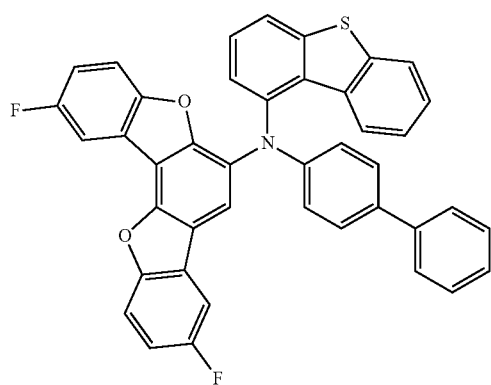
A131
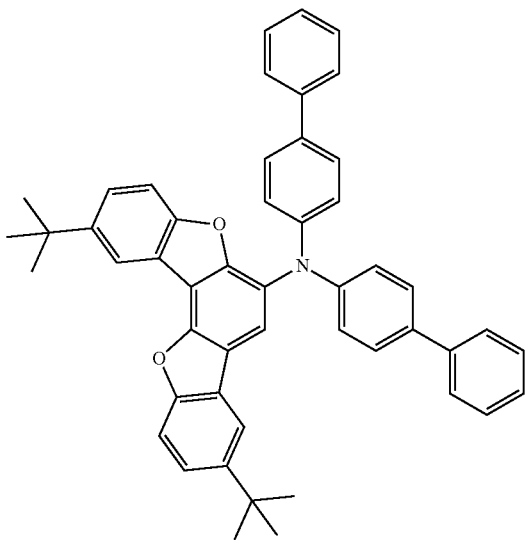
A132
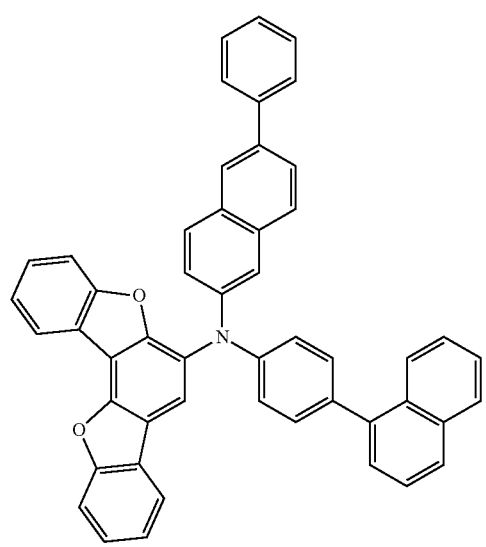
A133
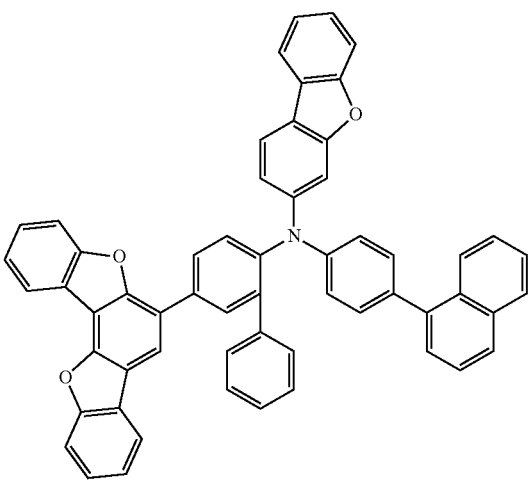

-continued
A134
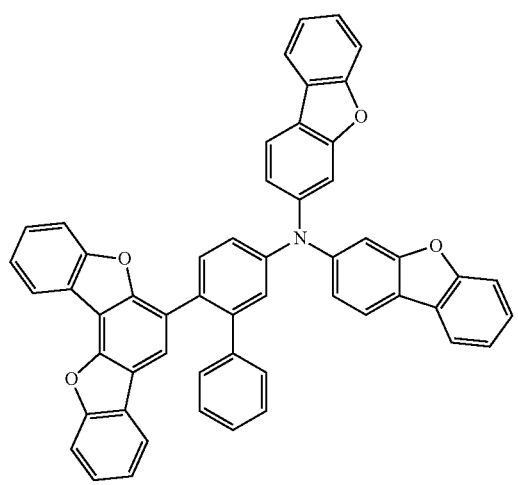
A135
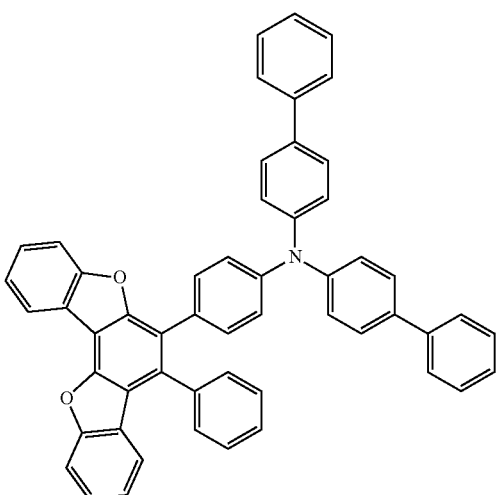
A136
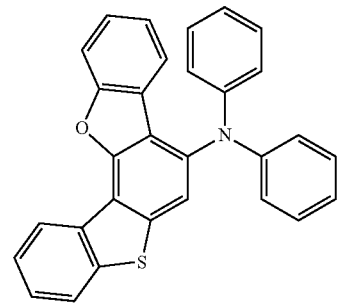
-continued
A137
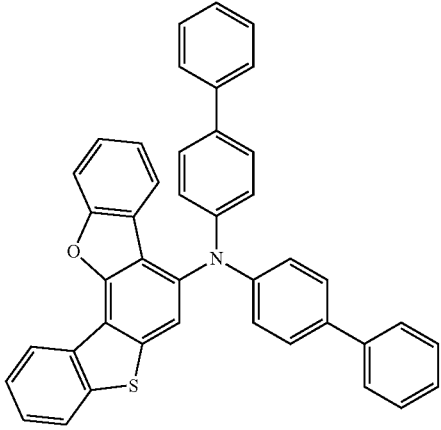
A138
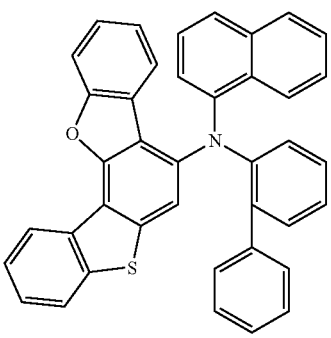
A139
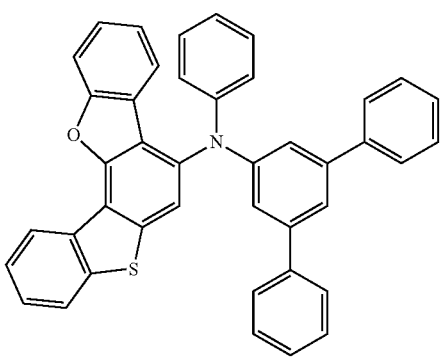
A140
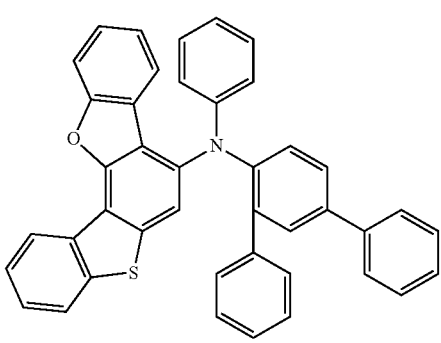

-continued
A141
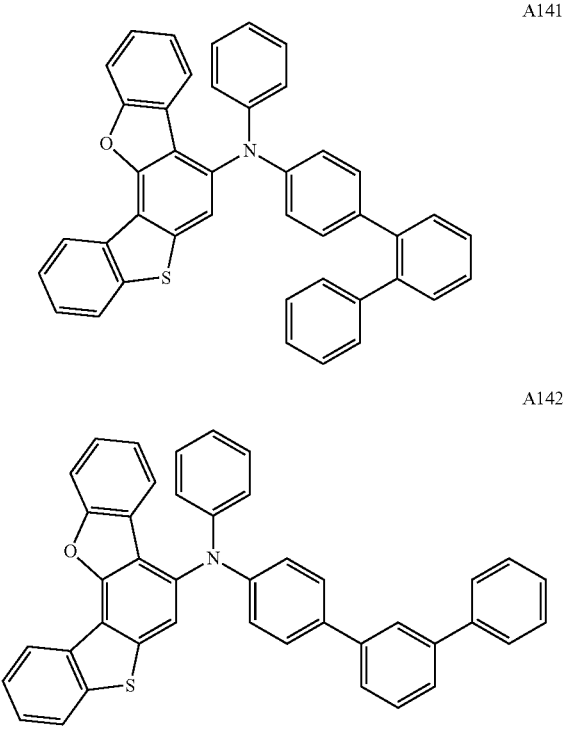
A142
A143
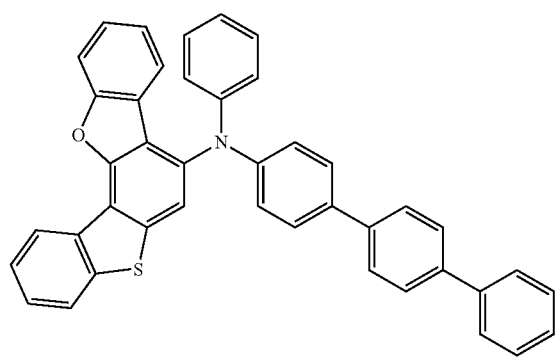
A144
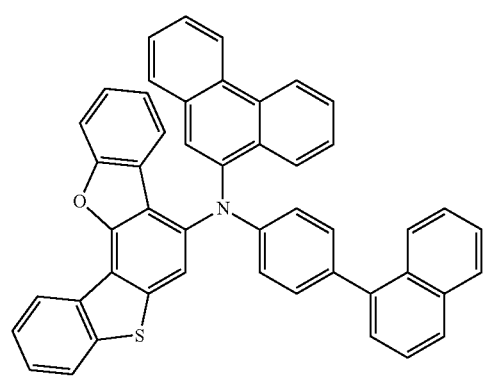
A145
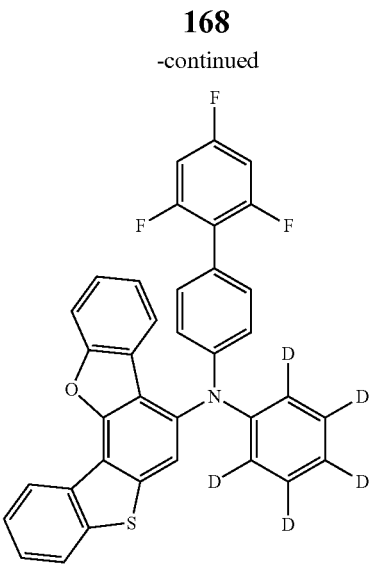
A146
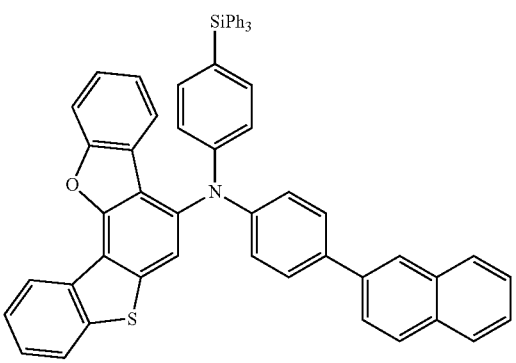
A147
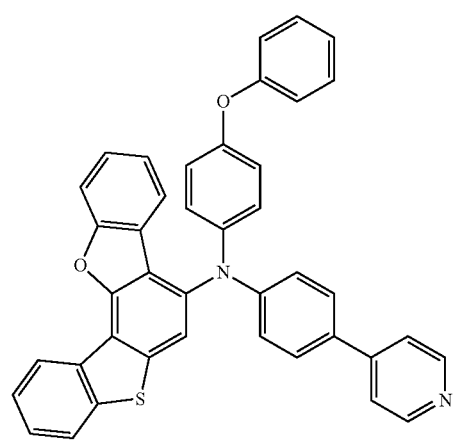

-continued
A148
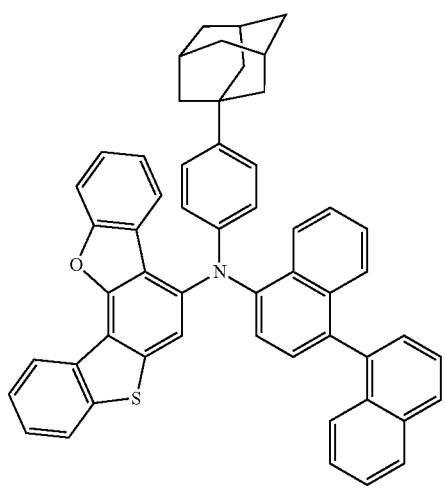
A149
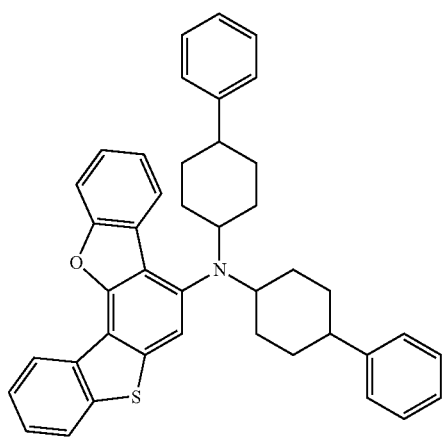
A150
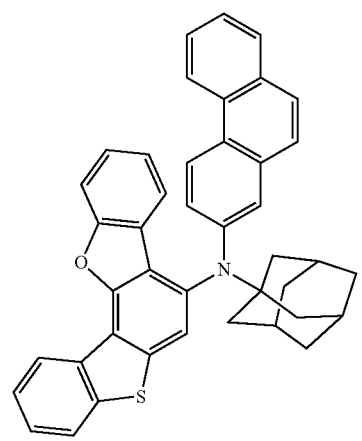
-continued
A151
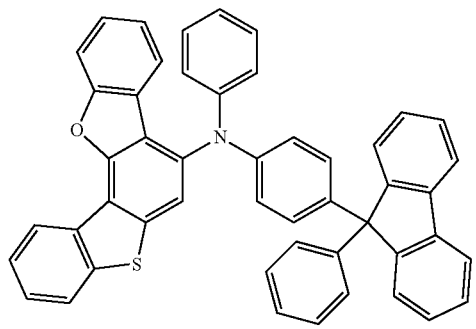
A152
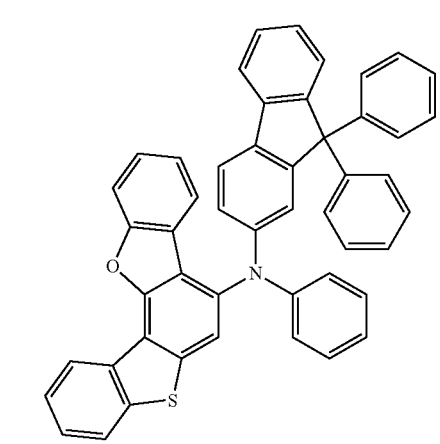
A153
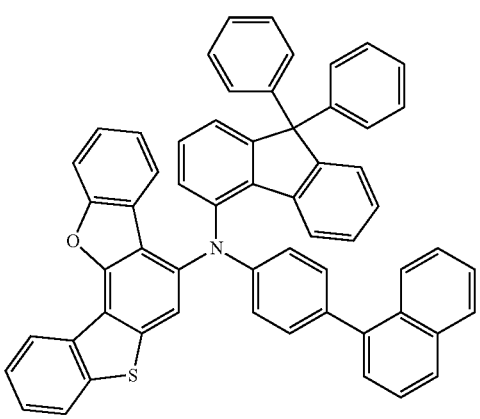
A154
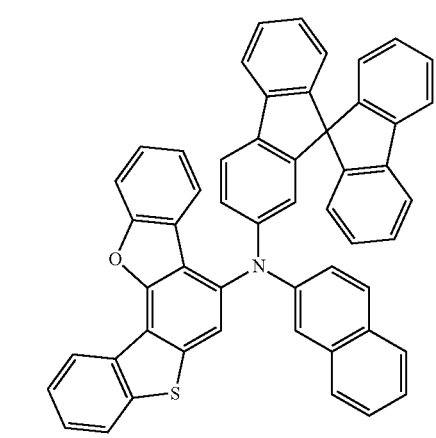

A155
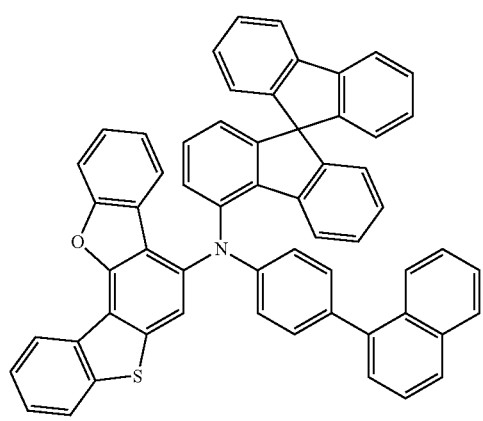
A156
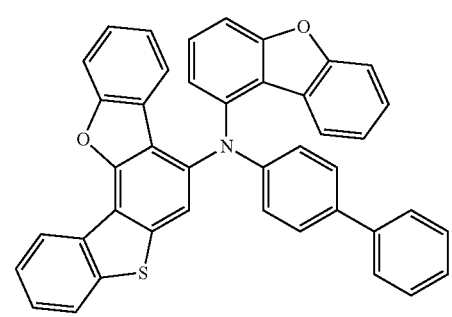
A157
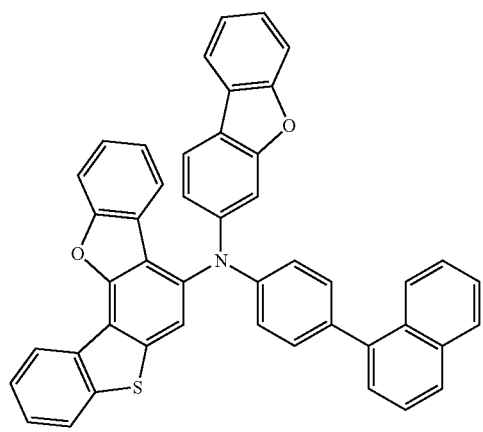
A158
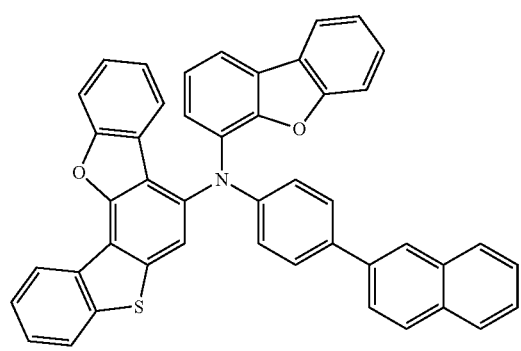
A159
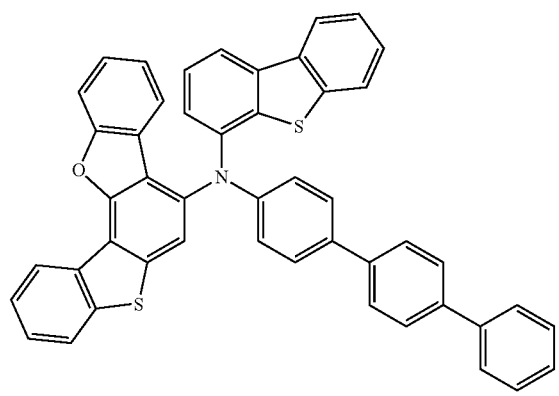
A160
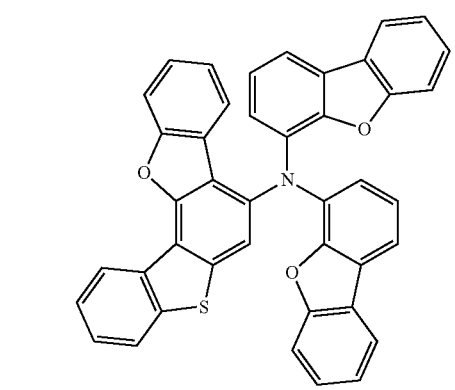
A161
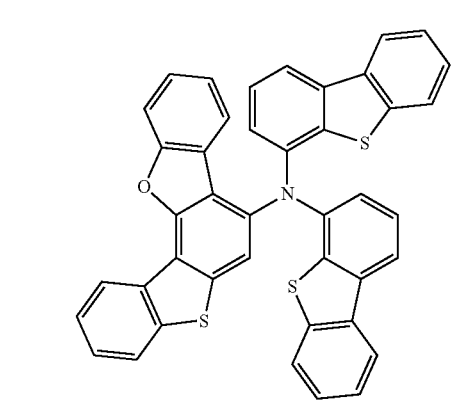
A162
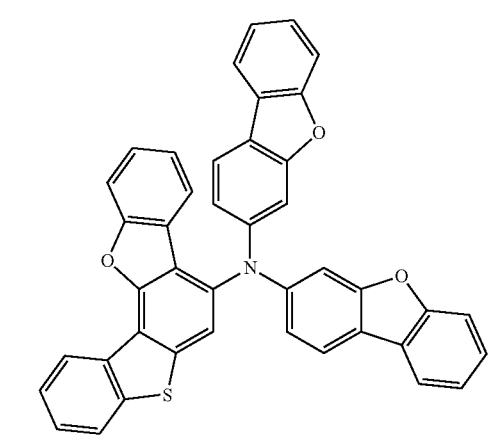

-continued
A163
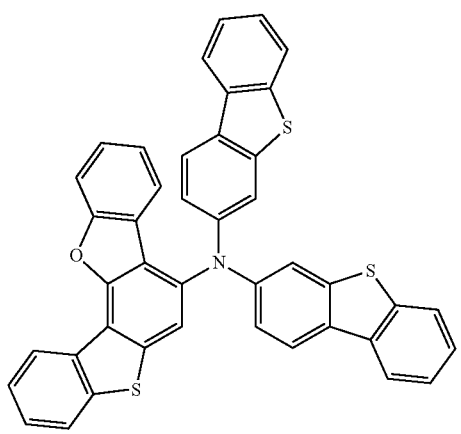
A164
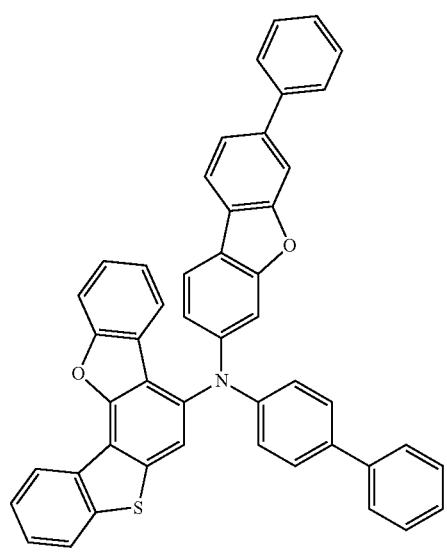
A165
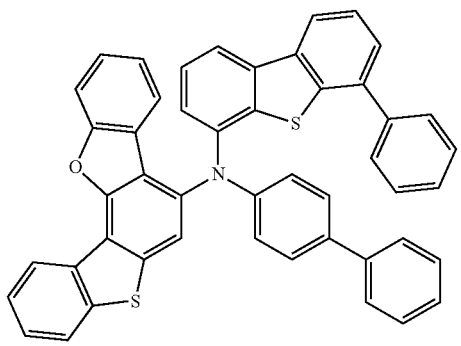
-continued
A166
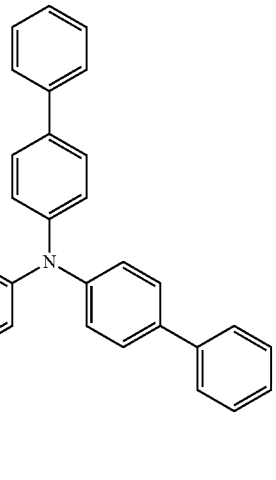
A167
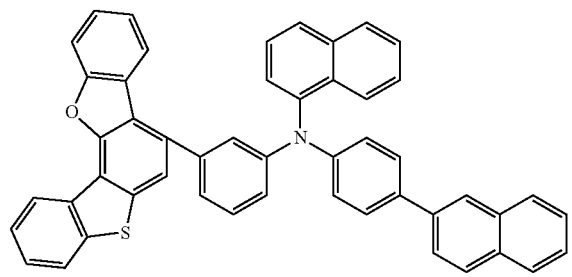
A168
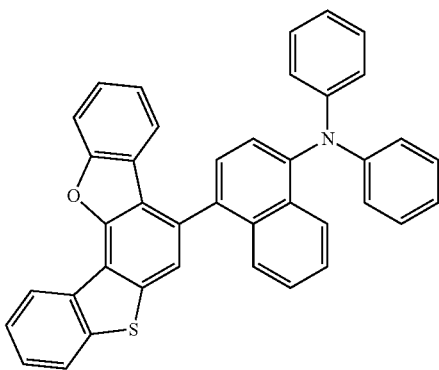
A169
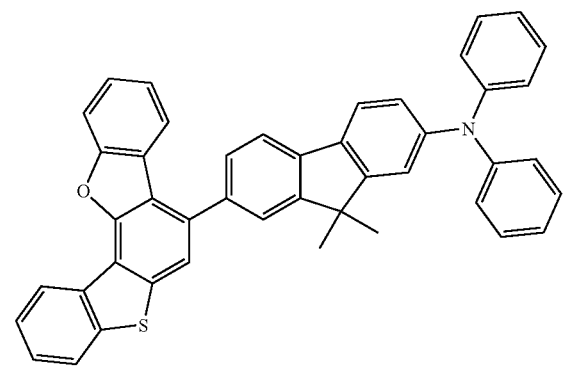

-continued
A170
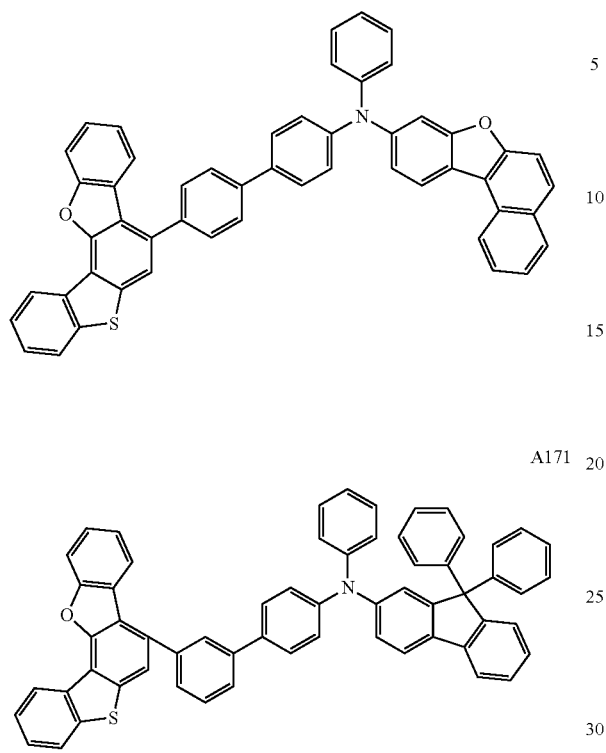
A171
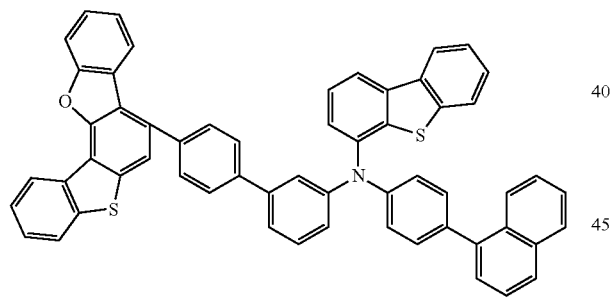
A172
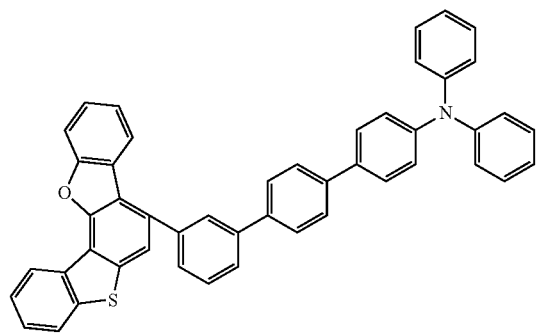
A173
-continued
A174
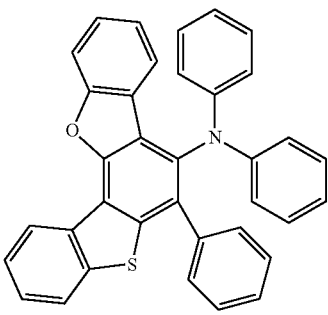
A175
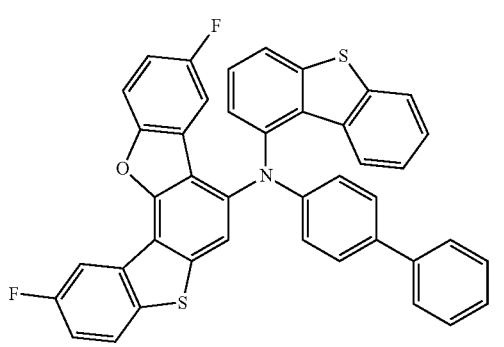
A176
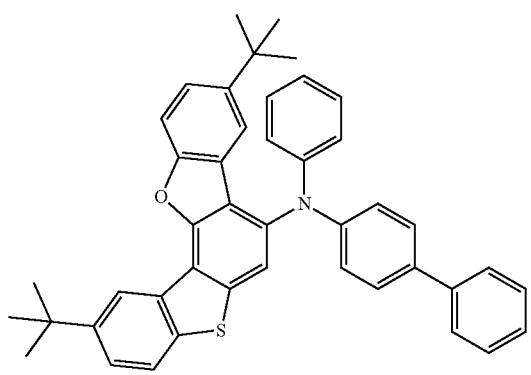
A177
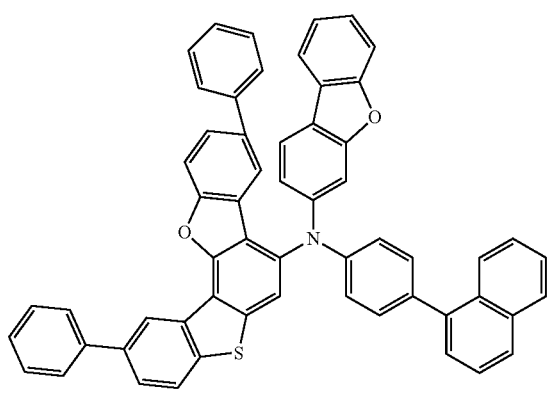

Compound Group B
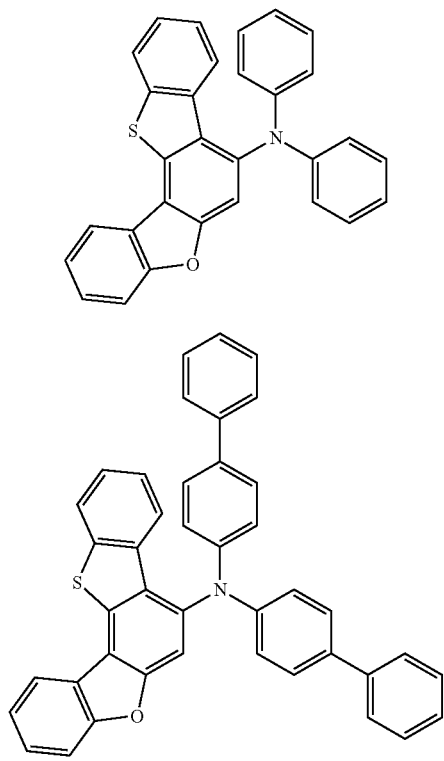
B1
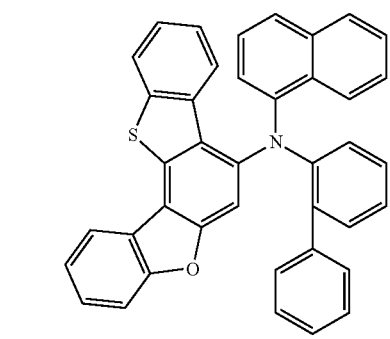
B2
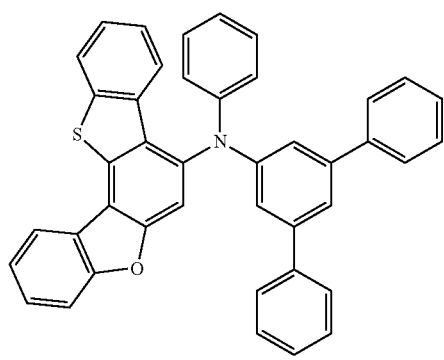
B3
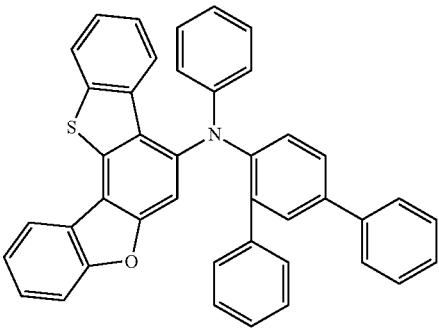
B4
-continued
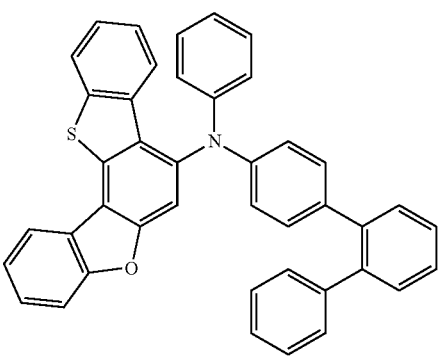
B5
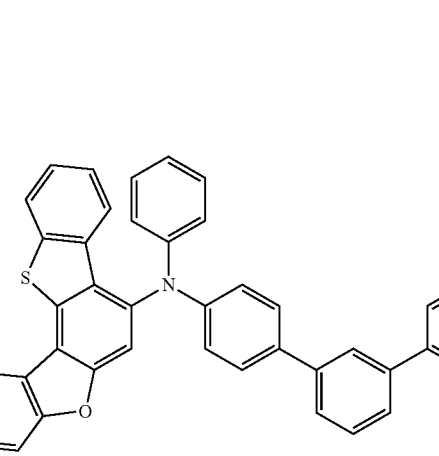
B6
B7
B8

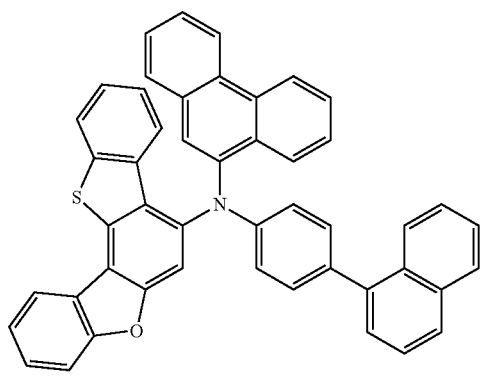
B9
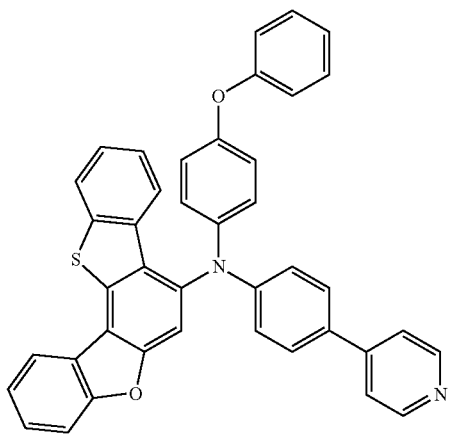
B12
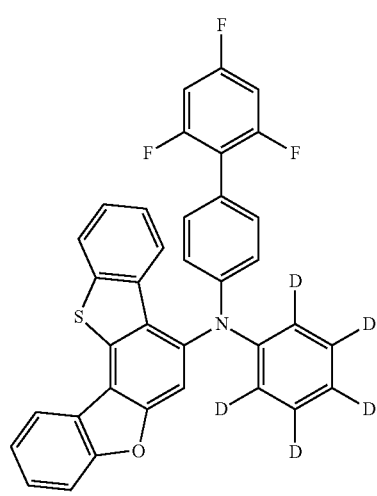
B10
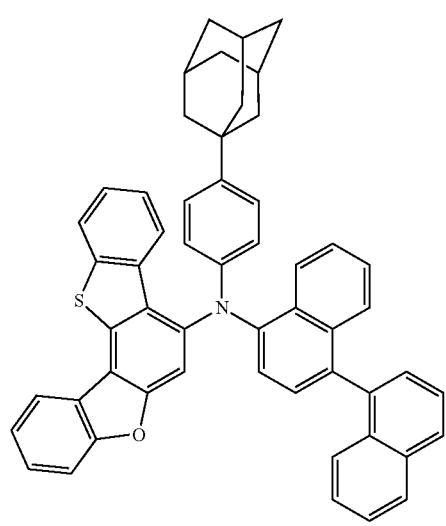
B13
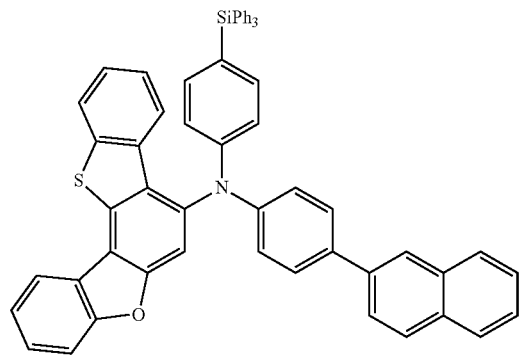
B11
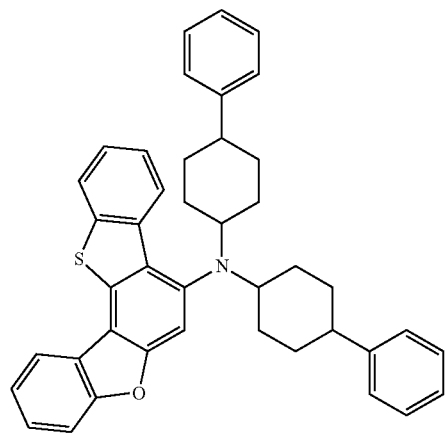
B14

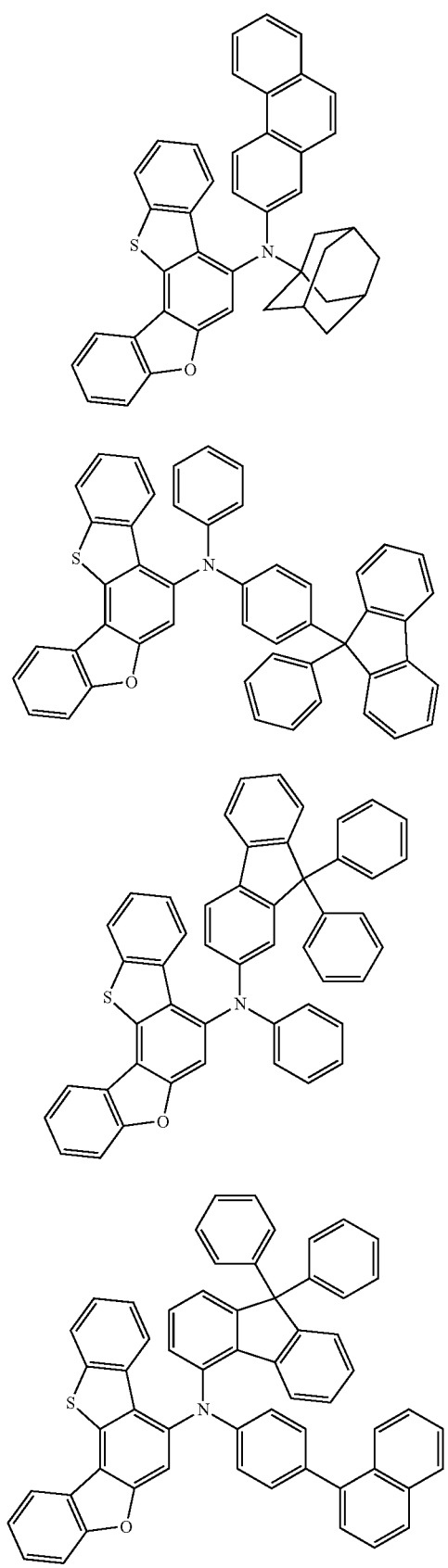
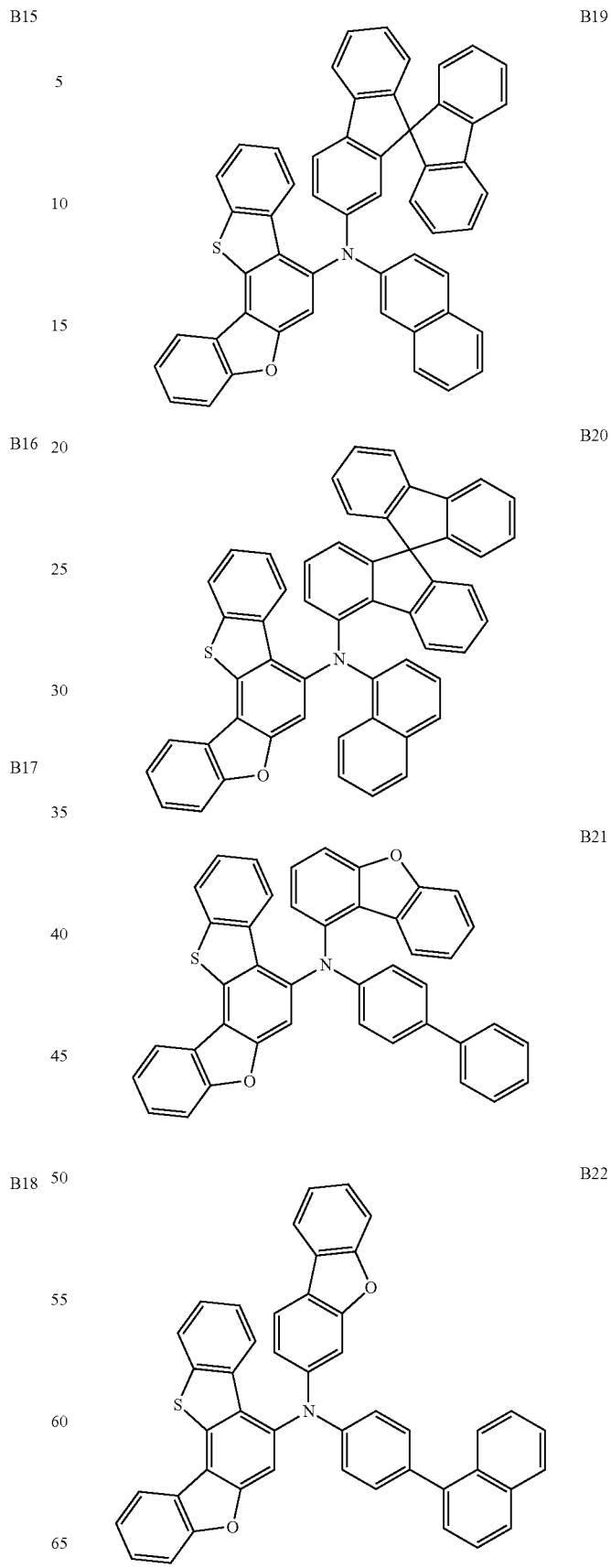

-continued
B23
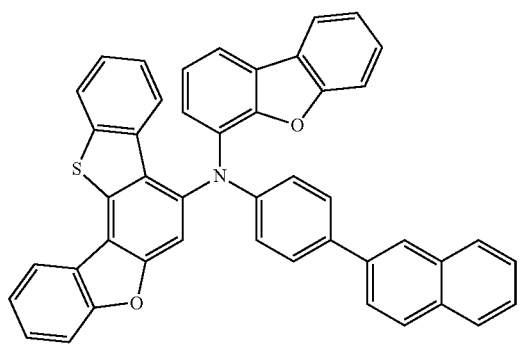
B24
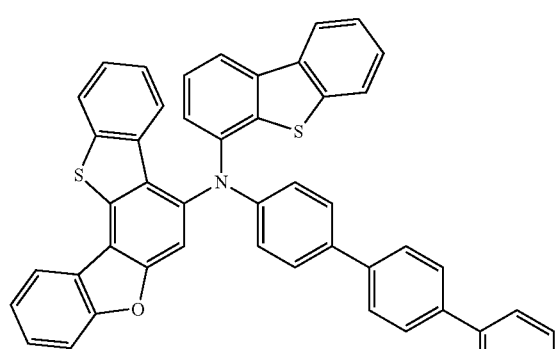
B25
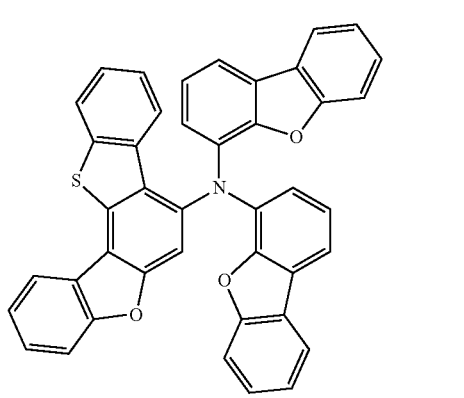
B26
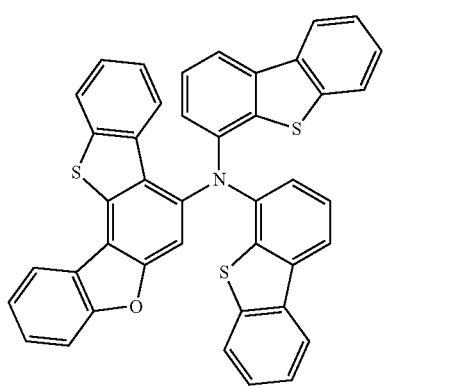
-continued
B27
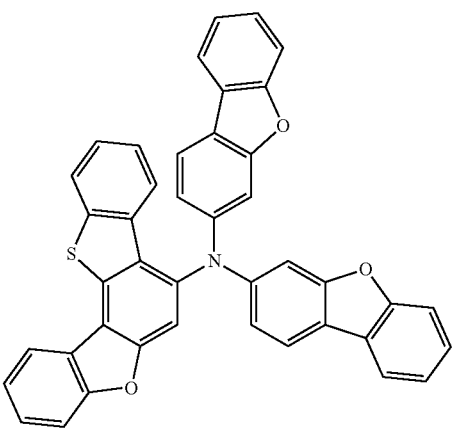
B28
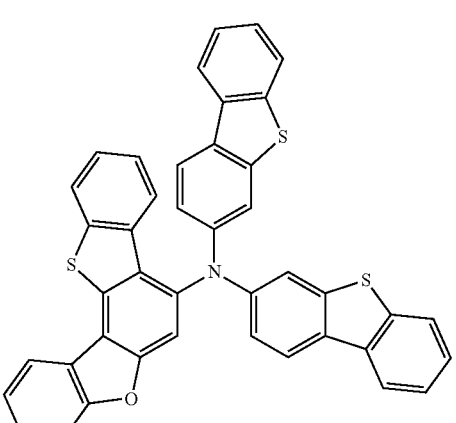
B29
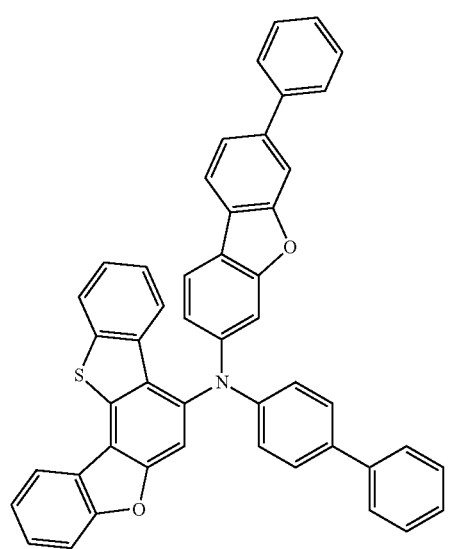

B30
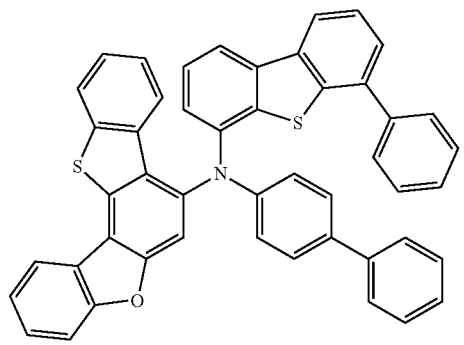
B34
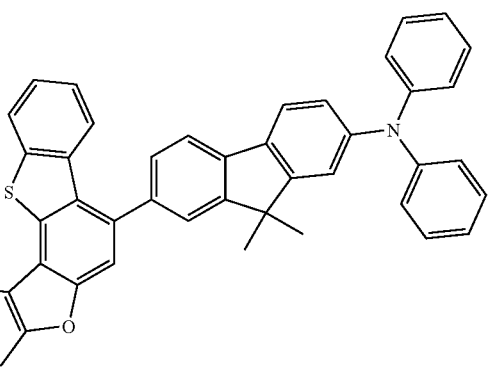
B31
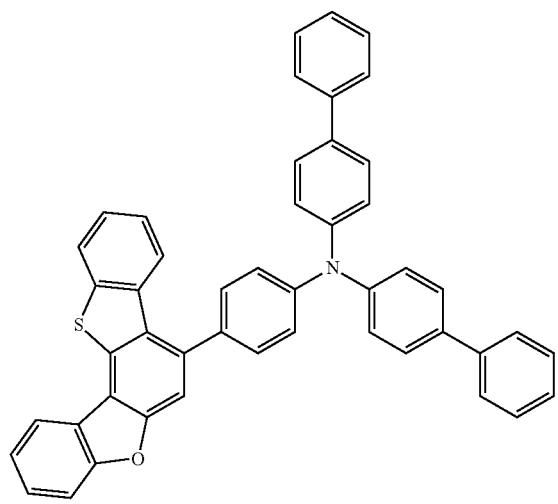
B35
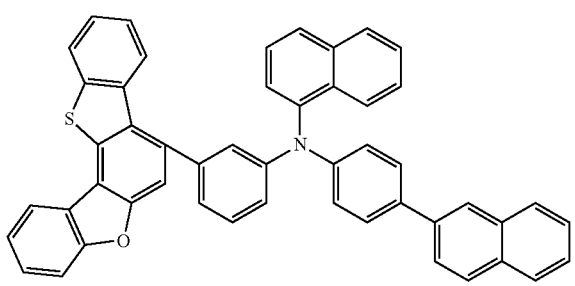
B32
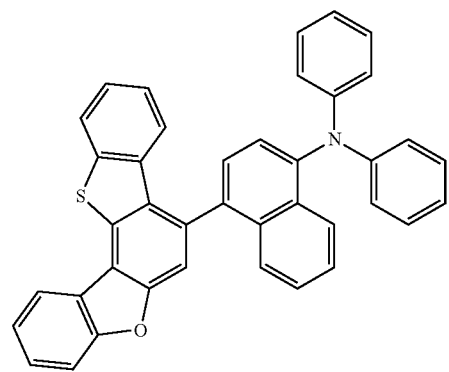
B36
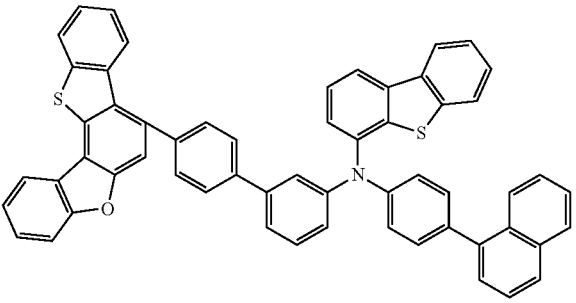
B33
B37

B38
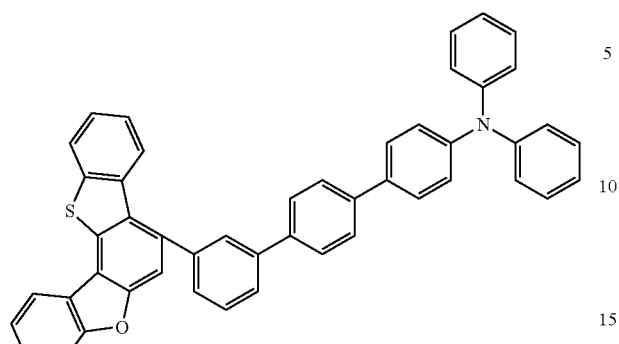
B39
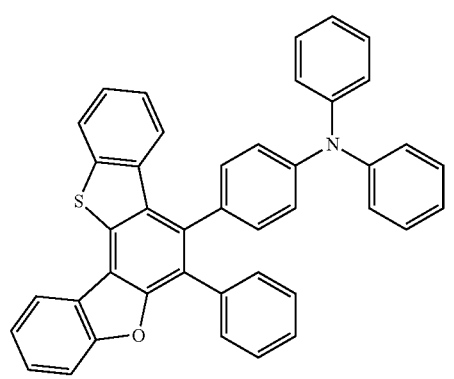
B40
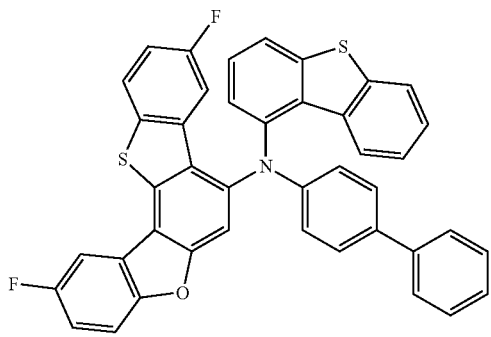
B41
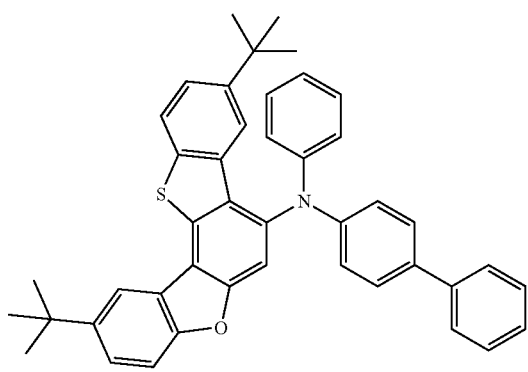
B42
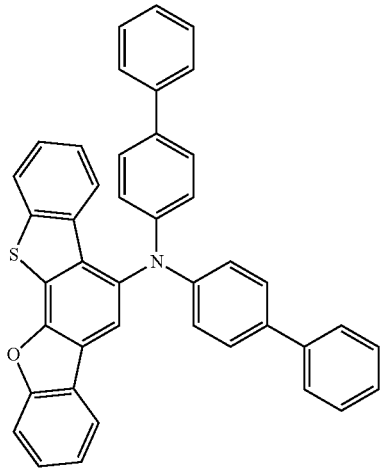
Compound Group C
C1
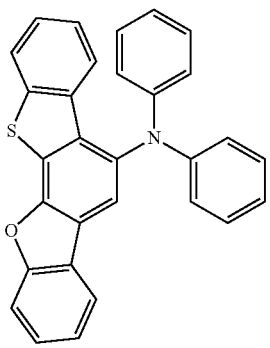
C2

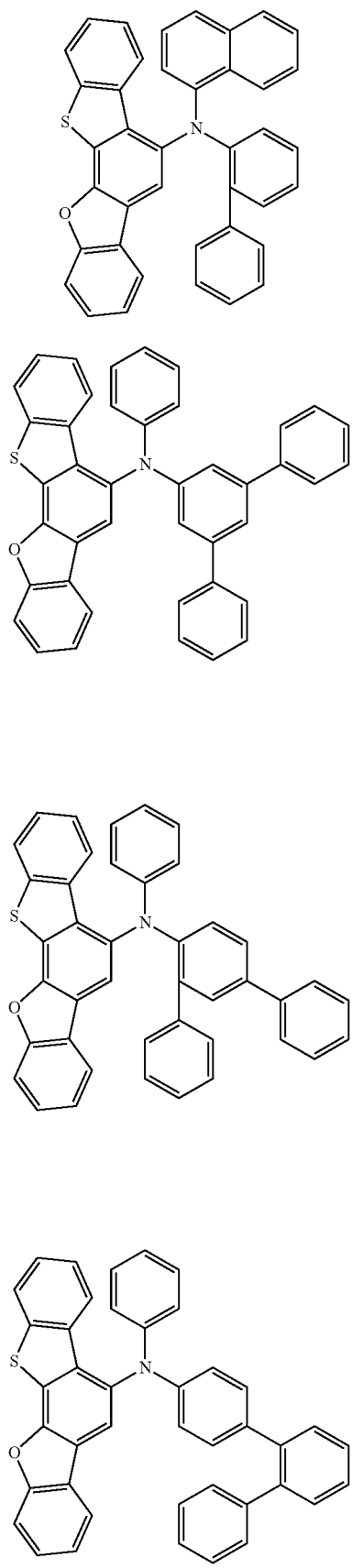
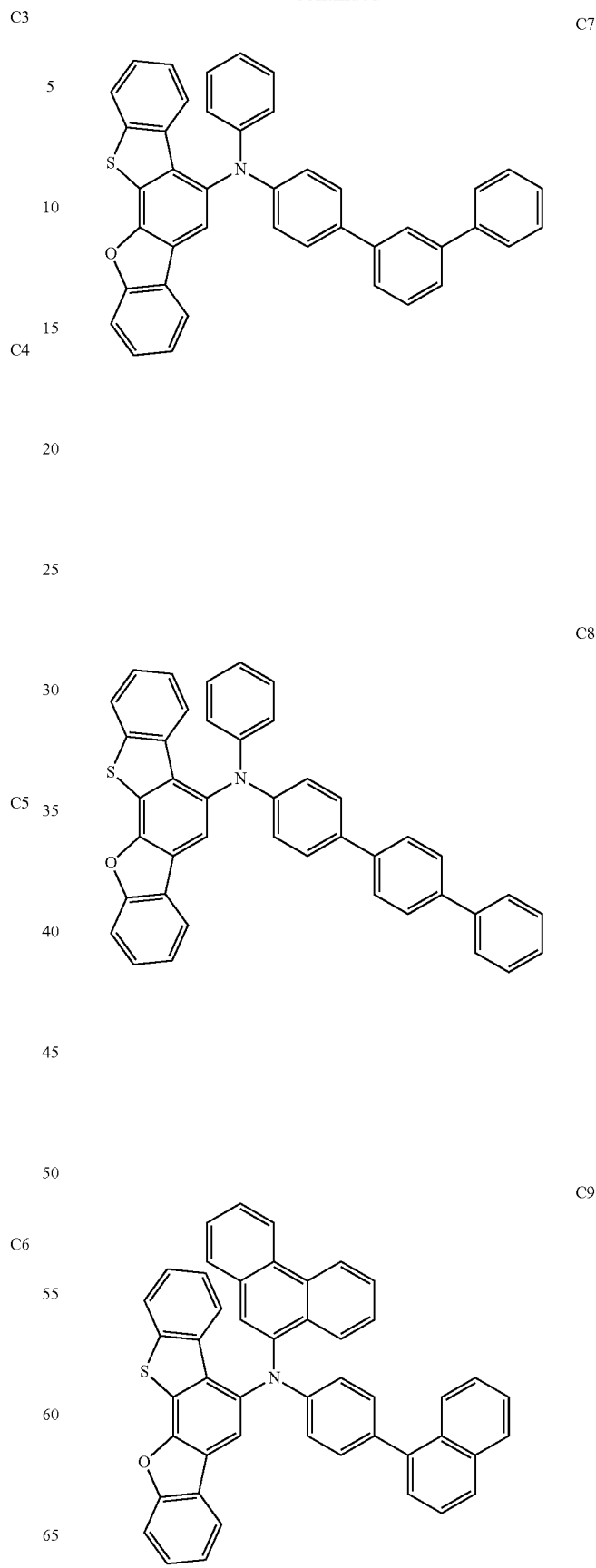

C10
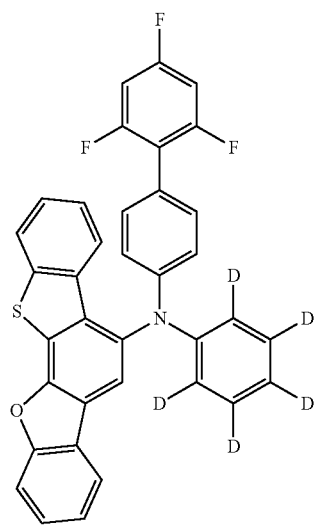
C11
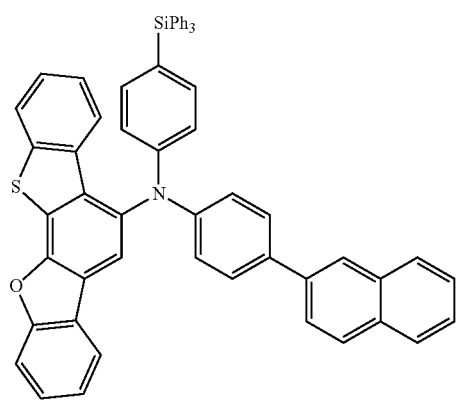
C12
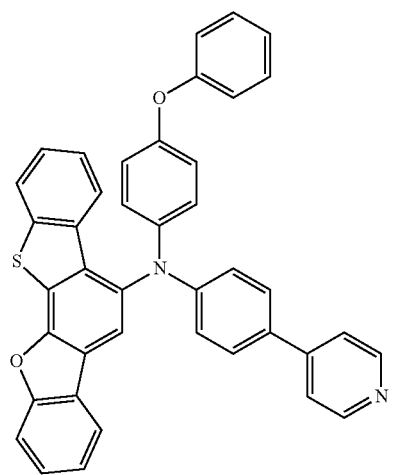
C13
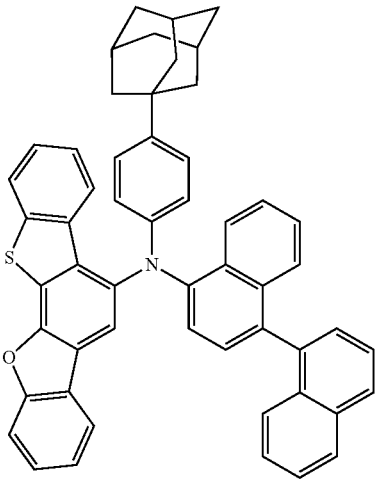
C14
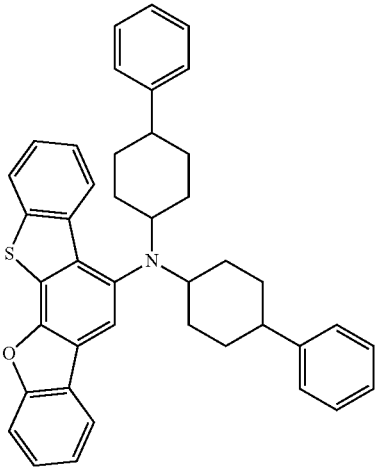
C15
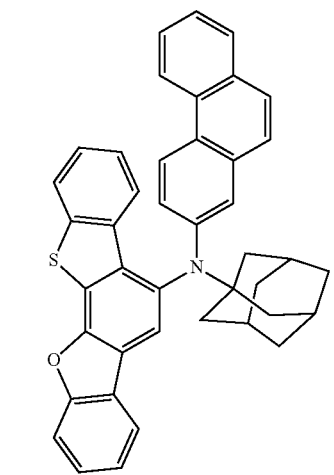

C16
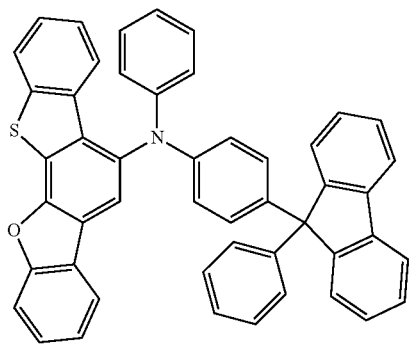
C17
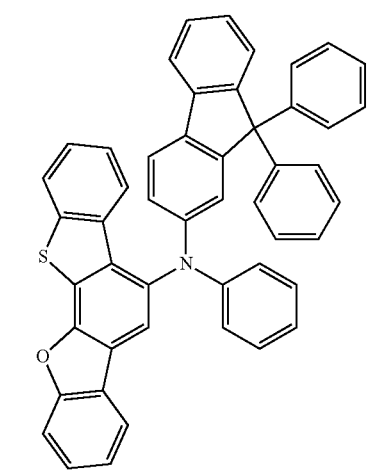
C18
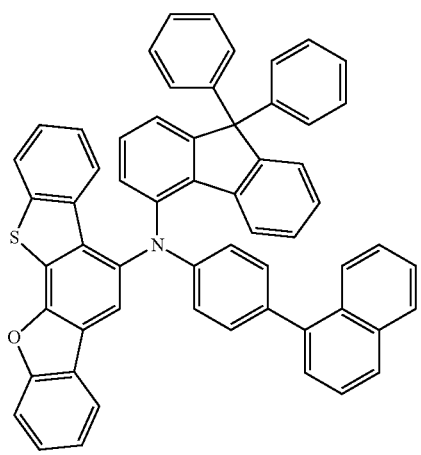
C19
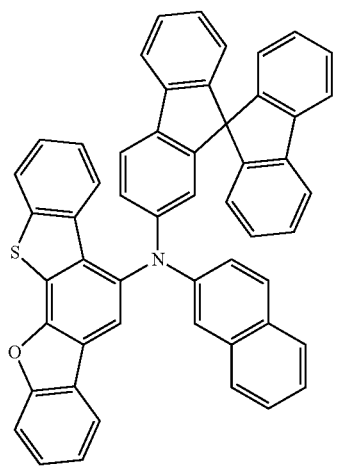
C20
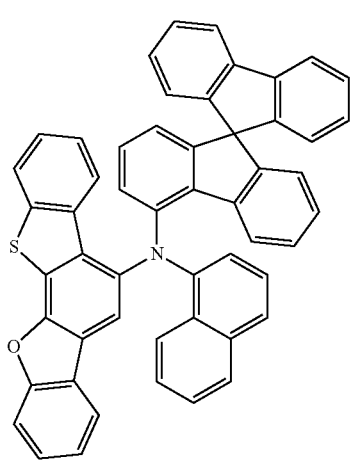
C21
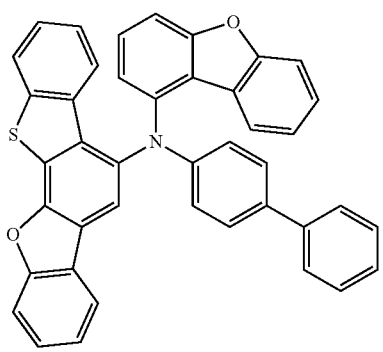

C22
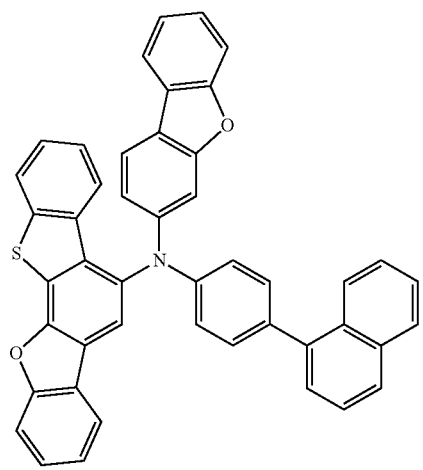
C23
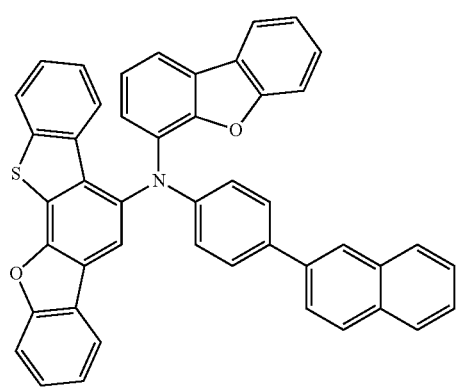
C24
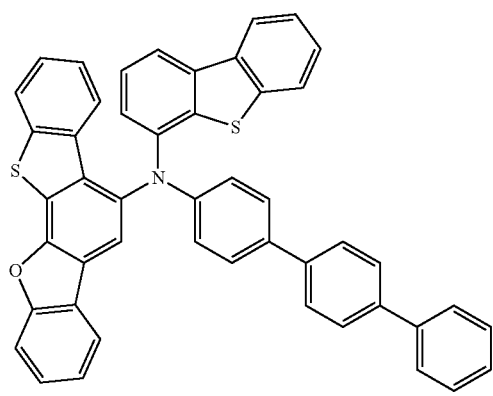
C25
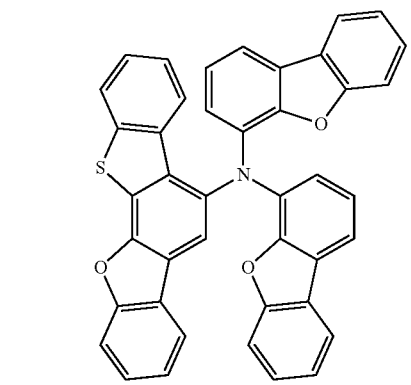
C26
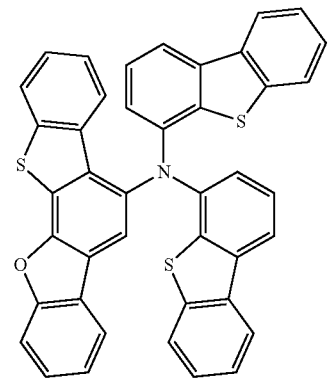
C27
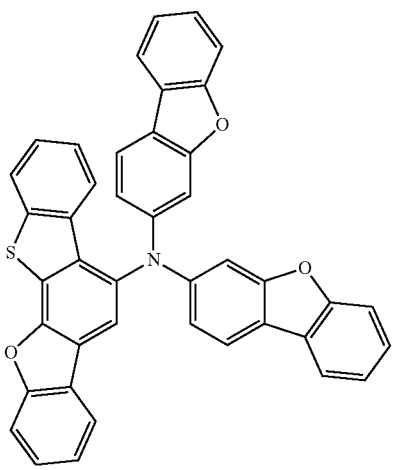
C28
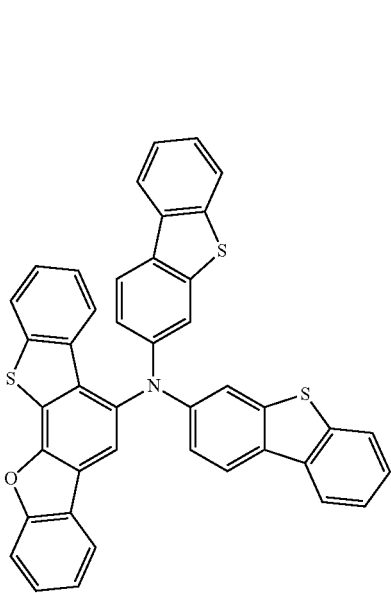

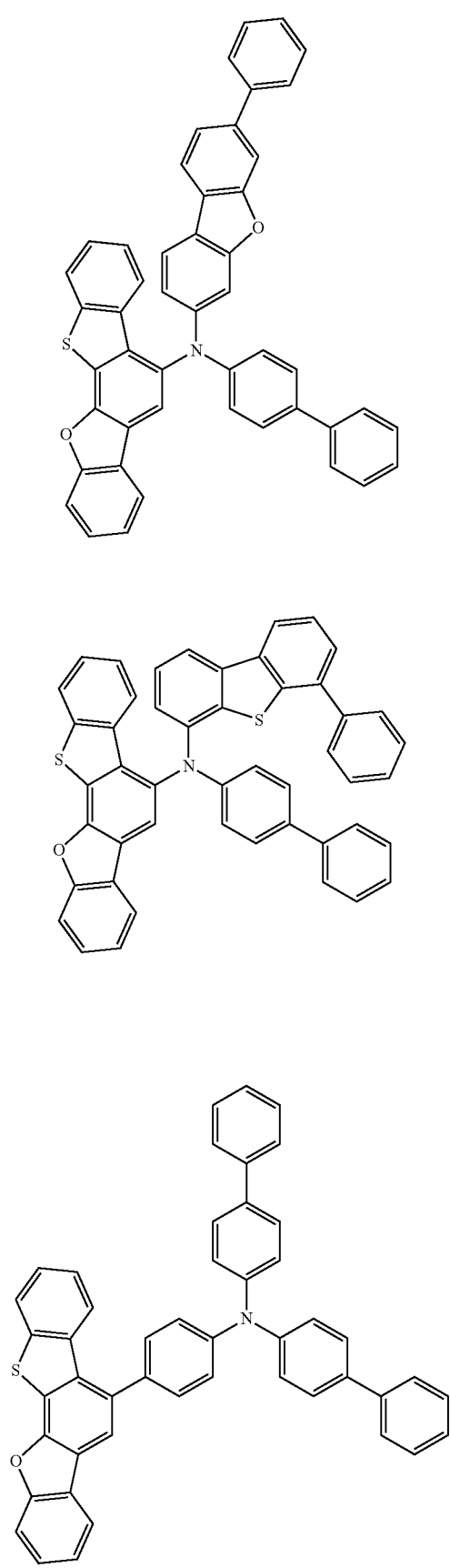
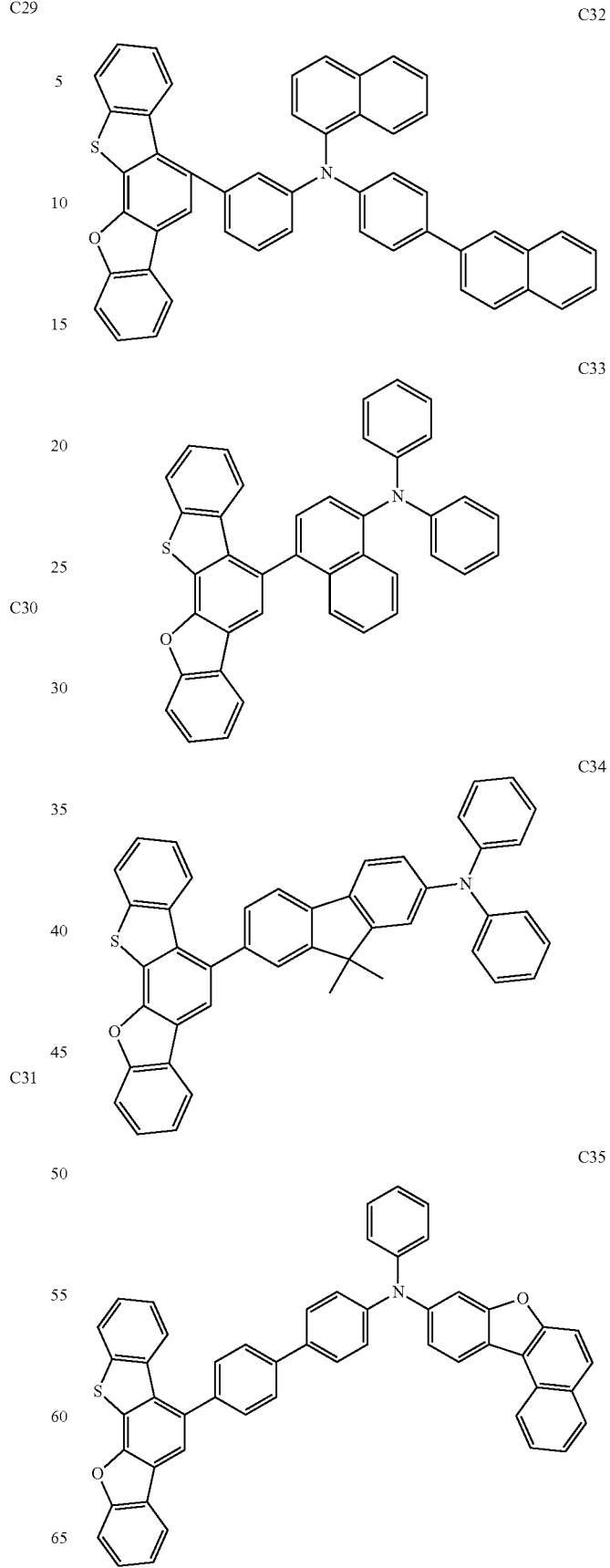

C36
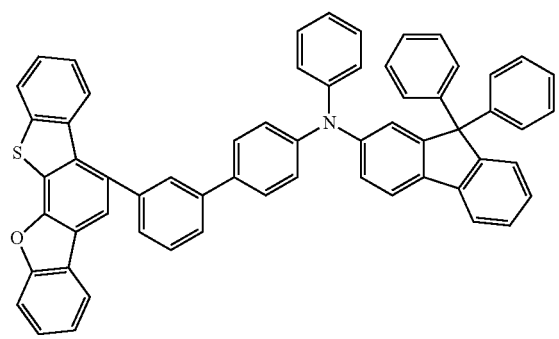
C37
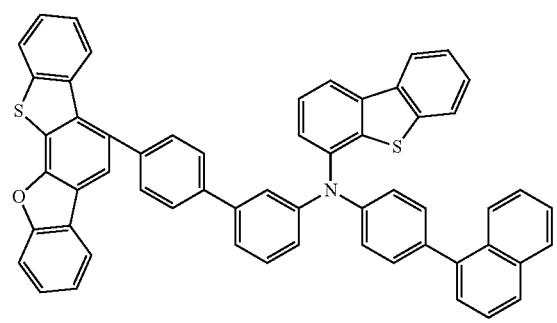
C38
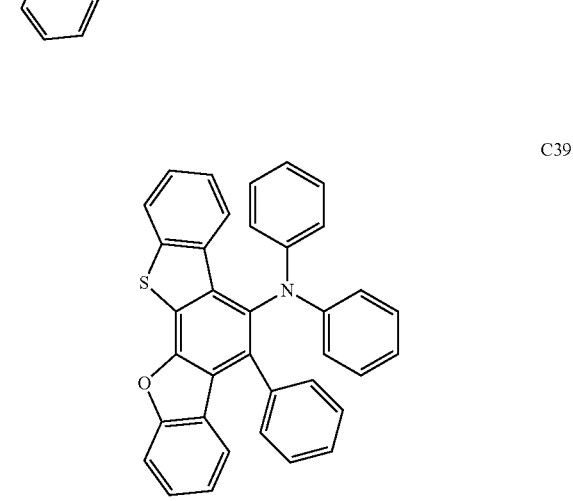
C39
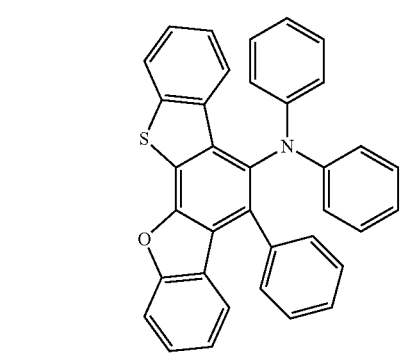
C40
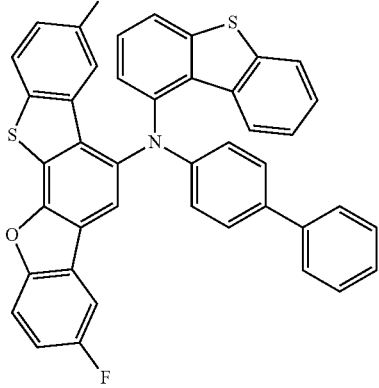
C41
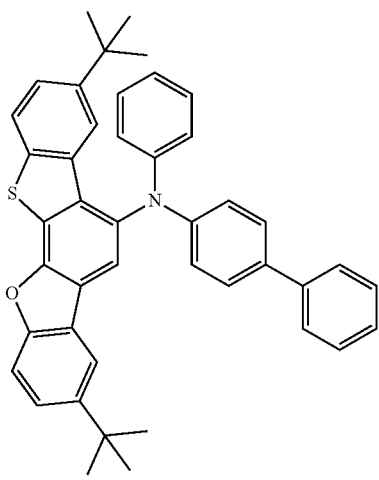
C42
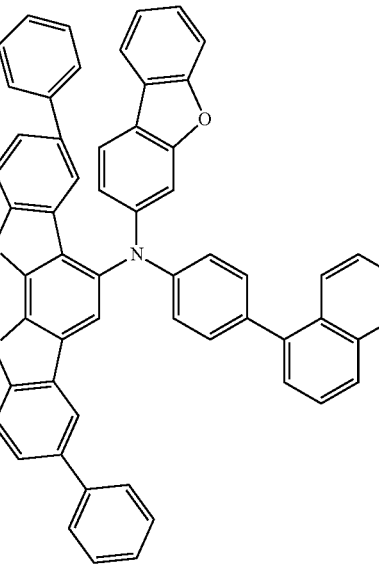

Compound Group D
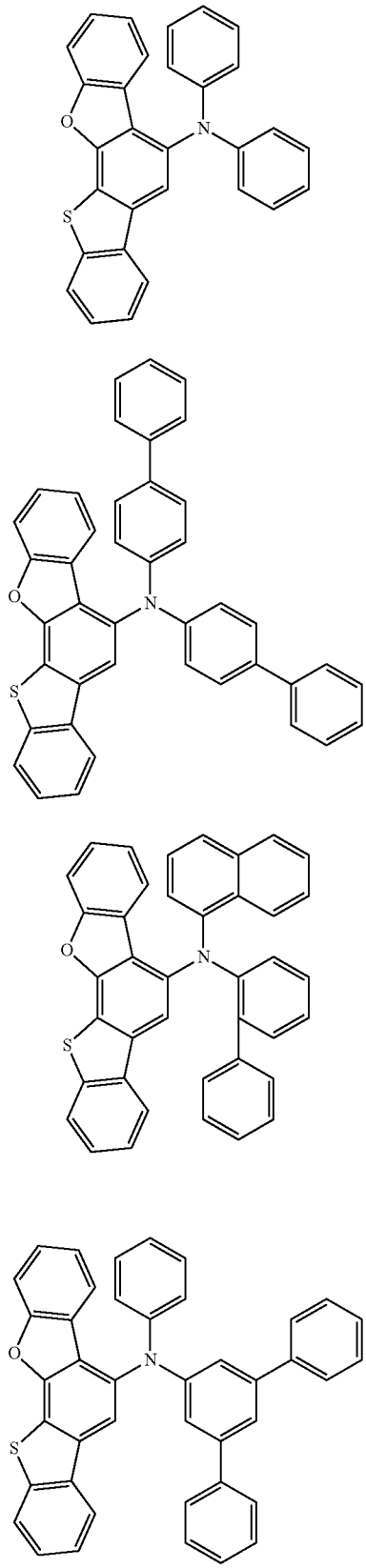
D1
D2
D3
D4
-continued
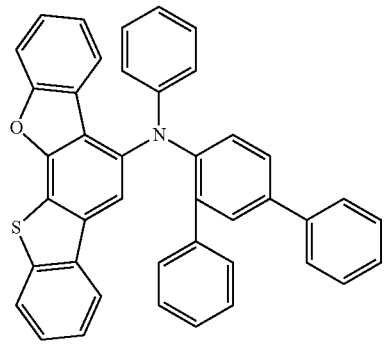
D5
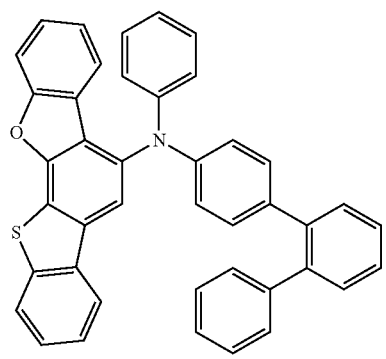
D6
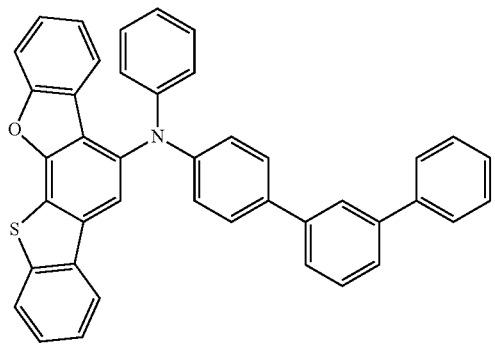
D7
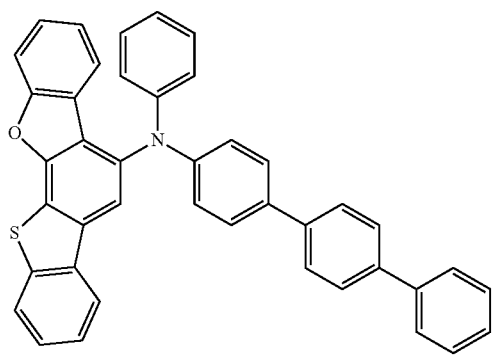
D8

D9
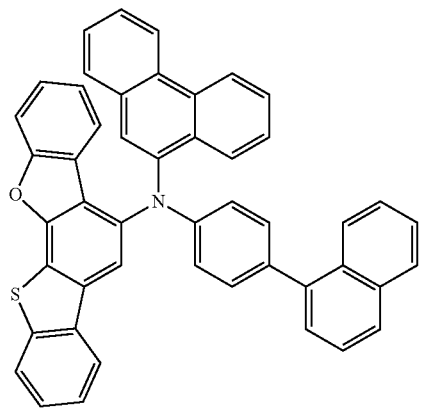
D12
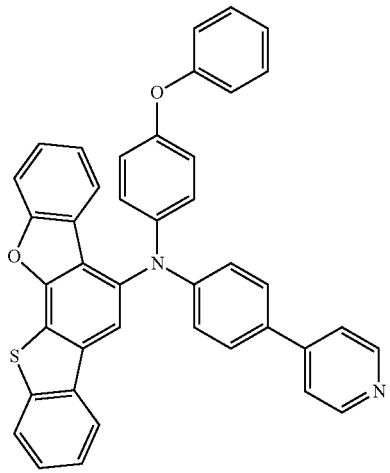
D10
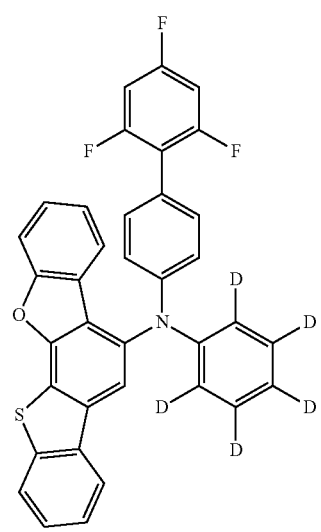
D13
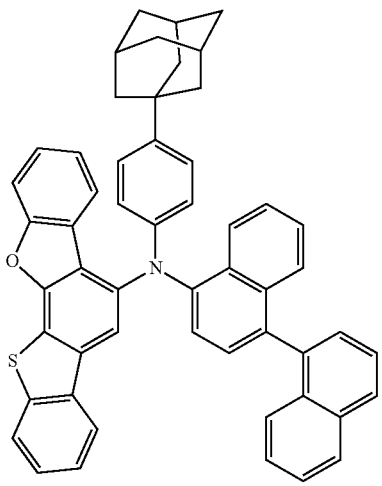
D11
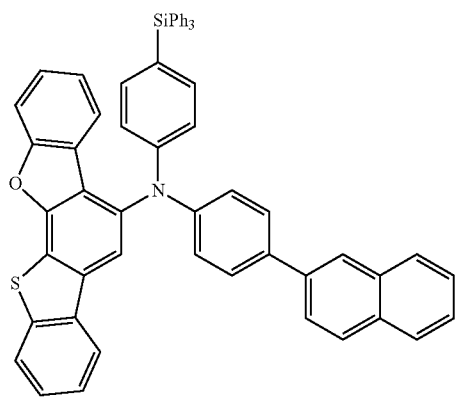
D14
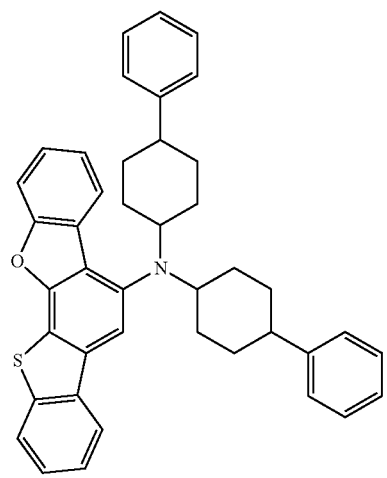

D15
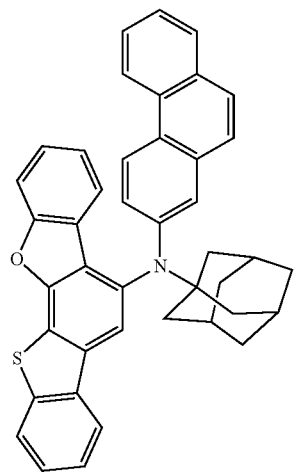
D16
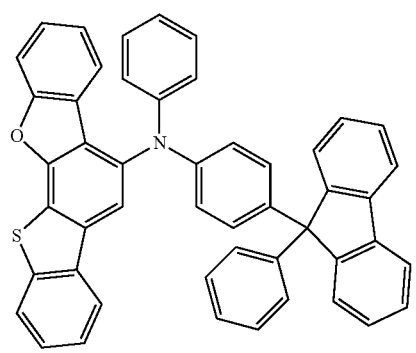
D17
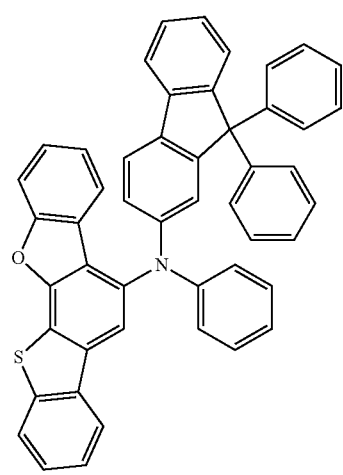
D18
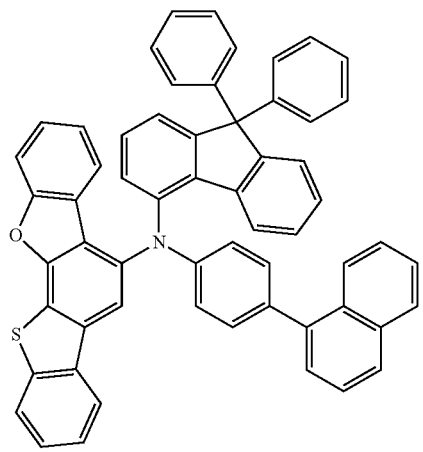
D19
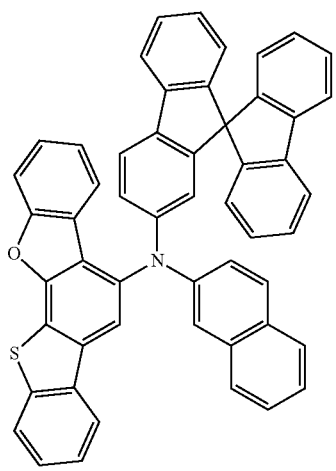
D20
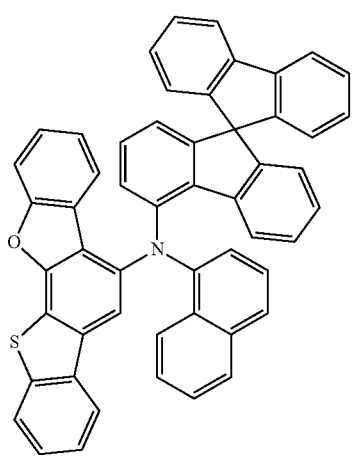

D21
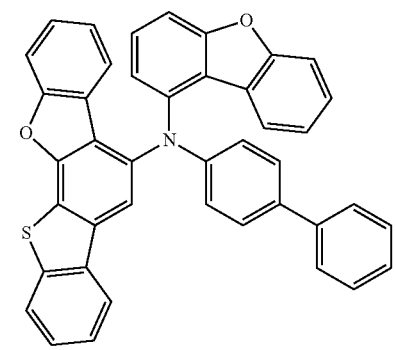
D22
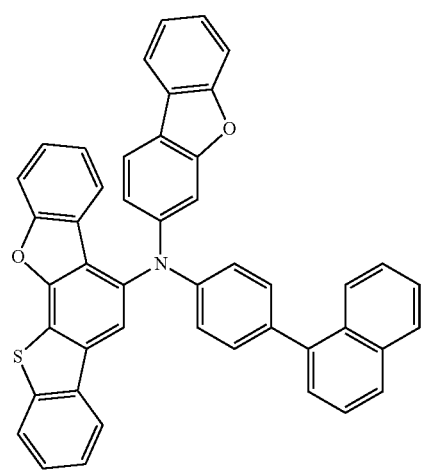
D23
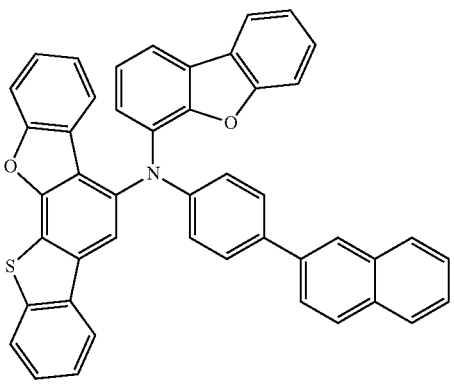
D24
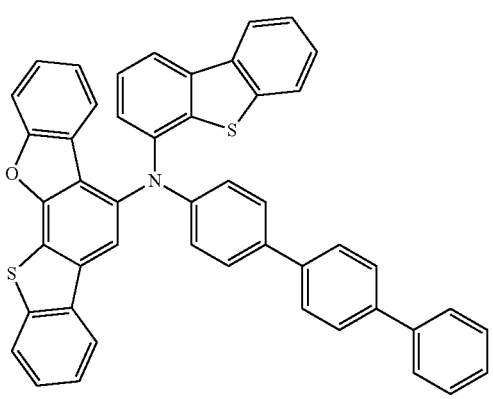
D25
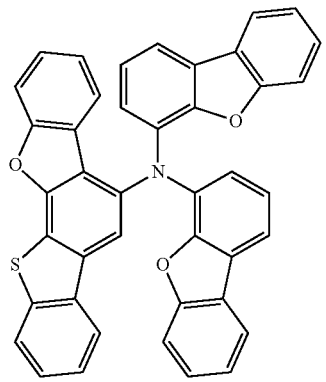
D26
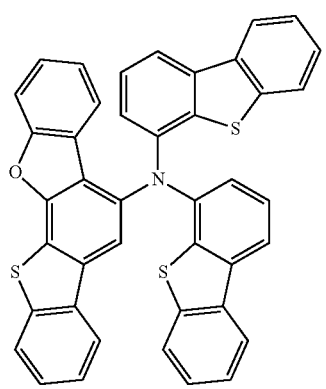
D27
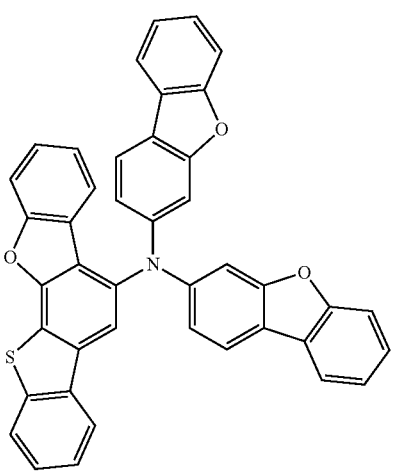

D28
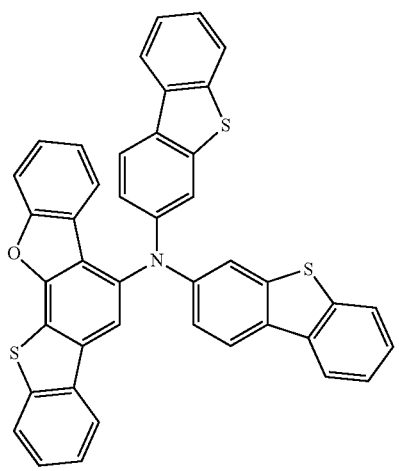
D29
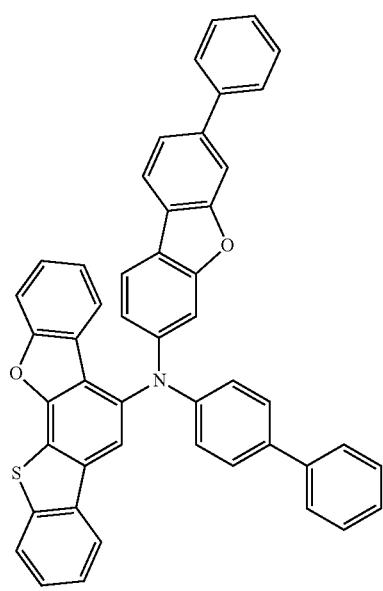
D30
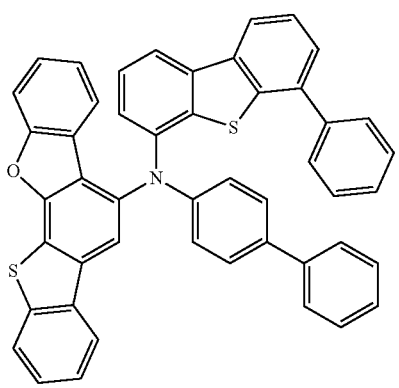
D31
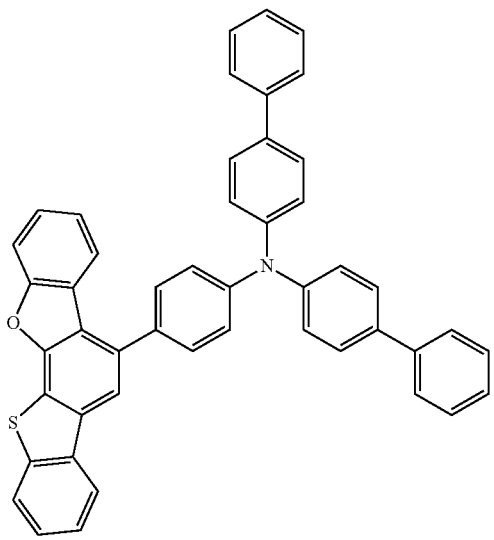
D32
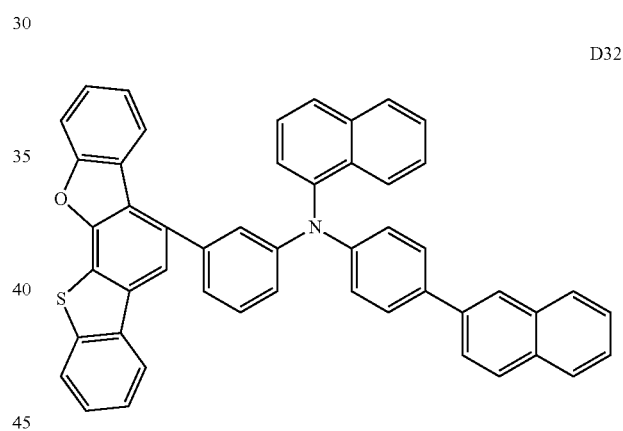
D33
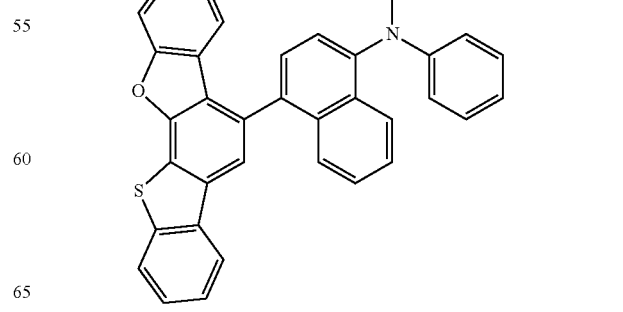

D34
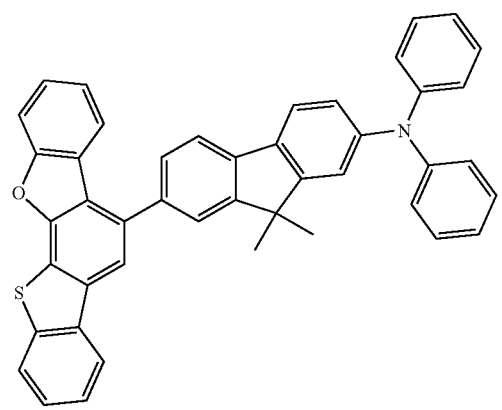
D35
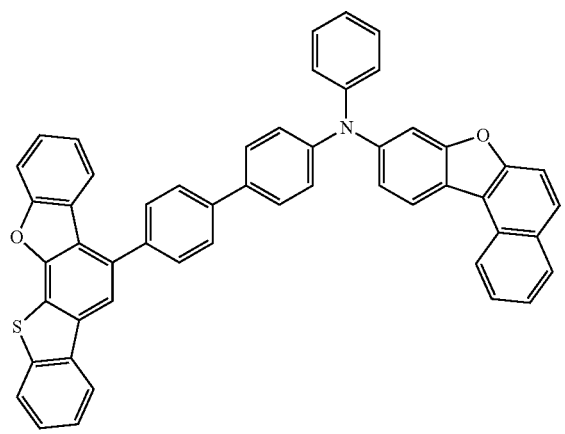
D36
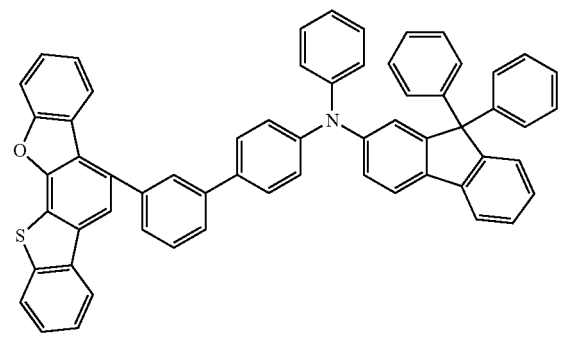
D37
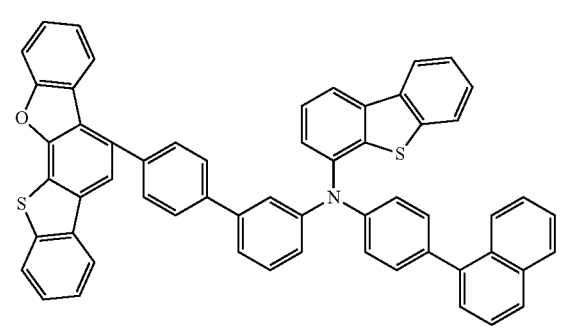
D38
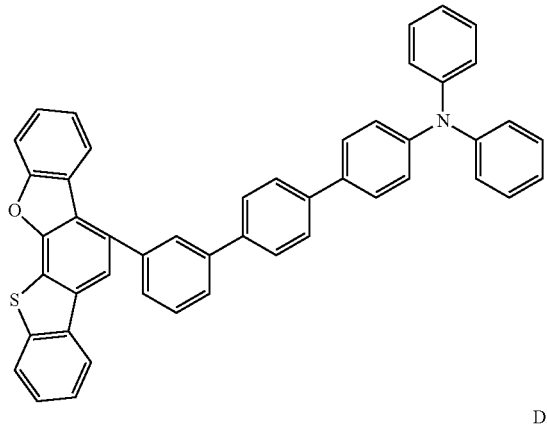
D39
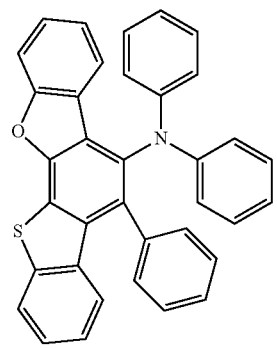
D40
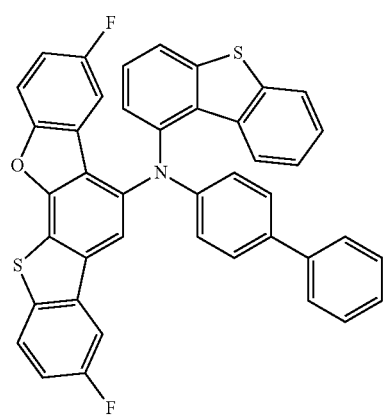
D41
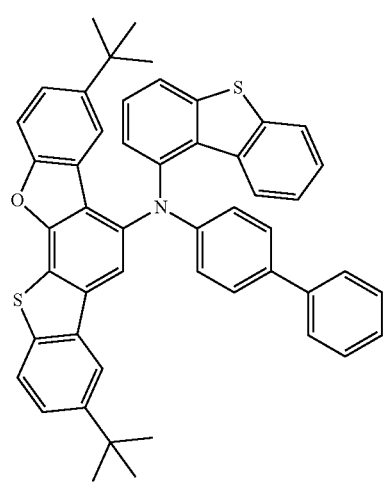

-continued
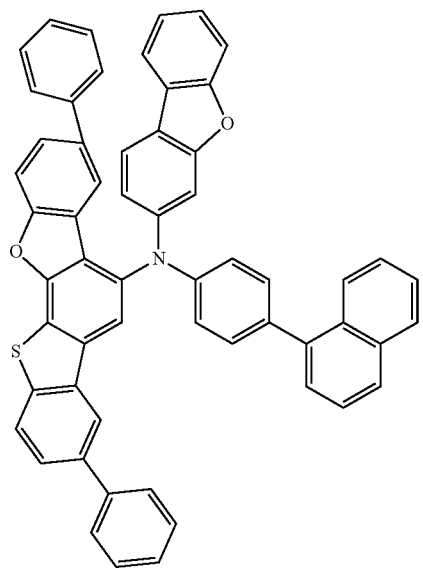
D42
Compound Group E
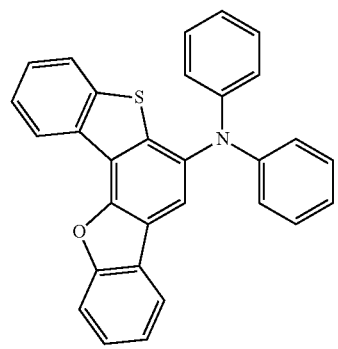
E1
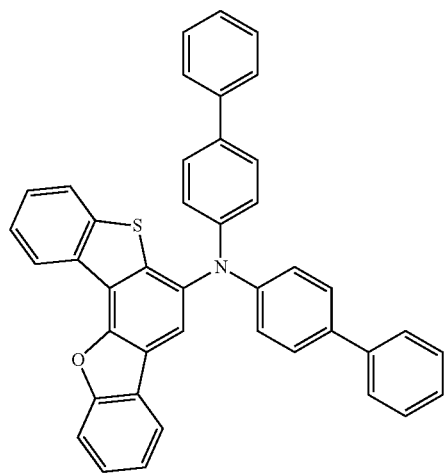
E2
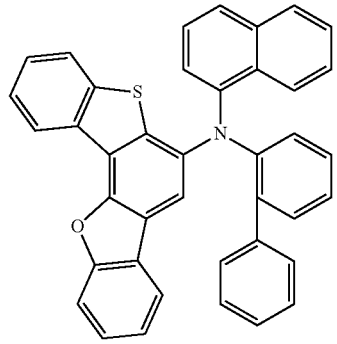
E3
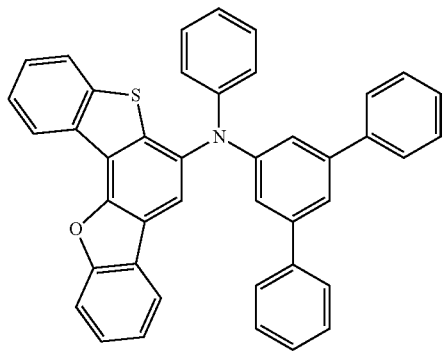
E4
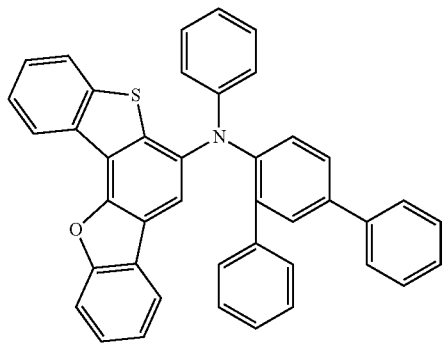
E5
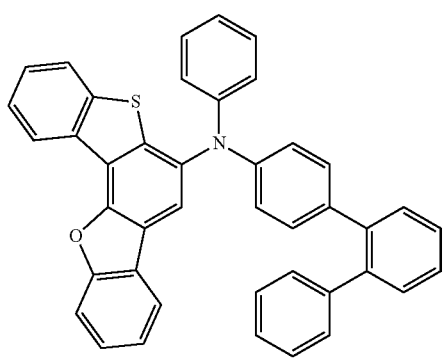
E6

E7
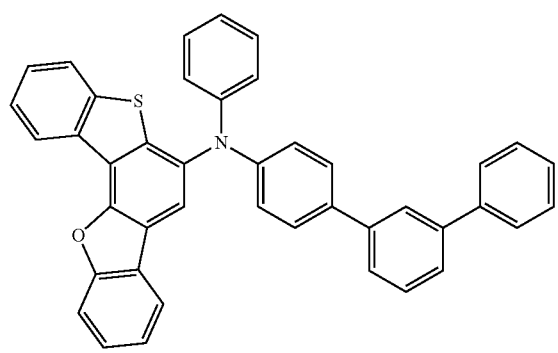
E8
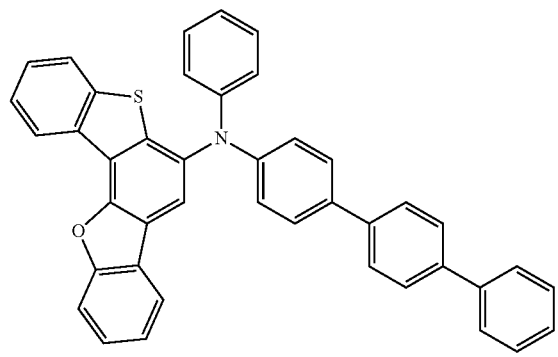
E9
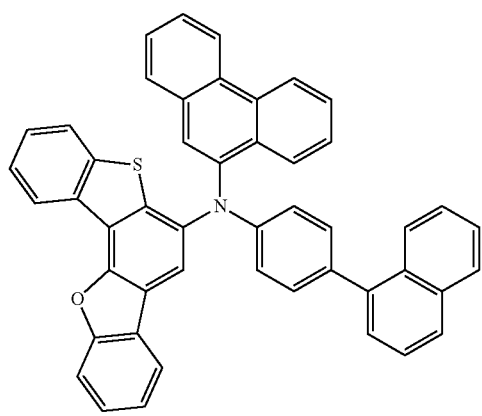
E10
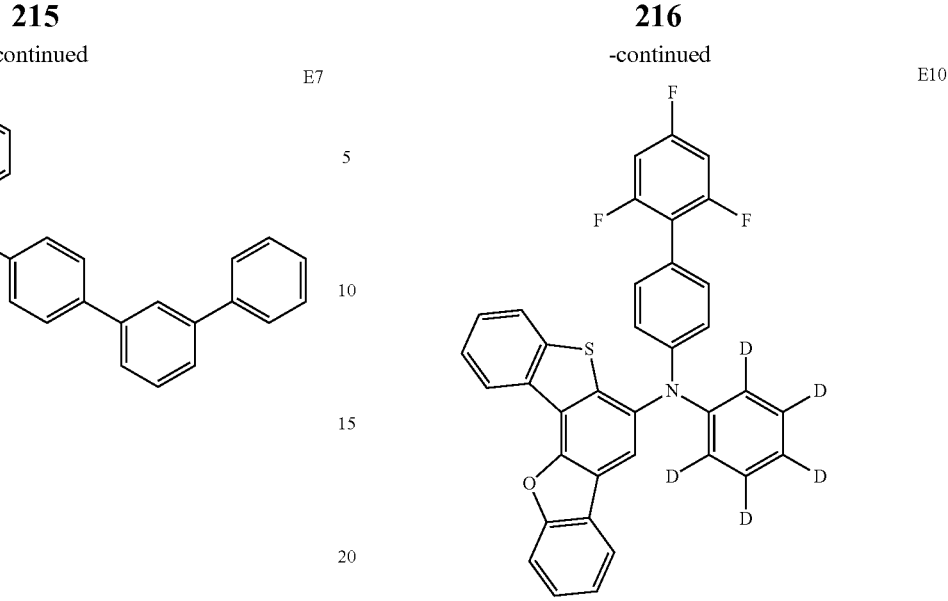
E11
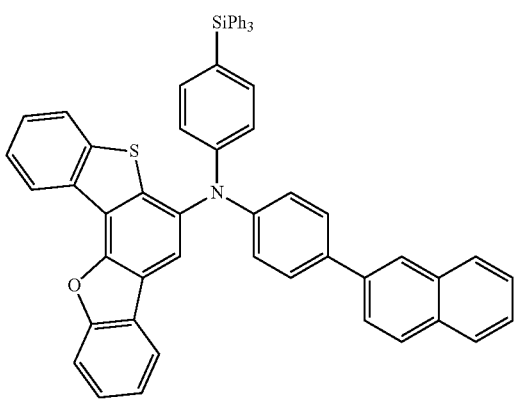
E12
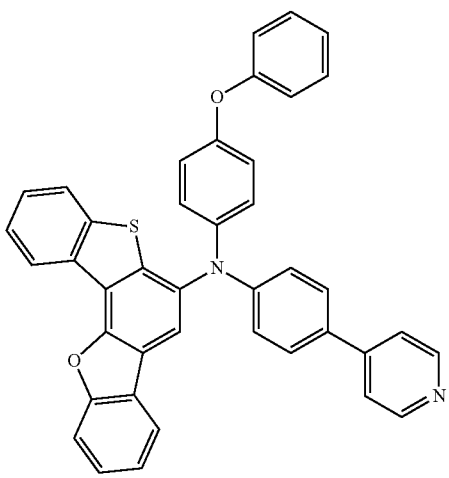

E13
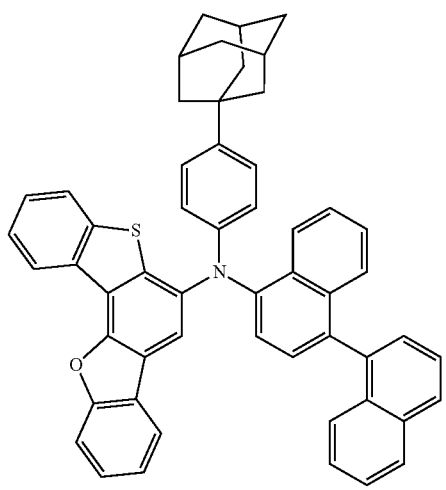
E14
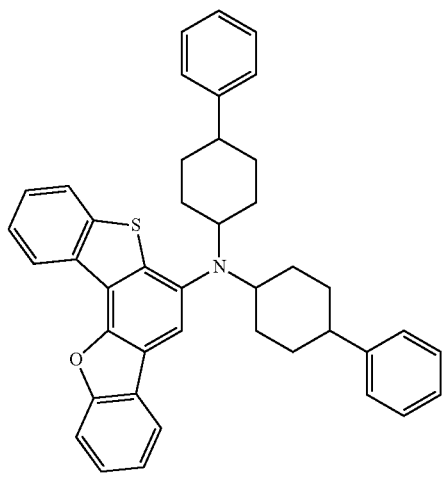
E15
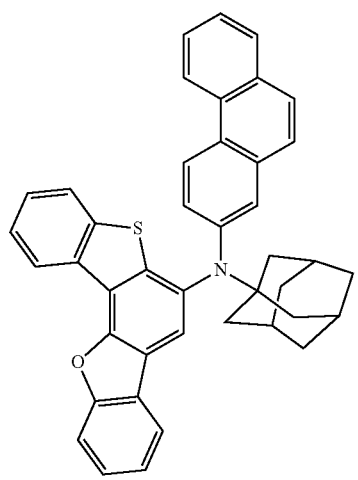
E16
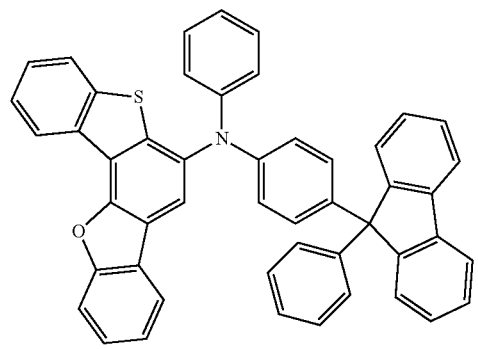
E17
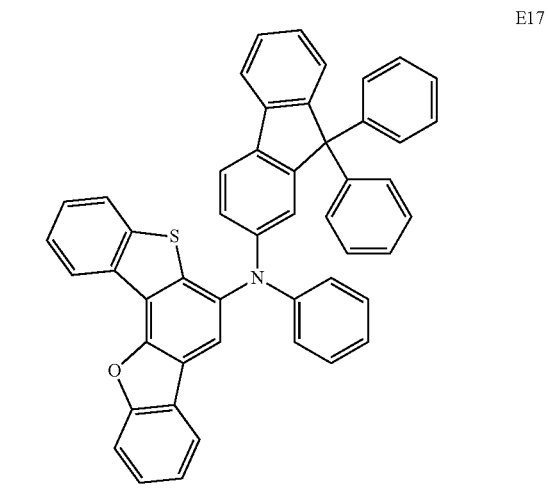
E18
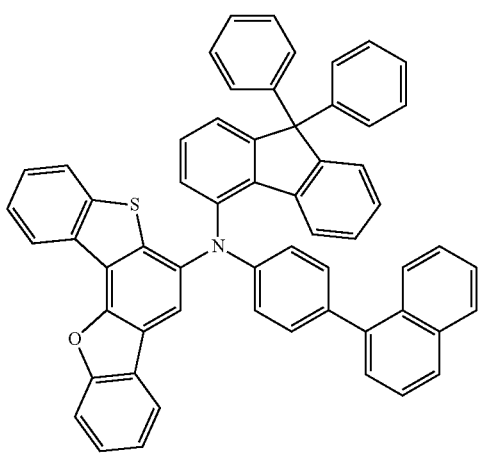

-continued
E19
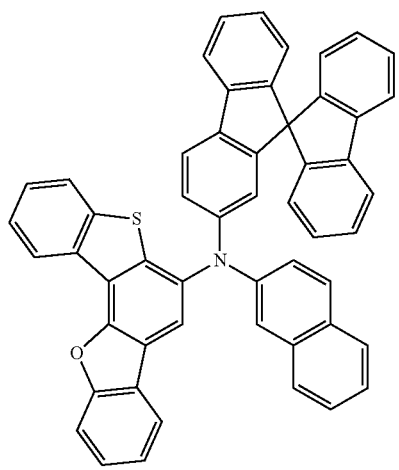
E22
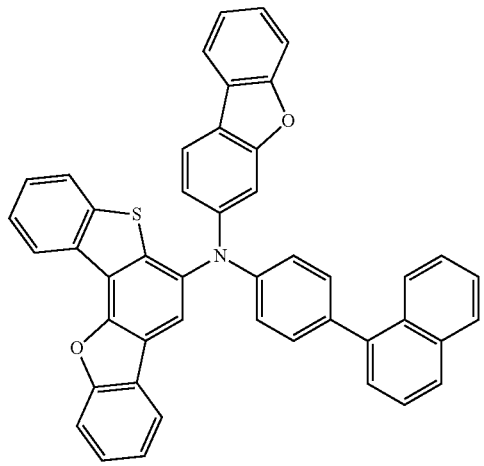
E20
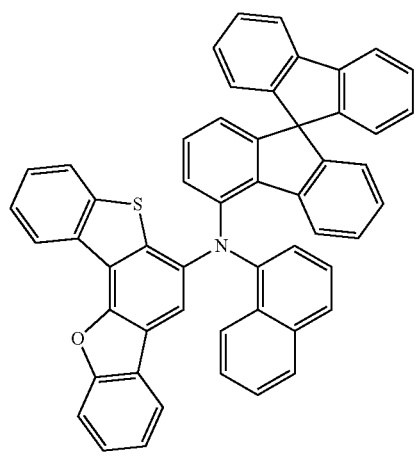
E23
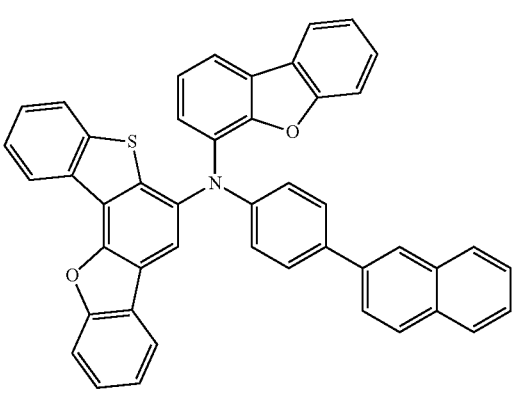
E21
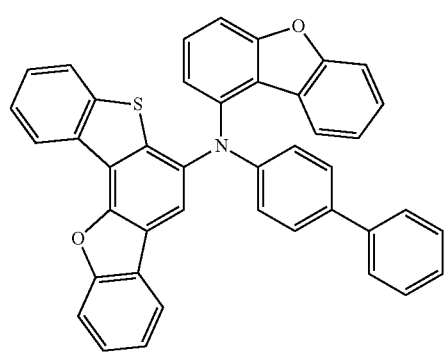
E24
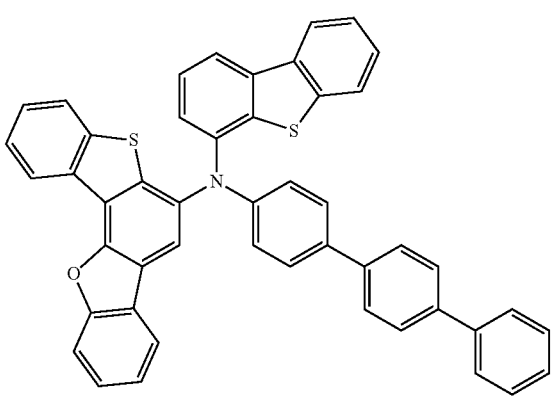

E25
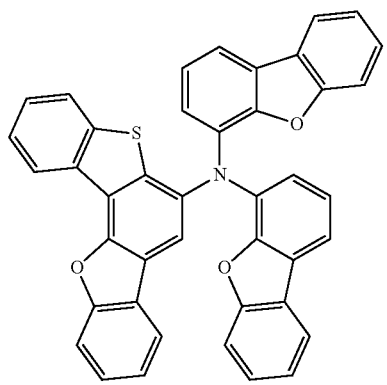
E28
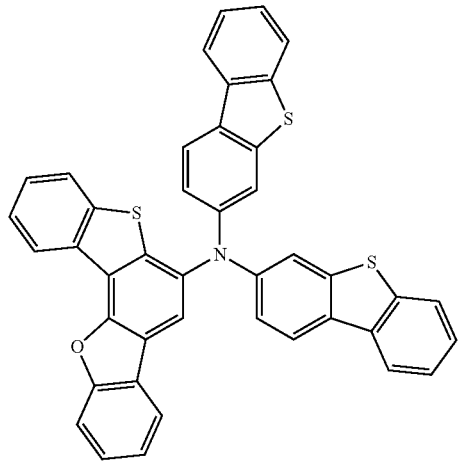
E26
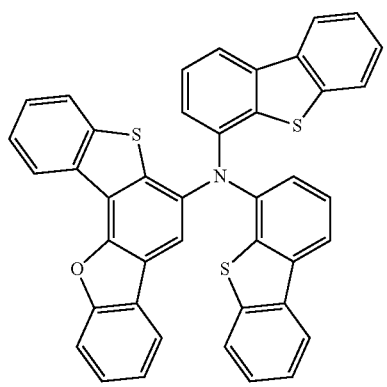
E29
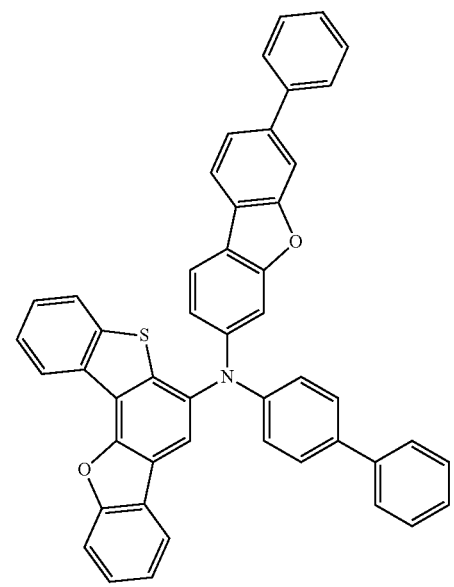
E27
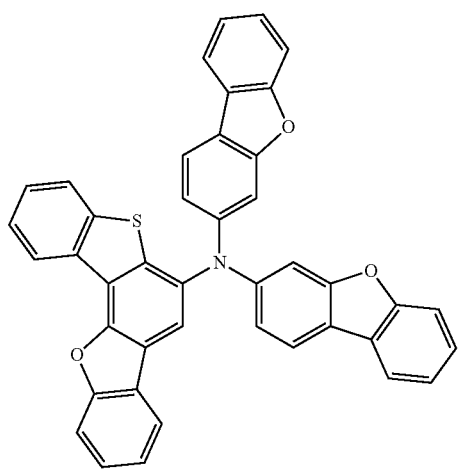
E30
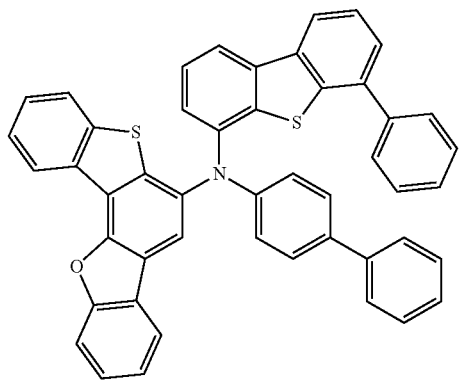

E31
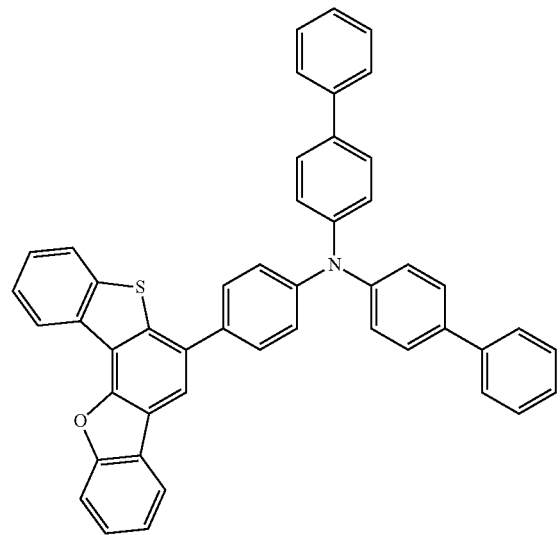
E32
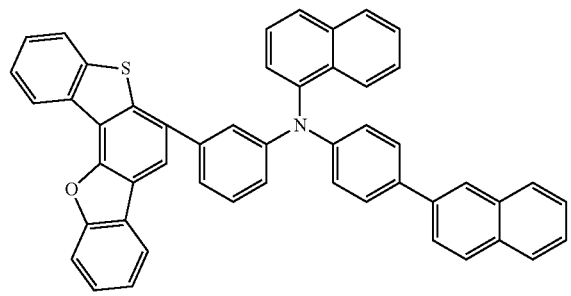
E33
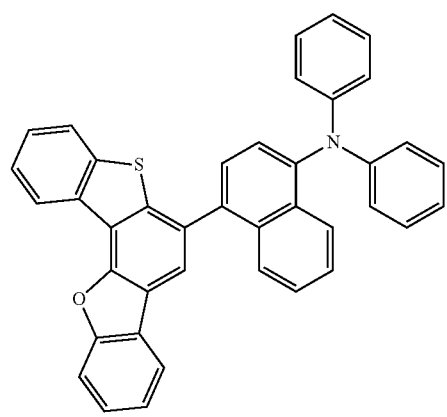
E34
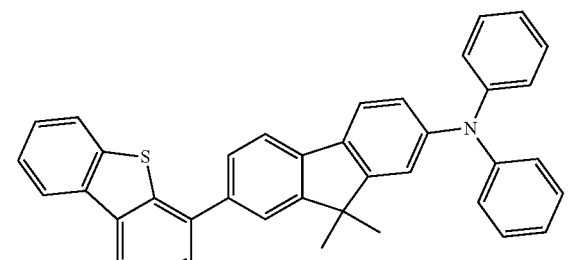
E35
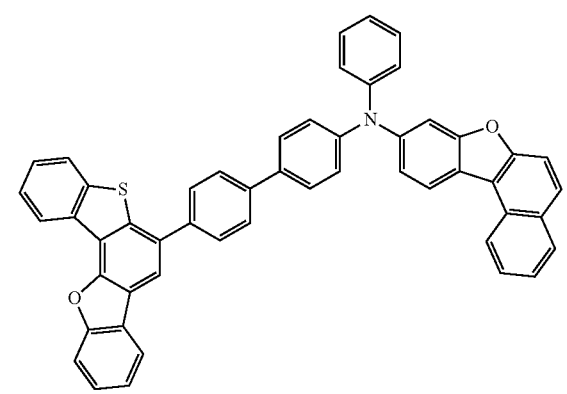
E36
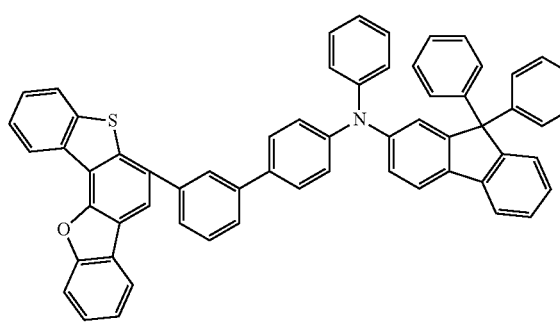
E37
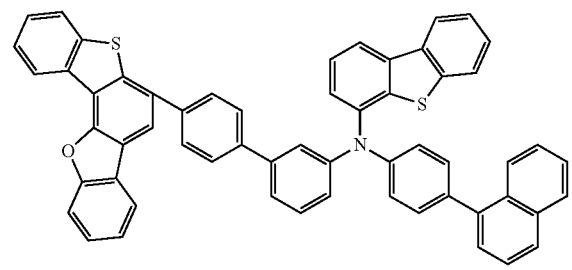

E38
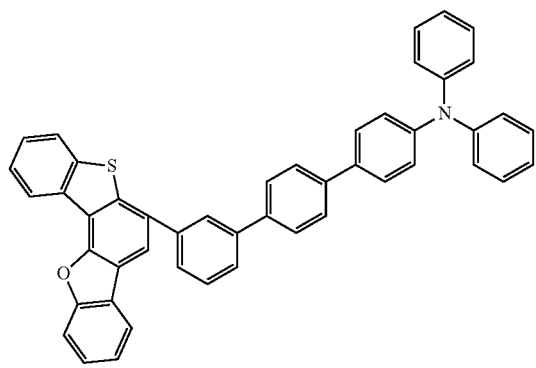
E39
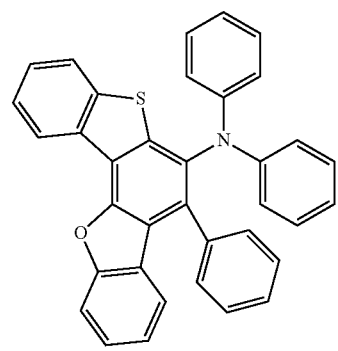
E40
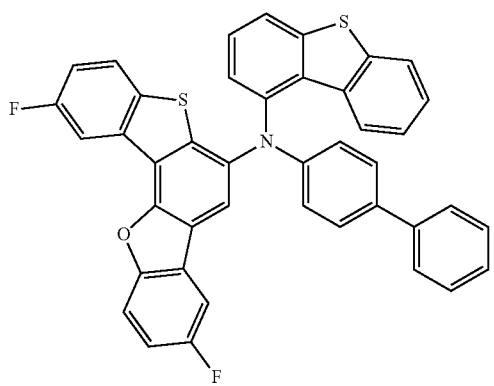
E41
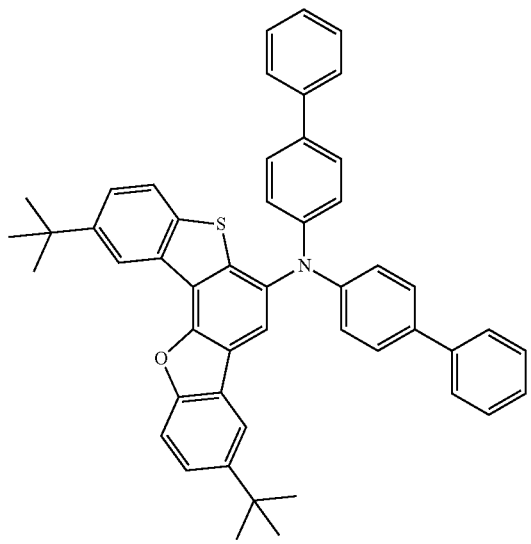
E42
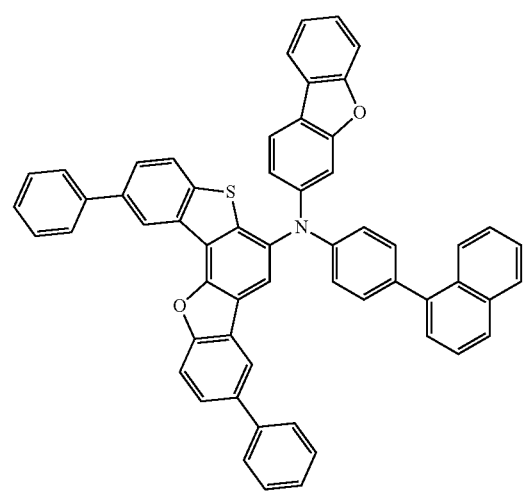
Compound Group F
F1
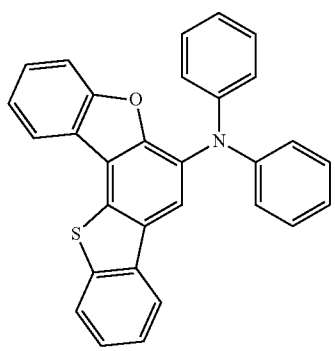

F2
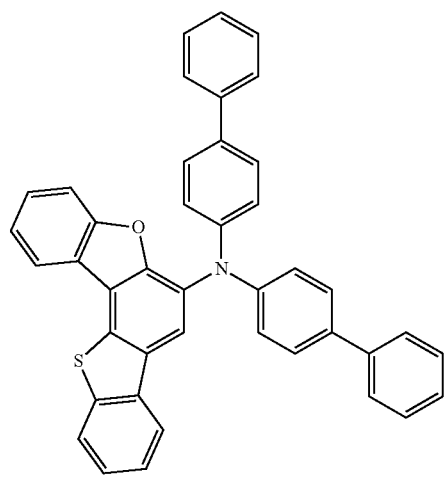
F3
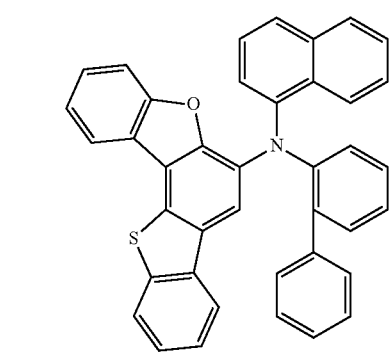
F4
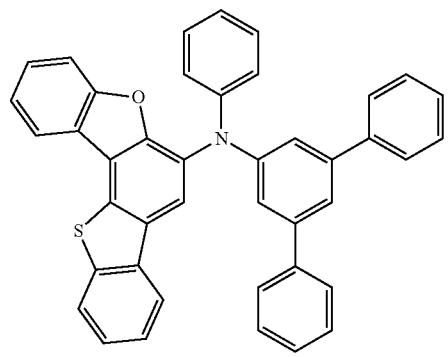
F5
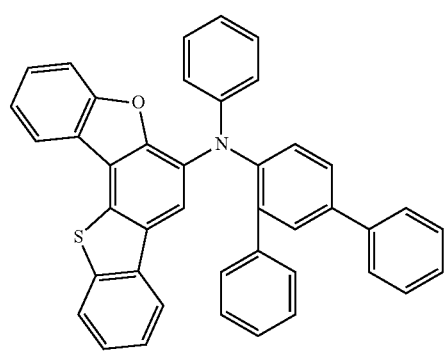
F6
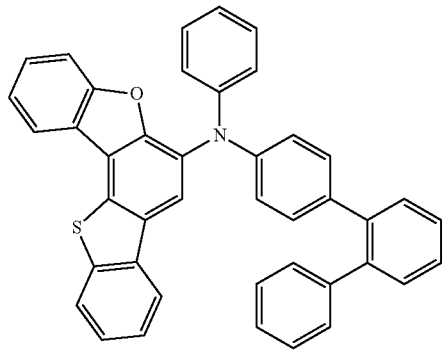
F7
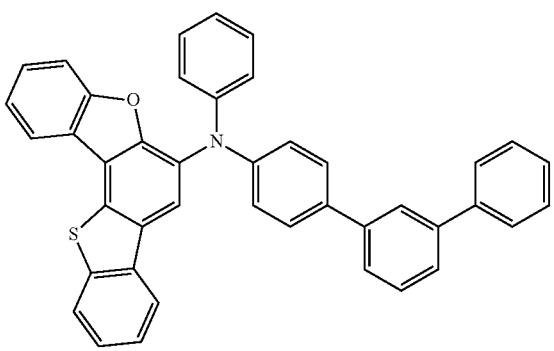
F8
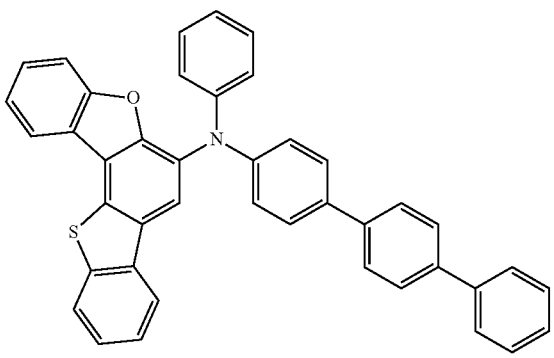
F9
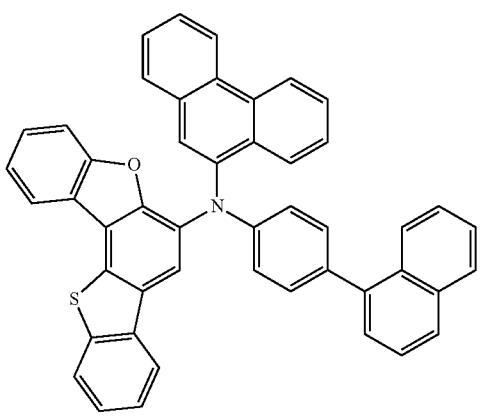

229
-continued
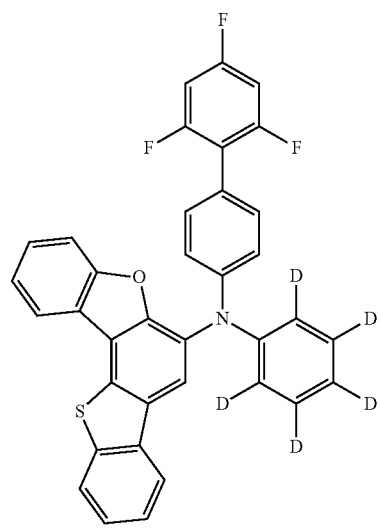
F10
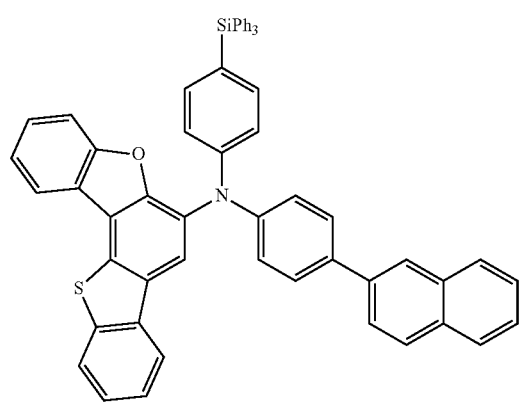
F11
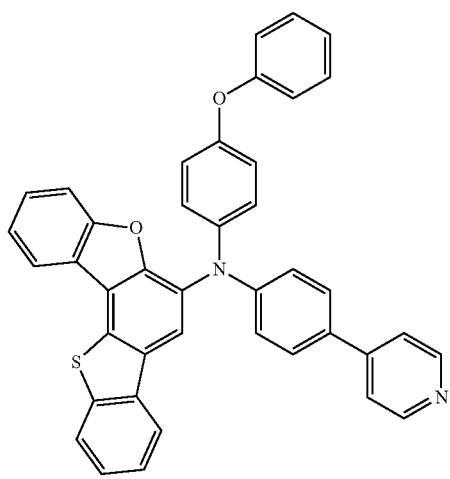
F12
230
-continued
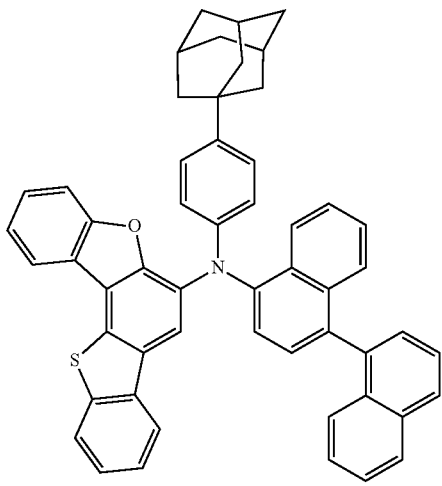
F13
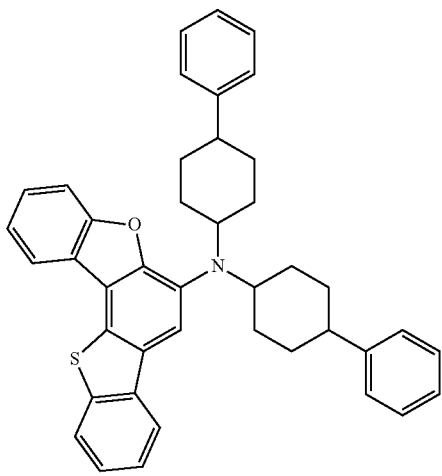
F14
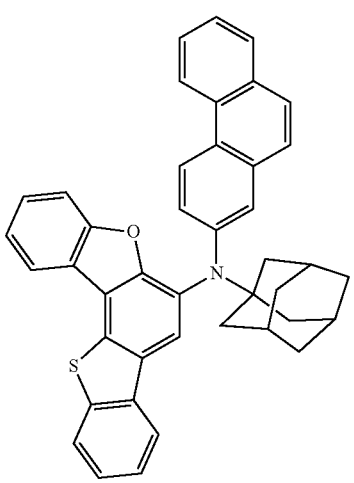
F15

F16
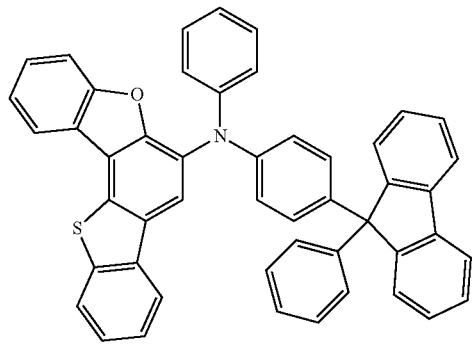
F17
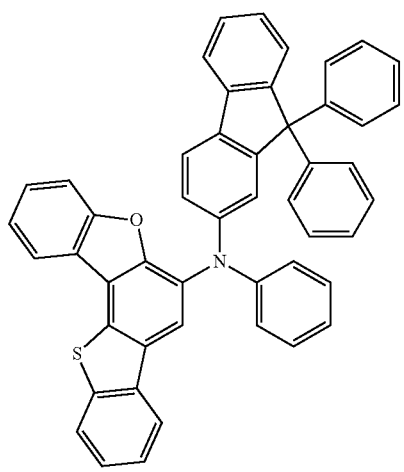
F18
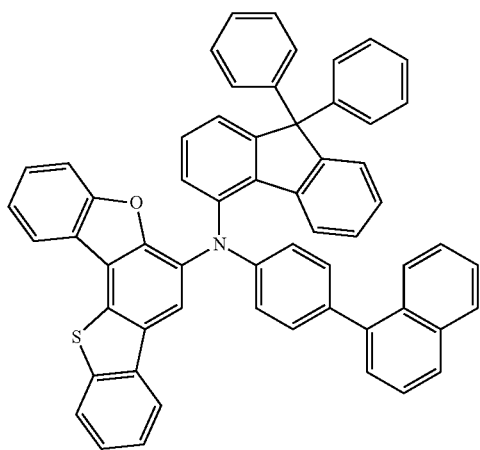
F19
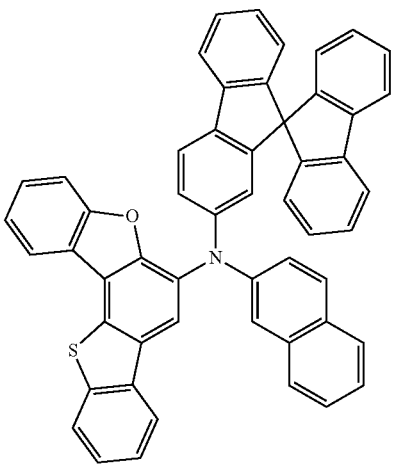
F20
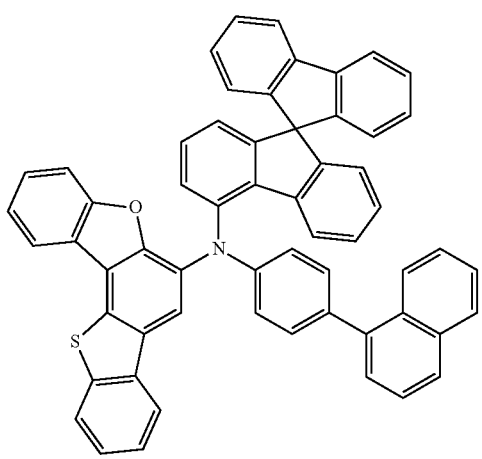
F21
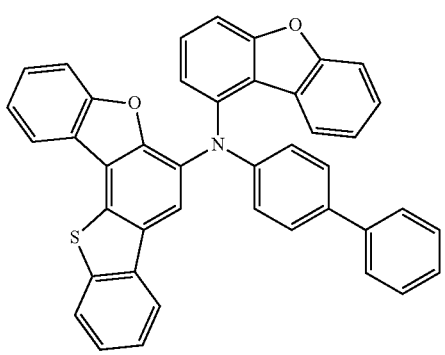

F22
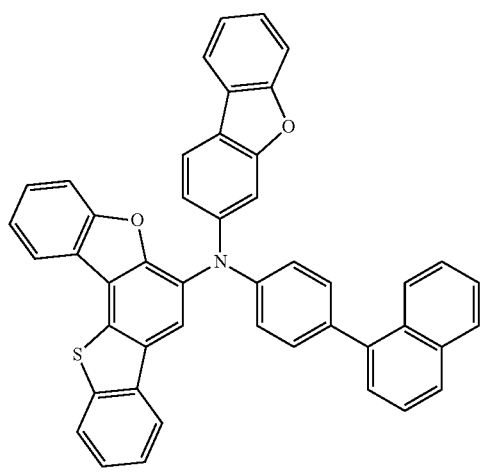
F23
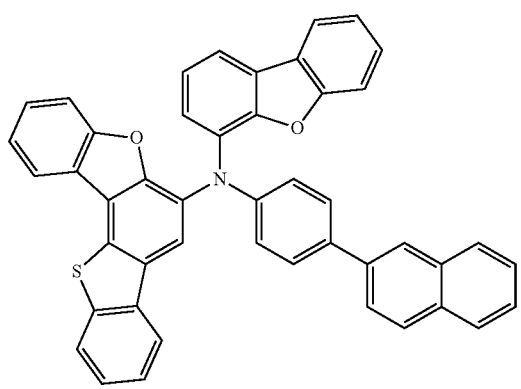
F24
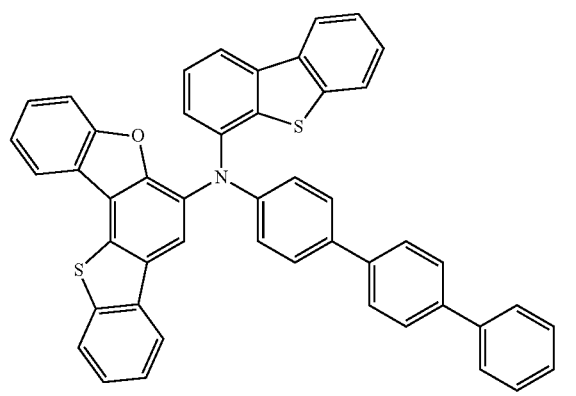
F25
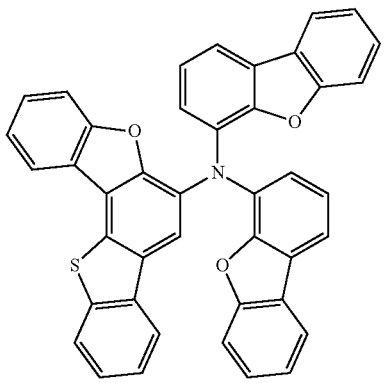
F26
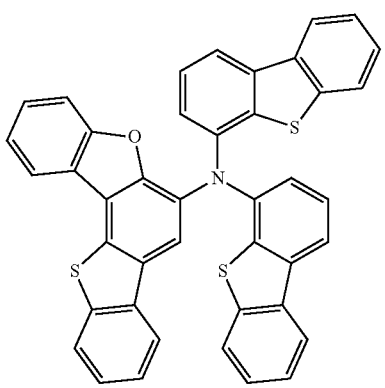
F27
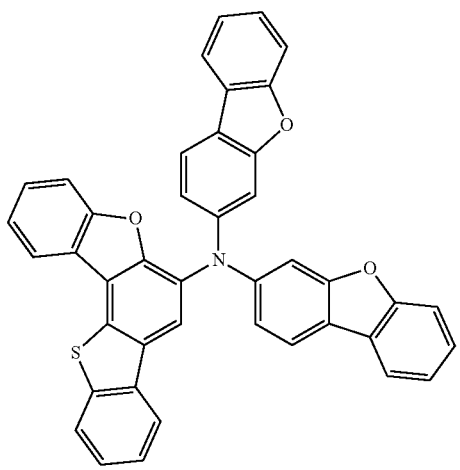

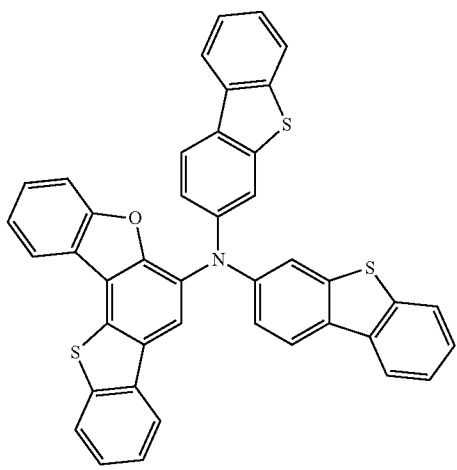
F28
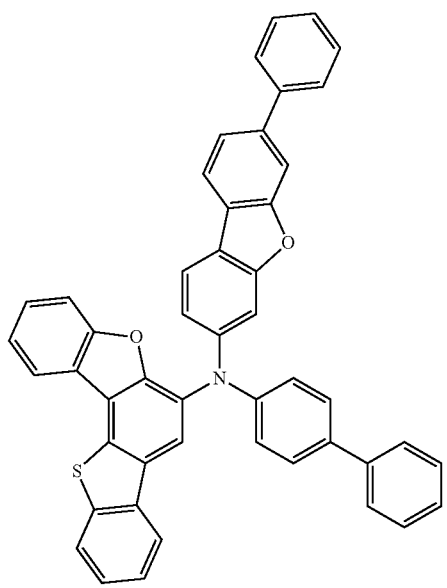
F29
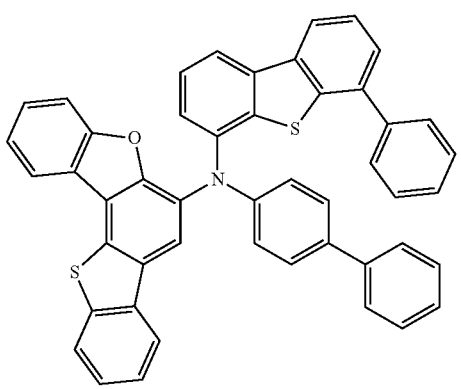
F30
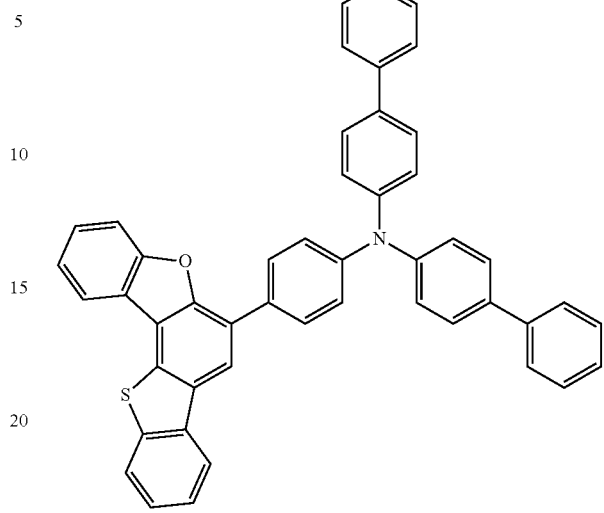
F31
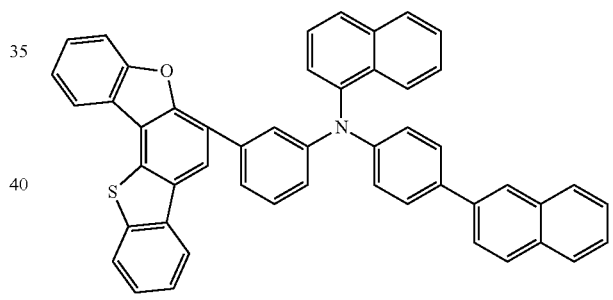
F32
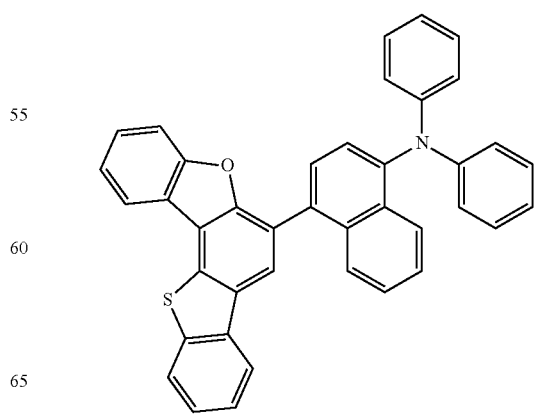
F33

237
-continued
F34
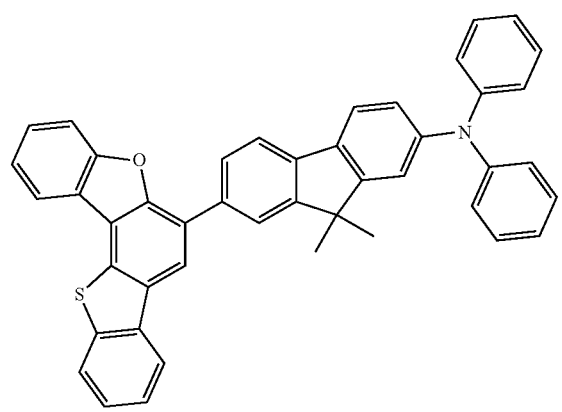
F35
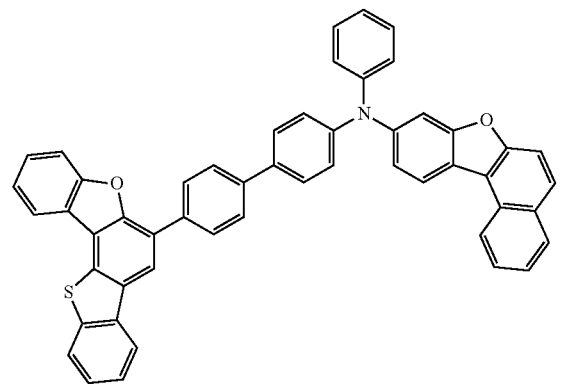
F36
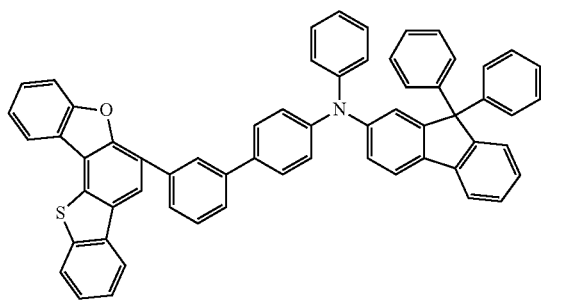
F37
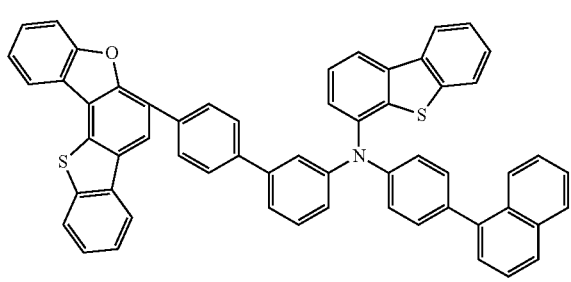
238
-continued
F38
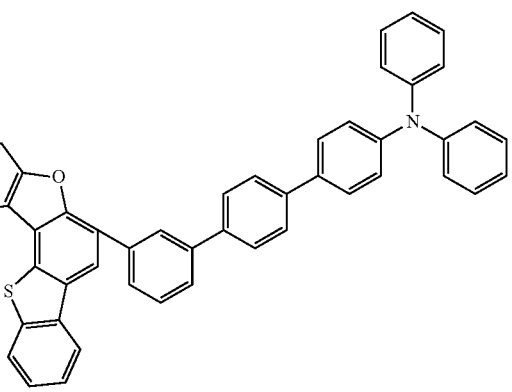
F39
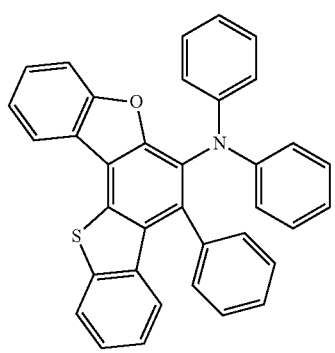
F40
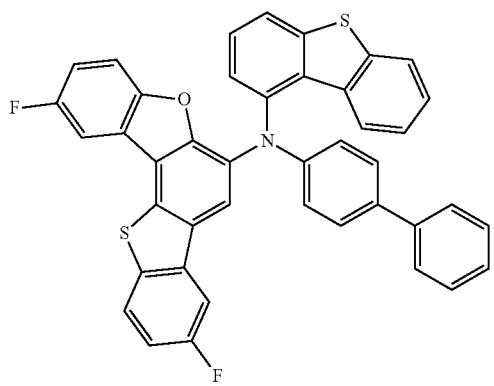

-continued

F41

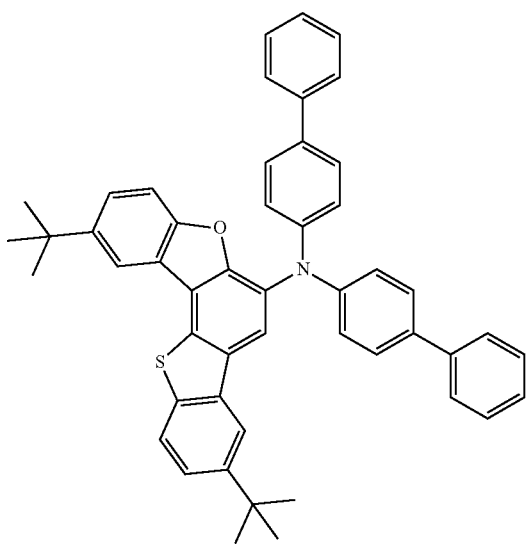

F42

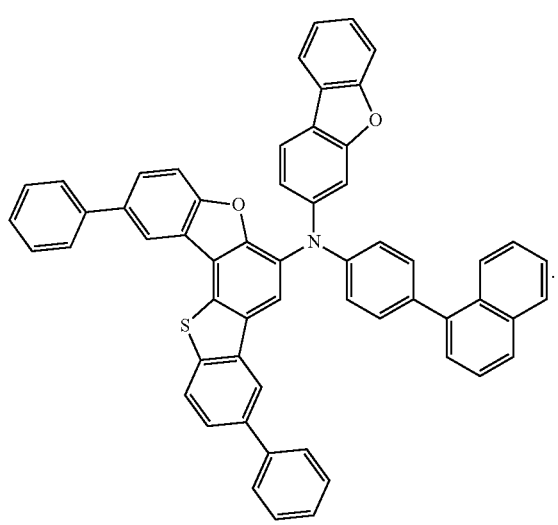

In the organic electroluminescence devices 10 shown in FIG. 1 to FIG. 4, the hole transport region HTR may include the amine compound represented by Formula 1 (e.g., the amine compound may be used as a material to form one or more layers in the hole transport region HTR). For example, a hole transport layer HTL may include the amine compound represented by Formula 1. However, embodiments of the present disclosure are not limited thereto. For example, the hole injection layer HIL of the hole transport region HTR may include the amine compound represented by Formula 1.

In some embodiments, the hole transport region HTR may include one kind (structure), or two or more kinds of the above-described amine compounds represented in Compound Group A to Compound Group F. The hole transport region HTR may further include any suitable material in the art, addition to the above-described amine compound.

The hole injection layer HIL may include, for example, a phthalocyanine compound (such as copper phthalocyanine), N,N'-diphenyl-N,N'-bis-[4-(phenyl-m-tolyl-amino)-phenyl]-biphenyl-4,4'-diamine (DNTPD), 4,4',4"-[tris(3-methylphenyl)phenylamino] triphenylamine (m-MTDATA), 4,4',4"-tris(N,N-diphenylamino)triphenylamine (TDATA), 4,4',4"-tris{N,-(2-naphthyl)-N-phenylamino}-triphenylamine (2-TNATA), poly(3,4-ethylene dioxythiophene)/poly(4-styrene sulfonate) (PEDOT/PSS), polyaniline/dodecylbenzene sulfonic acid (PANI/DBSA), polyaniline/camphor sulfonic acid (PANI/CSA), polyaniline/poly(4-styrene sulfonate) (PANI/PSS), N,N'-di(naphthalene-1-yl)-N,N'-diphenyl-benzidine (NPB), triphenylamine-containing polyether ketone (TPAPEK), 4-isopropyl-4'-methyldiphenyliodonium [tetrakis(pentafluorophenyl)borate], and/or dipyrazino[2,3-f:2',3'-h]quinoxaline-2,3,6,7,10,11-hexacarbonitrile (HAT-CN).

The hole transport layer HTL may include, for example, a carbazole derivative (such as N-phenyl carbazole and/or polyvinyl carbazole), a fluorene-based derivative, N,N'-bis (3-methylphenyl)-N,N'-diphenyl-[1,1-biphenyl]-4,4'-diamine (TPD), a triphenylamine-based derivative (such as 4,4',4"-tris(N-carbazolyl)triphenylamine (TCTA)), N,N'-di (1-naphthalene-1-yl)-N,N'-diphenyl-benzidine (NPB), 4,4'-cyclohexylidene bis[N,N-bis(4-methylphenyl)benzenamine (TAPC), 4,4'-bis[N,N'-(3-tolyl)amino]-3,3'-dimethylbiphenyl (HMTPD), 1,3-bis(N-carbazolyl)benzene (mCP), etc.

The thickness of the hole transport region HTR may be about 50 Å to about 10,000 Å, for example, about 100 Å to about 5,000 Å. The thickness of the hole injection region HIL may be, for example, about 30 Å to about 1,000 Å, and the thickness of the hole transport layer HTL may be about 30 Å to about 1,000 Å. For example, the thickness of the electron blocking layer EBL may be about 10 Å to about 1,000 Å. When the thicknesses of the hole transport region HTR, the hole injection layer HIL, the hole transport layer HTL, and the electron blocking layer EBL satisfy the above-described ranges, satisfactory hole transport properties may be achieved without substantial increase of a driving voltage.

The hole transport region HTR may further include a charge generating material in addition to the above-described materials to increase conductivity. The charge generating material may be dispersed substantially uniformly or non-uniformly in the hole transport region HTR. The charge generating material may be, for example, a p-dopant. The p-dopant may be selected from quinone derivatives, metal oxides, and cyano group-containing compounds, without limitation. Non-limiting examples of the p-dopant include quinone derivatives (such as tetracyanoquinodimethane (TCNQ) and/or 2,3,5,6-tetrafluoro-7,7',8,8'-tetracyanoquinodimethane (F4-TCNQ)), metal oxides (such as tungsten oxide and/or molybdenum oxide).

As described above, the hole transport region HTR may further include at least one of a hole buffer layer or an electron blocking layer EBL in addition to the hole injection layer HIL and the hole transport layer HTL. The hole buffer layer may compensate for an optical resonance distance of the wavelength of light emitted from an emission layer EML, and may thereby increase light emission efficiency. Materials that may be included in the hole transport region HTR may also be included in the hole buffer layer. The electron blocking layer EBL may prevent or reduce electron injection from the electron transport region ETR to the hole transport region HTR.

The emission layer EML is provided on the hole transport region HTR. The emission layer EML may have a thickness of, for example, about 100 Å to about 1,000 Å or about 100 Å to about 300 Å. The emission layer EML may have a single layer formed using a single material, a single layer formed using a plurality of different materials, or a multilayer structure having a plurality of layers formed using a plurality of different materials.

In the luminescence device 10 of an embodiment, the emission layer EML may include anthracene derivatives, pyrene derivatives, fluoranthene derivatives, chrysene derivatives, dihydrobenzanthracene derivatives, and/or triphenylene derivatives. For example, the emission layer EML may include anthracene derivatives or pyrene derivatives.

The emission layer EML may include an anthracene derivative represented by Formula 5:

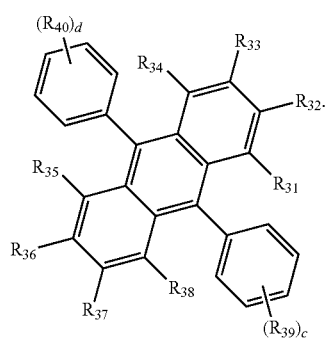

Formula 5

In the formula, $R_{31}$ to $R_{40}$ may each independently be a hydrogen atom, a deuterium atom, a halogen atom, a substituted or unsubstituted silyl group, a substituted or unsubstituted alkyl group of 1 to 10 carbon atoms, a substituted or unsubstituted aryl group of 6 to 30 carbon atoms for forming a ring, or a substituted or unsubstituted heteroaryl group of 2 to 30 carbon atoms for forming a ring, and/or combined with an adjacent group to form a ring. In some embodiments, $R_{31}$ to $R_{40}$ may be combined with an adjacent group to form a saturated hydrocarbon ring or an unsaturated hydrocarbon ring.

In Formula 5, "c" and "d" may each independently be an integer of 0 to 5.

Formula 5 may be represented by at least one among Compound G-1 to Compound G-16:

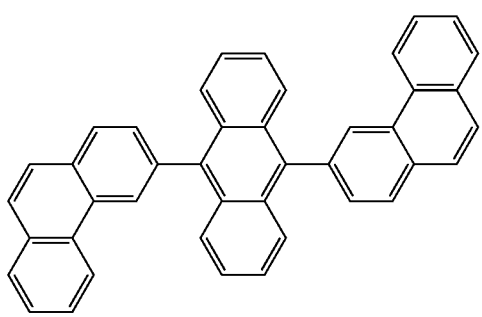

G-1

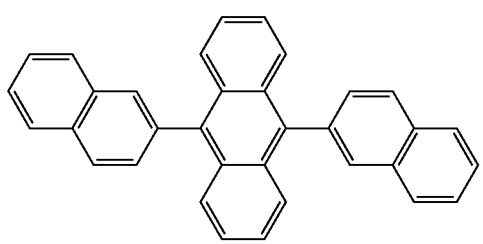

G-2

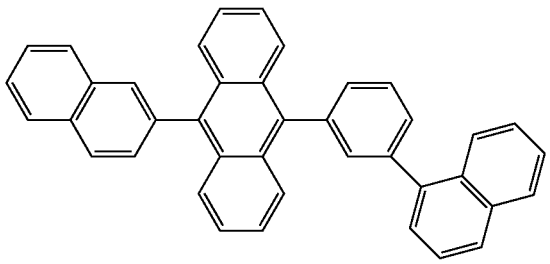

G-3

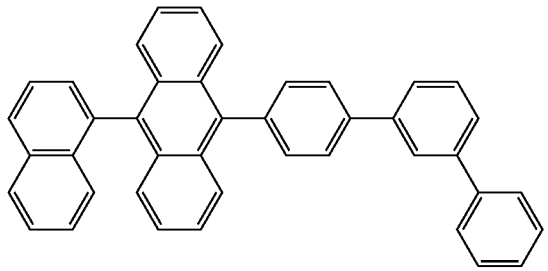

G-4

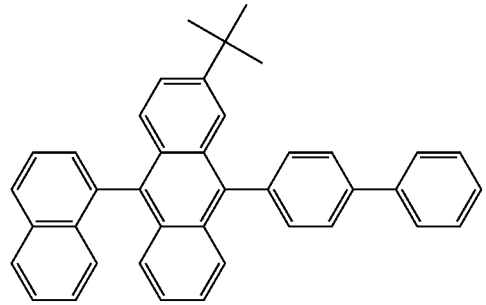

G-5

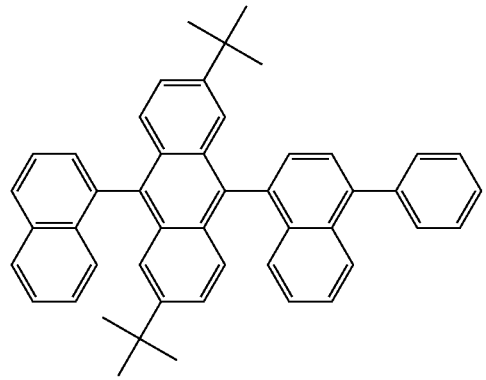

G-6

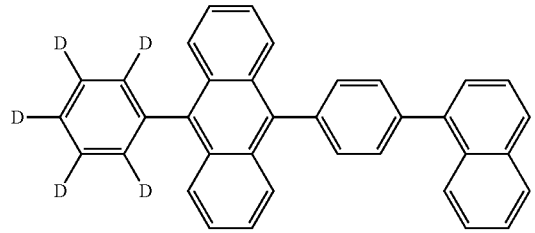

G-7

-continued

G-8
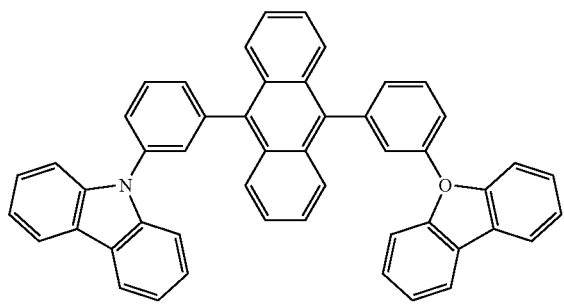

G-9
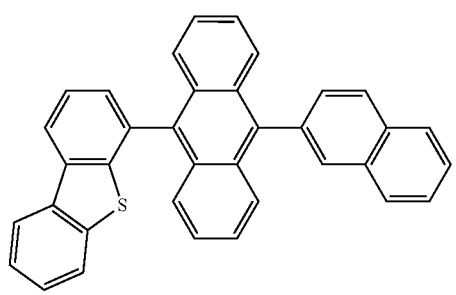

G-10
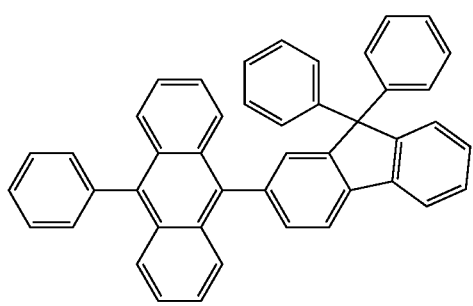

G-11
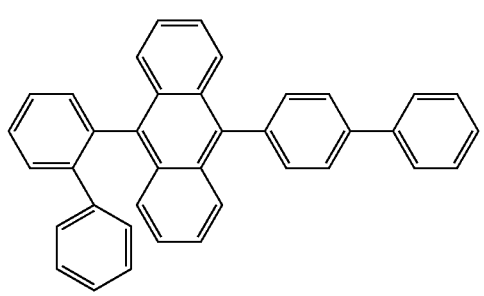

G-12
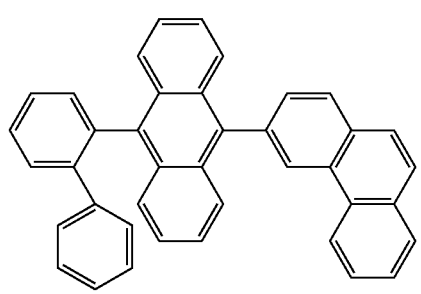

-continued

G-13
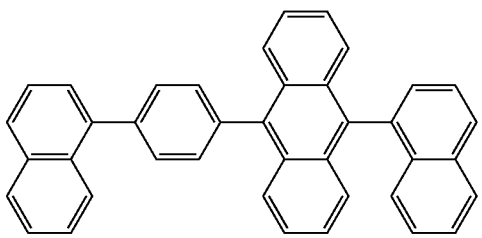

G-14
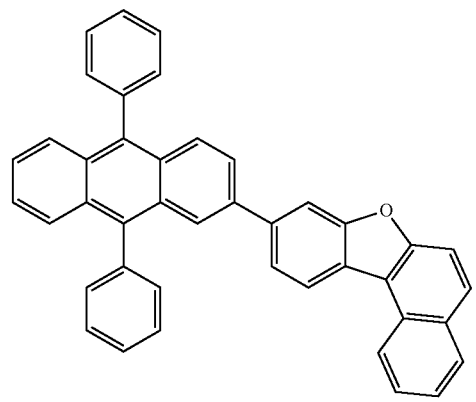

G-15
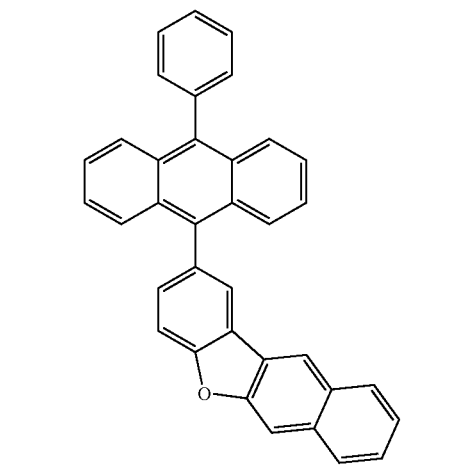

G-16
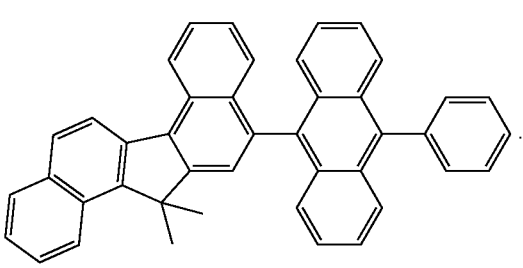

The emission layer EML may include any suitable materials available in the art as a host material. For example, the emission layer EML may include as the host material, at least one of bis[2-(diphenylphosphino)phenyl]ether oxide (DPEPO), 4,4'-bis(carbazol-9-yl)biphenyl (CBP), 1,3-bis(carbazol-9-yl)benzene (mCP), 2,8-bis(diphenylphosphoryl)dibenzo[b,d]furan (PPF), 4,4',4"-tris(carbazol-9-yl)triphenylamine (TcTa), or 1,3,5-tris(1-phenyl-1H-benz[d]imidazole-2-yl)benzene (TPBi). However, embodiments of the present disclosure are not limited thereto. For example, tris(8-hydroxyquinolino)aluminum (Alq$_3$), poly(N-vinylcarbazole) (PVK), 9,10-di(naphthalene-2-yl)anthracene (ADN), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), hexaphenyl cyclotriphosphazene (CP1), 1,4-bis(triphenylsilyl)benzene (UGH2), hexaphenylcyclotrisiloxane (DPSiO$_3$), octaphenylcyclotetrasiloxane (DPSiO$_4$), etc., may be used as the host material.

In an embodiment, the emission layer EML may further include any suitable dopant material, including styryl derivatives (for example, 1,4-bis[2-(3-N-ethylcarbazolyl)vinyl]benzene (BCzVB), 4-(di-p-tolylamino)-4'-[(di-p-tolylamino)styryl]stilbene (DPAVB), and/or N-(4-((E)-2-(6-((E)-4-(diphenylamino)styryl)naphthalen-2-yl)vinyl)phenyl)-N-phenylbenzenamine (N-BDAVBi)), perylene and/or derivatives thereof (for example, 2,5,8,11-tetra-t-butylperylene (TBP)), pyrene and/or derivatives thereof (for example, 1,1-dipyrene, 1,4-dipyrenylbenzene, 1,4-bis(N,N-diphenylamino)pyrene), etc.

The emission layer EML may include any suitable phosphorescent dopant material. For example, the phosphorescent dopant may use or be a metal complex including iridium (Ir), platinum (Pt), osmium (Os), gold (Au), titanium (Ti), zirconium (Zr), hafnium (Hf), europium (Eu), terbium (Tb) or thulium (Tm). In some embodiments, iridium(III) bis(4,6-difluorophenylpyridinato-N,C2' (FIrpic), iridium (III) bis(2,4-difluorophenylpyridinato (Fir6), and/or platinum octaethyl porphyrin (PtOEP) may be used as the phosphorescent dopant. However, embodiments of the present disclosure are not limited thereto.

In some embodiments, the emission layer EML may further include a phosphorescent host material, for example, bis(4-(9H-carbazol-9-yl)phenyl)diphenylsilane (BCPDS).

In the organic electroluminescence device 10 of an embodiment, as shown in FIGS. 1 to 4, the electron transport region ETR may be provided on the emission layer EML. The electron transport region ETR may include at least one of an electron blocking layer HBL, an electron transport layer ETL, or an electron injection layer EIL. However, embodiments of the present disclosure are not limited thereto.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of an electron injection layer EIL or an electron transport layer ETL, or a single layer structure formed using an electron injection material and an electron transport material. In some embodiments, the electron transport region ETR may have a single layer structure having a plurality of different materials, or a structure stacked from the emission layer EML of electron transport layer ETL/electron injection layer EIL, or hole blocking layer HBL/electron transport layer ETL/electron injection layer EIL, without limitation. The thickness of the electron transport region ETR may be, for example, about 1,000 Å to about 1,500 Å.

The electron transport region ETR may be formed using any suitable method (such as a vacuum deposition method, a spin coating method, a cast method, a Langmuir-Blodgett (LB) method, an inkjet printing method, a laser printing method, and/or a laser induced thermal imaging (LITI) method).

When the electron transport region ETR includes an electron transport layer ETL, the electron transport region ETR may include an anthracene-based compound. The electron transport region may include, for example, tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzimidazolyl-1-yl)phenyl)-9,10-dinaphthylanthracene, 1,3,5-tri(1-phenyl-1H-benz[d]imidazol-2-yl)benzene (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), beryllium bis(benzoquinolin-10-olate (Bebq2), 9,10-di(naphthalene-2-yl)anthracene (ADN), 1,3-bis[3,5-di(pyridine-3-yl)phenyl]benzene (BmPyPhB)), or a mixture thereof, without limitation. The thickness of the electron transport layer ETL may be about 100 Å to about 1,000 Å and may be, for example, about 150 Å to about 500 Å. When the thickness of the electron transport layer ETL satisfies the above-described range, satisfactory electron transport properties may be obtained without substantial increase of a driving voltage.

When the electron transport region ETR includes the electron injection layer EIL, the electron transport region ETR may include metal halides (such as LiF, NaCl, CsF, RbCl, RbI, and/or CuI), a lanthanide metal (such as ytterbium (Yb), or a metal oxide (such as Li$_2$O and/or BaO), or lithium quinolate (LiQ). However, embodiments of the present disclosure are not limited thereto. In some embodiments, the electron injection layer EIL may be formed using a mixture of an electron transport material and an insulating organo metal salt. The organo metal salt may be a material having an energy band gap of about 4 eV or more. For example, the organo metal salt may include metal acetates, metal benzoates, metal acetoacetates, metal acetylacetonates, and/or metal stearates. The thickness of the electron injection layer EIL may be about 1 Å to about 100 Å, and about 3 Å to about 90 Å. When the thickness of the electron injection layer EIL satisfies the above described range, satisfactory electron injection properties may be obtained without inducing substantial increase of a driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), or 4,7-diphenyl-1,10-phenanthroline (Bphen). However, embodiments of the present disclosure are not limited thereto.

The second electrode EL2 may be provided on the electron transport region ETR. The second electrode EL2 may be a common electrode or a cathode. The second electrode EL2 may be a transmissive electrode, a transflective electrode, or a reflective electrode. When the second electrode EL2 is a transmissive electrode, the second electrode EL2 may include a transparent metal oxide, for example, ITO, IZO, ZnO, ITZO, etc.

When the second electrode EL2 is a transflective electrode or a reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In some embodiments, the second electrode EL2 may have a multi-layered structure including a reflective layer or a transflective layer formed using the above-described materials and a transparent conductive layer formed using ITO, IZO, ZnO, ITZO, etc.

In some embodiments, the second electrode EL2 may be connected with an auxiliary electrode. When the second electrode EL2 is connected with the auxiliary electrode, the resistance of the second electrode EL2 may decrease.

In some embodiments, a capping layer (CPL) may be further disposed on the second electrode EL2 of the organic electroluminescence device 10 of an embodiment. The capping layer CPL may have a multilayer structure or a monolayer structure.

In an embodiment, the capping layer CPL may be an organic layer or an inorganic layer. For example, when the capping layer CPL includes an inorganic material, the inorganic material may include an alkali metal compound (such as LiF) and/or an alkaline earth metal compound (such as SiON, $SiN_x$, $SiO_y$, etc.)

For example, when the capping layer (CPL) includes an organic material, the organic material may include α-NPD, NPB, TPD, m-MTDATA, $Alq_3$, CuPc, N4,N4,N4',N4'-tetra (biphenyl-4-yl) biphenyl-4,4'-diamine (TPD15), 4,4',4"-tris (carbazol-9-yl) triphenylamine (TCTA), etc., or may include an epoxy resin, or an acrylate (such as methacrylate). However, embodiments of the present disclosure are not limited thereto, and in some embodiments, one or more of Compounds P1 to P5 may be included:

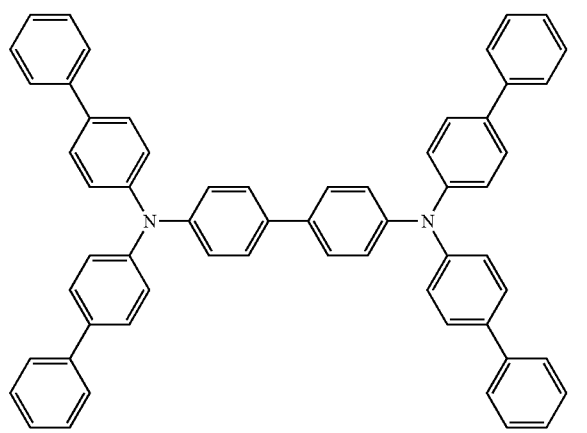

P1

P2

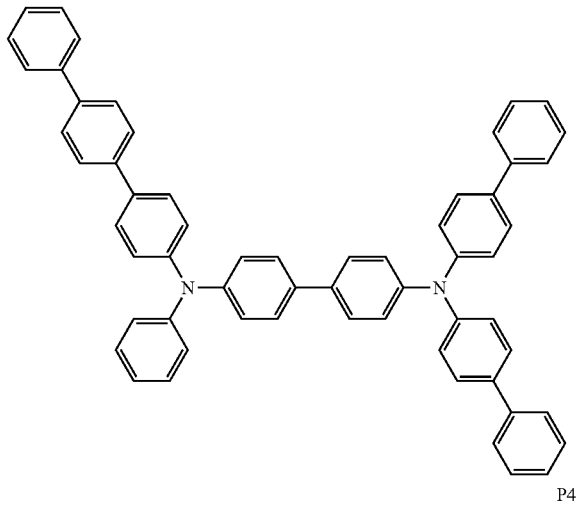

P3

P4

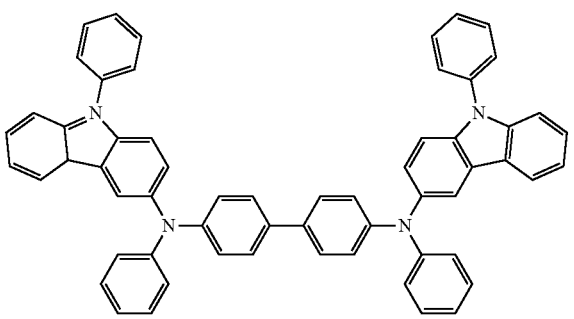

P5

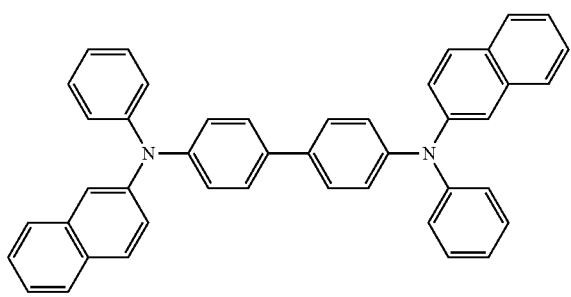

The organic electroluminescence device 10 according to an embodiment of the present disclosure includes the amine compound of an embodiment in the hole transport region HTR disposed between the first electrode EL1 and the second electrode EL2, and thereby exhibits improved emission efficiency in the blue and (to) green light-emitting wavelength region, and improved life span characteristics.

In some embodiments, the compound of an embodiment may be included in an organic layer other than the hole transport region HTR as a material for the organic electroluminescence device 10. For example, the organic electroluminescence device 10 according to an embodiment of the present disclosure may include the above-described amine compound in at least one functional layer disposed between the first electrode EL1 and the second electrode EL2, and/or in a capping layer CPL disposed on the second electrode EL2.

The amine compound of an embodiment includes a terphenyl group that is additionally crosslinked via two heteroatoms (e.g., three phenyl groups connected by two cross-linkages, each including a single bond and a heteroatom bond) and has a structure in which a nitrogen atom is substituted at a benzene ring in the middle of the terphenyl group (e.g., to the phenyl group in the middle), which structure enables the high efficiency and/or long-life characteristics of the organic electroluminescence device. Without being bound by the correctness of any theory or explanation, it is thought that the amine compound of an embodiment may have improved charge tolerance due to the crosslinked terphenyl group skeleton, improved hole transport properties along the whole molecule due to the two heteroatoms, and improved device life due to the amine group.

Hereinafter, the amine compound according to an embodiment and the organic electroluminescence device of an embodiment of the present disclosure will be explained in more detail with reference to embodiments and comparative embodiments. The following embodiments are only illustrations to assist the understanding of the present disclosure, and the scope of the present disclosure is not limited thereto.

A. Synthetic Examples

The amine compound according to an embodiment may be synthesized, for example, as follows. However, the synthetic method of the amine compound explained hereinafter is an embodiment, and the synthetic method of the amine compound according to an embodiment of the present disclosure is not limited thereto.

The molecular weight of each compound was measured by FAB-MS using JMS-700V of JEOL Co.

1. Synthesis of Compound A24

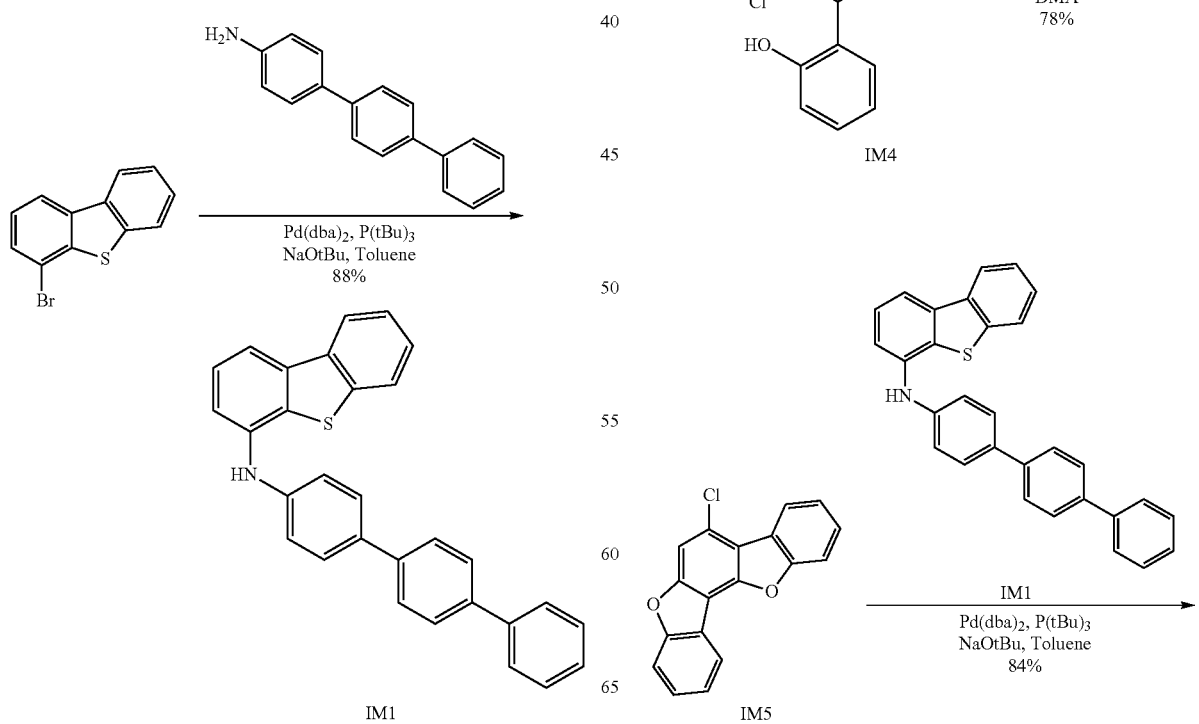
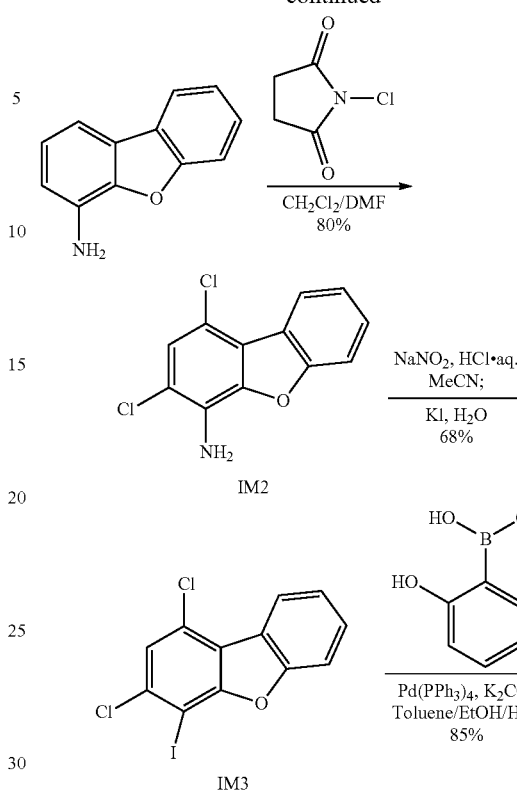
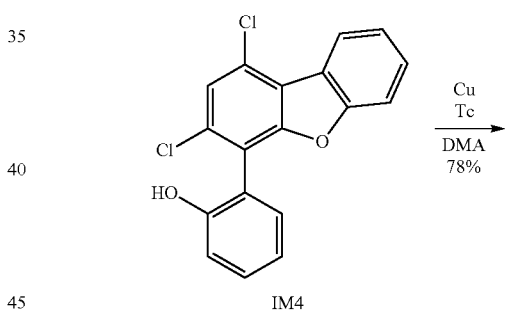
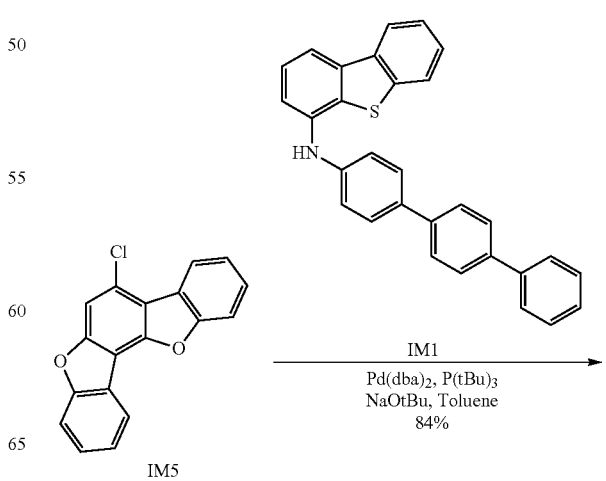

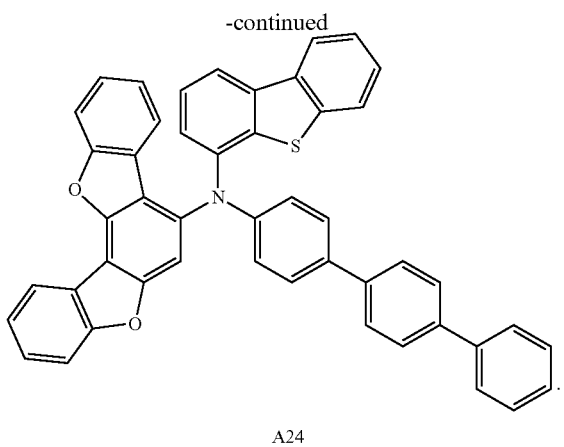

A24

Synthesis of Intermediate IM1

Under an Ar atmosphere, to a 2,000 mL three-neck flask, 23.00 g (87.40 mmol) of 4-bromodibenzothiophene, 2.51 g (0.05 eq, 4.37 mmol) of Pd(dba)$_2$, 8.40 g (1.0 eq, 87.40 mmol) of NaOtBu, 874 mL of toluene, 21.44 g (1.0 eq, 87.40 mmol) of 4-aminoterphenyl and 3.54 g (0.2 eq, 17.48 mmol) of $^t$Bu$_3$P were added in order, followed by heating, refluxing, and stirring. After cooling to room temperature, water was added to the reaction, and an organic layer was extracted. Toluene was added to an aqueous layer, and an organic layer was further extracted. The organic layers were collected, washed with a saline solution, and dried with MgSO$_4$. The MgSO$_4$ was separated by filtering, and the organic layer was concentrated. The crude product thus obtained was separated by silica gel column chromatography (using a mixture solvent of hexane and toluene as an eluent) to obtain Intermediate IM1 (32.89 g, yield 88%).

Synthesis of Intermediate IM2

Under an Ar atmosphere, to a 1,000 mL three neck flask, 30.00 g (163.75 mmol) of 4-aminodibenzofuran, 250 mL of CH$_2$Cl$_2$, and 250 mL of DMF were added, and then cooled in an ice bath. Then, 43.37 g (2.0 eq, 327.49 mmol) of N-chlorosuccinimide (NCS) was added thereto over about 30 minutes. After adding the reagent, the temperature was elevated to room temperature, and the reactants were stirred. After finishing the reaction, water and CH$_2$Cl$_2$ were added, and an organic layer was extracted. The organic layer was washed with a saline solution and dried with MgSO$_4$. The MgSO$_4$ was separated by filtering, and the organic layer was concentrated. The crude product thus obtained was washed with MeOH to obtain Intermediate IM2 (33.00 g, yield 80%).

By FAB-MS measurement, mass number of m/z=251 was observed as a molecular ion peak, and Intermediate IM2 was identified.

Synthesis of Intermediate IM3

Under an atmospheric atmosphere, to a 1,000 mL three-neck flask, 33.00 g (130.91 mmol) of IM2, 220 mL of a 10% HCl aqueous solution, and 420 mL of MeCN were added and then, cooled in an ice bath. 9.03 g (1.0 eq, 130.91 mmol) of NaNO$_2$ was added thereto over about 30 minutes. After adding the reagent, the reaction solution was put in a flask in which 43.46 g (2.0 eq, 261.81 mmol) of KI was dissolved in 50 mL of H$_2$O and cooled, and the temperature was allowed to reach room temperature, and then, the mixture was stirred. After the reaction was complete, water and CH$_2$Cl$_2$ were added, and an organic layer was extracted. The organic layer was washed with a saline solution and dried with MgSO$_4$. The MgSO$_4$ was separated by filtering, and the organic layer was concentrated. The crude product thus obtained was washed with EtOH to obtain Intermediate IM3 (32.31 g, yield 68%).

By FAB-MS measurement, mass number of m/z=362 was observed as a molecular ion peak, and Intermediate IM3 was identified.

Synthesis of Intermediate IM4

Under an Ar atmosphere, to a 1,000 mL three neck flask, 32.00 g (88.16 mmol) of IM3, 13.38 g (1.1 eq, 96.98 mmol) of 2-hydroxyphenylboronic acid, 36.55 g (3.0 eq, 264.5 mmol) of K$_2$CO$_3$, 5.09 g (0.05 eq, 4.41 mmol) of Pd(PPh$_3$)$_4$, and 600 mL of a mixture solution of toluene/EtOH/H$_2$O (mixing ratio of 4:2:1) were added in order, followed by heating to about 80° C. and stirring. After cooling to room temperature, the reaction solution was extracted with toluene. An aqueous layer was removed, and an organic layer was washed with a saturated saline solution and dried with MgSO$_4$. The MgSO$_4$ was separated by filtering, and the organic layer was concentrated. The crude product thus obtained was separated by silica gel column chromatography (using a mixture of hexane and toluene as an eluent) to obtain Intermediate IM4 (24.60 g, yield 85%).

By FAB-MS measurement, mass number of m/z=328 was observed as a molecular ion peak, and Intermediate IM4 was identified.

Synthesis of Intermediate IM5

Under an Ar atmosphere, to a 500 mL three neck flask, 24.60 g (74.73 mmol) of IM4, 14.25 g (1.0 eq, 74.73 mmol) of 2-thiophenecarboxylato-copper, and 250 mL of dimethylamine (DMA) were added in order, followed by heating and refluxing. After cooling to room temperature, ammonia water was added, and the reaction solution was extracted with CH$_2$Cl$_2$. An aqueous layer was removed, and an organic layer was washed with a saturated saline solution and dried with MgSO$_4$. The MgSO$_4$ was separated by filtering, and the organic layer was concentrated. The crude product thus obtained was separated by silica gel column chromatography (using a mixture of hexane and toluene as an eluent) to obtain Intermediate IM5 (17.06 g, yield 78%).

By FAB-MS measurement, mass number of m/z=294 was observed as a molecular ion peak, and Intermediate IM5 was identified.

Synthesis of Compound A24

Under an Ar atmosphere, to a 1,000 mL three neck flask, 17.00 g (58.08 mmol) of Intermediate IM5, 1.67 g (0.05 eq, 2.90 mmol) of Pd(dba)$_2$, 5.58 g (1.0 eq, 58.08 mmol) of NaOtBu, 580 mL of toluene, 24.83 g (1.0 eq, 58.08 mmol) of Intermediate IM1, and 2.35 g (0.2 eq, 11.62 mmol) of $^t$Bu$_3$P were added in order, followed by heating, refluxing, and stirring. After cooling to room temperature, water was added to the reaction solution, and an organic layer was extracted. Toluene was added to an aqueous layer, and an organic layer was further extracted. The organic layers were collected, washed with a saline solution, and dried with MgSO$_4$. The MgSO$_4$ was separated by filtering, and the organic layer was concentrated. The crude product thus obtained was separated by silica gel column chromatography (using a mixture solvent of hexane and toluene as an eluent) to obtain Compound A24 (33.3 g, yield 84%).

By FAB-MS measurement, mass number of m/z=683 was observed as a molecular ion peak, and Compound A24 was identified.

2. Synthesis of Compound A31

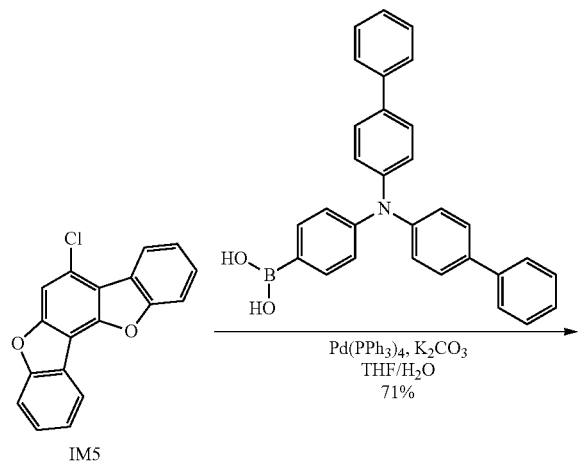

IM5

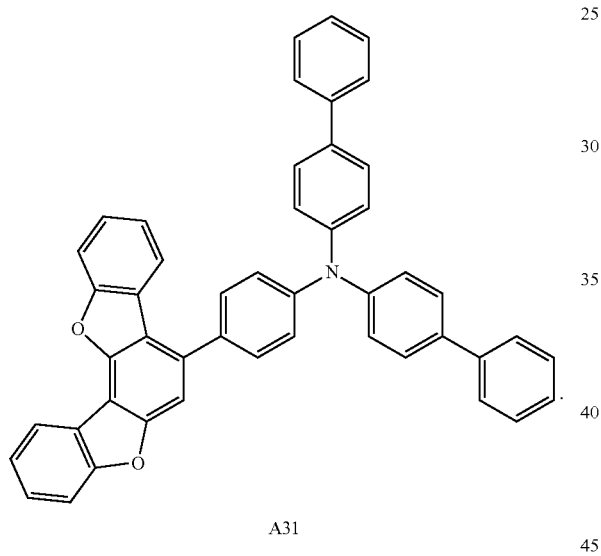

A31

Synthesis of Compound A31

Under an Ar atmosphere, to a 300 mL three neck flask, 5.00 g (17.08 mmol) of IM5, 9.04 g (1.2 eq, 20.50 mmol) of [4-[di([1,1'-biphenyl]-4-yl)amino]phenyl]boronic acid, 7.08 g (3.0 eq, 51.2 mmol) of $K_2CO_3$, 0.99 g (0.05 eq, 0.85 mmol) of $Pd(PPh_3)_4$, and 120 mL of a mixture of toluene/EtOH/$H_2O$ (mixing ratio of 4:2:1) were added in order, followed by heating to about 80° C. and stirring. After cooling to room temperature, the reaction solution was extracted with toluene. An aqueous layer was removed, and an organic layer was washed with a saturated saline solution and dried with $MgSO_4$. The $MgSO_4$ was separated by filtering, and the organic layer was concentrated. The crude product thus obtained was separated by silica gel column chromatography (using a mixture solvent of hexane and toluene as an eluent) to obtain Compound A31 (7.93 g, yield 71%).

By FAB-MS measurement, mass number of m/z=653 was observed as a molecular ion peak, and Compound A31 was identified.

3. Synthesis of Compound A48

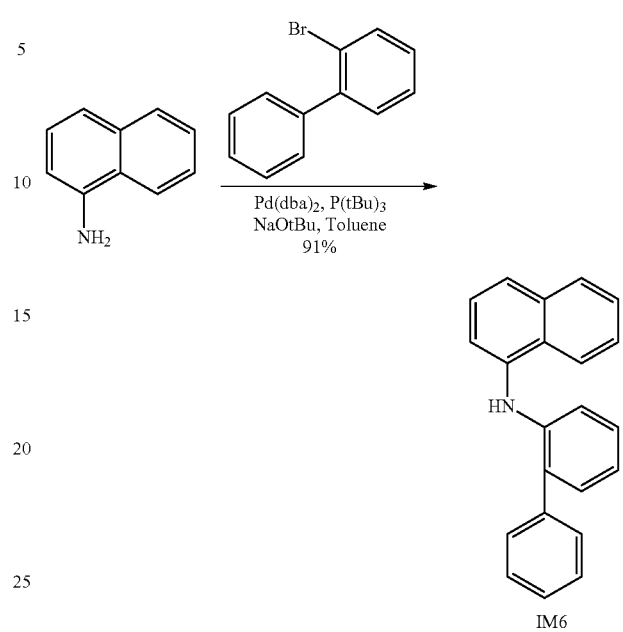

IM6

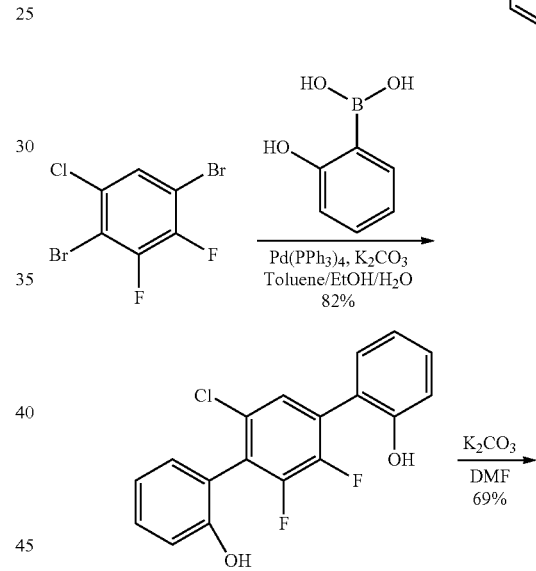

IM7

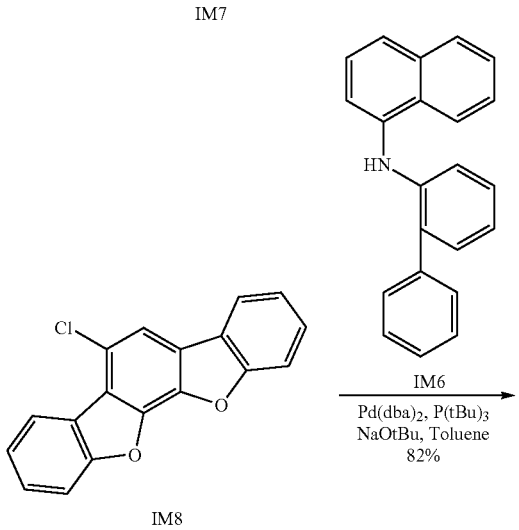

IM8

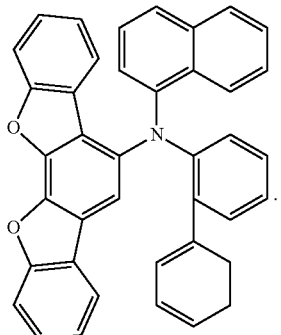

A48

Synthesis of Intermediate IM6

Under an Ar atmosphere, to a 2,000 mL three neck flask, 20.00 g (139.467 mmol) of 1-aminonaphthalene, 4.02 g (0.05 eq, 6.98 mmol) of Pd(dba)$_2$, 13.42 g (1.0 eq, 139.67 mmol) of NaOtBu, 1.4 L of toluene, 32.56 g (1.0 eq, 139.67 mmol) of 2-bromobiphenyl, and 5.65 g (0.2 eq, 27.93 mmol) of $^t$Bu$_3$P were added in order, followed by heating, refluxing, and stirring. After cooling to room temperature, water was added to the reaction solution, and an organic layer was extracted. Toluene was added to an aqueous layer, and an organic layer was further extracted. The organic layers were collected, washed with a saline solution and dried with MgSO$_4$. The MgSO$_4$ was separated by filtering, and the organic layer was concentrated. The crude product thus obtained was separated by silica gel column chromatography (using a mixture of hexane and toluene as an eluent) to obtain Intermediate IM6 (43.18 g, yield 91%).

By FAB-MS measurement, mass number of m/z=295 was observed as a molecular ion peak, and Intermediate IM6 was identified.

Synthesis of Intermediate IM7

Under an Ar atmosphere, to a 1,000 mL three neck flask, 20.00 g (65.29 mmol) of 1,4-dibromo-5-chloro-2,3-difluorobenzene, 10.80 g (1.2 eq, 78.35 mmol) of 2-hydroxyphenylboronic acid, 27.07 g (3.0 eq, 195.9 mmol) of K$_2$CO$_3$, 3.77 g (0.05 eq, 3.26 mmol) of Pd(PPh$_3$)$_4$, and 500 mL of a mixture of toluene/EtOH/H$_2$O (mixing ratio of 4:2:1) were added in order, followed by heating to about 80° C. and stirring. After cooling to room temperature, the reaction solution was extracted with toluene. An aqueous layer was removed, and an organic layer was washed with a saturated saline solution and dried with MgSO$_4$. The MgSO$_4$ was separated by filtering, and the organic layer was concentrated. The crude product thus obtained was separated by silica gel column chromatography (using a mixture solvent of hexane and toluene as an eluent) to obtain Intermediate IM7 (17.81 g, yield 82%).

By FAB-MS measurement, mass number of m/z=332 was observed as a molecular ion peak, and Intermediate IM7 was identified.

Synthesis of Intermediate IM8

Under an Ar atmosphere, to a 500 mL three neck flask, 17.81 g (53.53 mmol) of IM7, 14.80 g (2.0 eq, 107.1 mmol) of K$_2$CO$_3$, and 180 mL of dimethylformamide (DMF) were added in order, followed by heating and refluxing. After cooling to room temperature, water was added, and the reaction solution was extracted with CH$_2$Cl$_2$. An aqueous layer was removed, and an organic layer was washed with a saturated saline solution and dried with MgSO$_4$. The MgSO$_4$ was separated by filtering, and the organic layer was concentrated. The crude product thus obtained was separated by silica gel column chromatography (using a mixture solvent of hexane and toluene as an eluent) to obtain Intermediate IM8 (10.78 g, yield 69%).

By FAB-MS measurement, mass number of m/z=292 was observed as a molecular ion peak, and Intermediate IM8 was identified.

Synthesis of Compound A48

Under an Ar atmosphere, to a 300 mL three neck flask, 5.00 g (17.08 mmol) of Intermediate IM8, 0.49 g (0.05 eq, 0.85 mmol) of Pd(dba)$_2$, 1.64 g (1.0 eq, 17.08 mmol) of NaOtBu, 170 mL of toluene, 5.05 g (1.0 eq, 17.08 mmol) of Intermediate IM6, and 0.69 g (0.2 eq, 3.42 mmol) of $^t$Bu$_3$P were added in order, followed by heating, refluxing, and stirring. After cooling to room temperature, water was added to the reaction solution, and an organic layer was extracted. Toluene was added to an aqueous layer, and an organic layer was further extracted. The organic layers were collected, washed with a saline solution and dried with MgSO$_4$. The MgSO$_4$ was separated by filtering, and the organic layer was concentrated. The crude product thus obtained was separated by silica gel column chromatography (using a mixture solvent of hexane and toluene as an eluent) to obtain Compound A48 (7.73 g, yield 82%).

By FAB-MS measurement, mass number of m/z=551 was observed as a molecular ion peak, and Compound A48 was identified.

4. Synthesis of Compound A76

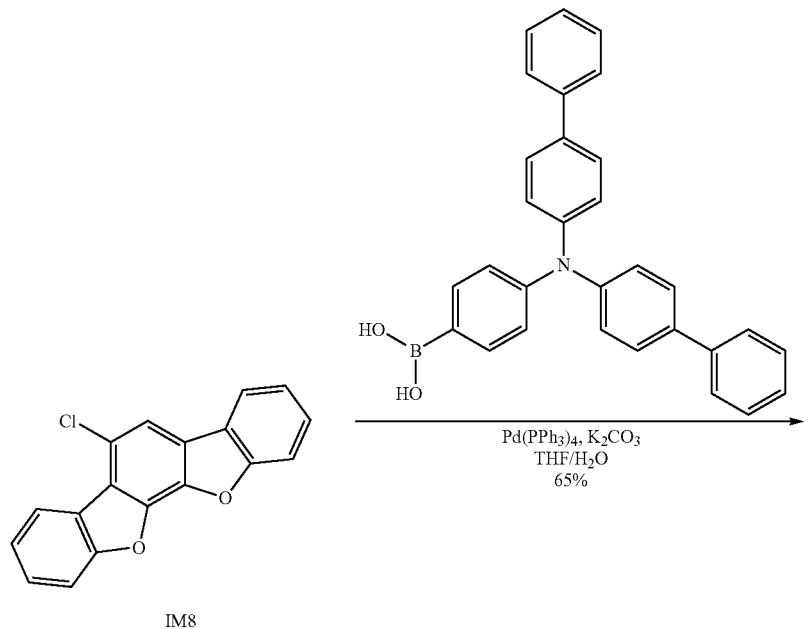

IM8

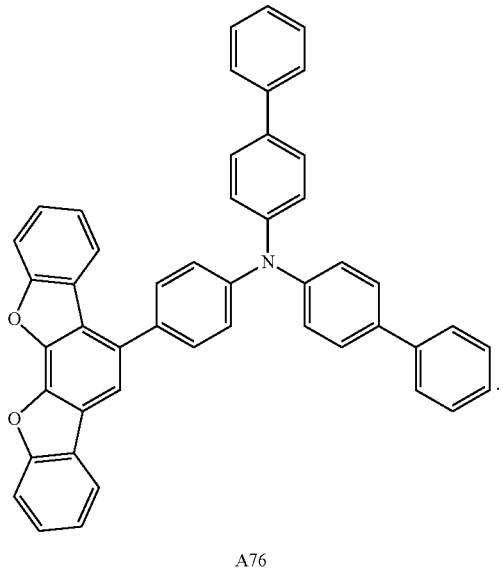

A76

Under an Ar atmosphere, to a 300 mL three neck flask, 5.00 g (17.08 mmol) of IM8, 9.04 g (1.2 eq, 20.50 mmol) of [4-[di([1,1'-biphenyl]-4-yl)amino]phenyl]boronic acid, 7.08 g (3.0 eq, 51.2 mmol) of $K_2CO_3$, 0.99 g (0.05 eq, 0.85 mmol) of $Pd(PPh_3)_4$, and 120 mL of a mixture solution of toluene/EtOH/$H_2O$ (mixing ratio of 4:2:1) were added in order, followed by heating to about 80° C. and stirring. After cooling to room temperature, the reaction solution was extracted with toluene. An aqueous layer was removed, and an organic layer was washed with a saturated saline solution and dried with $MgSO_4$. The $MgSO_4$ was separated by filtering, and the organic layer was concentrated. The crude product thus obtained was separated by silica gel column chromatography (using a mixture solvent of hexane and toluene as an eluent) to obtain Compound A76 (7.22 g, yield 65%).

By FAB-MS measurement, mass number of m/z=653 was observed as a molecular ion peak, and Compound A76 was identified.

5. Synthesis of Compound A113

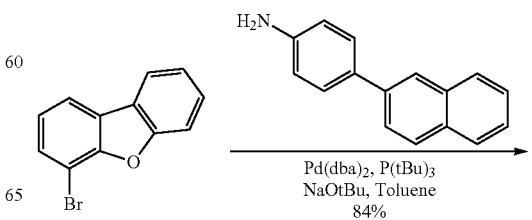

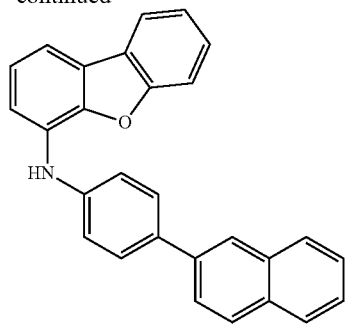

IM9

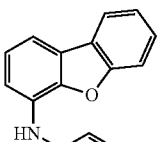

IM9
Pd(dba)₂, P(tBu)₃
NaOtBu, Toluene
80%

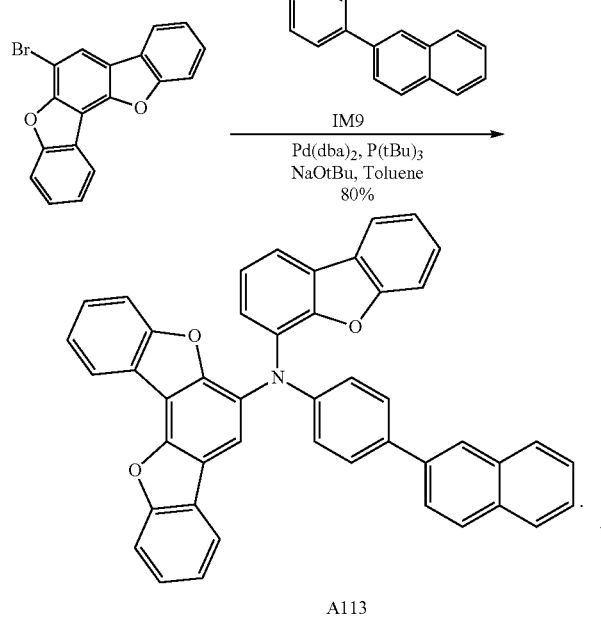

A113

Synthesis of Intermediate IM9

Under an Ar atmosphere, to a 1,000 mL three neck flask, 15.00 g (60.71 mmol) of 4-bromodibenzofuran, 1.75 g (0.05 eq, 3.04 mmol) of Pd(dba)₂, 5.83 g (1.0 eq, 60.71 mmol) of NaO$^t$Bu, 600 mL of toluene, 13.31 g (1.0 eq, 60.71 mmol) of 4-(naphthalen-2-yl)aniline, and 2.46 g (0.2 eq, 12.14 mmol) of $^t$Bu₃P were added in order, followed by heating, refluxing, and stirring. After cooling to room temperature, water was added to the reaction solution, and an organic layer was extracted. Toluene was added to an aqueous layer, and an organic layer was further extracted. The organic layers were collected, washed with a saline solution and dried with MgSO₄. The MgSO₄ was separated by filtering, and the organic layer was concentrated. The crude product thus obtained was separated by silica gel column chromatography (using a mixture solvent of hexane and toluene as an eluent) to obtain Intermediate IM9 (19.69 g, yield 84%).

By FAB-MS measurement, mass number of m/z=385 was observed as a molecular ion peak, and Intermediate IM9 was identified.

Synthesis of Compound A113

Under an Ar atmosphere, to a 500 mL three neck flask, 15.00 g (29.66 mmol) of 6-bromobenzo[1,2-b:3,4-b']bisbenzofuran, 0.85 g (0.05 eq, 1.5 mmol) of Pd(dba)₂, 2.85 g (1.0 eq, 29.66 mmol) of NaO$^t$Bu, 300 mL of toluene, 11.43 g (1.0 eq, 29.66 mmol) of Intermediate IM9, and 1.20 g (0.2 eq, 5.93 mmol) of $^t$Bu₃P were added in order, followed by heating, refluxing, and stirring. After cooling to room temperature, water was added to the reaction solution, and an organic layer was extracted. Toluene was added to an aqueous layer, and an organic layer was further extracted. The organic layers were collected, washed with a saline solution and dried with MgSO₄. The MgSO₄ was separated by filtering, and the organic layer was concentrated. The crude product thus obtained was separated by silica gel column chromatography (using a mixture of hexane and toluene as an eluent) to obtain Compound A113 (15.23 g, yield 80%).

By FAB-MS measurement, mass number of m/z=641 was observed as a molecular ion peak, and Compound A113 was identified.

6. Synthesis of Compound A121

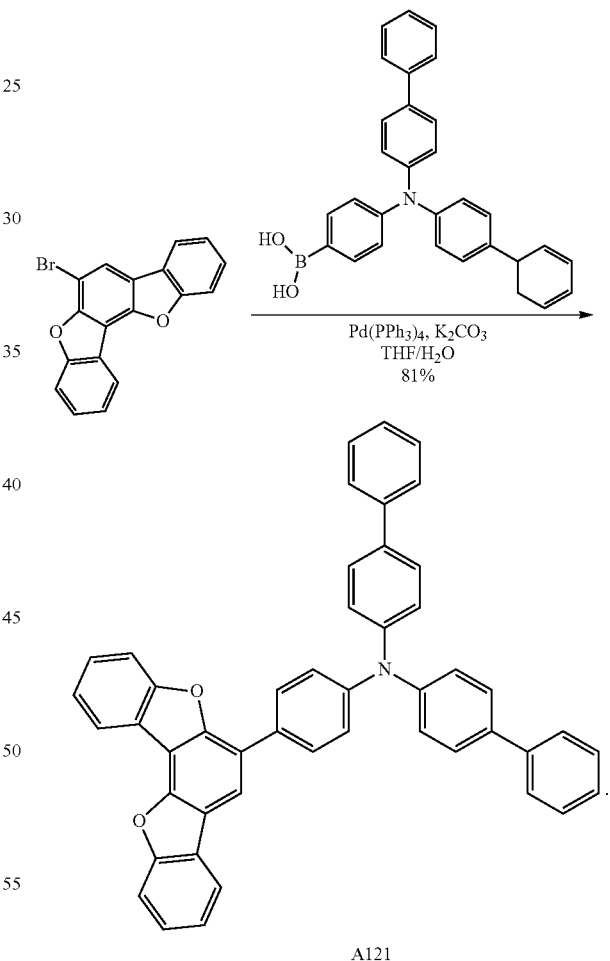

A121

Under an Ar atmosphere, to a 500 mL three neck flask, 10.00 g (29.66 mmol) of 6-bromobenzo[1,2-b:3,4-b']bisbenzofuran, 15.70 g (1.2 eq, 35.59 mmol) of [4-[di([1,1'-biphenyl]-4-yl)amino]phenyl]boronic acid, 12.30 g (3.0 eq, 88.98 mmol) of K₂CO₃, 1.71 g (0.05 eq, 1.48 mmol) of Pd(PPh₃)₄, and 200 mL of a mixture of toluene/EtOH/H₂O (mixing ratio of 4:2:1) were added in order, followed by heating to about 80° C. and stirring. After cooling to room temperature, the reaction solution was extracted with toluene. An aqueous layer was removed, and an organic layer was washed with a saturated saline solution and dried with MgSO$_4$. The MgSO$_4$ was separated by filtering, and the organic layer was concentrated. The crude product thus obtained was separated by silica gel column chromatography (using a mixture solvent of hexane and toluene as an eluent) to obtain Compound A121 (15.70 g, yield 81%).

By FAB-MS measurement, mass number of m/z=653 was observed as a molecular ion peak, and Compound A121 was identified.

7. Synthesis of Compound B27

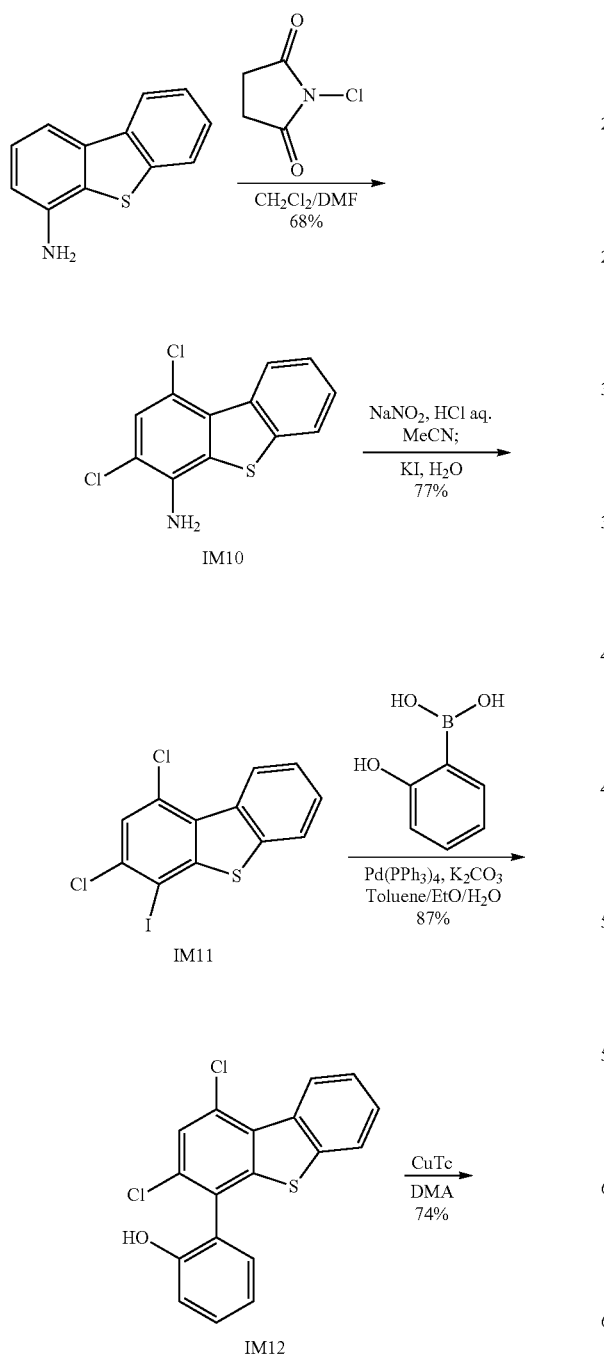

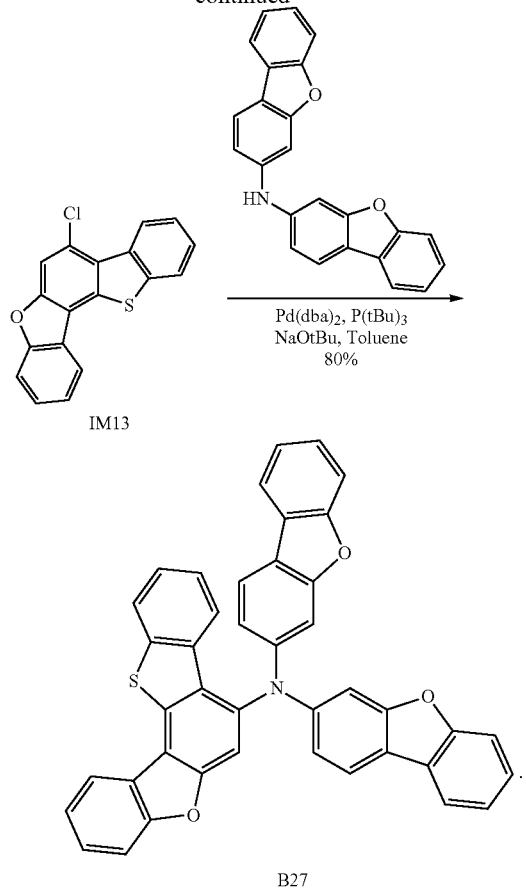

Synthesis of Intermediate IM10

Under an Ar atmosphere, to a 1,000 mL three neck flask, 30.00 g (150.55 mmol) of 4-aminodibenzothiophene, 230 mL of CH$_2$Cl$_2$, and 230 mL of DMF were added, and then cooled in an ice bath. Then, 40.21 g (2.0 eq, 301.10 mmol) of NCS was added thereto over about 30 minutes. After adding the reagent, the temperature was elevated to room temperature, and the reactants were stirred. After the reaction was complete, water and CH$_2$Cl$_2$ were added, and an organic layer was extracted. The organic layer was washed with a saline solution and dried with MgSO$_4$. The MgSO$_4$ was separated by filtering, and the organic layer was concentrated. The crude product thus obtained was washed with MeOH to obtain Intermediate IM10 (27.45 g, yield 68%).

By FAB-MS measurement, mass number of m/z=267 was observed as a molecular ion peak, and Intermediate IM10 was identified.

Synthesis of Intermediate IM11

Under an atmospheric atmosphere, to a 1,000 mL three-neck flask, 27.45 g (102.36 mmol) of IM10, 170 mL of a 10% HCl aqueous solution, and 340 mL of MeCN were added and then, cooled in an ice bath. 7.06 g (1.0 eq, 102.36 mmol) of NaNO$_2$ was added thereto over about 30 minutes. After adding the reagent, the reaction solution was put in a flask in which 33.98 g (2.0 eq, 204.73 mmol) of KI was dissolved in 50 mL of H$_2$O and cooled, and the temperature was elevated to room temperature, and then, the mixture was stirred. After finishing the reaction, water and CH$_2$Cl$_2$ were added, and an organic layer was extracted. The organic layer was washed with a saline solution and dried with MgSO$_4$. The MgSO$_4$ was separated by filtering, and the organic layer was concentrated. The crude product thus obtained was washed with EtOH to obtain Intermediate IM11 (29.88 g, yield 77%).

By FAB-MS measurement, mass number of m/z=378 was observed as a molecular ion peak, and Intermediate IM11 was identified.

Synthesis of Intermediate IM12

Under an Ar atmosphere, to a 1,000 mL three neck flask, 29.88 g (78.83 mmol) of IM11, 11.96 g (1.1 eq, 86.71 mmol) of 2-hydroxyphenylboronic acid, 32.69 g (3.0 eq, 236.5 mmol) of K$_2$CO$_3$, 4.55 g (0.05 eq, 3.94 mmol) of Pd(PPh$_3$)$_4$, 550 mL of a mixture of toluene/EtOH/H$_2$O (mixing ratio of 4:2:1) were added in order, followed by heating to about 80° C. and stirring. After cooling to room temperature, the reaction solution was extracted with toluene. An aqueous layer was removed, and an organic layer was washed with a saturated saline solution and dried with MgSO$_4$. The MgSO$_4$ was separated by filtering, and the organic layer was concentrated. The crude product thus obtained was separated by silica gel column chromatography (using a mixture solvent of hexane and toluene as an eluent) to obtain Intermediate IM12 (23.68 g, yield 87%).

By FAB-MS measurement, mass number of m/z=344 was observed as a molecular ion peak, and Intermediate IM12 was identified.

Synthesis of Intermediate IM13

Under an Ar atmosphere, to a 500 mL three neck flask, 23.68 g (68.59 mmol) of IM12, 13.08 g (1.0 eq, 68.59 mmol) of 2-thiophenecarboxylato-copper, and 240 mL of DMA were added in order, followed by heating and refluxing. After cooling to room temperature, ammonia water was added, and the reaction solution was extracted with CH$_2$Cl$_2$. An aqueous layer was removed, and an organic layer was washed with a saturated saline solution and dried with MgSO$_4$. The MgSO$_4$ was separated by filtering, and the organic layer was concentrated. The crude product thus obtained was separated by silica gel column chromatography (using a mixture solvent of hexane and toluene as an eluent) to obtain Intermediate IM13 (15.67 g, yield 74%).

By FAB-MS measurement, mass number of m/z=308 was observed as a molecular ion peak, and Intermediate IM13 was identified.

Synthesis of Compound B27

Under an Ar atmosphere, to a 1,000 mL three neck flask, 11.32 g (32.39 mmol) of bis(dibenzofuran-3-yl)amine, 0.93 g (0.05 eq, 1.6 mmol) of Pd(dba)$_2$, 3.11 g (1.0 eq, 32.4 mmol) of NaO$^t$Bu, 320 mL of toluene, 10.00 g (1.0 eq, 32.39 mmol) of Intermediate IM13, and 1.31 g (0.2 eq, 6.48 mmol) of $^t$Bu$_3$P were added in order, followed by heating, refluxing, and stirring. After cooling to room temperature, water was added to a reaction solvent, and an organic layer was extracted. Toluene was added to an aqueous layer, and an organic layer was further extracted. The organic layers were collected, washed with a saline solution, and dried with MgSO$_4$. The MgSO$_4$ was separated by filtering, and the organic layer was concentrated. The crude product thus obtained was separated by silica gel column chromatography (using a mixture of hexane and toluene as an eluent) to obtain Compound B27 (16.11 g, yield 80%).

By FAB-MS measurement, mass number of m/z=621 was observed as a molecular ion peak, and Compound B27 was identified.

8. Synthesis of Compound C19

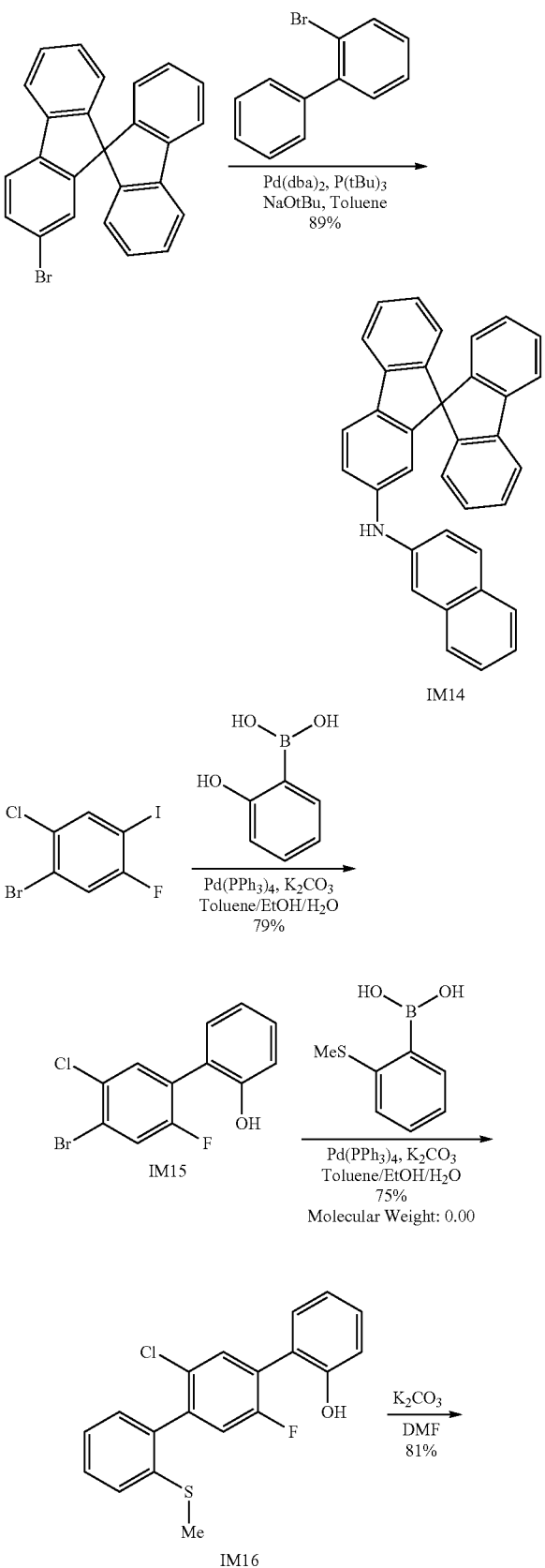

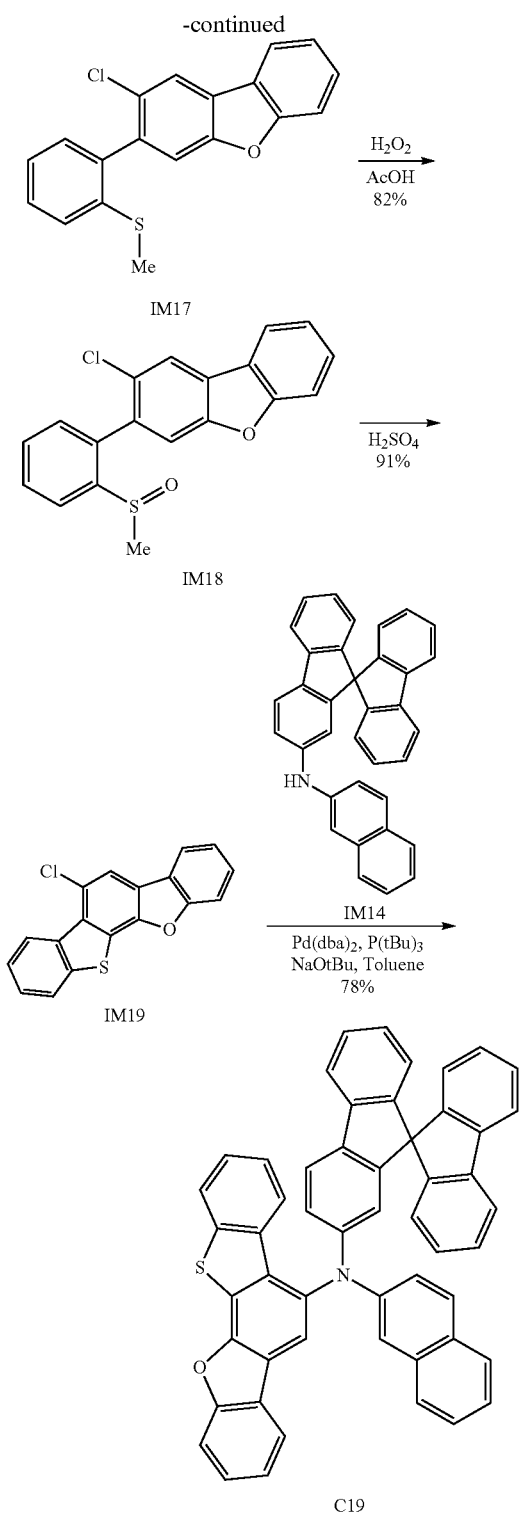

Synthesis of Intermediate IM14

Under an Ar atmosphere, to a 1,000 mL three neck flask, 15.00 g (37.95 mmol) of 2-bromo-9,9'-spirobifluorene, 1.09 g (0.05 eq, 1.90 mmol) of Pd(dba)$_2$, 3.65 g (1.0 eq, 37.95 mmol) of NaO$^t$Bu, 380 mL of toluene, 8.85 g (1.0 eq, 37.95 mmol) of 2-bromo-1,1'-biphenyl, and 1.54 g (0.2 eq, 7.59 mmol) of $^t$Bu$_3$P were added in order, followed by heating, refluxing, and stirring. After cooling to room temperature, water was added to the reaction solution, and an organic layer was extracted. Toluene was added to an aqueous layer, and an organic layer was further extracted. The organic layers were collected, washed with a saline solution, and dried with MgSO$_4$. MgSO$_4$ was separated by filtering, and the organic layer was concentrated. The crude product thus obtained was separated by silica gel column chromatography (using a mixture of hexane and toluene as an eluent) to obtain Intermediate IM14 (15.55 g, yield 89%).

By FAB-MS measurement, mass number of m/z=457 was observed as a molecular ion peak, and Intermediate IM14 was identified.

Synthesis of Intermediate IM15

Under an Ar atmosphere, to a 1,000 mL three neck flask, 20.00 g (59.64 mmol) of 1-bromo-2-chloro-5-fluoro-4-iodobenzene, 9.87 g (1.2 eq, 71.57 mmol) of 2-hydroxyphenylboronic acid, 24.73 g (3.0 eq, 178.9 mmol) of K$_2$CO$_3$, 3.45 g (0.05 eq, 2.98 mmol) of Pd(PPh$_3$)$_4$, and 420 mL of a mixture of toluene/EtOH/H$_2$O (mixing ratio of 4:2:1) were added in order, followed by heating to about 80° C. and stirring. After cooling to room temperature, the reaction solution was extracted with toluene. An aqueous layer was removed, and an organic layer was washed with a saturated saline solution and dried with MgSO$_4$. The MgSO$_4$ was separated by filtering, and the organic layer was concentrated. The crude product thus obtained was separated by silica gel column chromatography (using a mixture of hexane and toluene as an eluent) to obtain Intermediate IM15 (14.25 g, yield 79%).

By FAB-MS measurement, mass number of m/z=300 was observed as a molecular ion peak, and Intermediate IM15 was identified.

Synthesis of Intermediate IM16

Under an Ar atmosphere, to a 1,000 mL three neck flask, 14.20 g (47.09 mmol) of IM15, 9.49 g (1.2 eq, 56.51 mmol) of 2-(methylthio)phenylboronic acid, 19.53 g (3.0 eq, 141.3 mmol) of K$_2$CO$_3$, 2.72 g (0.05 eq, 2.35 mmol) of Pd(PPh$_3$)$_4$, and 330 mL of a mixture of toluene/EtOH/H$_2$O (mixing ratio of 4:2:1) were added in order, followed by heating to about 80° C. and stirring. After cooling to room temperature, the reaction solution was extracted with toluene. An aqueous layer was removed, and an organic layer was washed with a saturated saline solution and dried with MgSO$_4$. The MgSO$_4$ was separated by filtering, and the organic layer was concentrated. The crude product thus obtained was separated by silica gel column chromatography (using a mixture solvent of hexane and toluene as an eluent) to obtain Intermediate IM16 (12.14 g, yield 75%).

By FAB-MS measurement, mass number of m/z=344 was observed as a molecular ion peak, and Intermediate IM16 was identified.

Synthesis of Intermediate IM17

Under an Ar atmosphere, to a 500 mL three neck flask, 12.14 g (35.21 mmol) of IM16, 9.73 g (2.0 eq, 70.41 mmol) of K$_2$CO$_3$, and 120 mL of DMF were added in order, followed by heating and refluxing. After cooling to room temperature, water was added, and the reaction solution was extracted with CH$_2$Cl$_2$. An aqueous layer was removed, and an organic layer was washed with a saturated saline solution and dried with MgSO$_4$. The MgSO$_4$ was separated by filtering, and the organic layer was concentrated. The crude product thus obtained was separated by silica gel column chromatography (using a mixture solvent of hexane and toluene as an eluent) to obtain Intermediate IM17 (9.26 g, yield 81%).

By FAB-MS measurement, mass number of m/z=324 was observed as a molecular ion peak, and Intermediate IM17 was identified.

Synthesis of Intermediate IM18

Under an atmospheric atmosphere, to a 300 mL three neck flask, 8.00 g (24.6 mmol) of Intermediate IM17, and 80 mL of AcOH were added and stirred, and then, 3.0 mL of hydrogen peroxide ($H_2O_2$, 35%) was added dropwisely. After finishing the reaction, water and $CH_2Cl_2$ were added, and an organic layer was extracted. The organic layer was washed with a saline solution and dried with $MgSO_4$. The $MgSO_4$ was separated by filtering, and the organic layer was concentrated. The crude product thus obtained was separated by silica gel column chromatography (using a mixture solvent of hexane and toluene as an eluent) to obtain Intermediate IM18 (6.90 g, yield 82%).

By FAB-MS measurement, mass number of m/z=340 was observed as a molecular ion peak, and Intermediate IM18 was identified.

Synthesis of Intermediate IM19

Under an atmospheric atmosphere, in a 100 mL three neck flask, 20 mL of concentrated sulfuric acid was cooled and stirred in an ice bath. 6.88 g (20.2 mmol) of Intermediate IM18 was added thereto. After the temperature came to room temperature, stirring was further performed. After the reaction was complete, the reaction solution was added dropwisely to a 300 mL three neck flask cooled in an ice bath containing 120 mL of water. The solution was neutralized using saturated soda water, $CH_2Cl_2$ was added, and an organic layer was extracted. The organic layer was washed with a saline solution and dried with $MgSO_4$. The $MgSO_4$ was separated by filtering, and the organic layer was concentrated. The crude product thus obtained was separated by silica gel column chromatography (using a mixture solvent of hexane and toluene as an eluent) to obtain Intermediate IM19 (5.68 g, yield 91%).

By FAB-MS measurement, mass number of m/z=308 was observed as a molecular ion peak, and Intermediate IM19 was identified.

Synthesis of Compound C19

Under an Ar atmosphere, to a 500 mL three neck flask, 5.67 g (18.36 mmol) of Intermediate IM19, 0.53 g (0.05 eq, 0.92 mmol) of $Pd(dba)_2$, 1.76 g (1.0 eq, 18.4 mmol) of $NaO^tBu$, 180 mL of toluene, 8.40 g (1.0 eq, 18.36 mmol) of Intermediate IM14, and 0.74 g (0.2 eq, 3.67 mmol) of $^tBu_3P$ were added in order, followed by heating, refluxing, and stirring. After cooling to room temperature, water was added to the reaction solution, and an organic layer was extracted. Toluene was added to an aqueous layer, and an organic layer was further extracted. The organic layers were collected, washed with a saline solution, and dried with $MgSO_4$. $MgSO_4$ was separated by filtering, and the organic layer was concentrated. The crude product thus obtained was separated by silica gel column chromatography (using a mixture solvent of hexane and toluene as an eluent) to obtain Compound C19 (10.45 g, yield 78%).

By FAB-MS measurement, mass number of m/z=729 was observed as a molecular ion peak, and Compound C19 was identified.

9. Synthesis of Compound E2

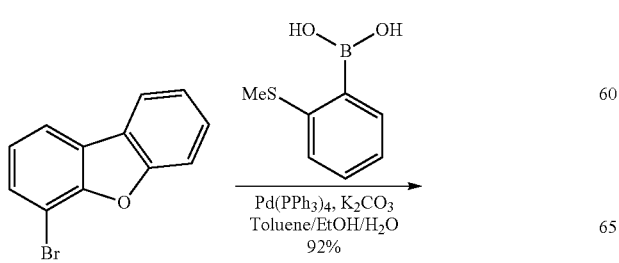

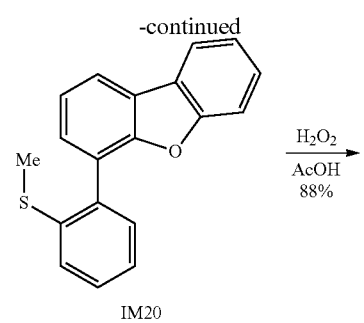

IM20

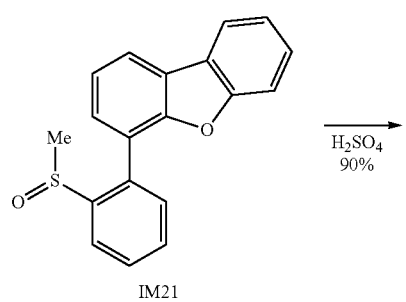

IM21

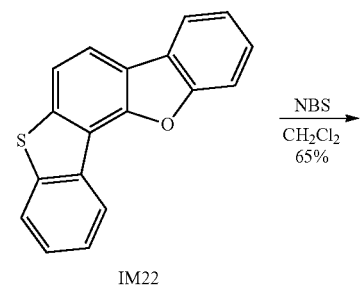

IM22

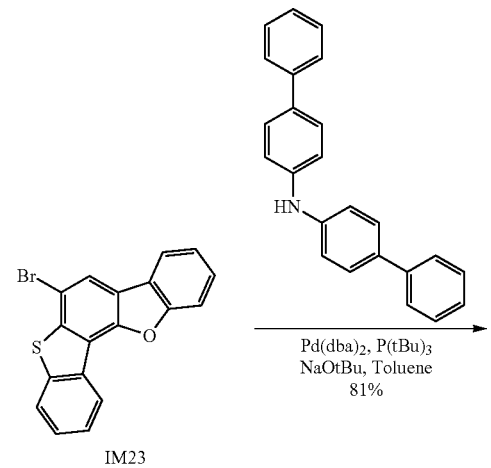

IM23

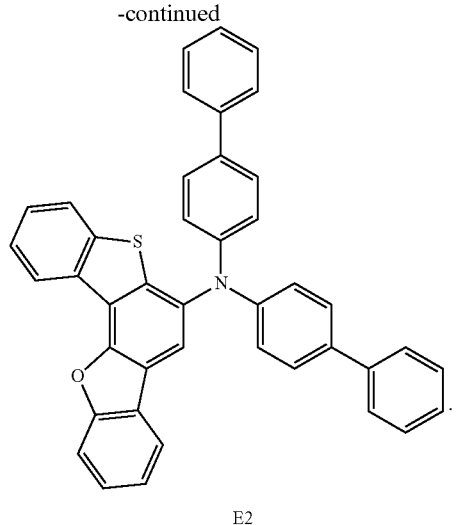

E2

Synthesis of Intermediate IM20

Under an Ar atmosphere, to a 1,000 mL three neck flask, 20.00 g (80.94 mmol) of 4-bromodibenzofuran, 16.32 g (1.2 eq, 97.13 mmol) of 2-(methylthio)phenylboronic acid, 33.56 g (3.0 eq, 242.83 mmol) of $K_2CO_3$, 4.68 g (0.05 eq, 4.05 mmol) of $Pd(PPh_3)_4$, and 560 mL of a mixture of toluene/EtOH/$H_2O$ (mixing ratio of 4:2:1) were added in order, followed by heating to about 80° C. and stirring. After cooling to room temperature, the reaction solution was extracted with toluene. An aqueous layer was removed, and an organic layer was washed with a saturated saline solution and dried with $MgSO_4$. The $MgSO_4$ was separated by filtering, and the organic layer was concentrated. The crude product thus obtained was separated by silica gel column chromatography (using a mixture of hexane and toluene as an eluent) to obtain Intermediate IM20 (21.52 g, yield 92%).

By FAB-MS measurement, mass number of m/z=290 was observed as a molecular ion peak, and Intermediate IM20 was identified.

Synthesis of Intermediate IM21

Under an atmospheric atmosphere, to a 500 mL three neck flask, 20.00 g (68.88 mmol) of Intermediate IM20, and 200 mL of AcOH were added and stirred, and then, 8.3 mL of hydrogen peroxide (35%) was added dropwisely. After finishing the reaction, water and $CH_2Cl_2$ were added, and an organic layer was extracted. The organic layer was washed with a saline solution and dried with $MgSO_4$. The $MgSO_4$ was separated by filtering, and an organic layer was concentrated. The crude product thus obtained was separated by silica gel column chromatography (using a mixture solvent of hexane and toluene as an eluent) to obtain Intermediate IM21 (18.60 g, yield 88%).

By FAB-MS measurement, mass number of m/z=306 was observed as a molecular ion peak, and Intermediate IM21 was identified.

Synthesis of Intermediate IM22

Under an atmospheric atmosphere, in a 200 mL three neck flask, 55 mL of concentrated sulfuric acid was cooled and stirred in an ice bath. 18.57 g (60.61 mmol) of Intermediate IM21 was added thereto. After elevating the temperature to room temperature, the stirring was further performed. After finishing the reaction, the reaction solution was added dropwisely to a 1,000 mL three neck flask cooled in an ice bath containing 330 ml of water. The solution was neutralized using saturated soda water, $CH_2Cl_2$ was added, and an organic layer was extracted. The organic layer was washed with a saline solution and dried with $MgSO_4$. The $MgSO_4$ was separated by filtering, and the organic layer was concentrated. The crude product thus obtained was separated by silica gel column chromatography (using a mixture solvent of hexane and toluene as an eluent) to obtain Intermediate IM22 (14.91 g, yield 90%).

By FAB-MS measurement, mass number of m/z=274 was observed as a molecular ion peak, and Intermediate IM22 was identified.

Synthesis of Intermediate IM23

Under an Ar atmosphere, in a 1,000 mL three neck flask, 14.91 g (54.35 mmol) of IM22, and 160 mL of $CH_2Cl_2$ were added and cooled in an ice bath. 9.67 g (1.0 eq, 54.35 mmol) of NBS was added over about 30 minutes. After adding the reagent, the temperature was elevated to room temperature, and the solution was stirred. After finishing the reaction, water and $CH_2Cl_2$ were added, and an organic layer was extracted. The organic layer was washed with a saline solution and dried with $MgSO_4$. The $MgSO_4$ was separated by filtering, and the organic layer was concentrated. The crude product thus obtained was separated by washing with EtOH to obtain Intermediate IM23 (12.44 g, yield 65%).

By FAB-MS measurement, mass number of m/z=352 was observed as a molecular ion peak, and Intermediate IM23 was identified.

Synthesis of Compound E2

Under an Ar atmosphere, to a 1,000 mL three neck flask, 12.44 g (35.22 mmol) of IM23, 1.01 g (0.05 eq, 1.76 mmol) of $Pd(dba)_2$, 3.38 g (1.0 eq, 35.2 mmol) of NaO$^t$Bu, 350 mL of toluene, 11.32 g (1.0 eq, 35.22 mmol) of di([1,1'-biphenyl]-4-yl)amine, and 1.43 g (0.2 eq, 7.04 mmol) of $^t$Bu$_3$P were added in order, followed by heating, refluxing, and stirring. After cooling to room temperature, water was added to the reaction solution, and an organic layer was extracted. Toluene was added to an aqueous layer, and an organic layer was further extracted. The organic layers were collected, washed with a saline solution, and dried with $MgSO_4$. The $MgSO_4$ was separated by filtering, and the organic layer was concentrated. The crude product thus obtained was separated by silica gel column chromatography (using a mixture of hexane and toluene as an eluent) to obtain Compound E2 (17.00 g, yield 81%).

By FAB-MS measurement, mass number of m/z=593 was observed as a molecular ion peak, and Compound E2 was identified.

B. Manufacture and Evaluation of Organic Electroluminescence Device Including Amine Compound The emission properties of an amine compound of an embodiment, and of an organic electroluminescence device including the amine compound of an embodiment in a hole transport layer were evaluated using the methods described below. The compounds used for the evaluation are shown below:

Example Compounds
A24
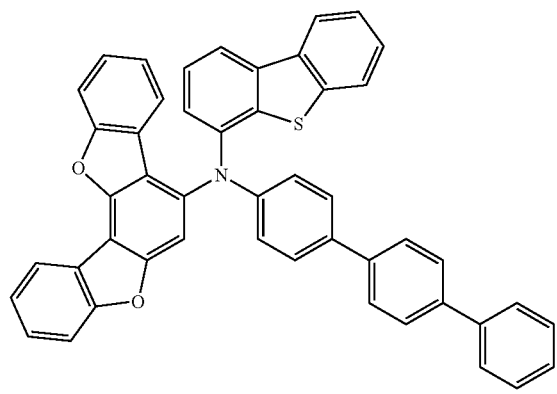
A31
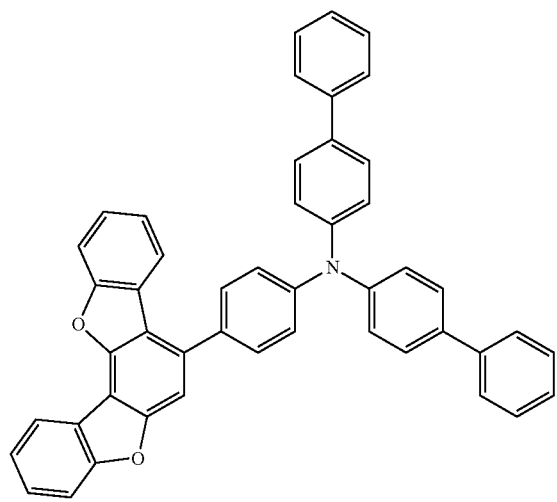
A48
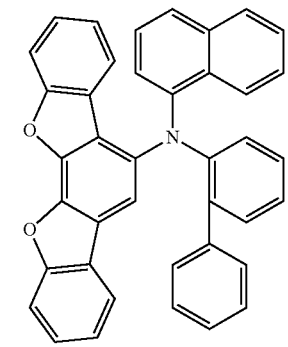
A76
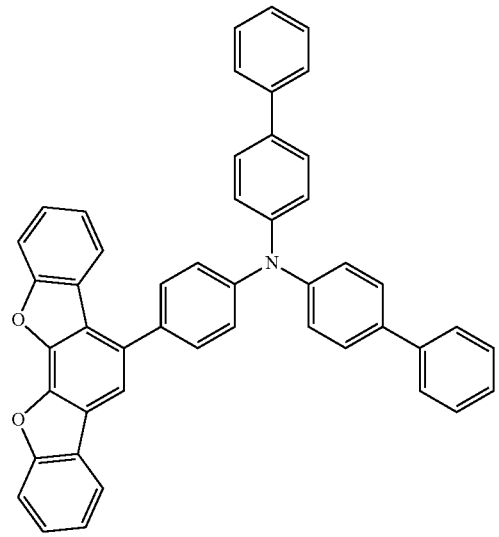
A113
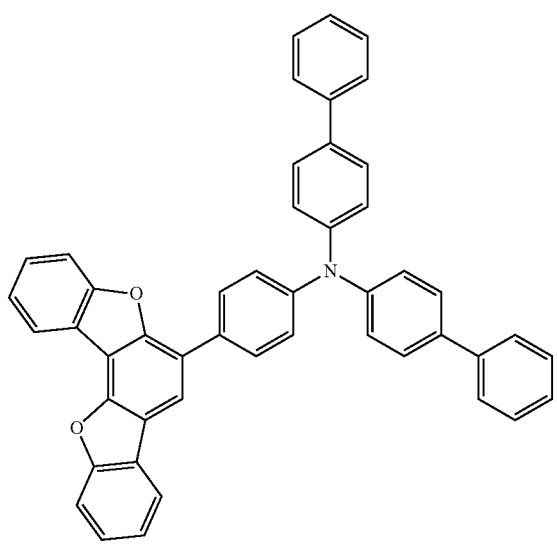
A121

B27
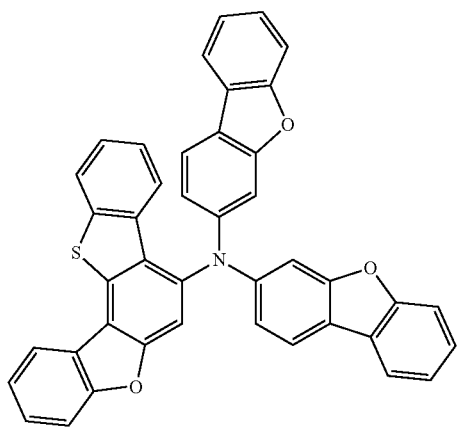
C19
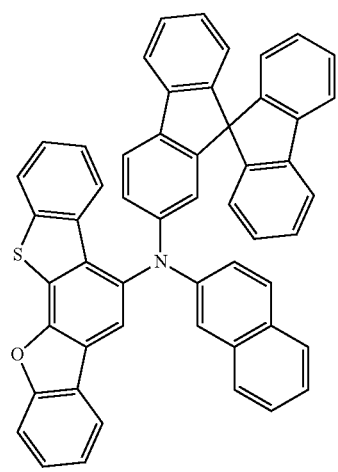
E2
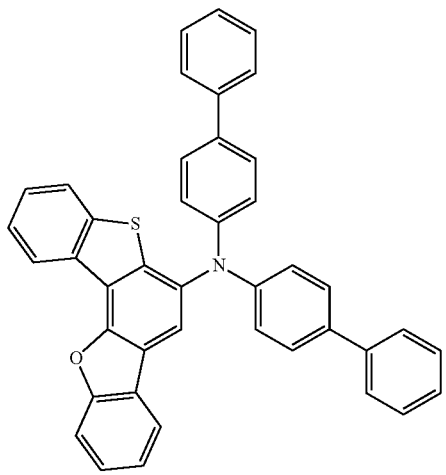
Comparative Compounds
R1
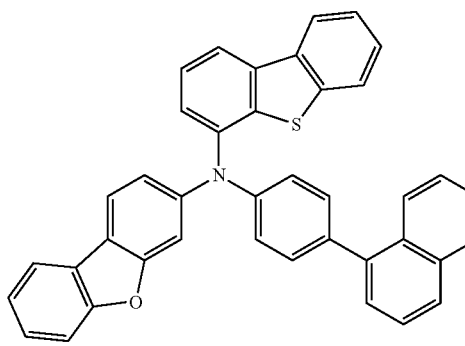
R2
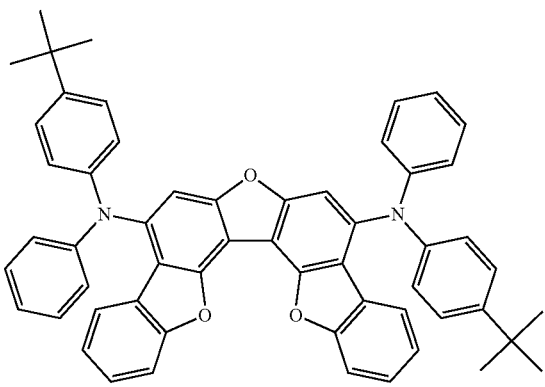
R3
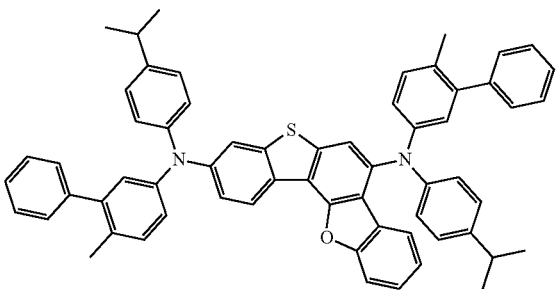
R4
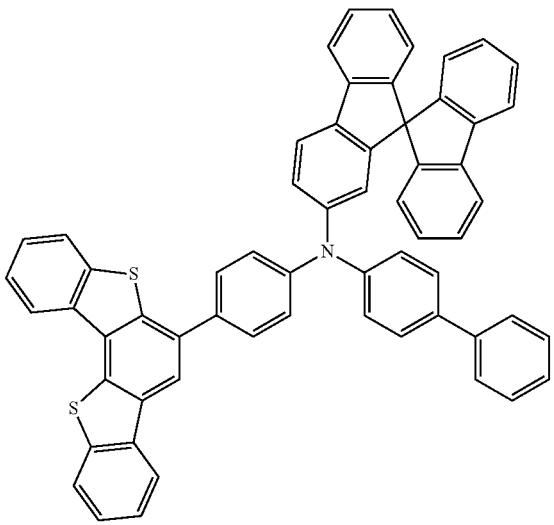

-continued
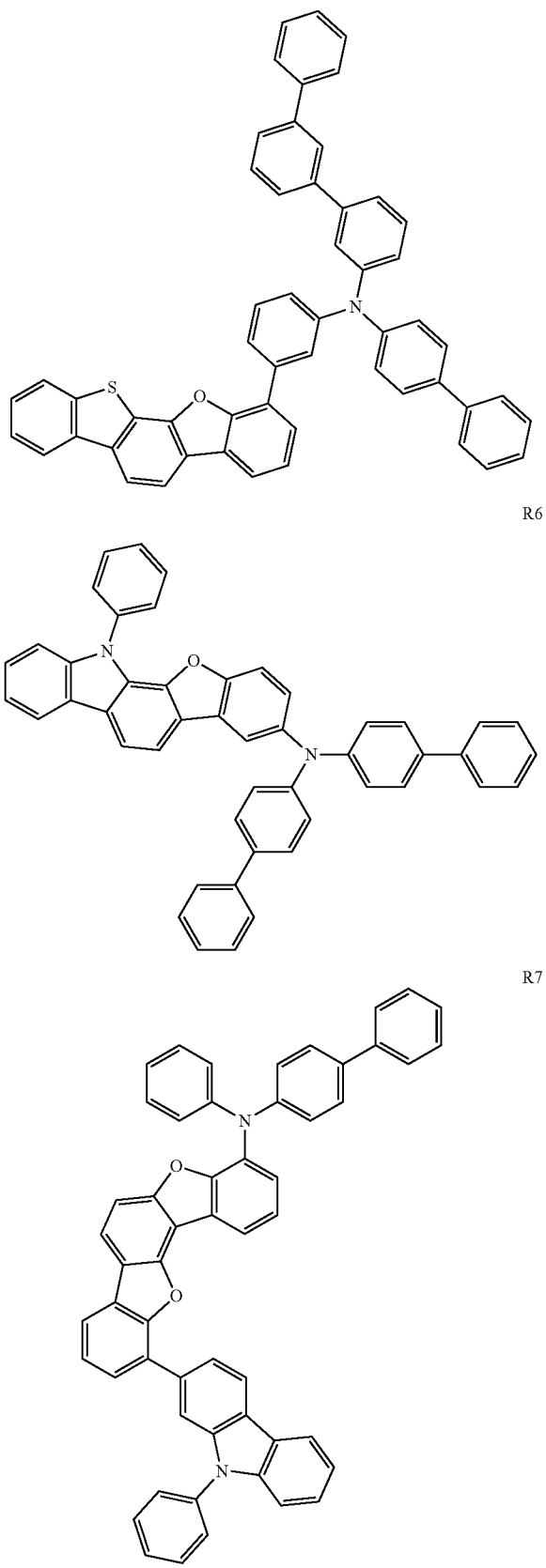
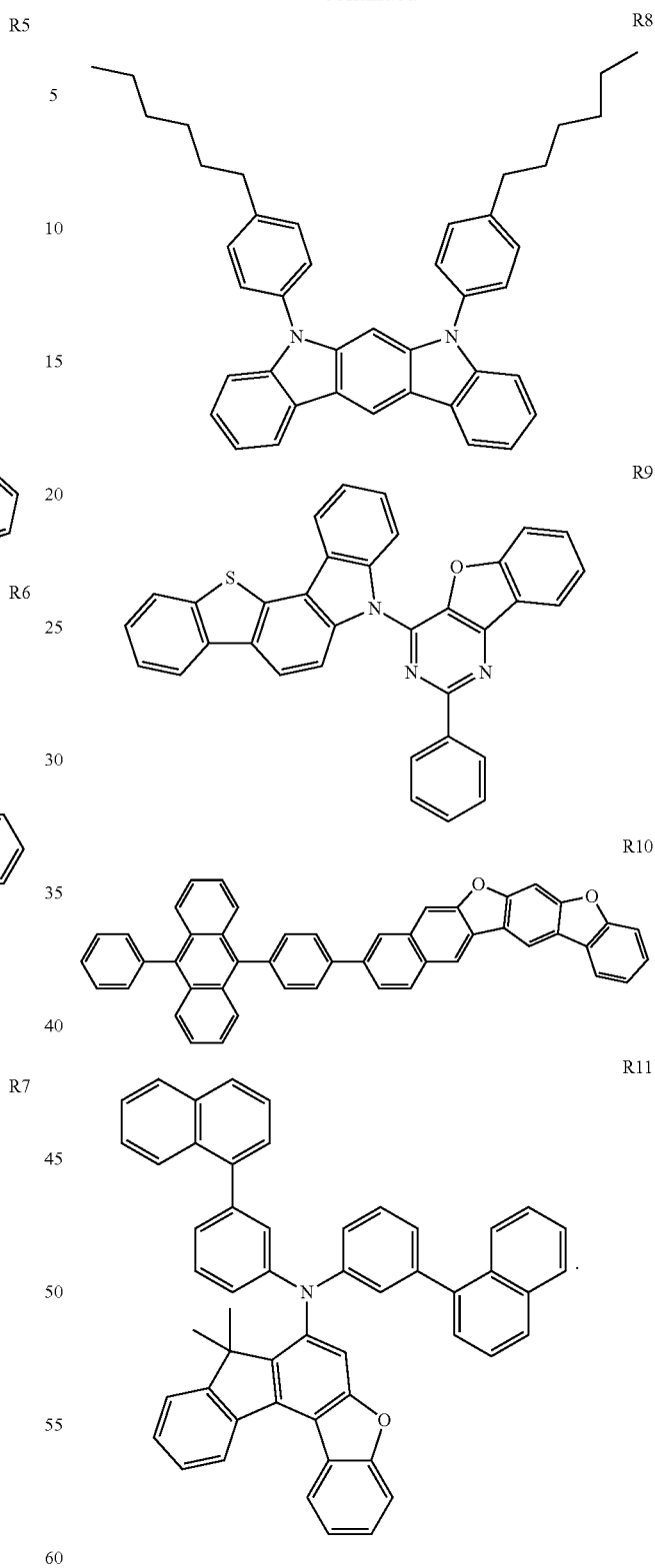
Example 1 to Example 9 correspond to organic electroluminescence devices manufactured using Compound A24, Compound A31, Compound A48, Compound A76, Compound A113, Compound A121, Compound B27, Compound C19, and Compound E2 as materials for a hole transport layer, respectively.

In Comparative Example 1 to Comparative Example 11, organic electroluminescence devices were manufactured using Comparative Compound R1 to Compound R11 as materials for a hole transport layer, respectively.

An example method of manufacturing an organic electroluminescence device for evaluating the device is described below.

Manufacture of Organic Electroluminescence Device

On a glass substrate, ITO with a thickness of about 1,500 Å was patterned, washed with ultra-pure water and ultrasonic waves, and treated with UV for about 30 minutes, followed by treatment with ozone. Then, 2-TNATA was deposited to a thickness of about 600 Å to form a hole injection layer. Then, the amine compound of an embodiment or the comparative compound was deposited to a thickness of about 300 Å to form a hole transport layer.

The hole transport layer thus formed was obtained by depositing Compound A24, Compound A31, Compound A48, Compound A76, Compound A113, Compound A121, Compound B27, Compound C19, and Compound E2 in Examples 1 to 9, respectively, and Comparative Compound R1 to Compound R11 in Comparative Examples 1 to 11, respectively.

After that, an emission layer was formed by co-depositing ADN and TBP in a ratio of 97:3 to a thickness of about 250 Å.

Then, an electron transport layer was formed on the emission layer using $Alq_3$ to a thickness of about 250 Å and then forming a layer using LiF to a thickness of about 10 Å. Then, a second electrode was formed by depositing aluminum (Al) to a thickness of about 1,000 Å.

Evaluation of Properties of Organic Electroluminescence Device

The voltage, emission efficiency, and life span of each of the organic electroluminescence devices manufactured in Example 1 to Example 9, and Comparative Example 1 to Comparative Example 11, are shown in Table 1. The current density, voltage, and emission efficiency of the organic electroluminescence devices were measured using a Source Meter of 2400 Series of Keithley Instrument Co., and a PC Program LabVIEW 2.0 for measurement of National Instrument Co. The emission efficiency is an efficiency value when the current density is about 10 $mA/cm^2$.

The device life span was obtained by measuring the time (half-life) elapsed for a decrease from an initial luminance to 50% luminance at a current density of about 1.0 $mA/cm^2$. The luminance was measured in a dark room using a luminance color meter of CS-200 (Konica Minolta Co.)

TABLE 1

| Division | Hole transport layer material | Voltage (V) | Emission efficiency (cd/A) | Life $LT_{50}$ (h) |
| --- | --- | --- | --- | --- |
| Example 1 | Example Compound A24 | 5.7 | 7.5 | 2250 |
| Example 2 | Example Compound A31 | 5.7 | 7.5 | 2200 |
| Example 3 | Example Compound A48 | 5.6 | 7.6 | 2100 |
| Example 4 | Example Compound A76 | 5.7 | 7.6 | 2150 |
| Example 5 | Example Compound A113 | 5.6 | 7.7 | 2050 |
| Example 6 | Example Compound A121 | 5.7 | 7.7 | 2100 |
| Example 7 | Example Compound B27 | 5.7 | 7.5 | 2200 |
| Example 8 | Example Compound C19 | 5.7 | 7.6 | 2100 |
| Example 9 | Example Compound E2 | 5.6 | 7.8 | 1950 |
| Comparative Example 1 | Comparative Compound R1 | 6.6 | 6.4 | 1800 |
| Comparative Example 2 | Comparative Compound R2 | 5.9 | 6.7 | 1500 |
| Comparative Example 3 | Comparative Compound R3 | 5.9 | 6.6 | 1450 |
| Comparative Example 4 | Comparative Compound R4 | 6.0 | 7.0 | 1850 |
| Comparative Example 5 | Comparative Compound R5 | 6.4 | 6.3 | 1750 |
| Comparative Example 6 | Comparative Compound R6 | 6.1 | 6.5 | 1550 |
| Comparative Example 7 | Comparative Compound R7 | 6.2 | 6.5 | 1700 |
| Comparative Example 8 | Comparative Compound R8 | 6.0 | 6.6 | 1450 |
| Comparative Example 9 | Comparative Compound R9 | 6.2 | 6.5 | 1400 |
| Comparative Example 10 | Comparative Compound R10 | 6.2 | 6.1 | 1600 |
| Comparative Example 11 | Comparative Compound R11 | 5.9 | 6.9 | 1850 |

Referring to the results of Table 1, it could be found that the organic electroluminescence devices of Example 1 to Example 9 each showed decreased driving voltage, increased emission efficiency, and increased device life span. compared with the organic electroluminescence devices of Comparative Example 1 to Comparative Example 11. Without being bound by the correctness of any explanation or theory, it is thought that because the HOMO orbitals of the Example Compounds are widely expanded to (delocalized in) a terphenyl skeleton, stability in a radical state was improved (e.g., a radical form of the molecule may be more stable), resulting in increased life span of a device including the molecule.

The Example Compounds of Examples 3, 4, 5, 6, 8 and 9 each have a structure in which an electron-donating heteroatom and a nitrogen atom are substituted at para positions (e.g., are located para to each other), which may result in improved hole transport properties, and when at least one compound is applied to a device, the recombination probability of holes and electrons in an emission layer may be improved. Accordingly, the organic electroluminescence devices of Examples 3, 4, 5, 6, 8, and 9 showed particularly improved emission efficiency when compared with the organic electroluminescence devices of the Comparative Examples.

Comparative Compound R1 includes a 3-dibenzofuranyl group and a 4-dibenzothiophenyl group, but the hole transport properties were decreased when compared with the terphenyl structure crosslinked by two heteroatoms of the present disclosure, and accordingly, it is thought that in case of applying to a device, emission efficiency was degraded.

Comparative Compounds R2 and R3 are amine compounds having a terphenyl group skeleton crosslinked by two heteroatoms, which are similar to the compound of the present disclosure. However, unlike the monoamine compound of the present disclosure, Comparative Compounds R2 and R3 included two amine groups. Without being bound by the correctness of any theory or explanation, it is believed that carrier balance was collapsed, and accordingly, the device life span was reduced.

Comparative Compound R4 is an amine compound having a terphenyl group skeleton crosslinked by two heteroatoms, which is similar to the compound of the present disclosure, but X and Y did not include an oxygen atom (e.g., the terphenyl group skeleton did not include oxygen), and sufficient hole transport properties were not obtained. Accordingly, it is thought that in case of applying to a device, emission efficiency was degraded.

Comparative Compound R5 is an amine compound having a terphenyl group skeleton crosslinked by two heteroatoms, which is similar to the compound of the present disclosure, but a substitution position of the terphenyl group of Comparative Compound R5 is different from a substitution position of the terphenyl group of the Example Compounds. Moreover, an additional benzene ring is inserted between the amine group and the terphenyl group skeleton, so that the conjugation distance is increased. Accordingly, sufficient hole transport properties could not be obtained, and it is thought that in case of applying to a device, emission device was degraded.

Comparative Compound R6 is a material having a benzofurocarbazole skeleton, in which a nitrogen atom is substituted at a para position with respect to the nitrogen atom of a carbazole skeleton when compared with the compound of the present disclosure. Without being bound by the correctness of any theory or explanation, it is believed that as a result, the hole transport properties were excessively increased, carrier balance was collapsed, and the emission efficiency and life span of a device including the compound were degraded when compared with the present disclosure.

Comparative Compound R7 is an amine compound having a terphenyl skeleton crosslinked by two heteroatoms, which is similar to the compound of the present disclosure, but a benzene ring substituted with only one heteroatom among three benzene rings of a crosslinked terphenyl group (e.g., one of the terminal benzene rings) is connected with a carbazole group. Accordingly, it is thought that sufficient hole transport properties could not be obtained, and in case of applying to a device, emission device was degraded.

Comparative Compounds R8 and R9 each have a terphenyl skeleton crosslinked by one or two nitrogen atoms, and when compared with the monoamine compound including an oxygen atom or a sulfur atom in the present disclosure, it is thought that hole transport properties were excessively increased, and carrier balance could be collapsed. Accordingly, it is thought that in case of applying to a device, device life was degraded when compared with the present disclosure.

Comparative Compound R10 has a terphenyl group skeleton crosslinked by two heteroatoms, which is similar to the compound of the present disclosure, but does not include an amine group. Accordingly, carrier balance was collapsed, and in case of applying to a device, emission efficiency and life span were both (e.g., simultaneously) degraded.

Comparative Compound R11 has a crosslinked terphenyl group skeleton, but is crosslinked using only one heteroatom, and sufficient hole transport properties could not be obtained. Accordingly, in case of applying to a device, emission efficiency was degraded.

Referring to the results of Table 1, it could be confirmed that the number and kind of the heteroatom of the hole transport layer material has an effect on the excellent device properties.

Referring to the evaluation results of the Example Compounds and the Examples of the organic electroluminescence devices, when the amine compound of an embodiment includes a terphenyl group crosslinked by two heteroatoms of oxygen or sulfur, and the middle benzene ring of the terphenyl group is substituted with a nitrogen atom, when the compound is used as a material for a hole transport region, the high efficiency and long-life characteristics of the organic electroluminescence devices may be achieved. For example, the amine compound of an embodiment may have improved charge tolerance due to a crosslinked terphenyl group skeleton, may have improved hole transport properties due to the two heteroatoms, and may impart improved device life span because of the amine group.

The organic electroluminescence device according to an embodiment of the present disclosure may exhibit excellent emission efficiency.

The amine compound according to an embodiment of the present disclosure may be applied to an organic electroluminescence device and may show excellent emission efficiency.

As used herein, the terms "substantially," "about," and similar terms are used as terms of approximation and not as terms of degree, and are intended to account for the inherent deviations in measured or calculated values that would be recognized by those of ordinary skill in the art.

Any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the example embodiments of the present disclosure have been described with reference to example embodiments of the present disclosure, it is understood that the present disclosure should not be limited to these example embodiments, but various changes and modifications can be made by one ordinary skilled in the art within the spirit and scope of the present disclosure as defined by the following claims and their equivalents.

What is claimed is:

1. An organic electroluminescence device, comprising:
    a first electrode;
    a second electrode opposite the first electrode; and
    a plurality of organic layers between the first electrode and the second electrode,
    wherein at least one functional layer among the plurality of organic layers comprises an amine compound represented by one of Formula 3-1 to Formula 3-3:

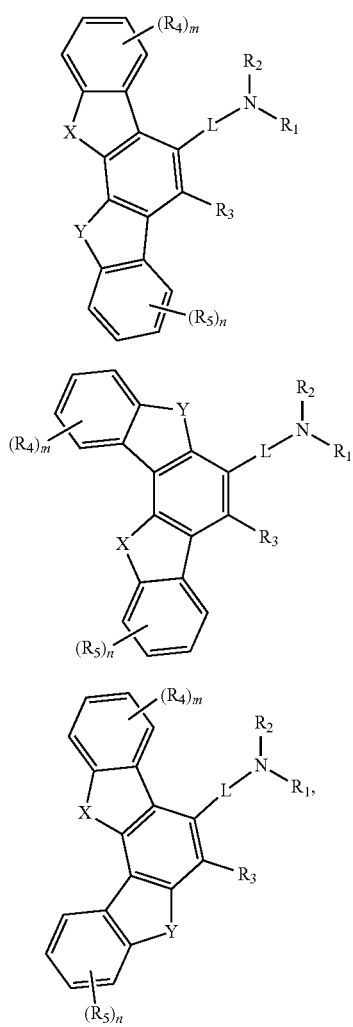

wherein
in Formulae 3-1 to 3-3,
X is O or S,
Y is O or S, where at least one of X or Y is O,
in Formulae 3-1,
R₁ and R₂ are each independently a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring,
in Formulae 3-2 and 3-3,
R₁ is a substituted or unsubstituted cyclohexyl group, a substituted or unsubstituted adamantyl group, a substituted or unsubstituted phenanthryl group, a substituted or unsubstituted dibenzofuran group, or a substituted or unsubstituted dibenzothiophene group,
R₂ is a substituted or unsubstituted alkyl group of 1 to 20 carbon atoms, a substituted or unsubstituted heteroaryl group of 2 to 30 carbon atoms for forming a ring, a substituted or unsubstituted cyclohexyl group, a substituted or unsubstituted adamantyl group, a substituted biphenyl group, a substituted or unsubstituted terphenyl group, a substituted or unsubstituted phenanthryl group, a substituted or unsubstituted naphthalene group, an unsubstituted phenyl group, or a substituted phenyl group substituted with a deuterium atom, a silyl group, an oxy group, a naphthalene group, or a pyridine group,
provided that in Formula 3-1, at least one of R₁ or R₂ comprises a substituted or unsubstituted cyclohexyl group or a substituted or unsubstituted adamantyl group,
provided that in Formula 3-2 and Formula 3-3, R₂ does not comprise a substituted or unsubstituted fluorenyl group,
R₃ to R₅ are each independently a hydrogen atom, a deuterium atom, a halogen atom, a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring, excluding a carbazolyl group,
provided that R₄ and R₅ do not combine with an adjacent group to form a ring,
L is a direct linkage,
"m" is an integer of 0 to 4, and
"n" is an integer of 0 to 4.

2. The organic electroluminescence device of claim 1, wherein the amine compound is a monoamine compound.

3. The organic electroluminescence device of claim 1, wherein in Formulae 3-2 and 3-3, R₂ is a substituted or unsubstituted heteroaryl group of 2 to 30 carbon atoms for forming a ring.

4. The organic electroluminescence device of claim 1, wherein R₂ is a substituted or unsubstituted cyclohexyl group, a substituted or unsubstituted adamantyl group, an unsubstituted phenyl group, a substituted biphenyl group, a substituted or unsubstituted terphenyl group, a substituted or unsubstituted naphthalene group, a substituted or unsubstituted phenanthryl group, a substituted or unsubstituted dibenzofuran group, or a substituted or unsubstituted dibenzothiophene group,
provided that in Formula 3-1, at least one of R₁ or R₂ comprises a substituted or unsubstituted cyclohexyl group or a substituted or unsubstituted adamantyl group.

5. The organic electroluminescence device of claim 1, wherein R₄ and R₅ are each independently a hydrogen atom, a deuterium atom, or a phenyl group.

6. The organic electroluminescence device of claim 1, wherein the amine compound represented by one of Formula 3-1 to Formula 3-3 is represented by one of Formula 4-1 to Formula 4-9:

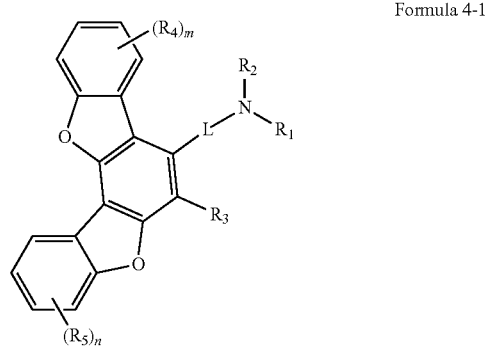

Formula 4-1 wherein in Formula 4-1 to Formula 4-9, $R_1$ to $R_5$, L, "m" and "n" are each independently the same as defined in Formula 3-1 to Formula 3-3, provided that in Formulae 4-1, 4-3, 4-4, 4-5, 4-8, and 4-9, $R_2$ does not comprise a substituted or unsubstituted fluorenyl group, provided that in Formulae 4-2, 4-6, and 4-7, at least one of $R_1$ or $R_2$ comprises a substituted or unsubstituted cyclohexyl group or a substituted or unsubstituted adamantyl group, and $R_4$ and $R_5$ do not combine with an adjacent group to form a ring.

7. The organic electroluminescence device of claim 1, wherein the plurality of organic layers comprise a hole transport region, an emission layer, and an electron transport region, and
the hole transport region comprises the amine compound.

8. The organic electroluminescence device of claim 7, wherein the hole transport region comprises a hole injection layer, a hole transport layer, and an electron blocking layer, and
the hole transport layer comprises the amine compound.

9. The organic electroluminescence device of claim 1, wherein the amine compound represented by one of Formula 3-1 to Formula 3-3 is at least one compound in Compound Group A to Compound Group F:

Compound Group A

A9
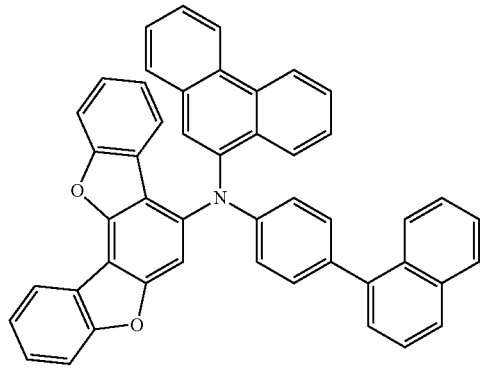

A14
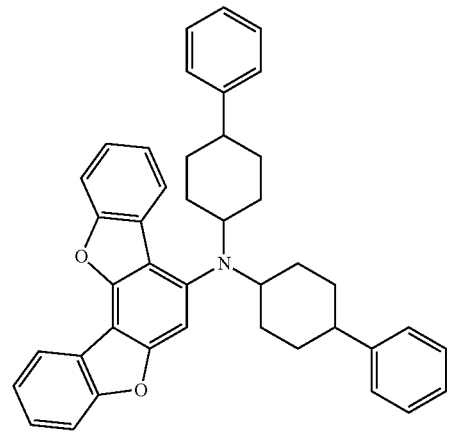

A15
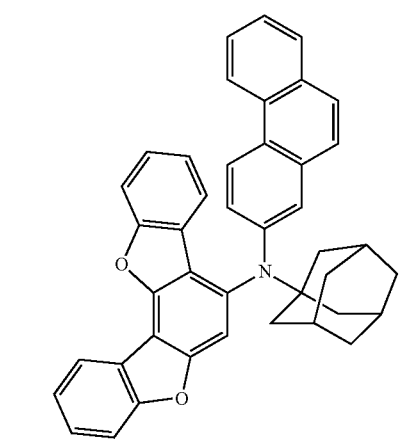

-continued

A22
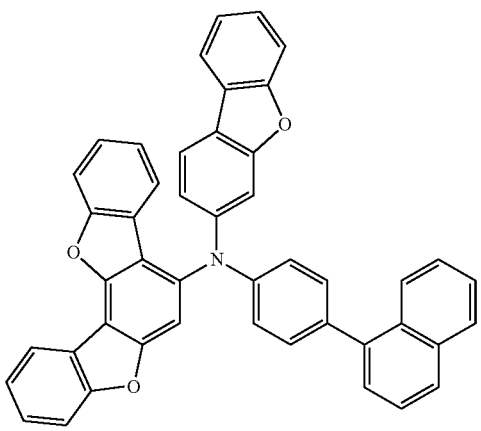

A23
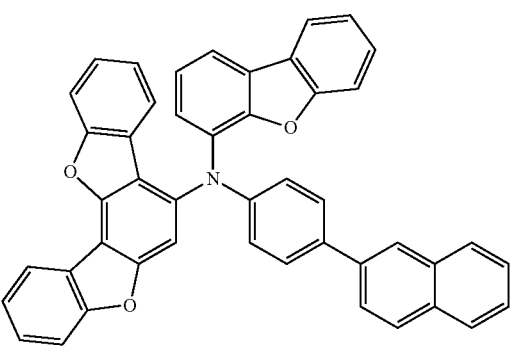

A24
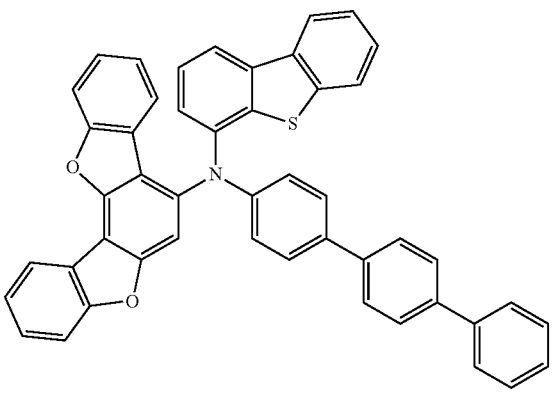

A25
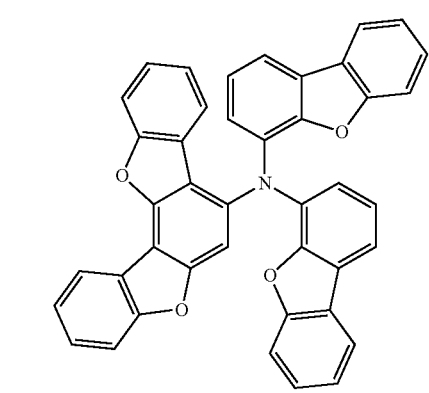

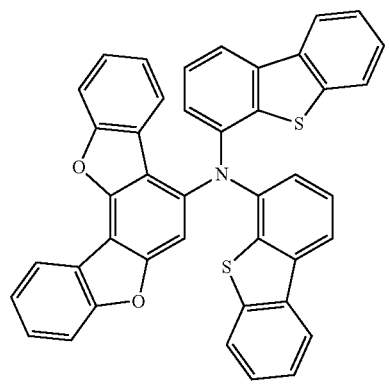 A26
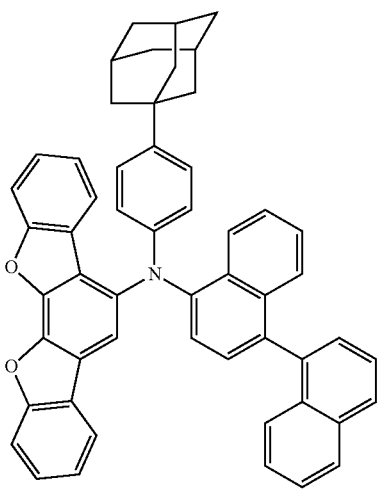 A58
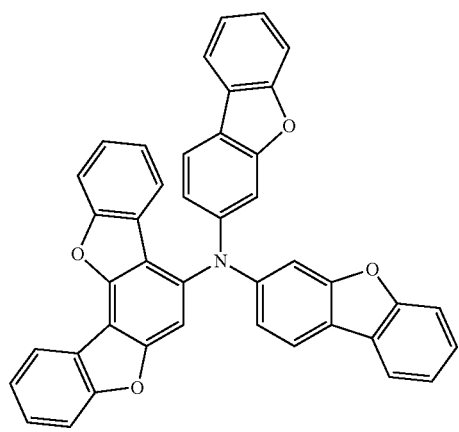 A27
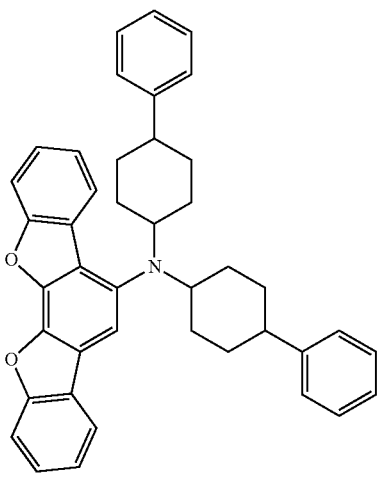 A59
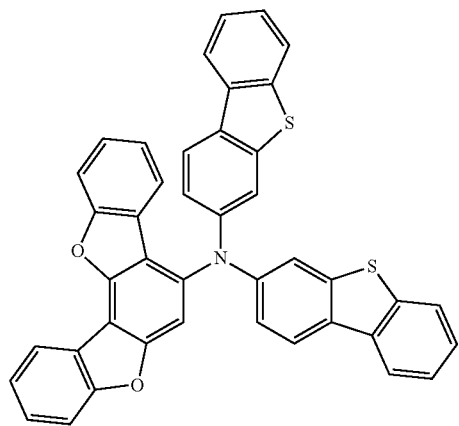 A28
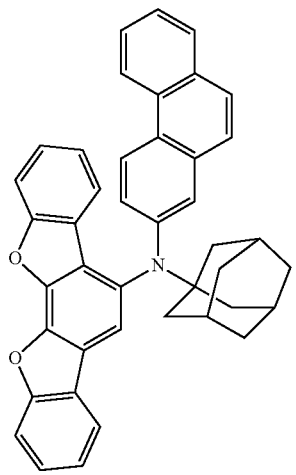 A60

-continued
A99
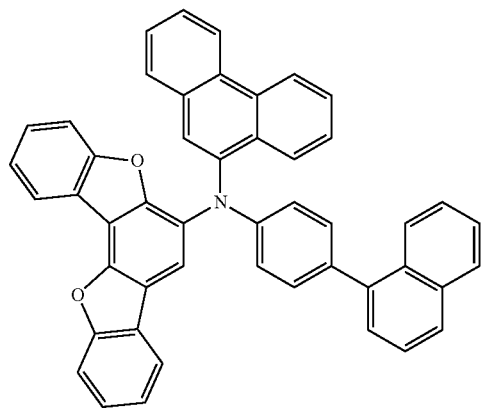
A104
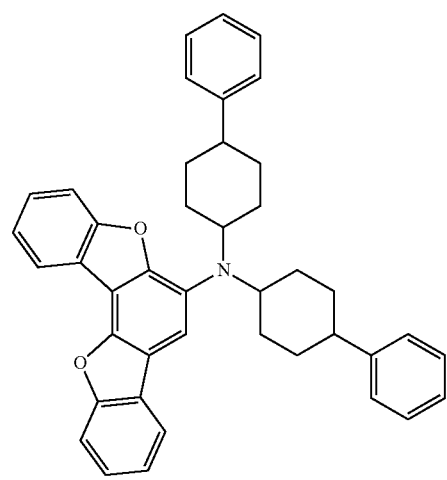
A105
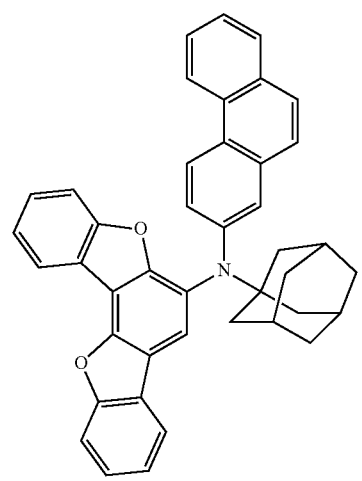
-continued
A112
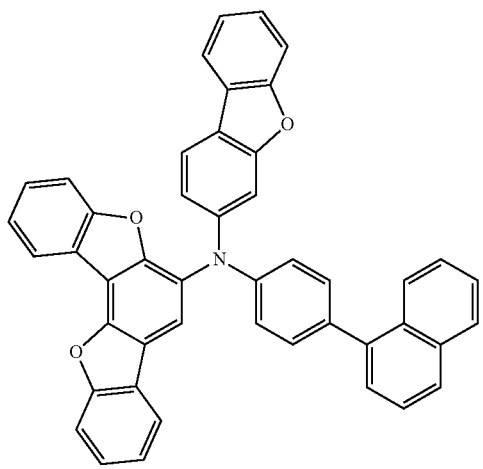
A113
A114
A115
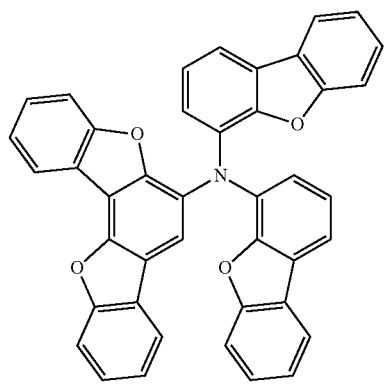

A116
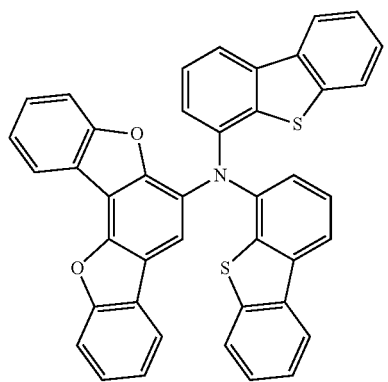
A144
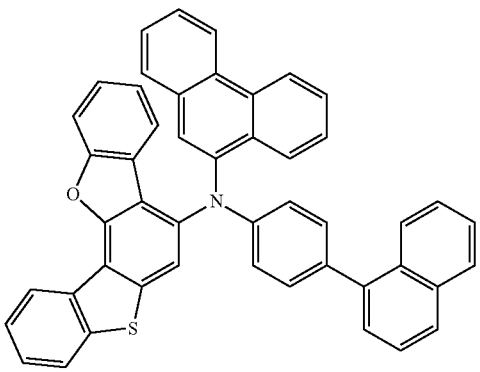
A117
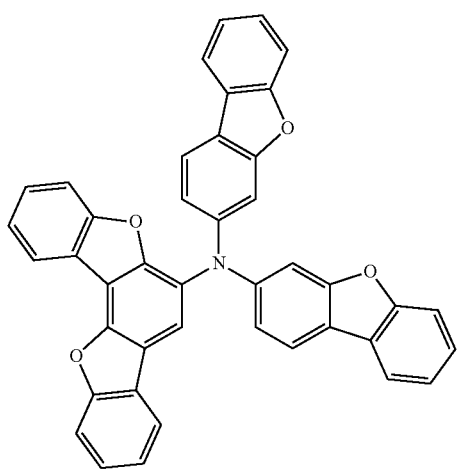
A149
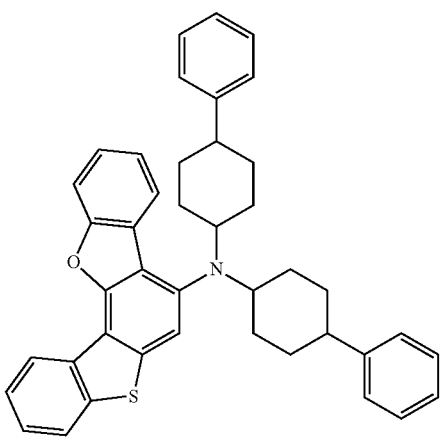
A118
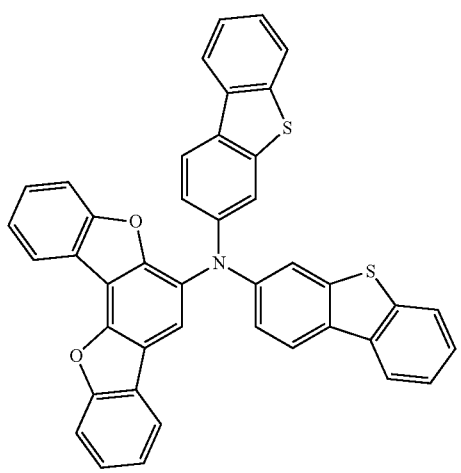
A150
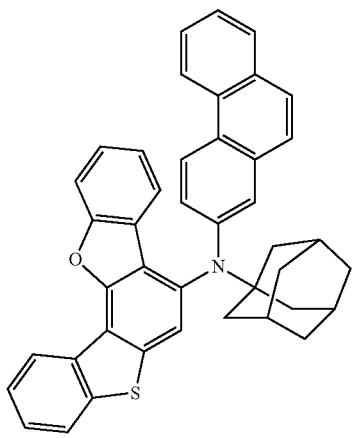

A157 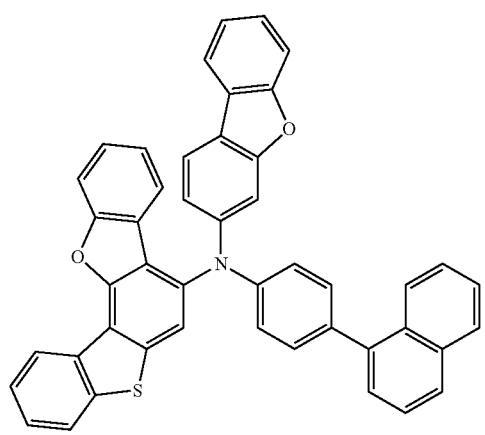
A161 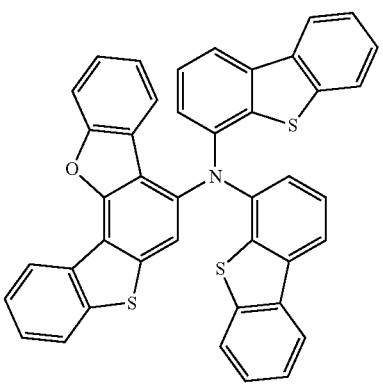
A158
A162 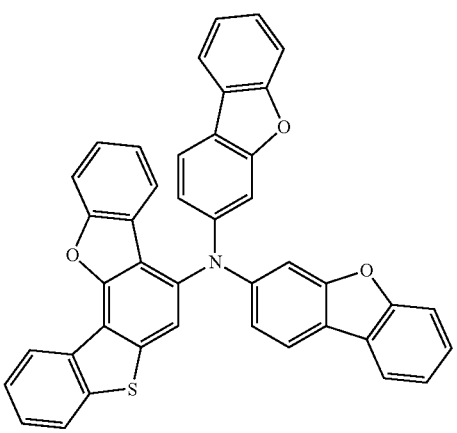
A159
A163 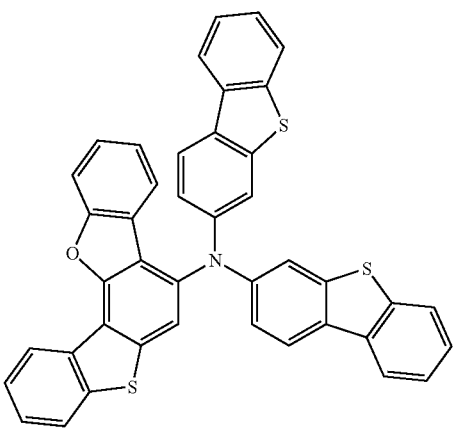
A160
A177 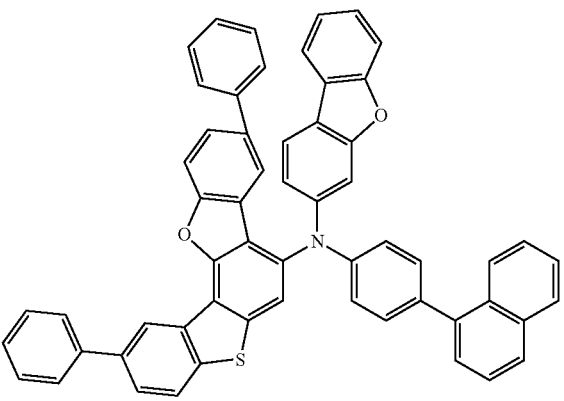

B9
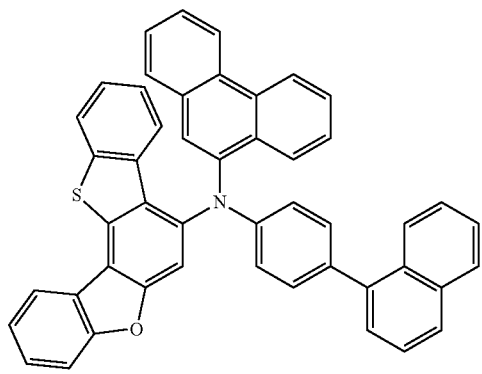
B14
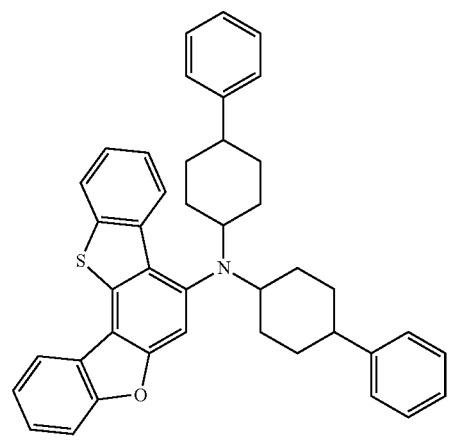
B15
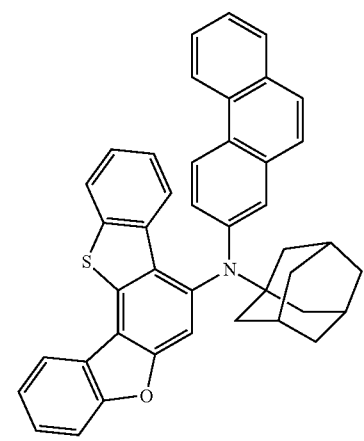
B22
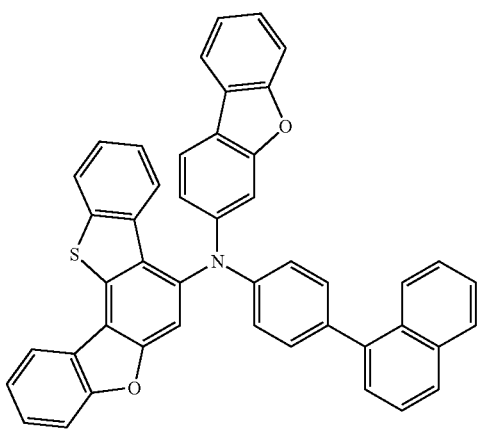
B23
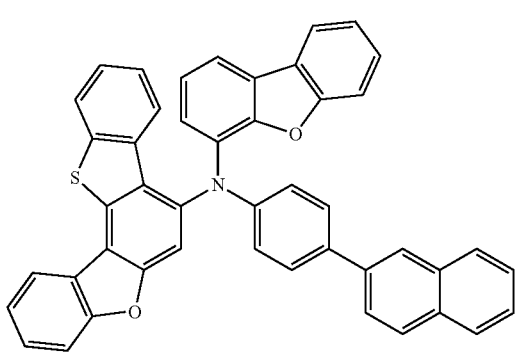
B24
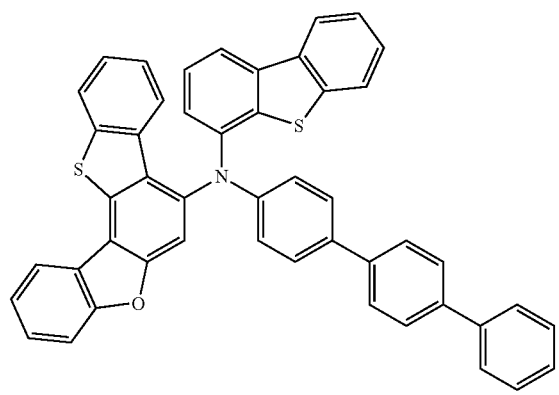
B25
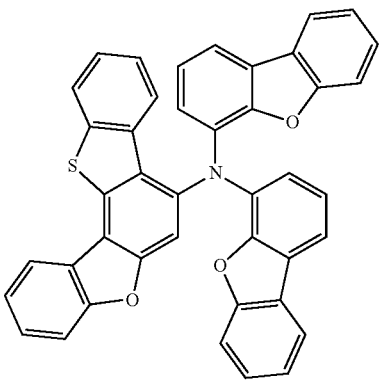

-continued
B26
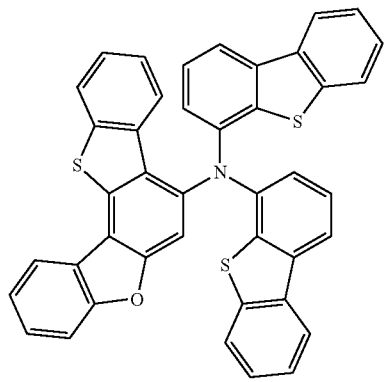
B27
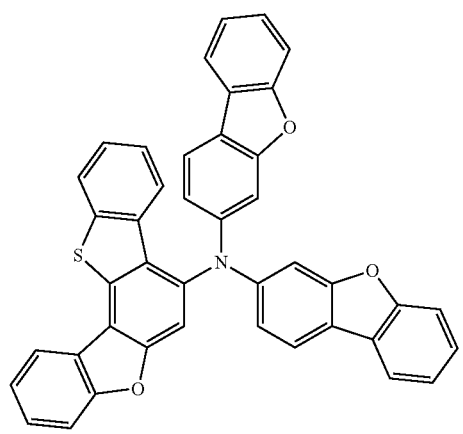
B28
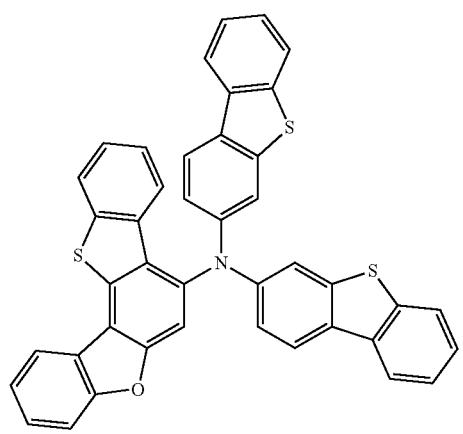
-continued
B29
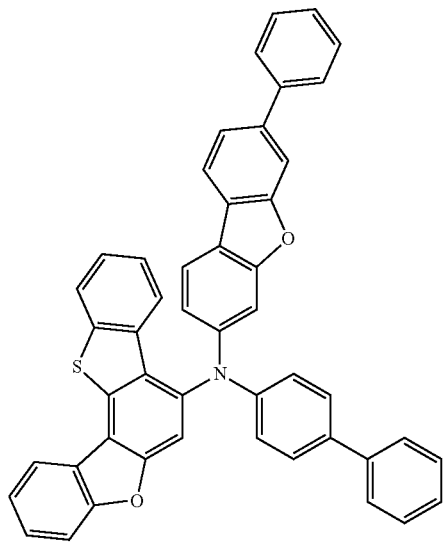
B30
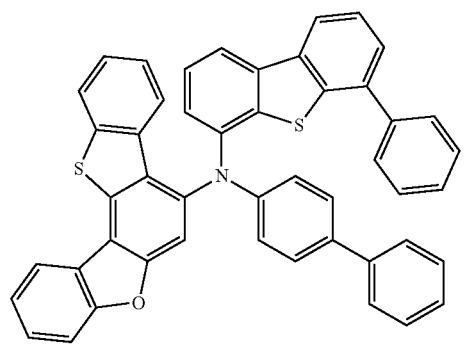
B42
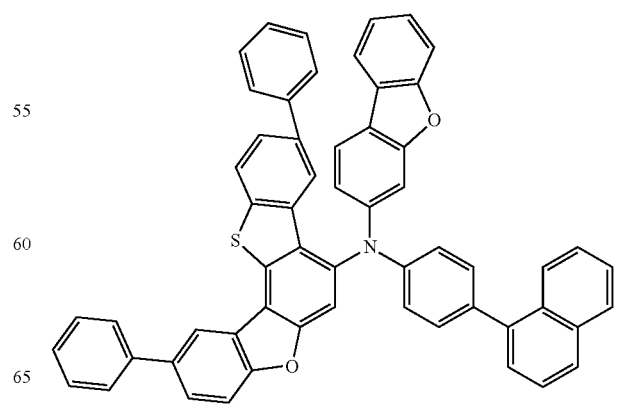

Compound Group C
C14
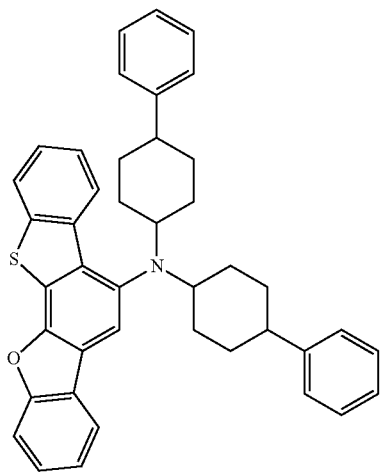
C15
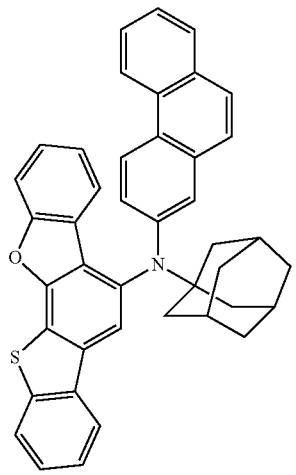
Compound Group D
D14
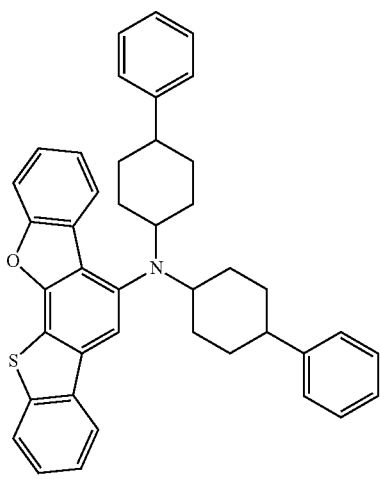
D15
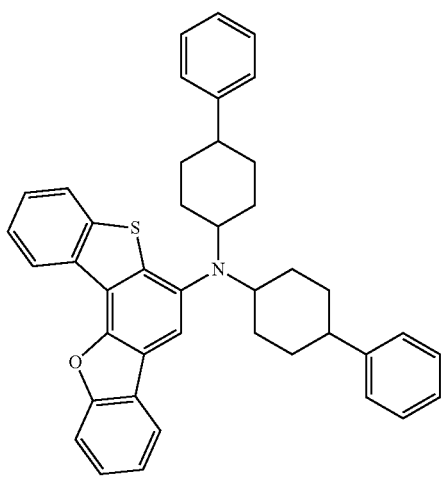
Compound Group E
E14
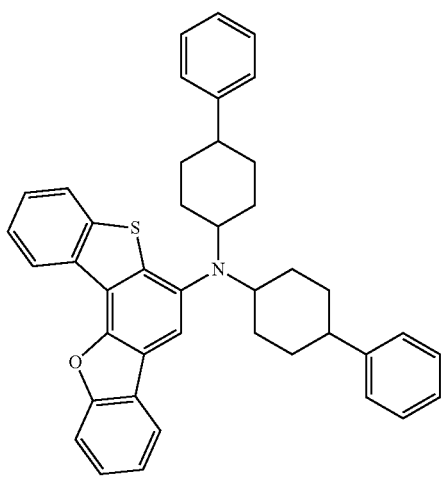
E15
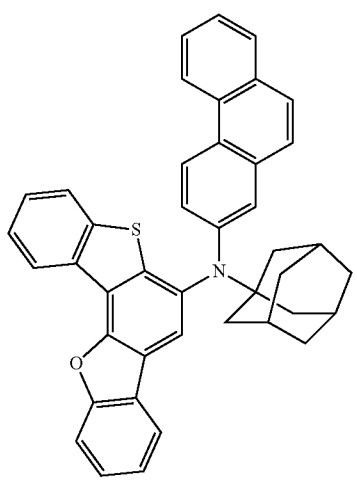

301
-continued
E22
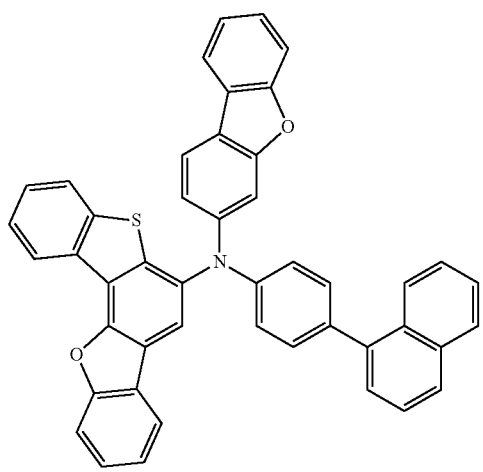
E23
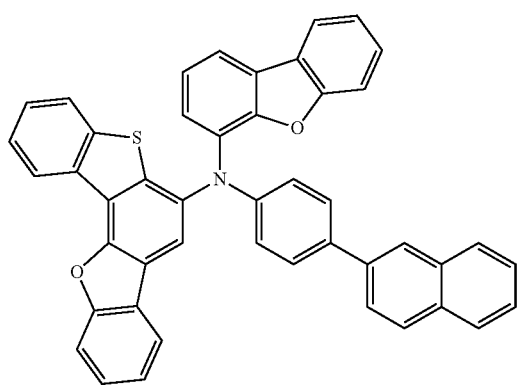
E24
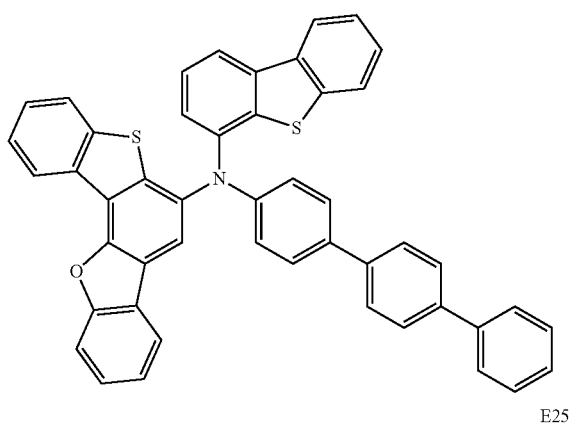
E25
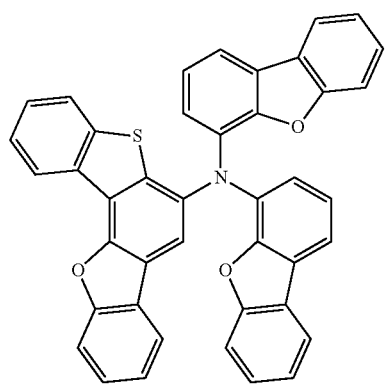
302
-continued
E26
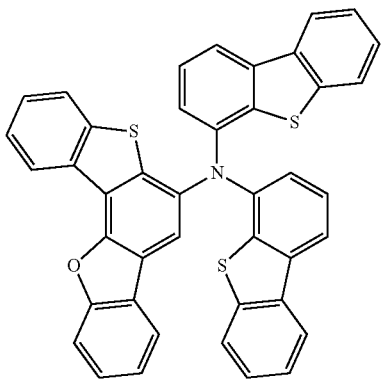
E27
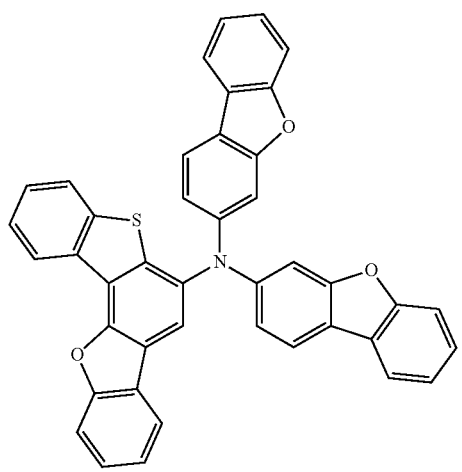
E28
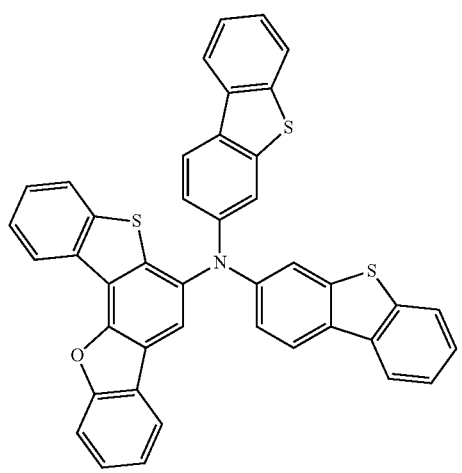

E42
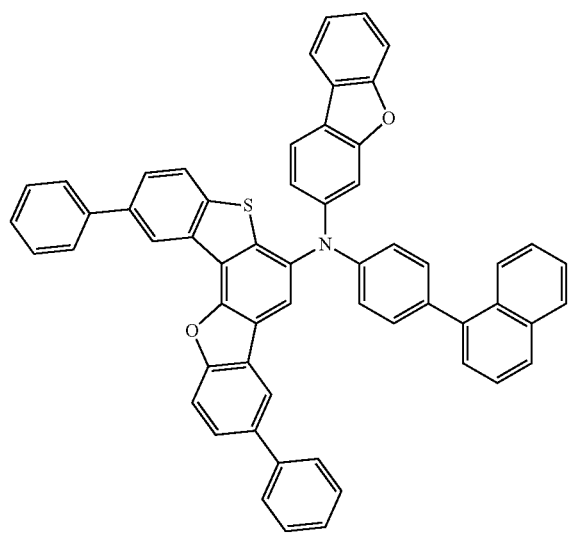
Compound Group F
F9
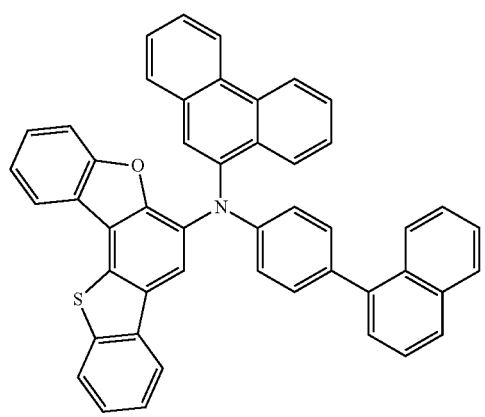
F15
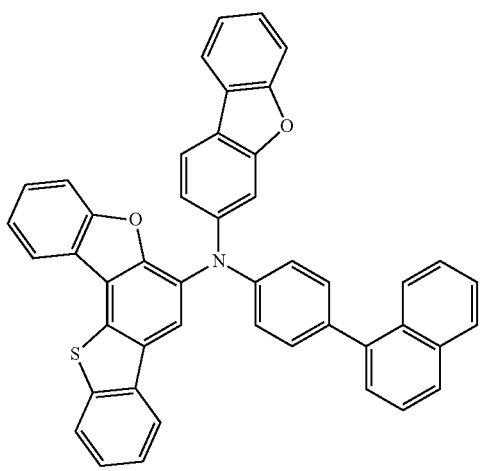
F22
F14
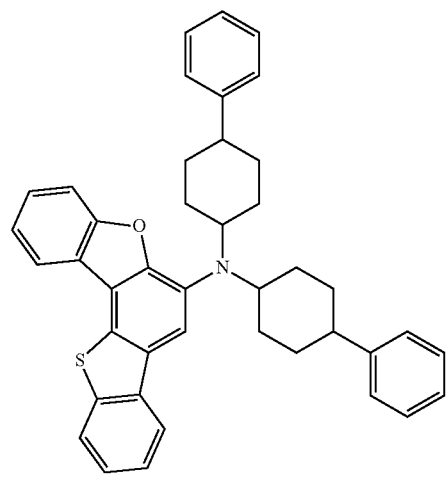
F23
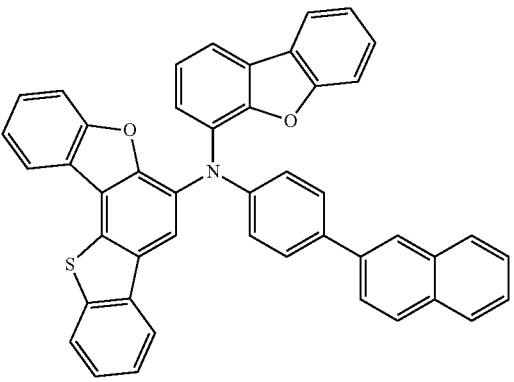

-continued
F24
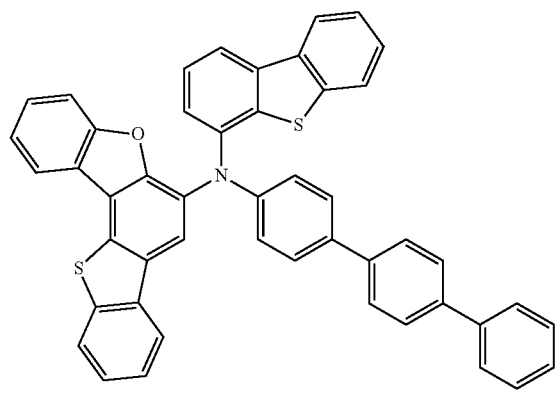
F25
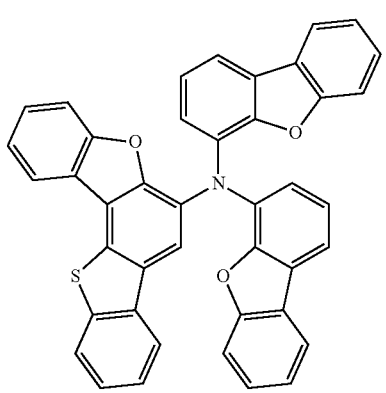
F26
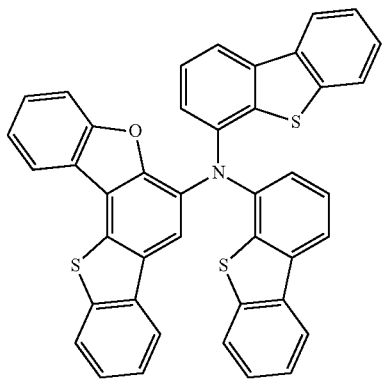
F27
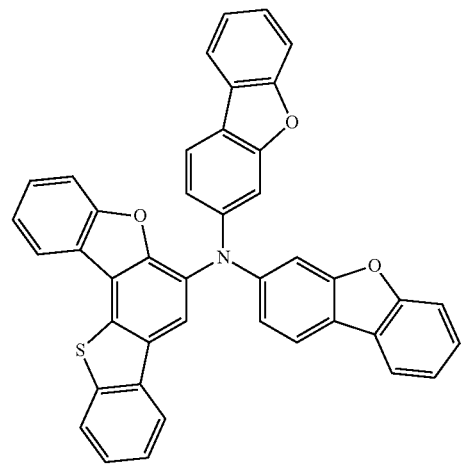
-continued
F28
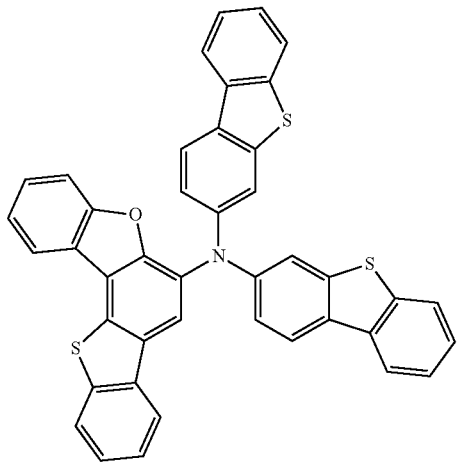
F42
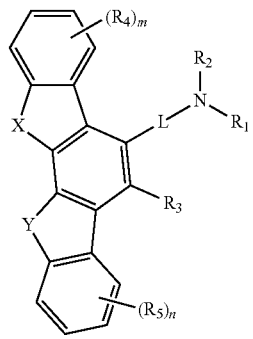
10. An amine compound represented by one of Formula 3-1 to Formula 3-3:
Formula 3-1

Formula 3-2

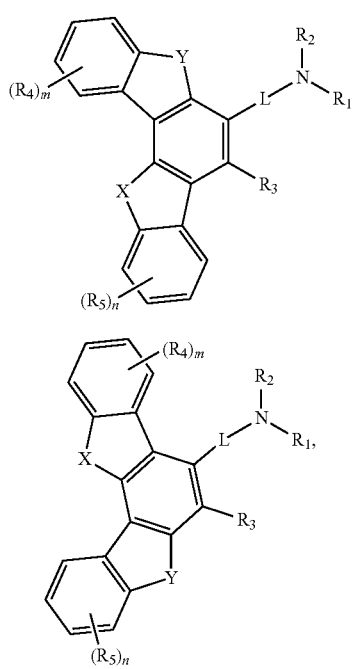

Formula 3-3 carbon atoms for forming a ring, or a substituted or unsubstituted heteroaryl group of 2 to 30 carbon atoms for forming a ring, excluding a carbazolyl group,
provided that $R_4$ and $R_5$ do not combine with an adjacent group to form a ring,
L is a direct linkage,
"m" is an integer of 0 to 4, and
"n" is an integer of 0 to 4.

11. The amine compound of claim 10, wherein the amine compound is a monoamine compound.

12. The amine compound of claim 10, wherein in Formulae 3-2 and 3-3, $R_2$ is a substituted or unsubstituted heteroaryl group of 2 to 30 carbon atoms for forming a ring.

13. The amine compound of claim 10, wherein $R_2$ is an unsubstituted phenyl group, a substituted biphenyl group, a substituted or unsubstituted naphthalene group, a substituted or unsubstituted phenanthryl group, a substituted or unsubstituted dibenzofuran group, or a substituted or unsubstituted dibenzothiophene group,
provided that in Formula 3-1, at least one of $R_1$ or $R_2$ comprises a substituted or unsubstituted cyclohexyl group or a substituted or unsubstituted adamantyl group.

14. The amine compound of claim 10, wherein the amine compound represented by one of Formula 3-1 to Formula 3-3 is represented by one of Formula 4-1 to Formula 4-9:

wherein in Formulae 3-1 to 3-3,
X is O or S,
Y is O or S, where at least one of X or Y is O,
in Formulae 3-1,
$R_1$ and $R_2$ are each independently a substituted or unsubstituted alkyl group of 1 to 20 carbon atoms, a substituted or unsubstituted aryl group of 6 to 30 carbon atoms for forming a ring, or a substituted or unsubstituted heteroaryl group of 2 to 30 carbon atoms for forming a ring,
in Formulae 3-2 and 3-3,
$R_1$ is a substituted or unsubstituted cyclohexyl group, a substituted or unsubstituted adamantyl group, a substituted or unsubstituted phenanthryl group, a substituted or unsubstituted dibenzofuran group, or a substituted or unsubstituted dibenzothiophene group,
$R_2$ is a substituted or unsubstituted alkyl group of 1 to 20 carbon atoms, a substituted or unsubstituted heteroaryl group of 2 to 30 carbon atoms for forming a ring, a substituted or unsubstituted cyclohexyl group, a substituted or unsubstituted adamantyl group, a substituted biphenyl group, a substituted or unsubstituted terphenyl group, a substituted or unsubstituted phenanthryl group, a substituted or unsubstituted naphthalene group, an unsubstituted phenyl group, or a substituted phenyl group substituted with a deuterium atom, a silyl group, an oxy group, a naphthalene group, or a pyridine group,
provided that in Formula 3-1, at least one of $R_1$ or $R_2$ comprises a substituted or unsubstituted cyclohexyl group or a substituted or unsubstituted adamantyl group,
provided that in Formula 3-2 and Formula 3-3, $R_2$ does not comprise a substituted or unsubstituted fluorenyl group,
$R_3$ to $R_5$ are each independently a hydrogen atom, a deuterium atom, a halogen atom, a substituted or unsubstituted alkyl group of 1 to 20 carbon atoms, a substituted or unsubstituted aryl group of 6 to 30

Formula 4-1

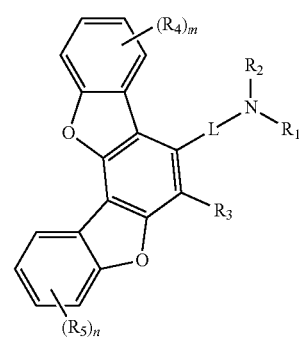

Formula 4-2

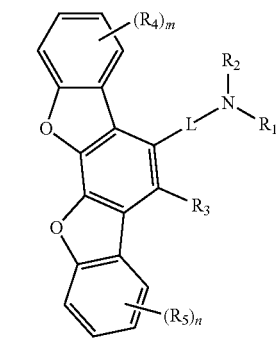

Formula 4-3

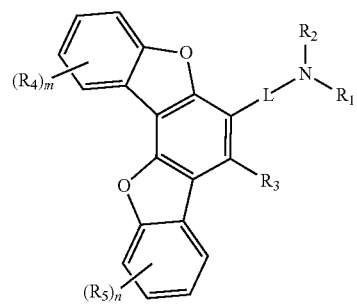

Formula 4-4

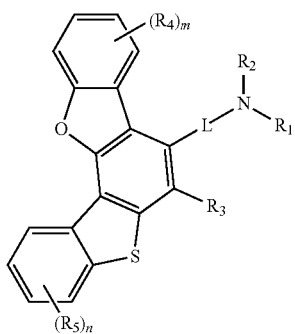

Formula 4-5

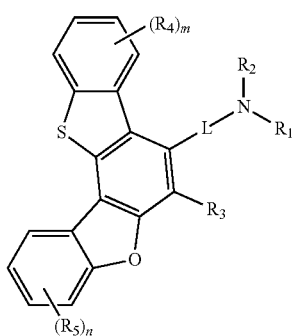

Formula 4-6

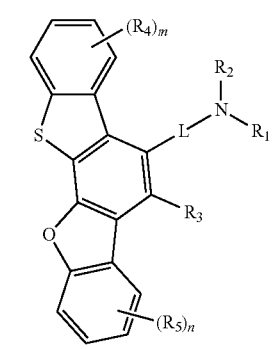

Formula 4-7

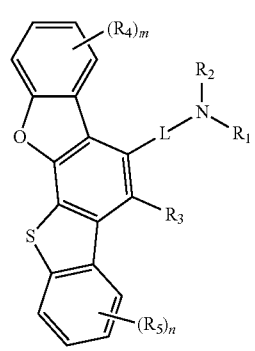

Formula 4-8

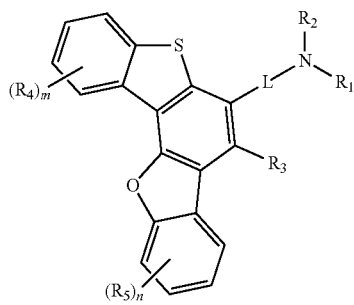

Formula 4-9

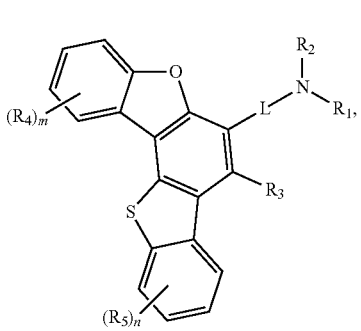

wherein in Formula 4-1 to Formula 4-9, $R_1$ to $R_5$, L, "m" and "n" are each independently the same as defined in Formula 3-1 to Formula 3-3, provided that in Formulae 4-1, 4-3,4-4, 4-5, 4-8, and 4-9, $R_2$ does not comprise a substituted or unsubstituted fluorenyl group, provided that in Formulae 4-2, 4-6, and 4-7, at least one of $R_1$ or $R_2$ comprises a substituted or unsubstituted cyclohexyl group or a substituted or unsubstituted adamantyl group, and $R_4$ and $R_5$ do not combine with an adjacent group to form a ring.

15. An amine compound represented by at least one compound in Compound Group A to Compound Group F:

Compound Group A

A14

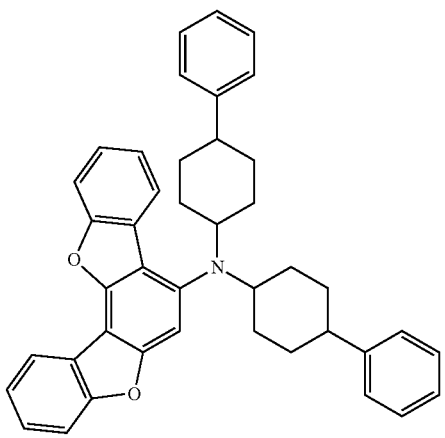

A16
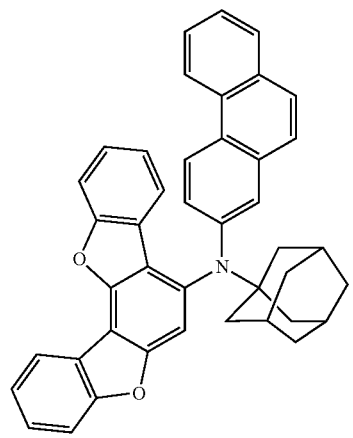
A25
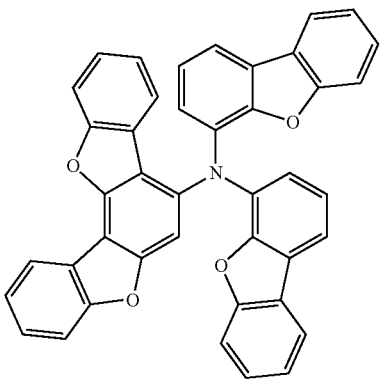
A22
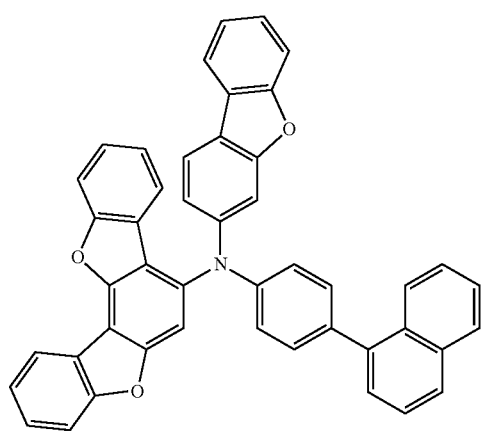
A26
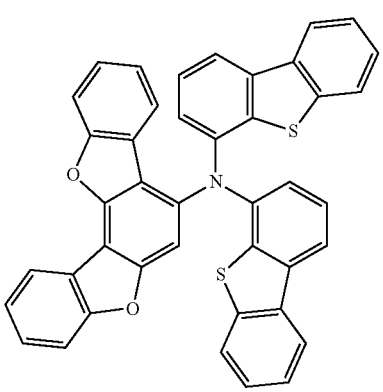
A23
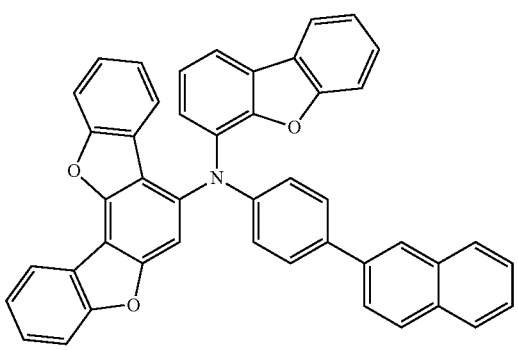
A27
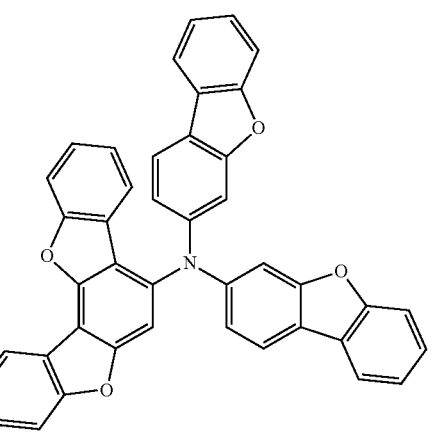
A24
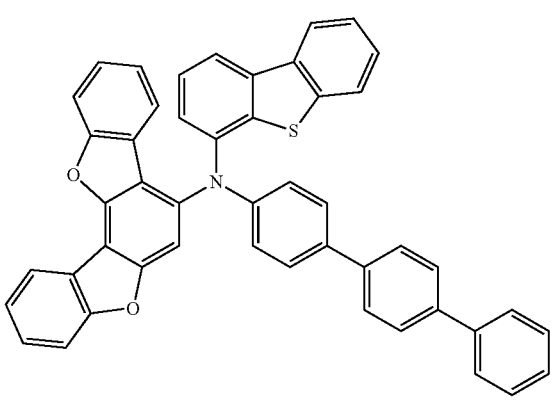
A28
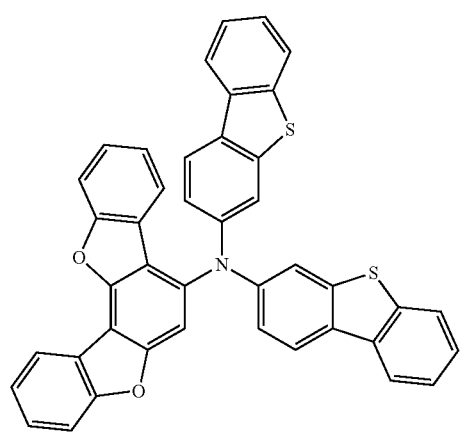

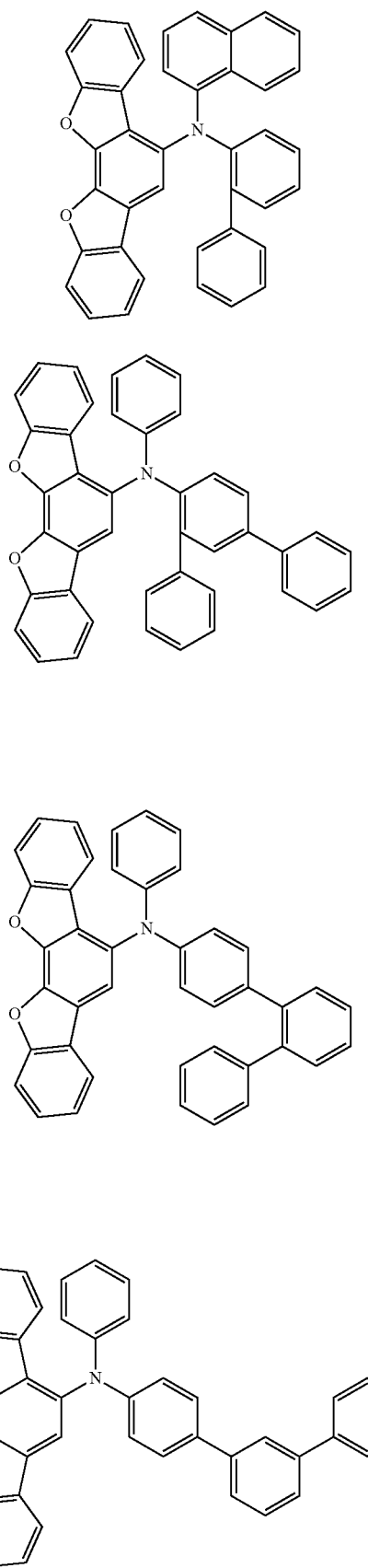
A48
A50
A51
A52
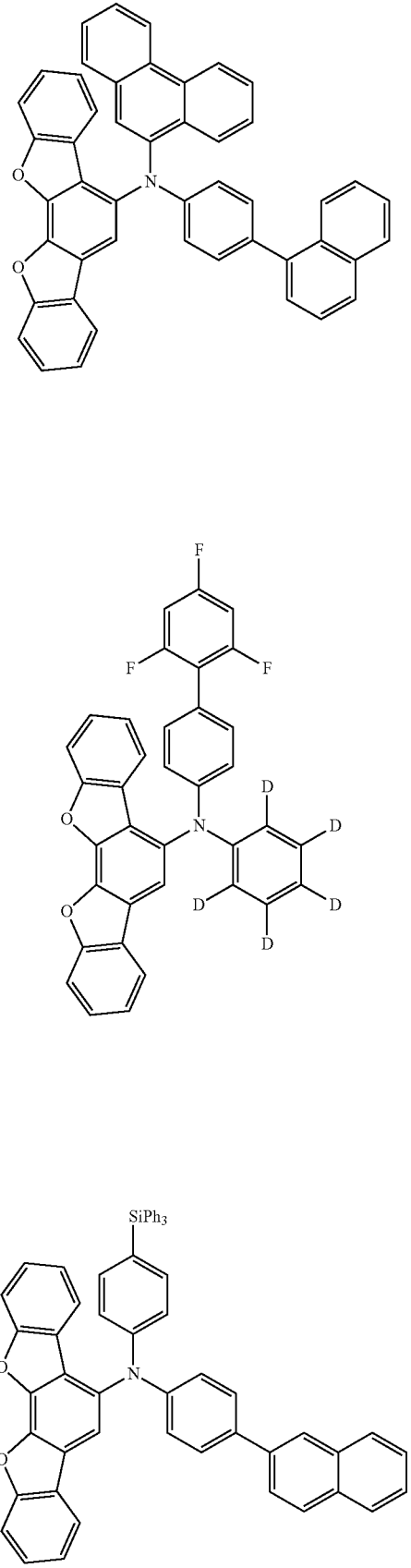
A54
A55
A56

A57
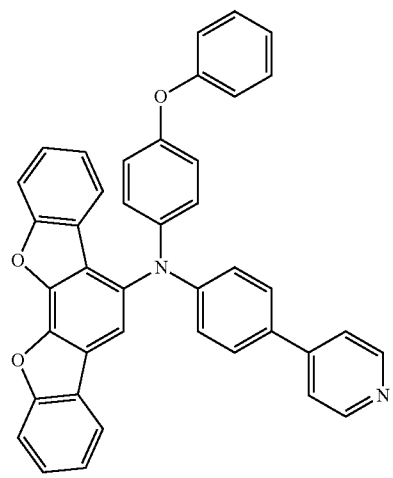
A63
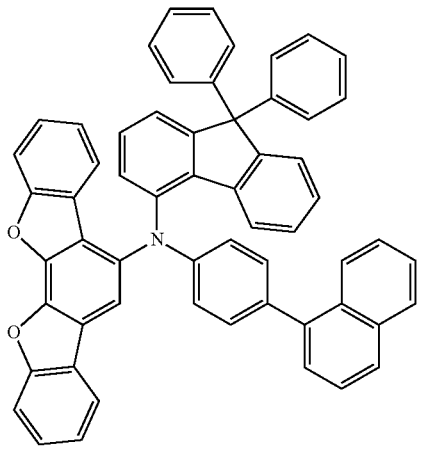
A61
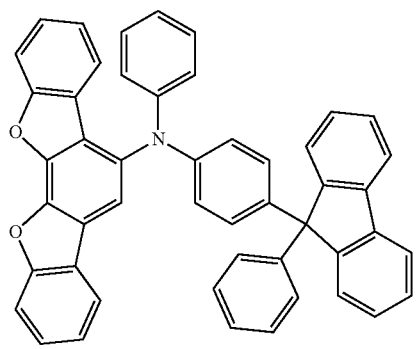
A64
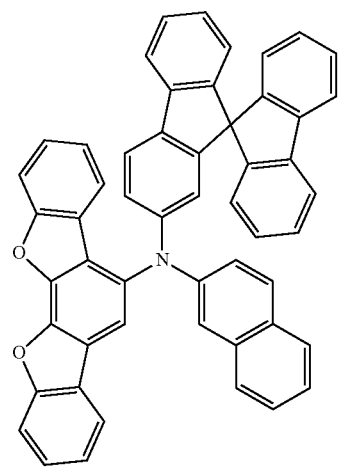
A62
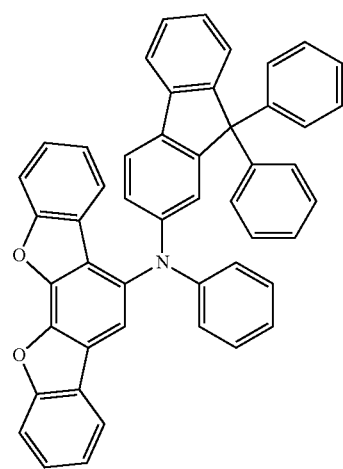
A65
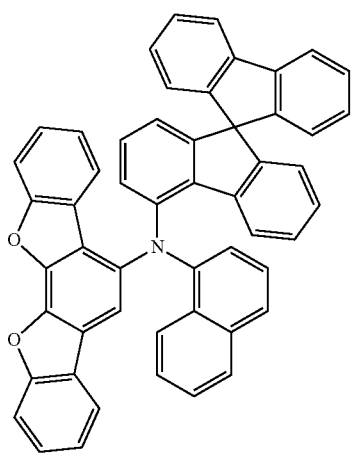

A67
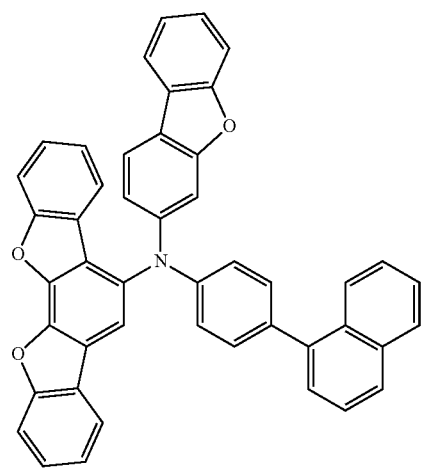
A68
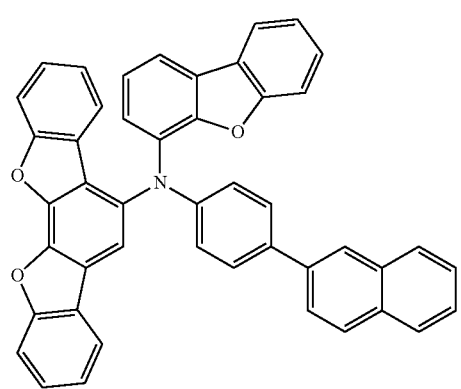
A69
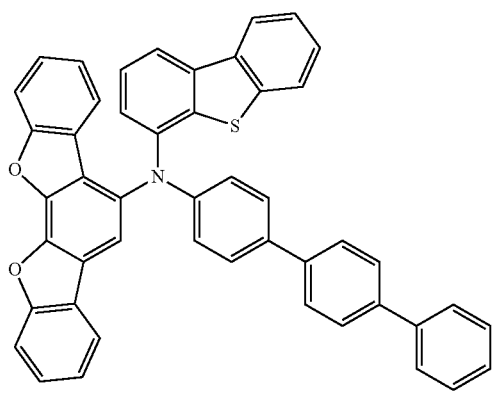
A70
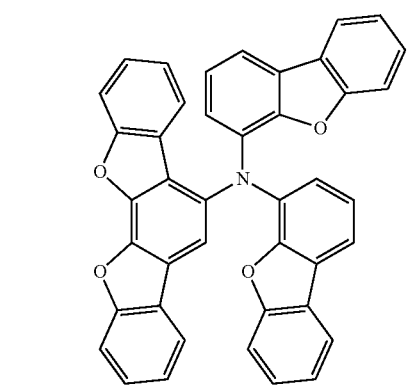
A71
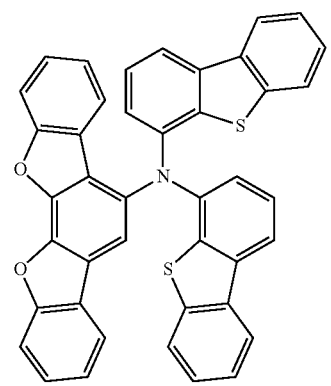
A72
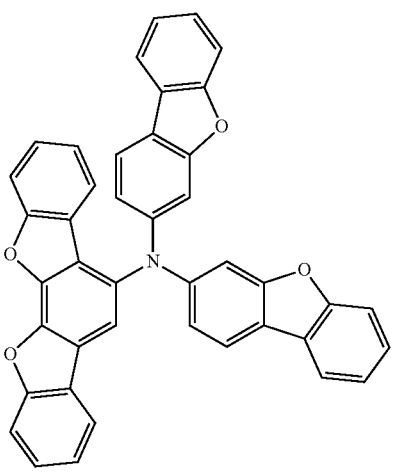
A73
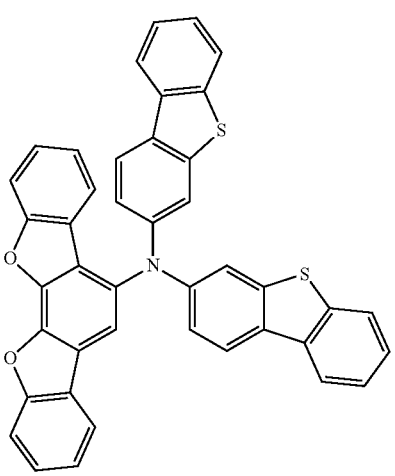

-continued
A74
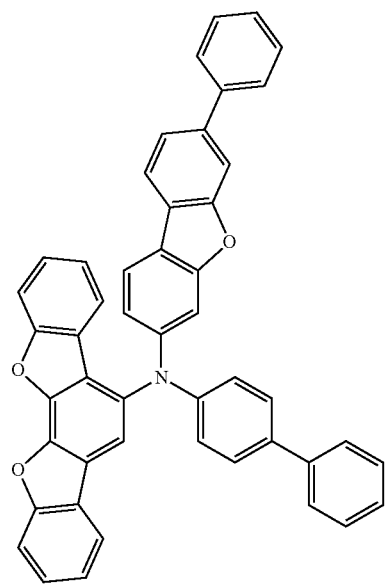
A75
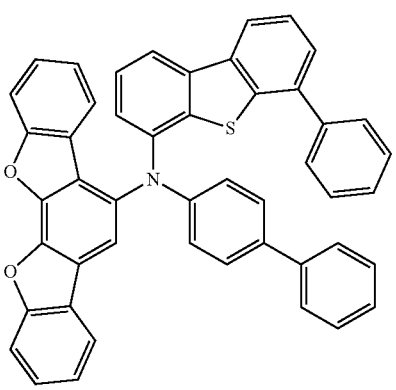
A84
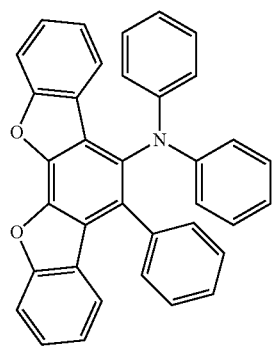
-continued
A85
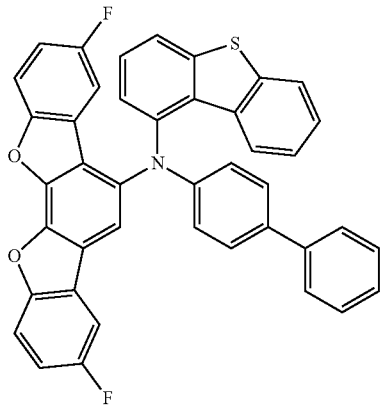
A86
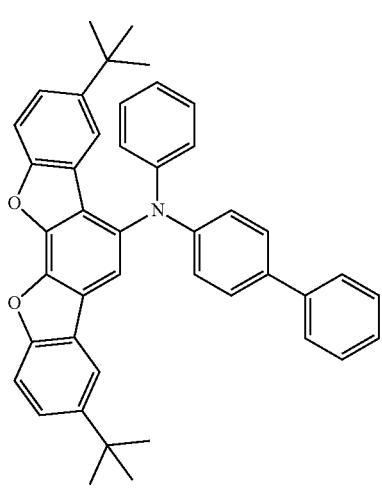
A87
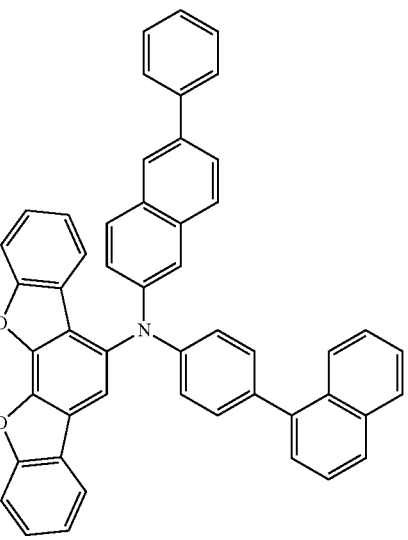

A99
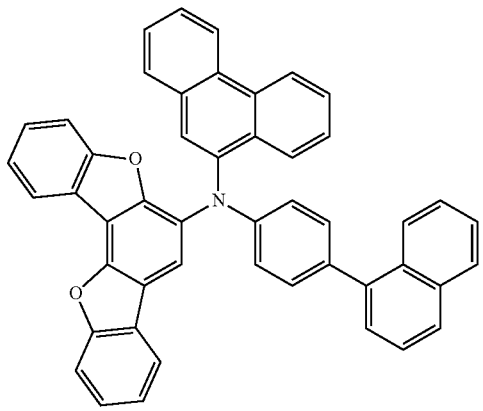
A103
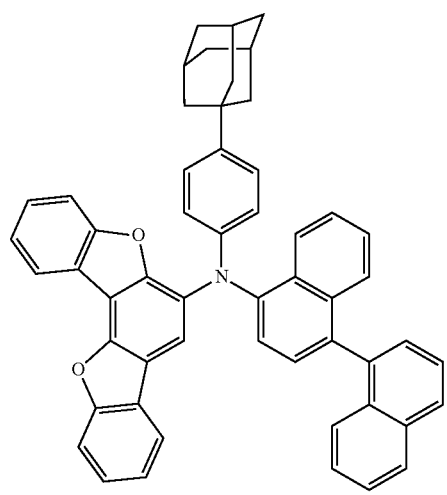
A104
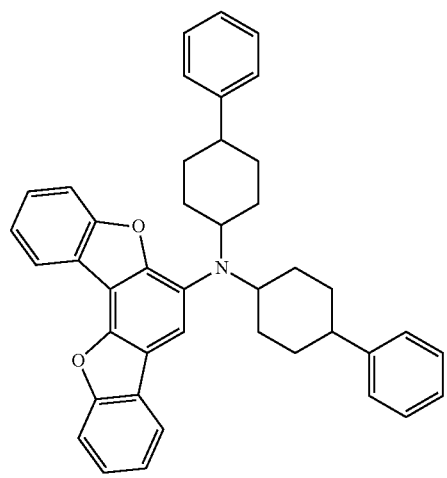
A105
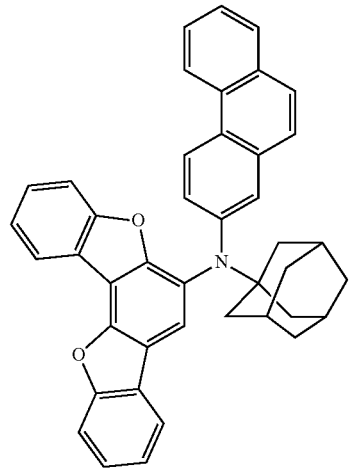
A107
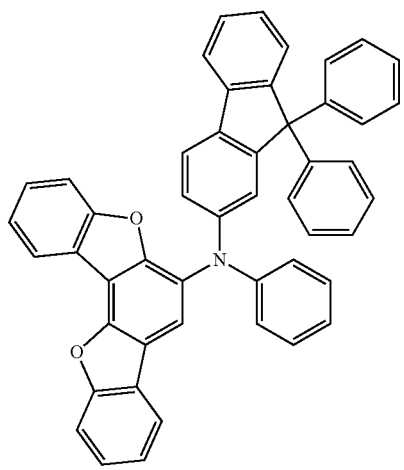
A108
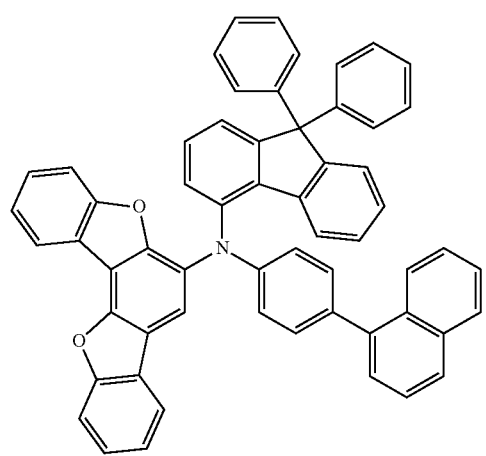

A109
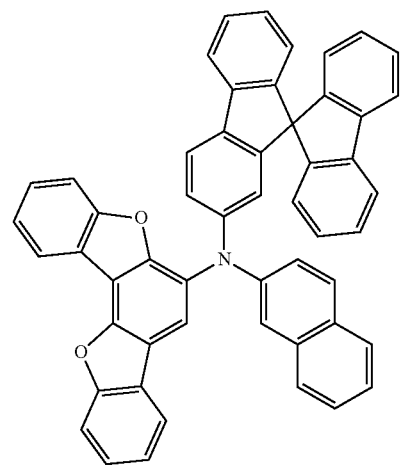
A110
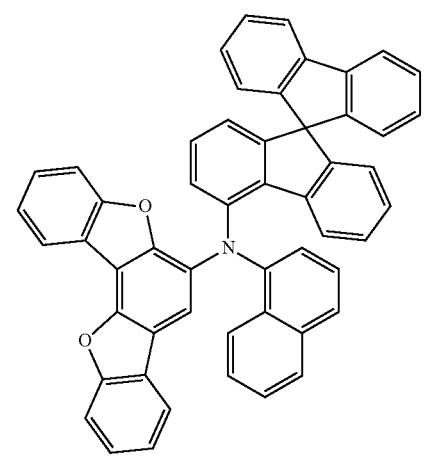
A112
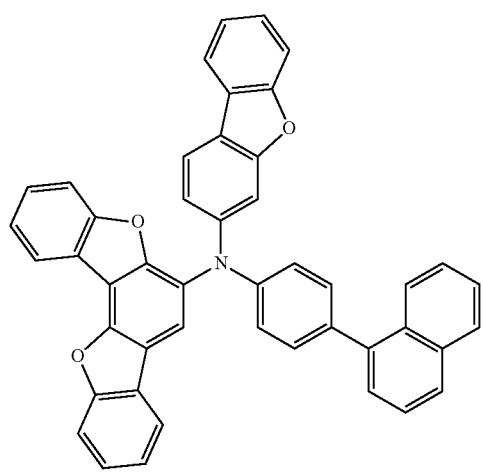
A113
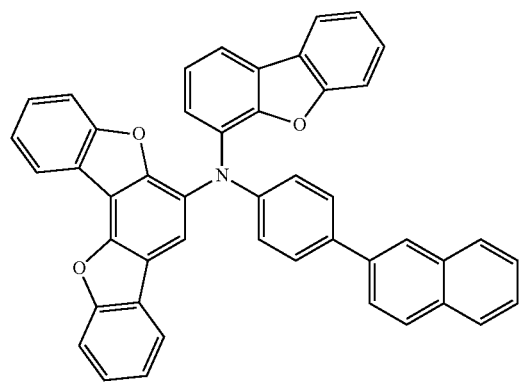
A114
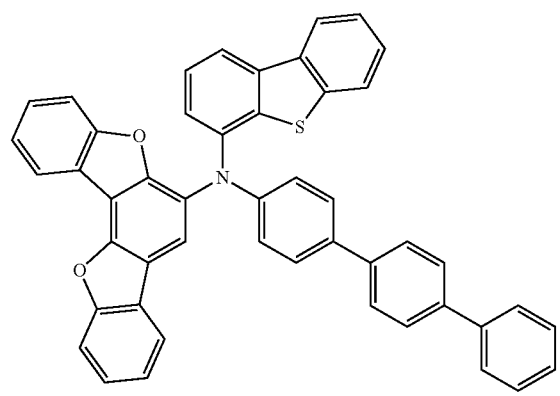
A115
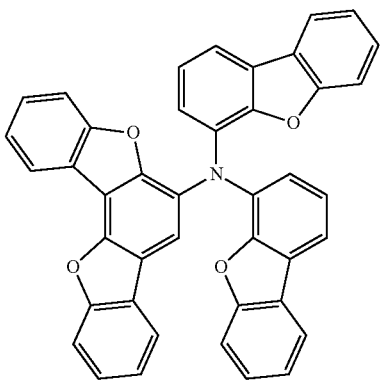
A116
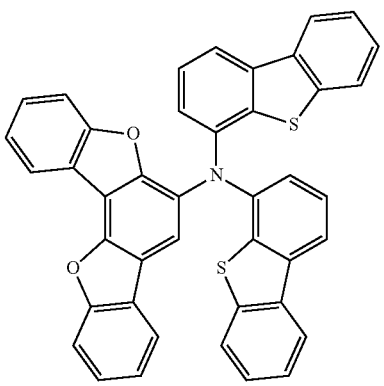

A117
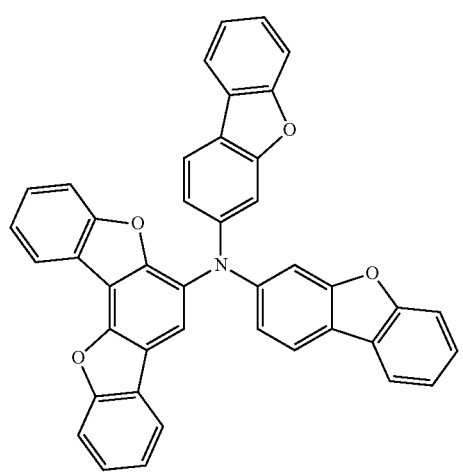
A149
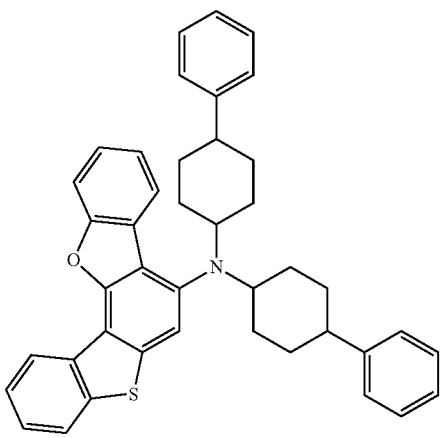
A118
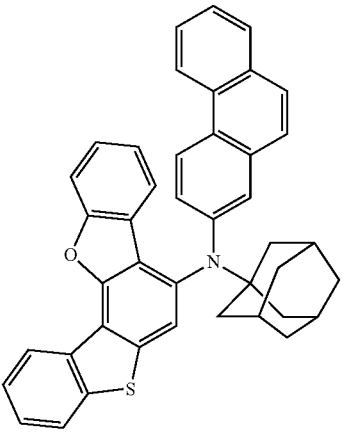
A150
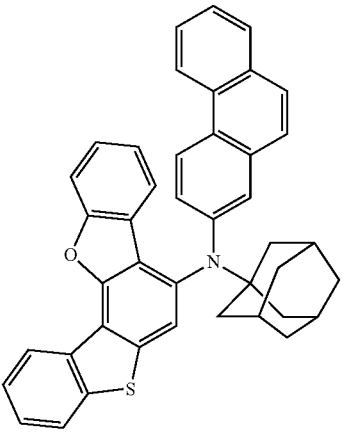
A144
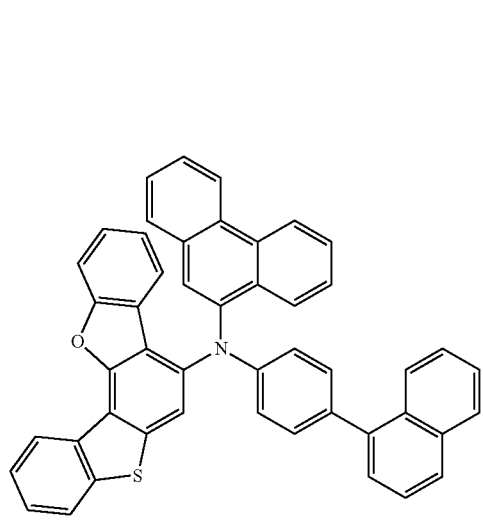
A152
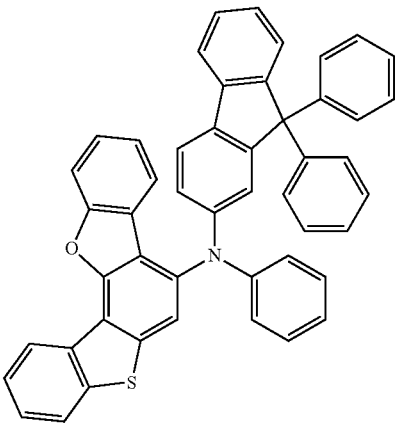

327
-continued
A153
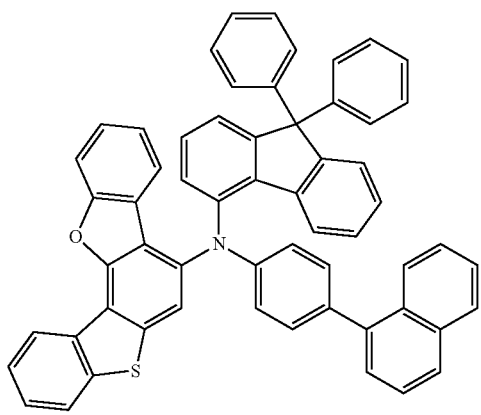
A154
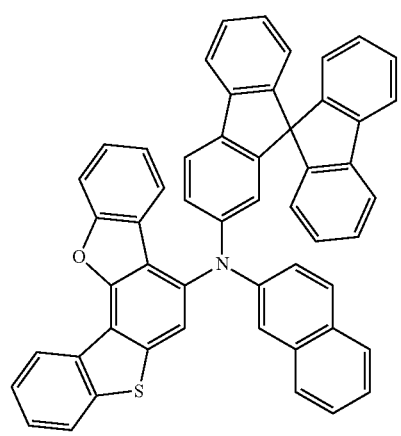
A155
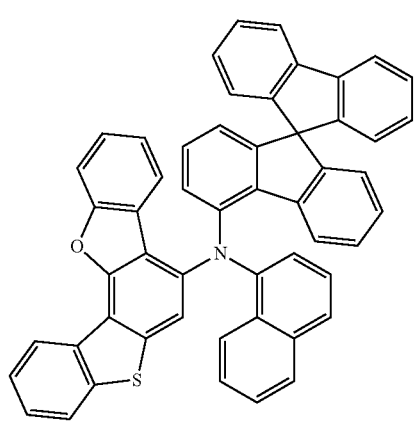
328
-continued
A157
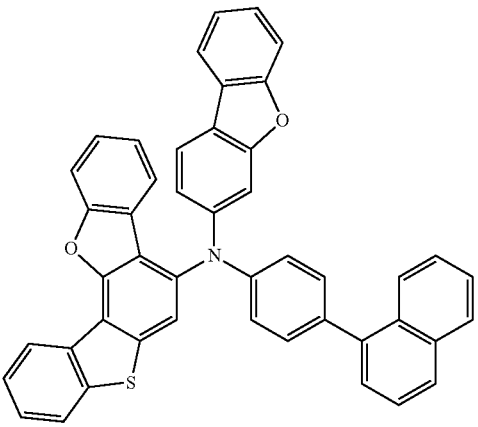
A158
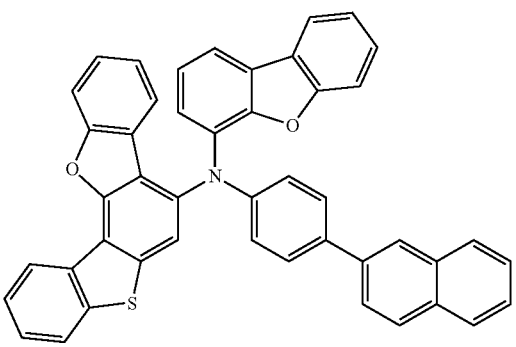
A159
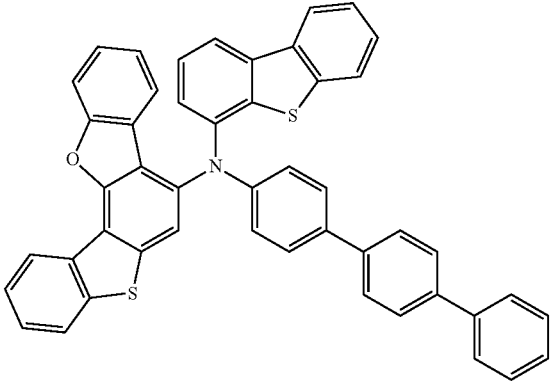
A160

-continued
A161
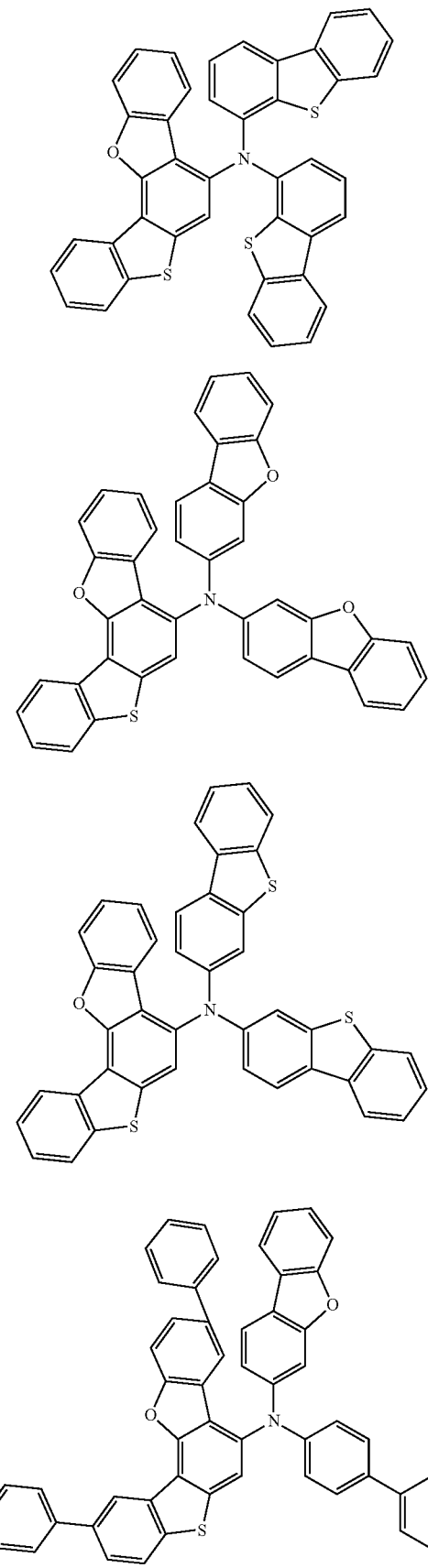
A162
A163
A177
-continued
Compound Group B
B9
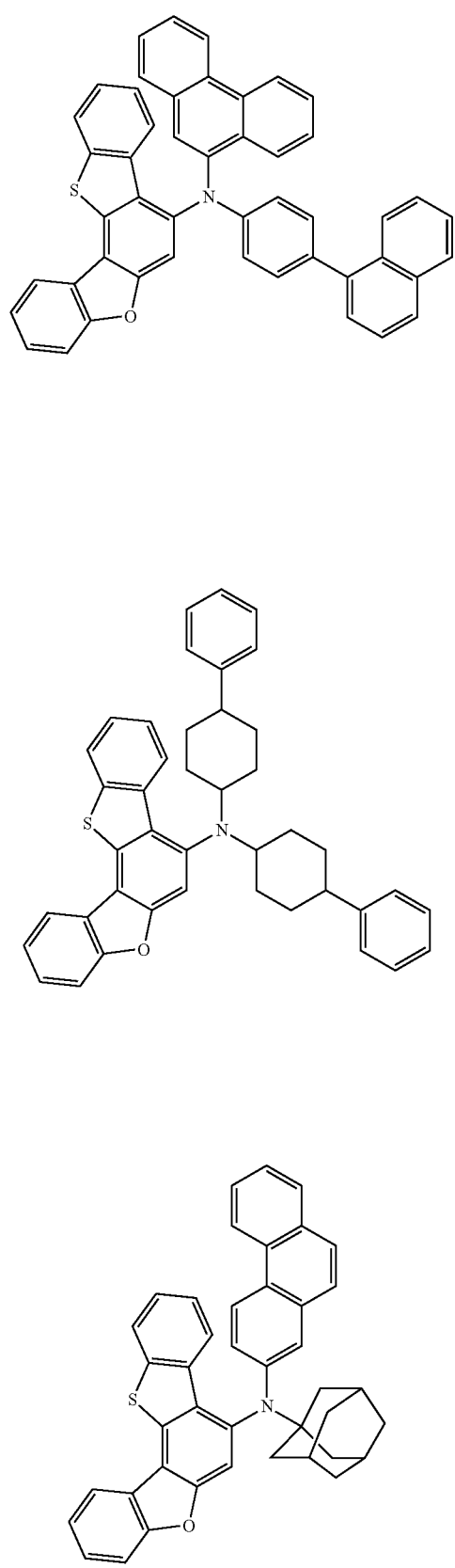
B14
B15

B17
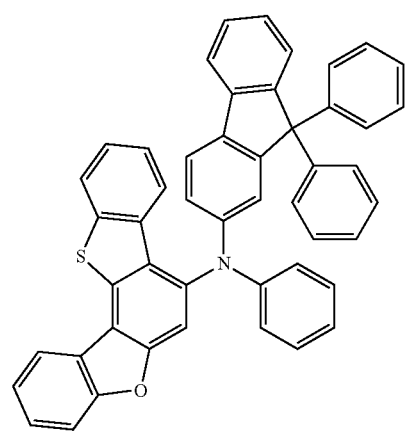
B18
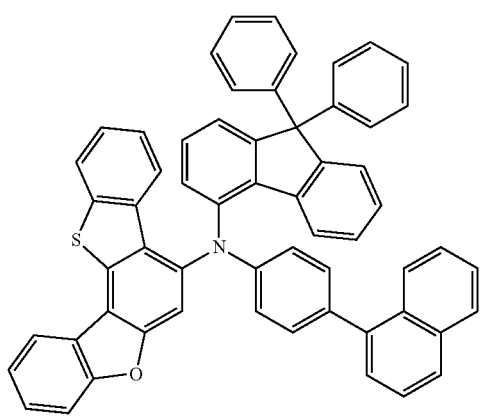
B19
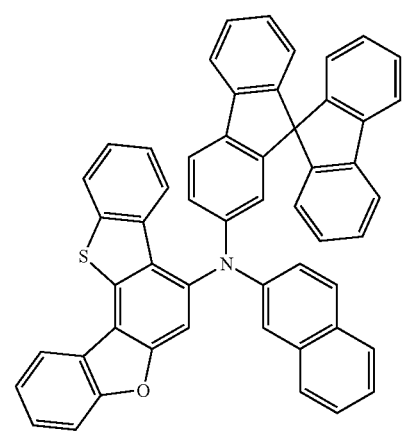
B20
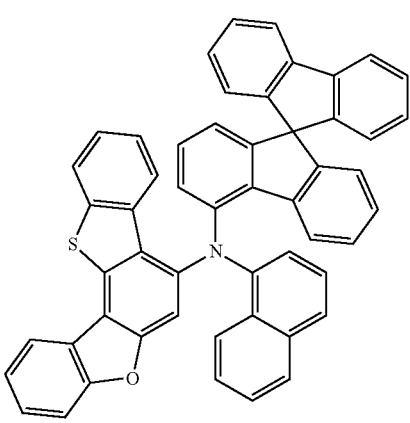
B21
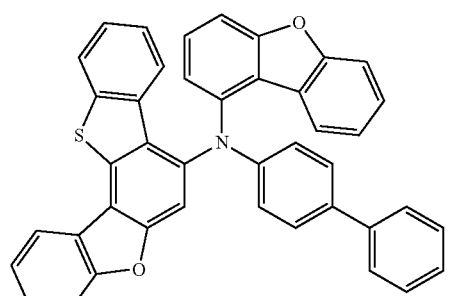
B22
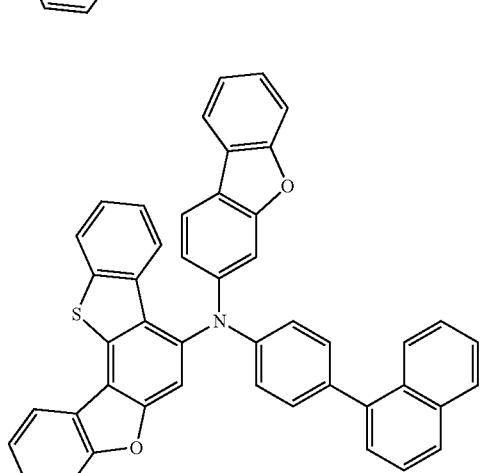
B23
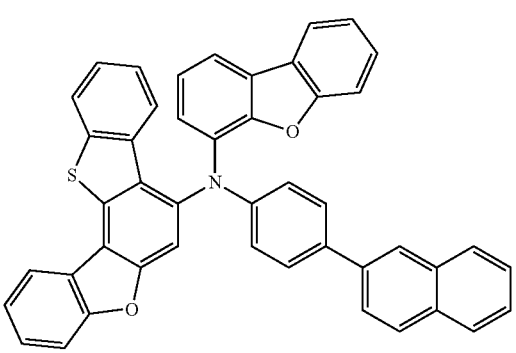

B24
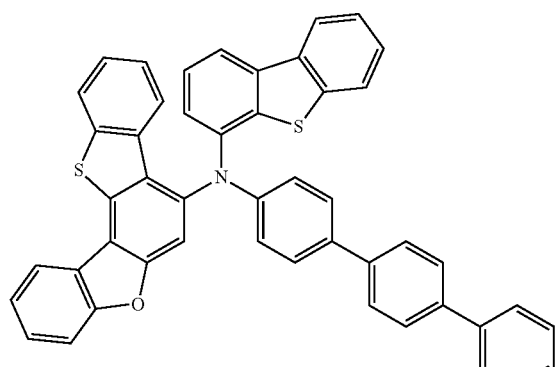
B25
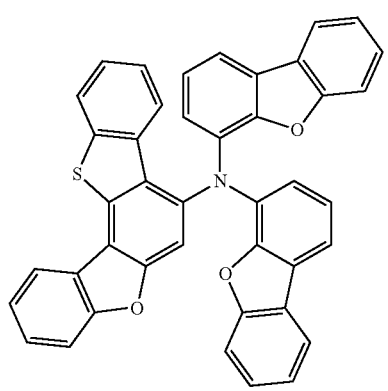
B26
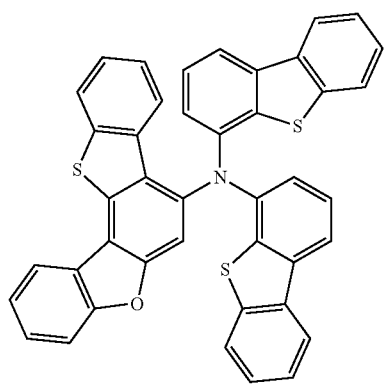
B27
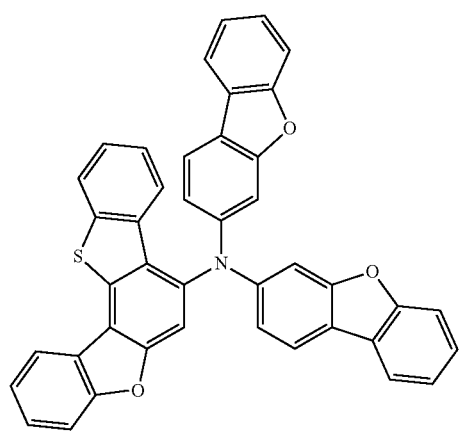
B28
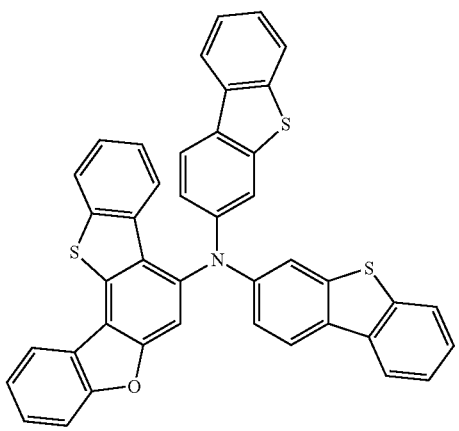
B42
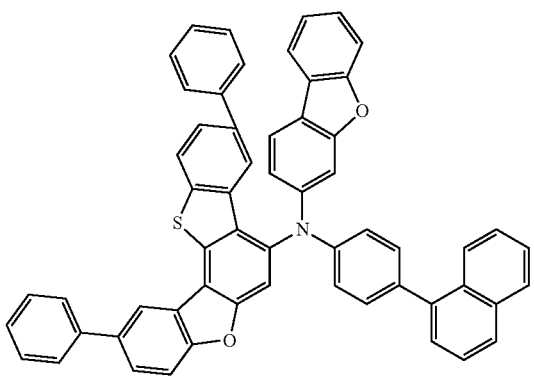
Compound Group C
C1
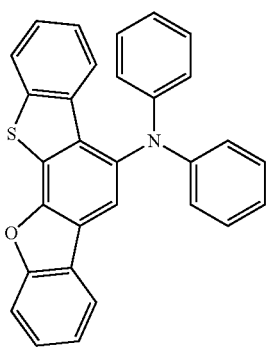

-continued
C2
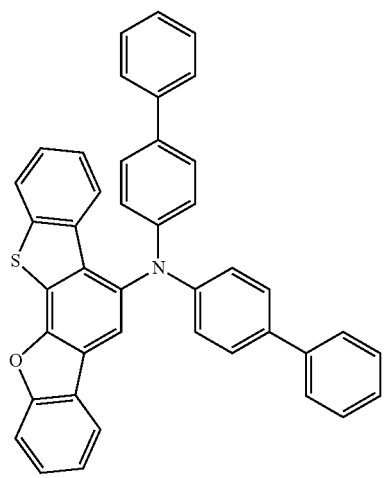
C3
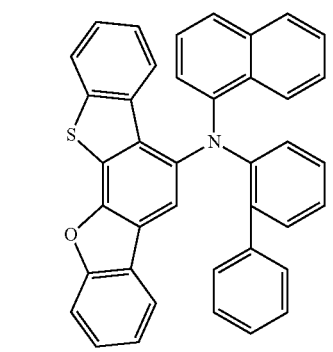
C4
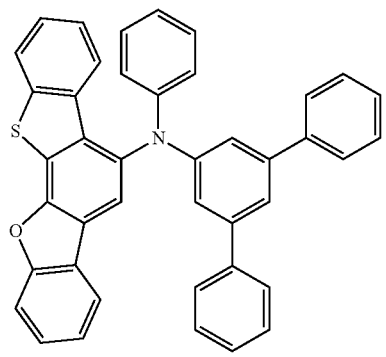
C5
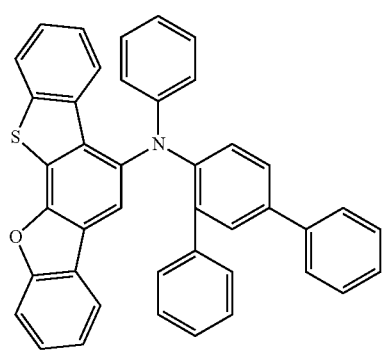
-continued
C6
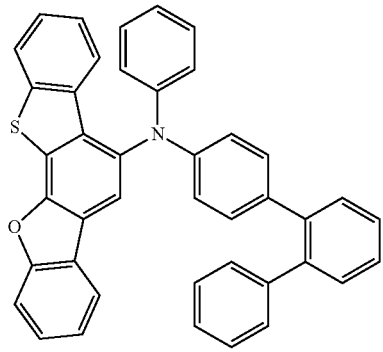
C7
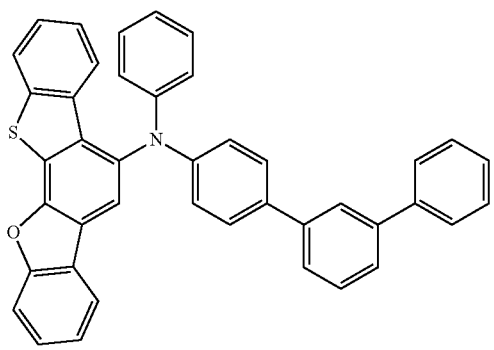
C8
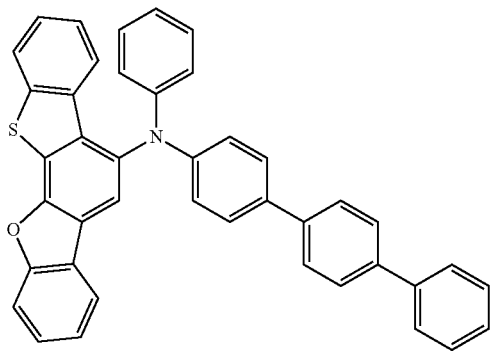
C9
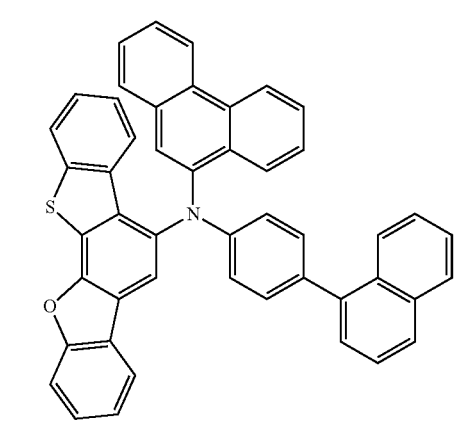

338
-continued
C10
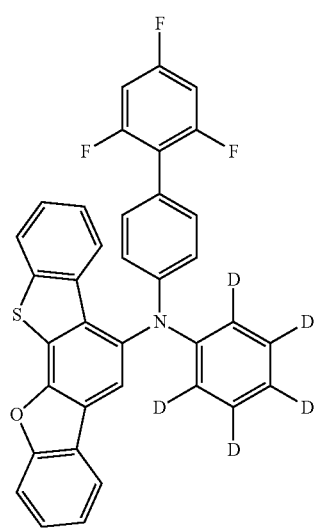
C11
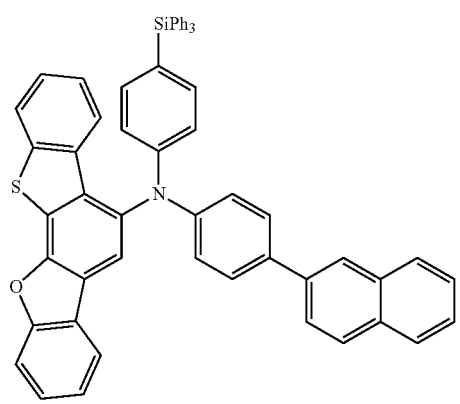
C12
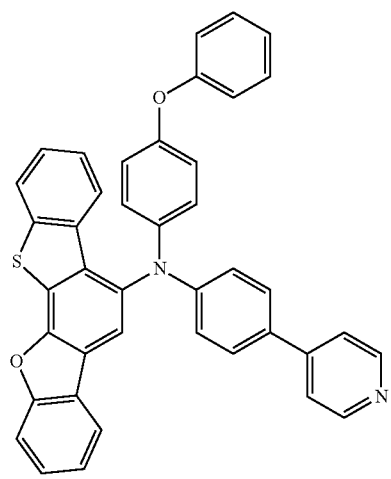
C14
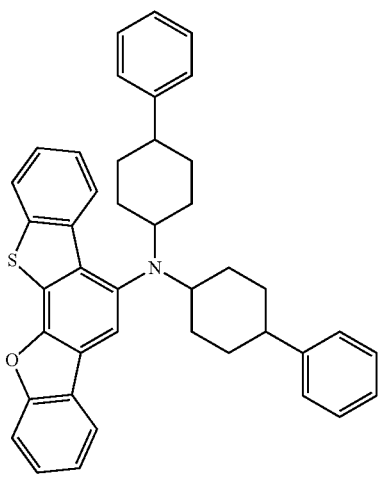
C15
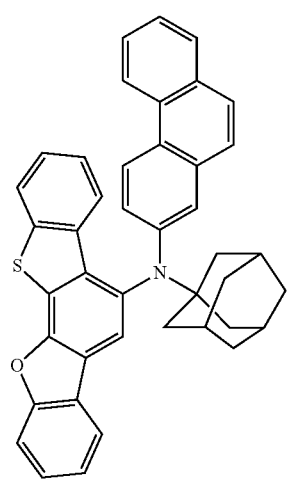
C16
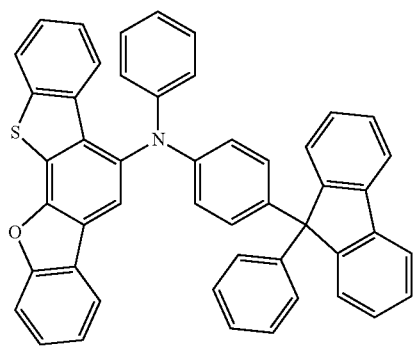

-continued
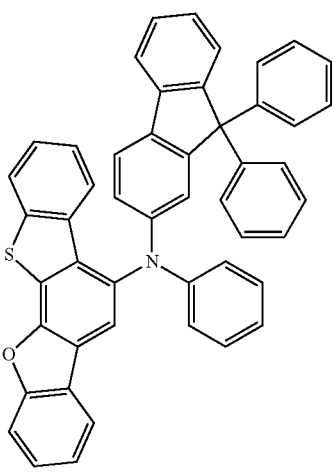
C17
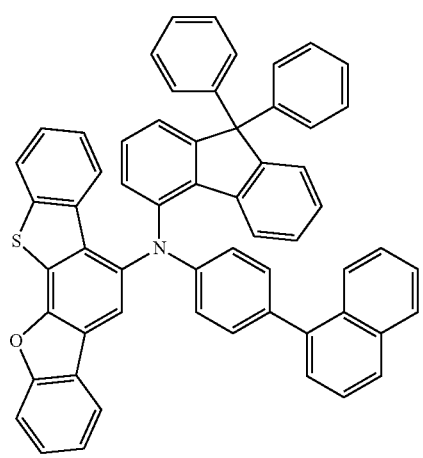
C18
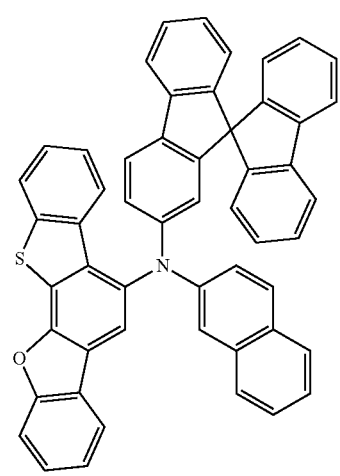
C19
-continued
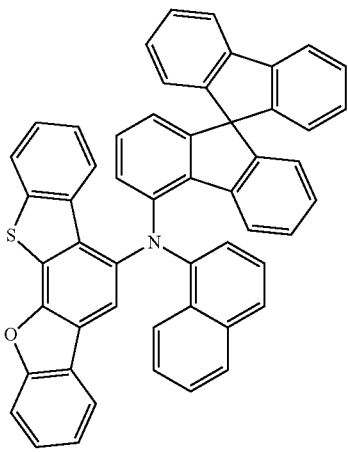
C20
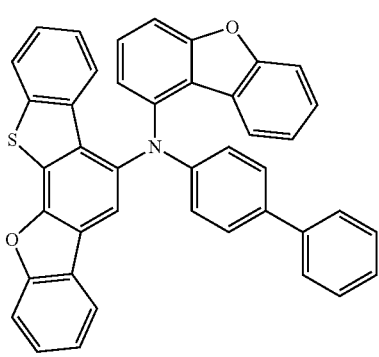
C21
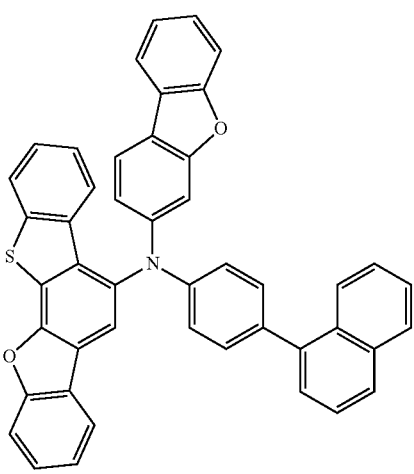
C22
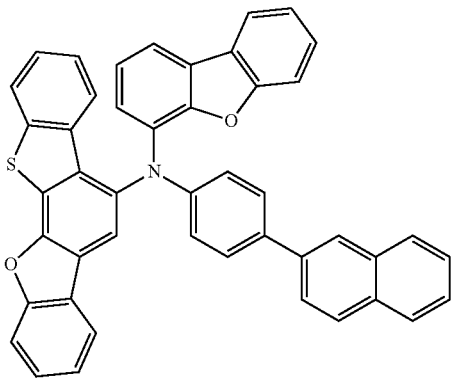
C23

C24
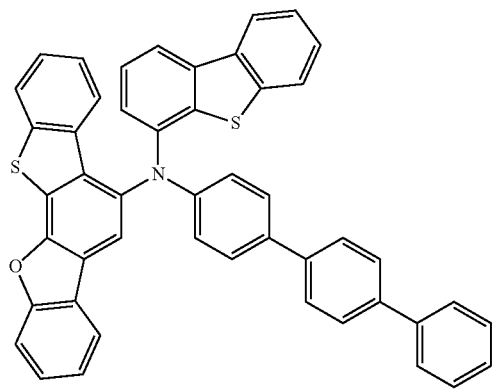
C25
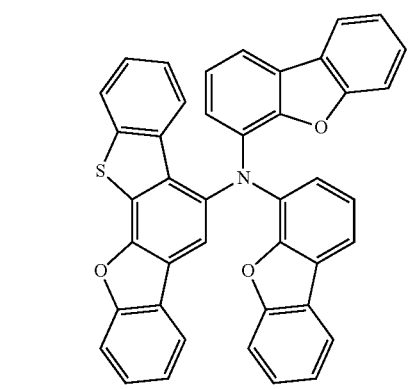
C26
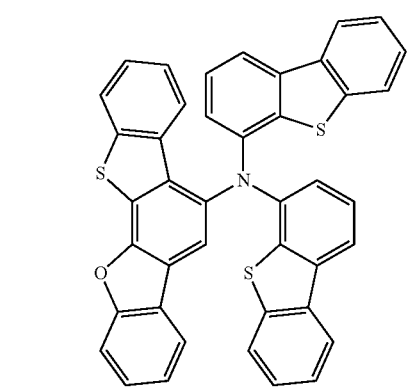
C27
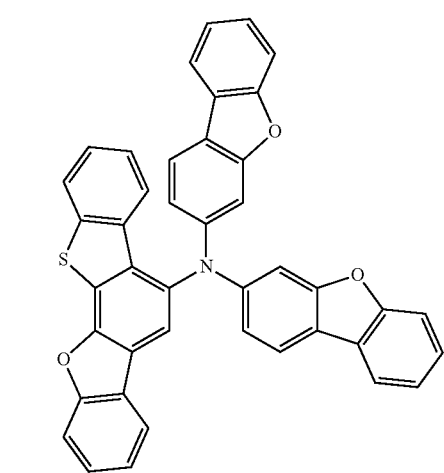
C28
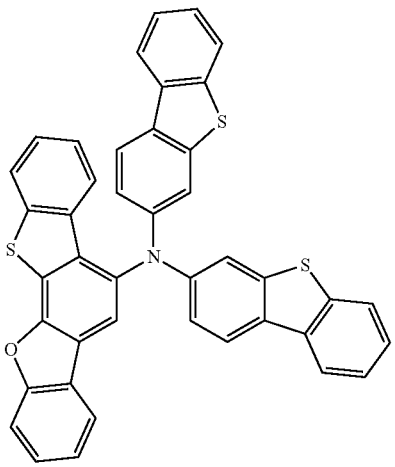
C29
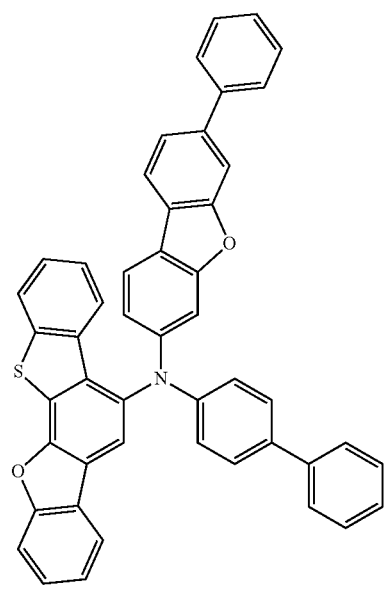
C30
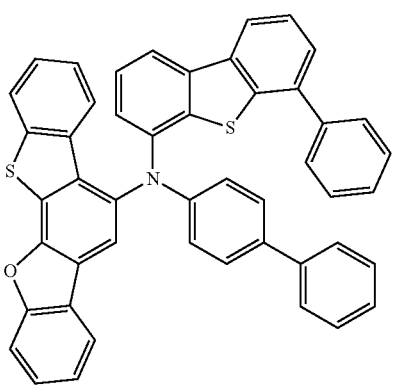

C39
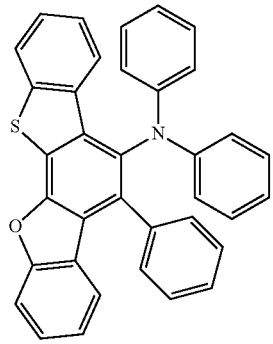
C40
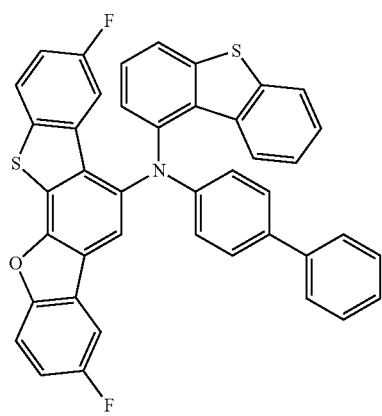
C41
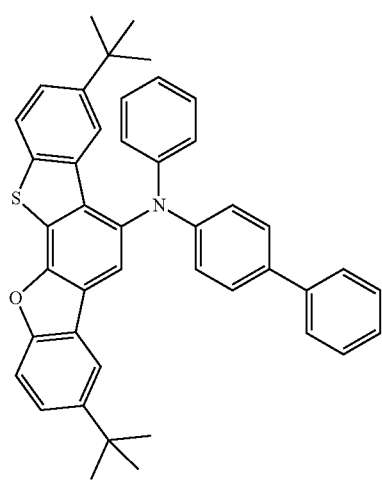
C42
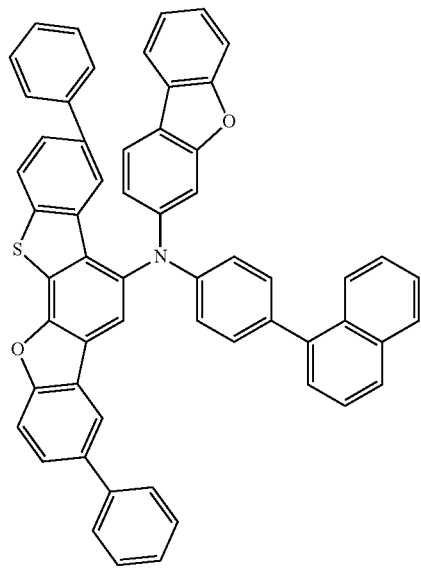
Compound Group D
D1
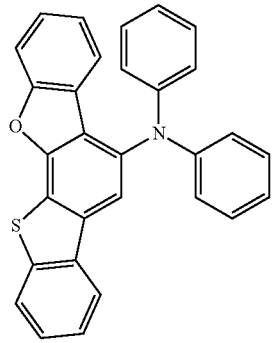
D2
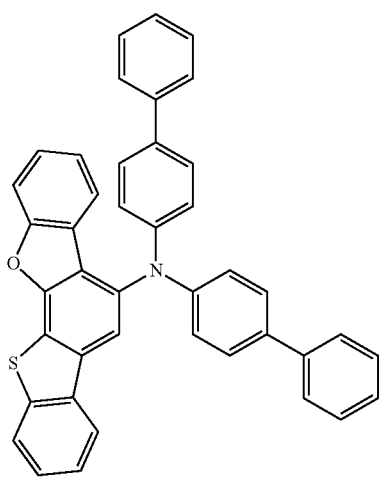

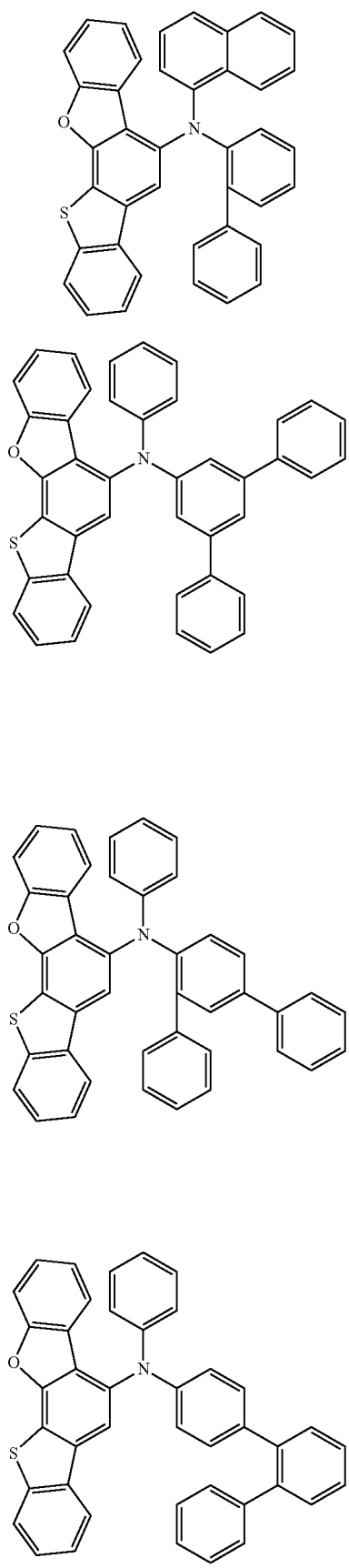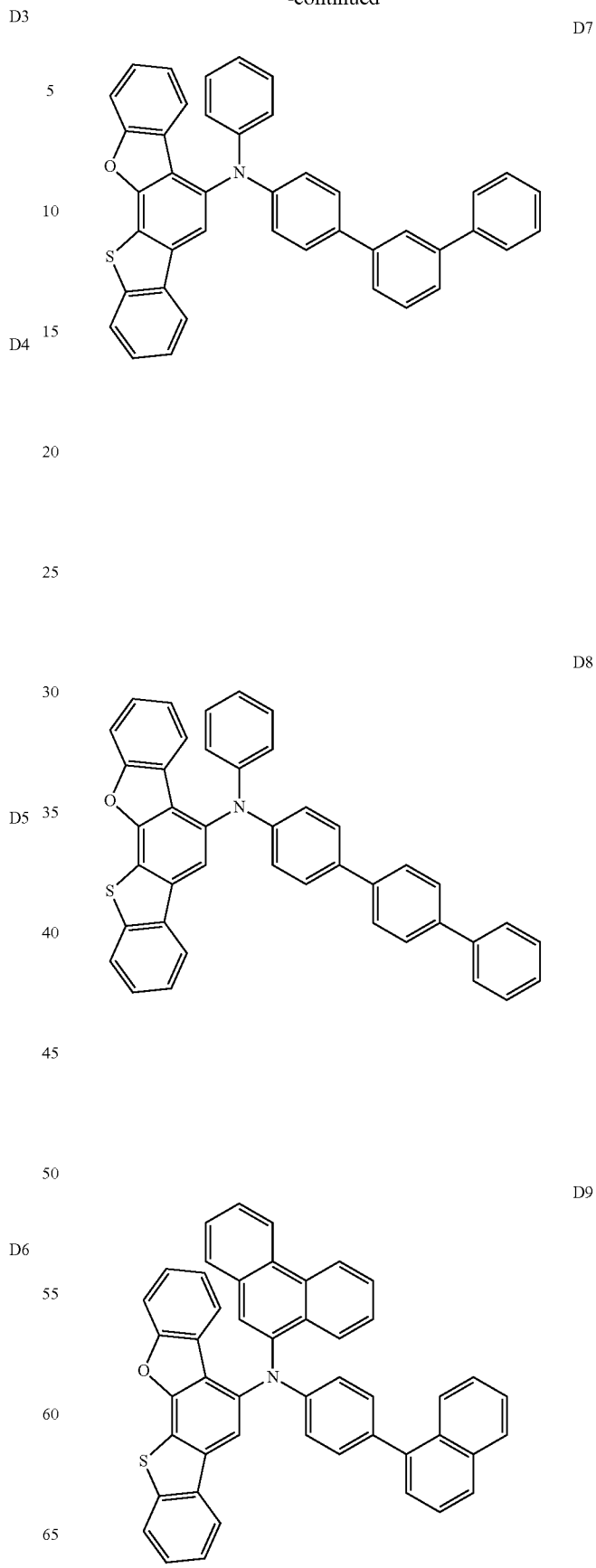

D10 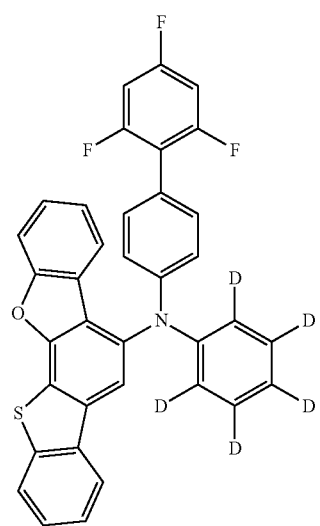
D11 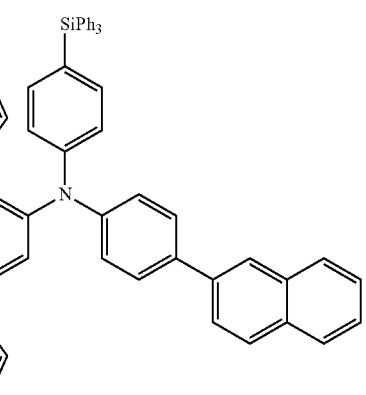
D14 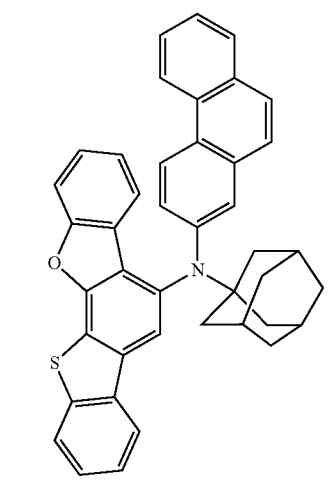
D12 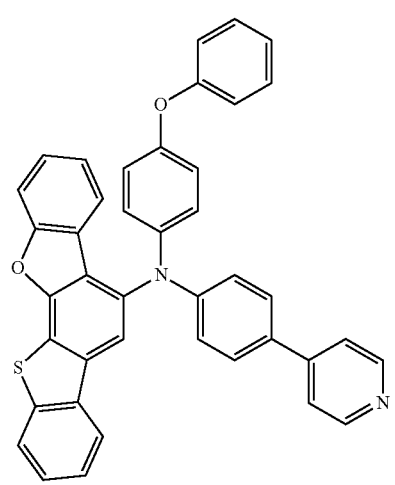
D15
D16 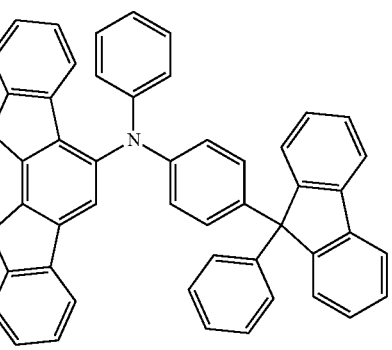

-continued
D17
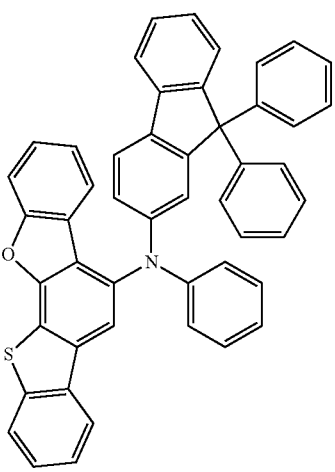
D18
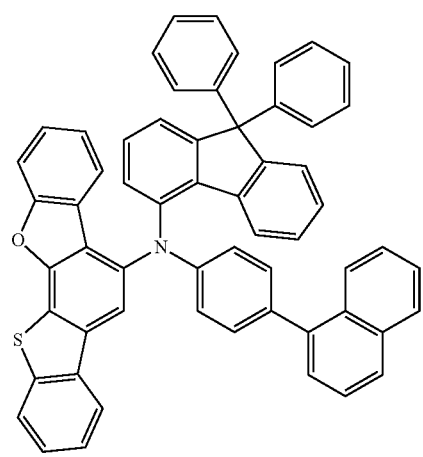
D19
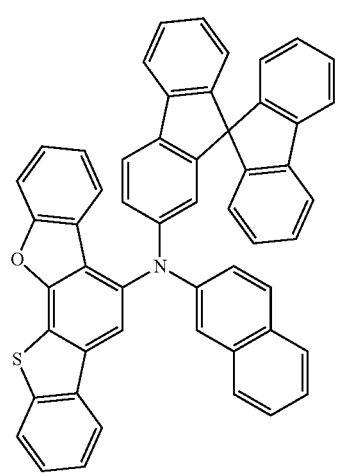
-continued
D20
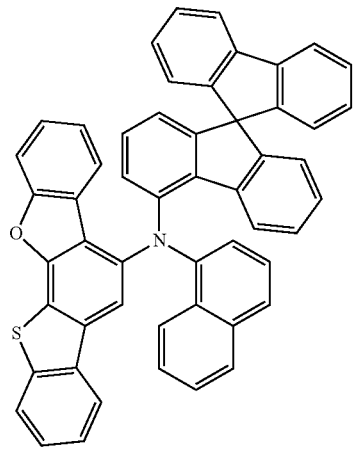
D21
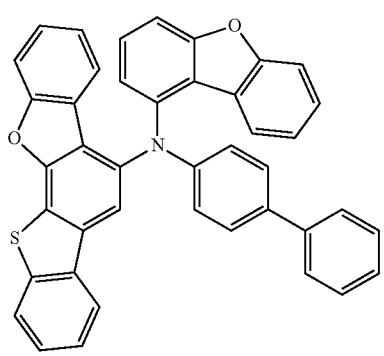
D22
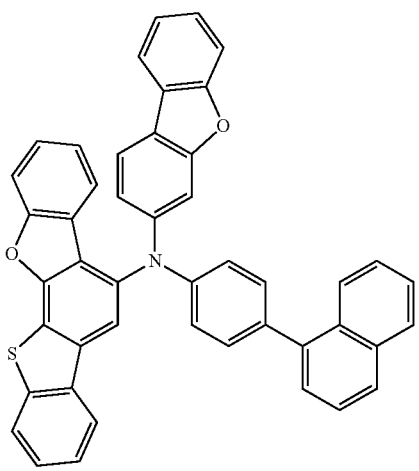
D23
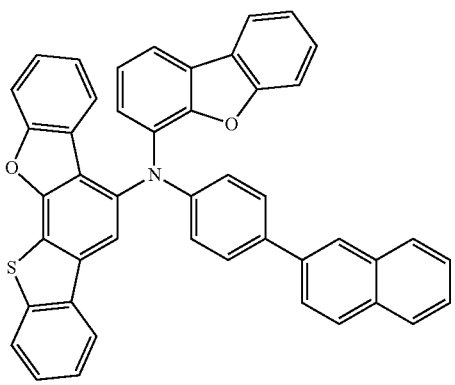

D24
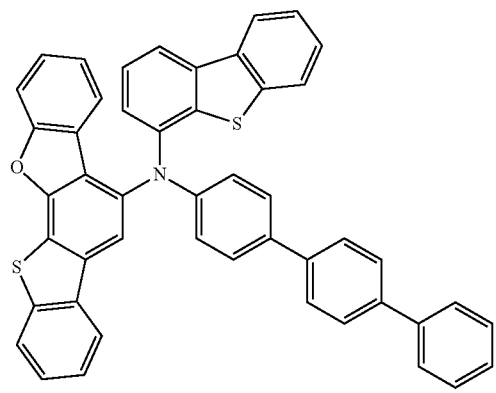
D25
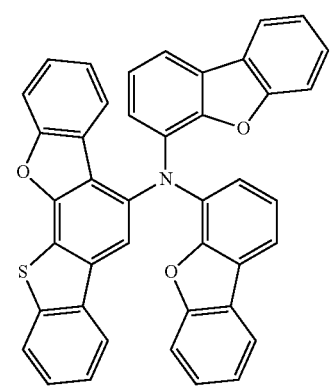
D26
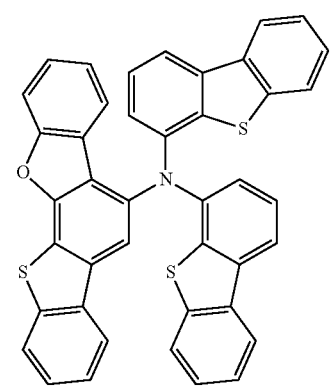
D27
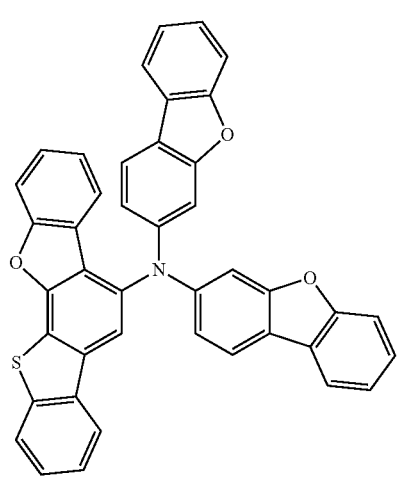
D28
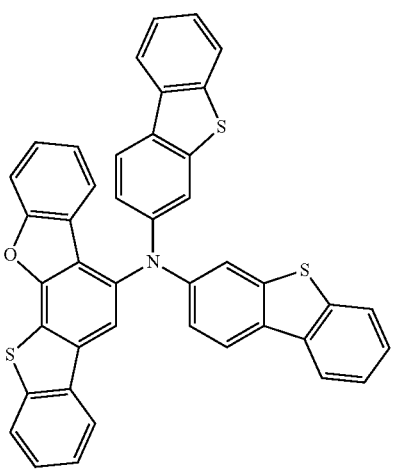
D29
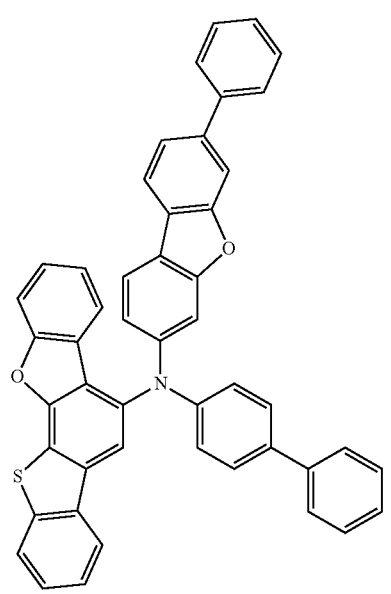
D30
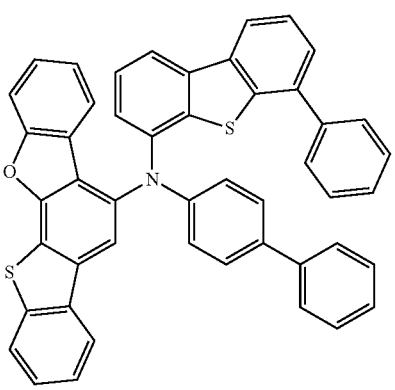

D39
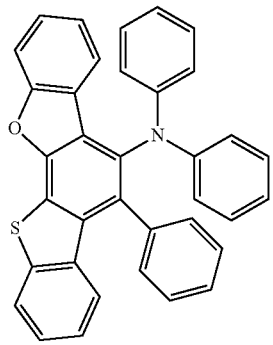
D40
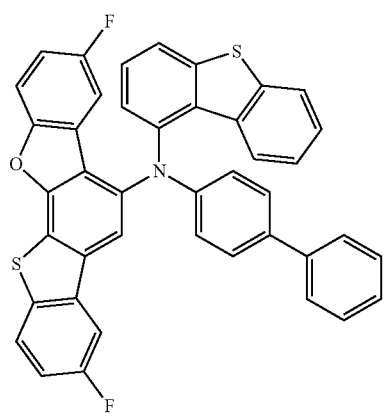
D41
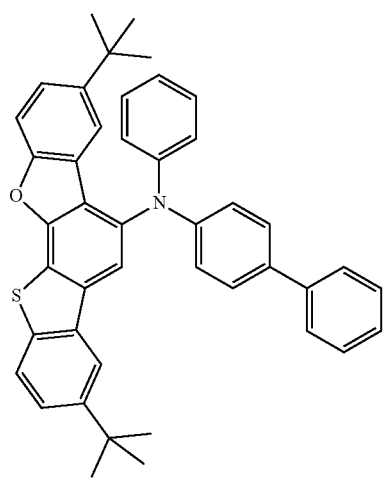
D42
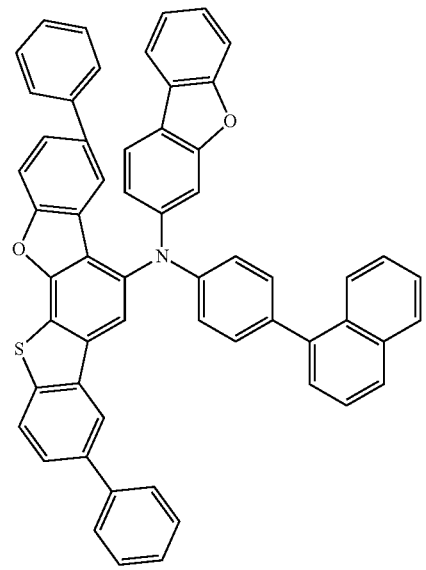
Compound Group E
E14
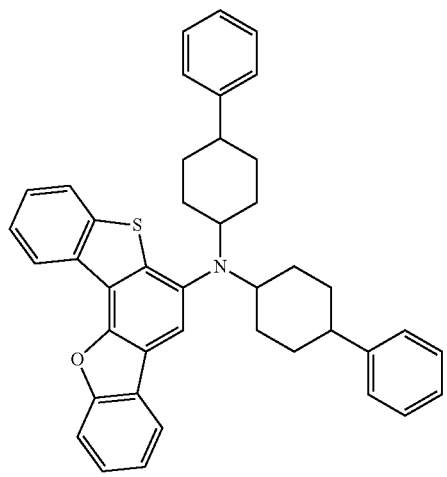
E15
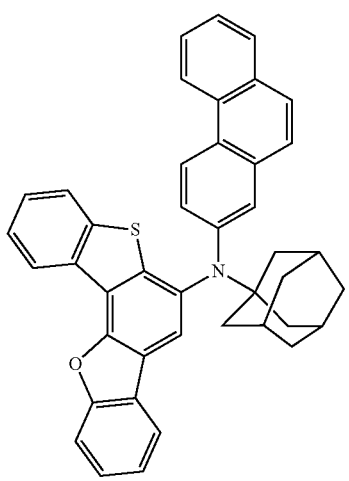

E17
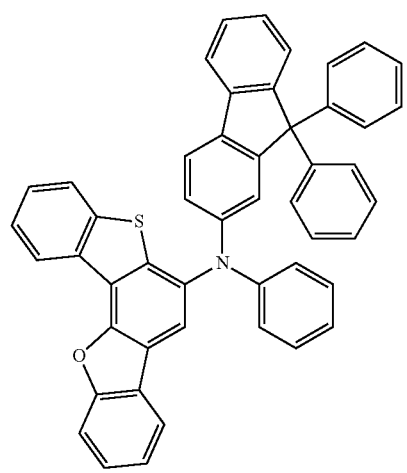
E18
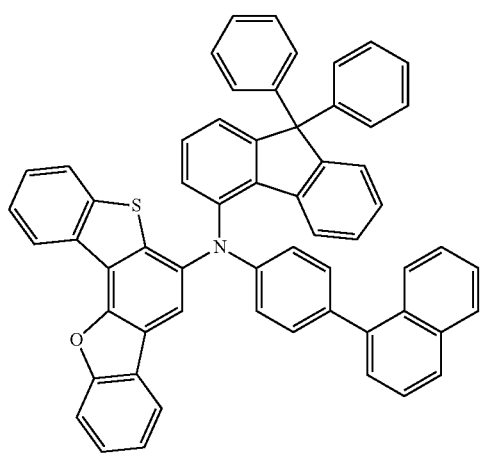
E19
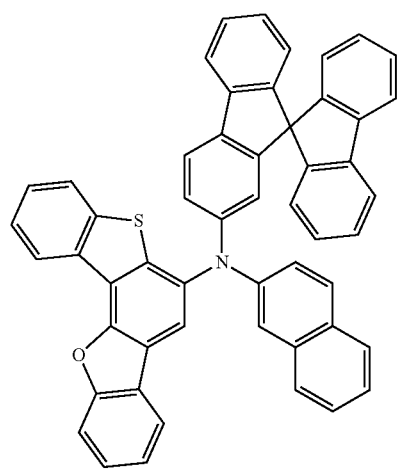
E20
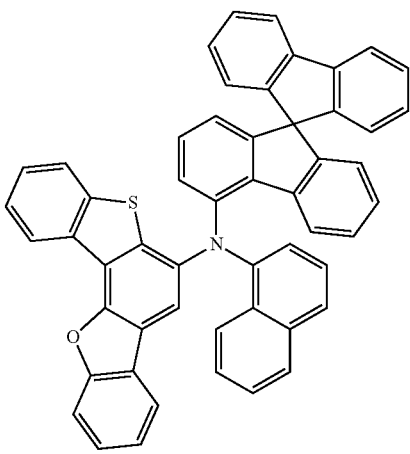
E22
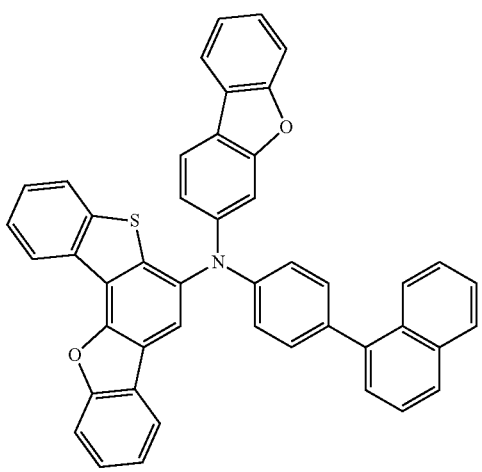
E23
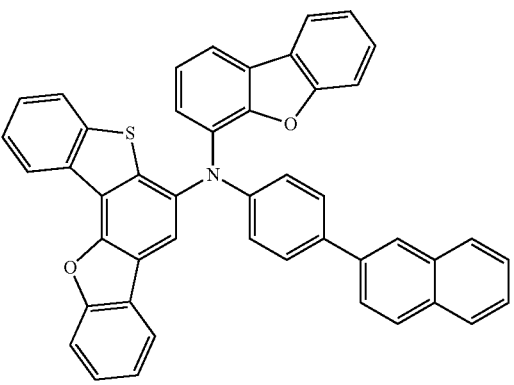

-continued
E24
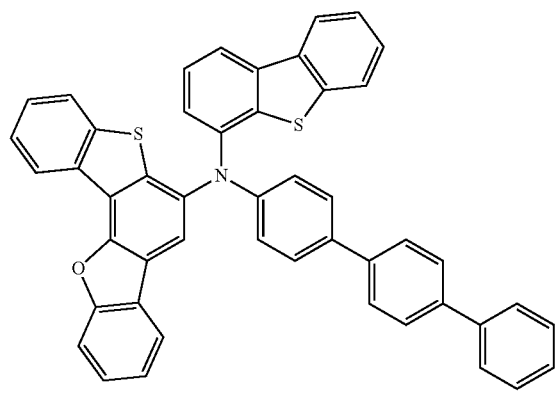
E25
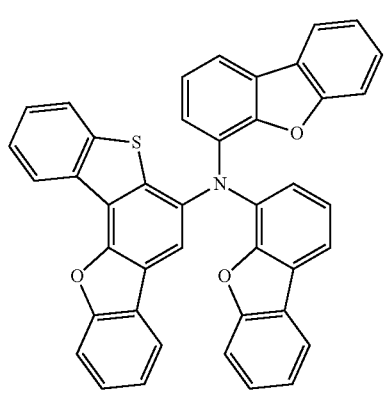
E26
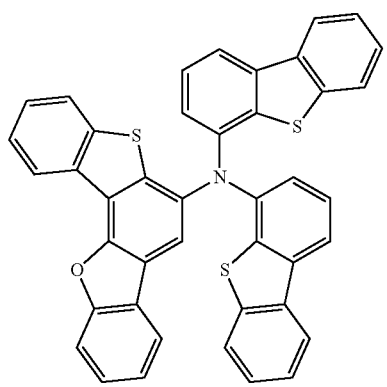
E27
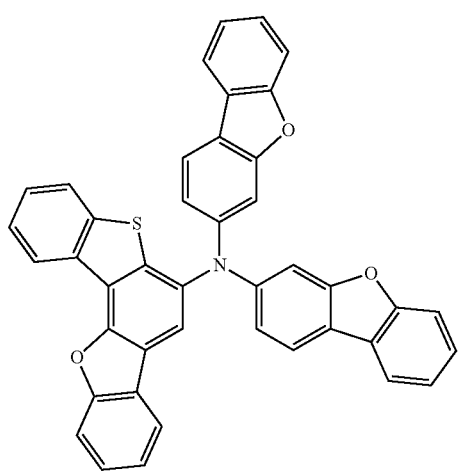
-continued
E28
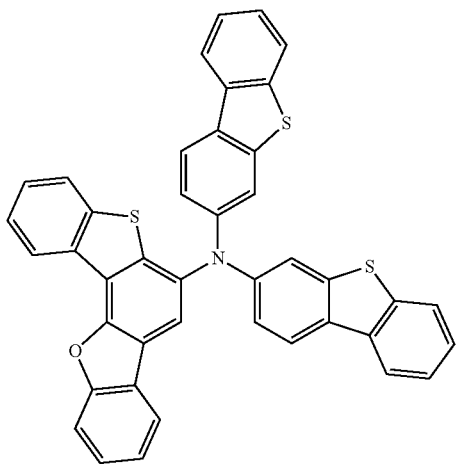
E42
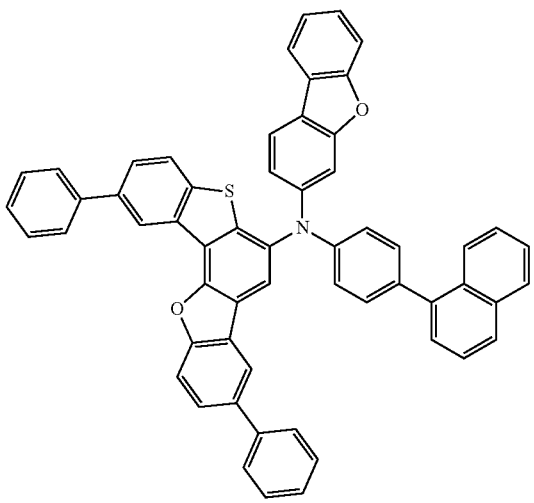
Compound Group F
F9
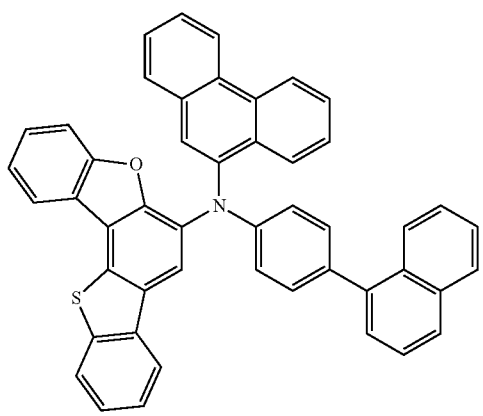

F14
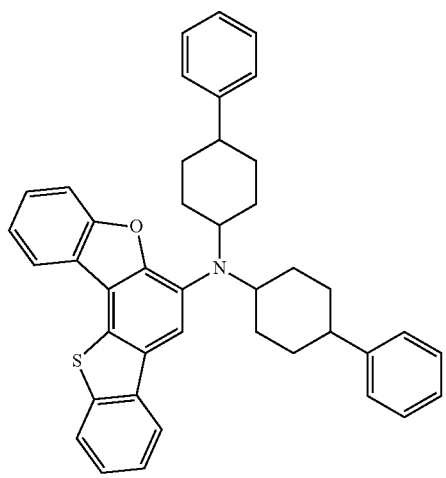
F15
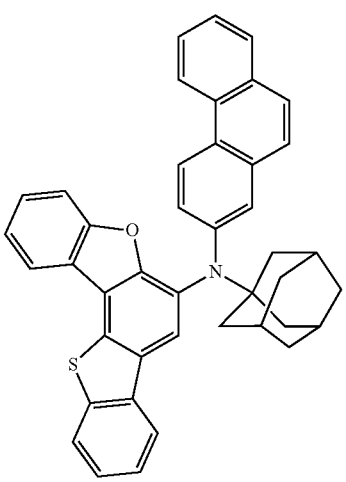
F17
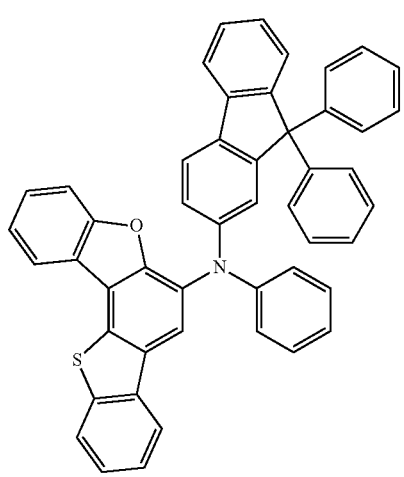
F18
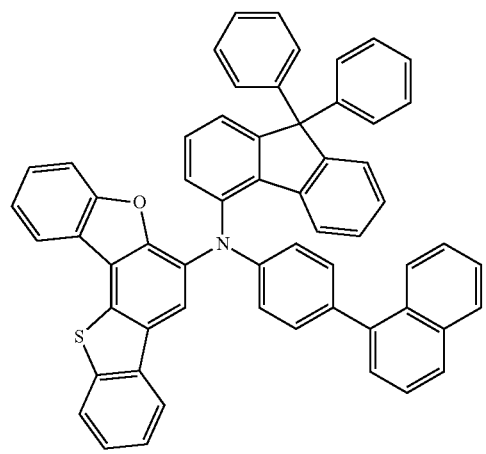
F19
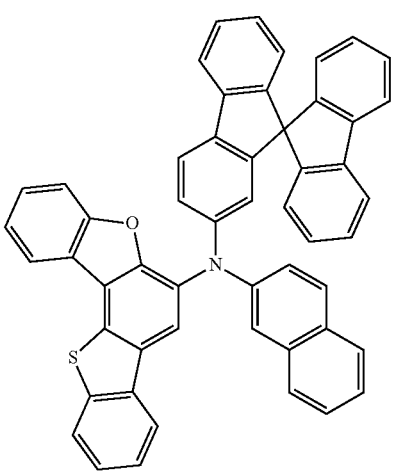
F20
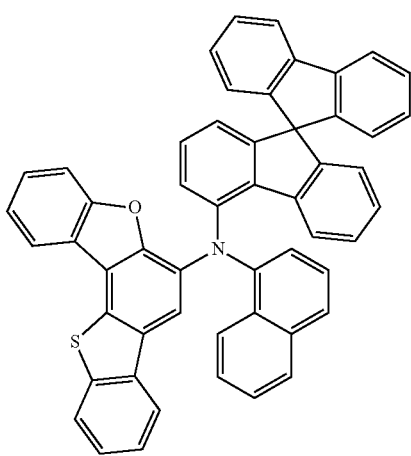

361
-continued
F22
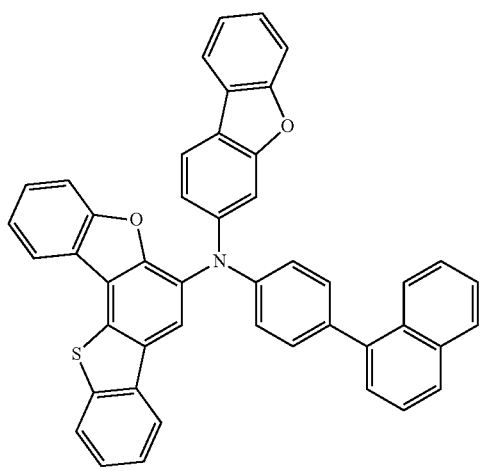
F23
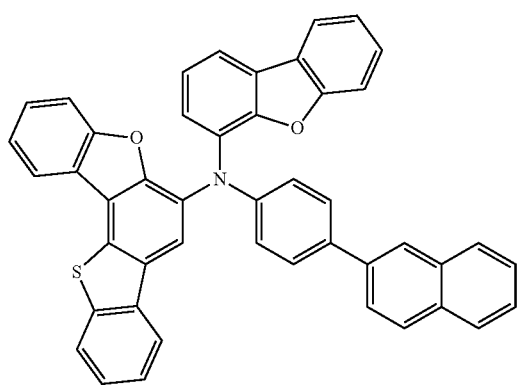
F24
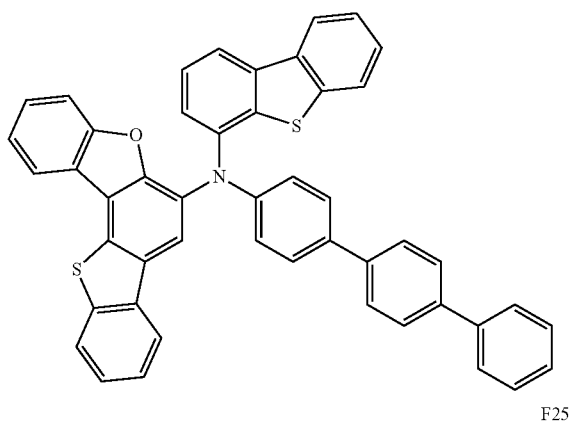
F25
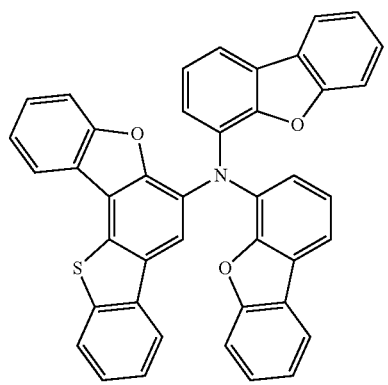
362
-continued
F26
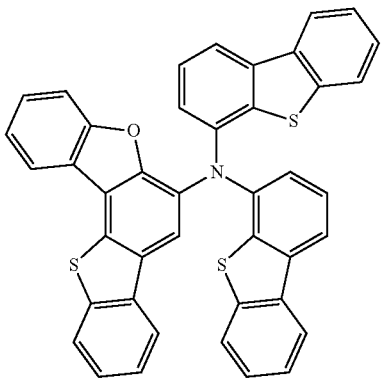
F27
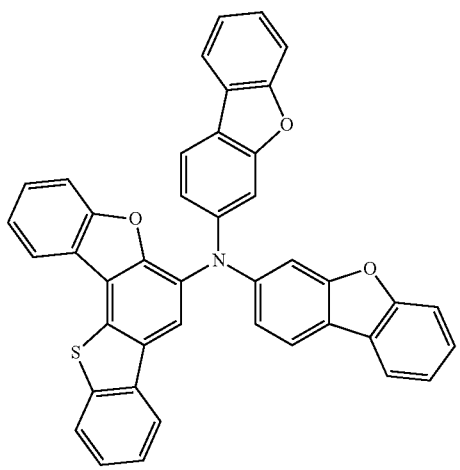
F28
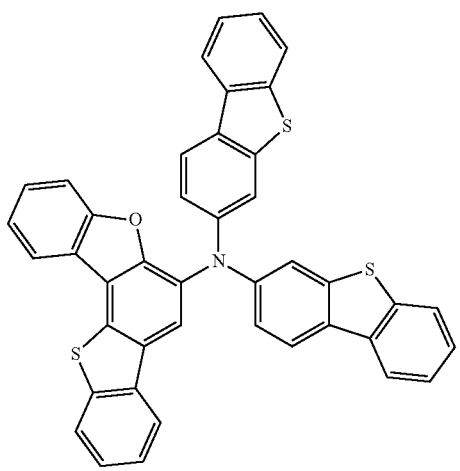

F42
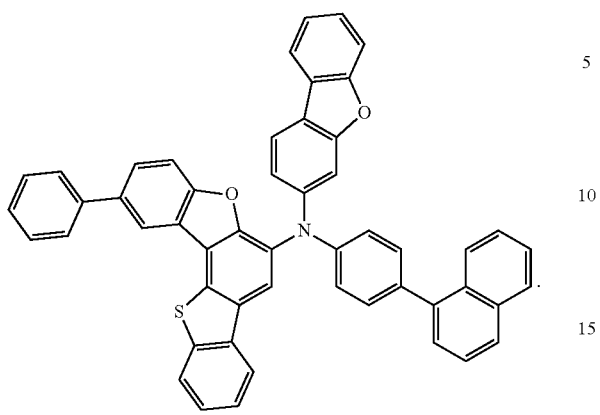
* * * * *

UNITED STATES PATENT AND TRADEMARK OFFICE
CERTIFICATE OF CORRECTION

PATENT NO. : 12,201,020 B2
APPLICATION NO. : 17/011843
DATED : January 14, 2025
INVENTOR(S) : Taku Imaizumi Page 1 of 1

It is certified that error appears in the above-identified patent and that said Letters Patent is hereby corrected as shown below:

In the Claims

In Column 284, Line 58, in Claim 6, delete "4-3,4-4," and insert -- 4-3, 4-4, --.

In Column 310, Line 34, in Claim 14, delete "4-3,4-4," and insert -- 4-3, 4-4, --.

In Column 310, Line 49, in Claim 15, below "Compound Group A" insert

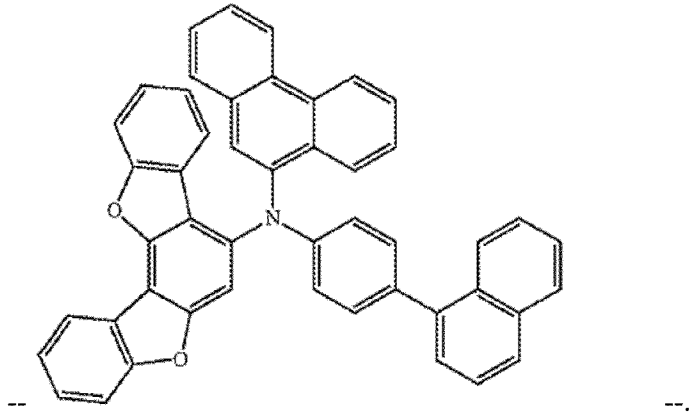

-- --.

Signed and Sealed this
Tenth Day of February, 2026

John A. Squires
*Director of the United States Patent and Trademark Office*